United States Patent [19]
Lucas et al.

[11] Patent Number: 5,698,411
[45] Date of Patent: Dec. 16, 1997

[54] METHOD FOR DETERMINING ACTIVITY OF ENZYMES IN METABOLICALLY ACTIVE WHOLE CELLS

[75] Inventors: Frank J. Lucas, Baca Raton; Gerald E. Jaffe; Steven E. Bott, both of Pembroke Pines; James H. Carter, Plantation, all of Fla.

[73] Assignee: Coulter Corporation, Miami, Fla.

[21] Appl. No.: 444,051

[22] Filed: May 18, 1995

[51] Int. Cl.$^6$ .............................. C12Q 1/02; C12Q 1/00
[52] U.S. Cl. ............................. 435/29; 435/4; 435/34
[58] Field of Search ................................. 435/4, 29, 24, 435/25, 34, 968

[56] References Cited

U.S. PATENT DOCUMENTS

| | | | |
|---|---|---|---|
| 3,786,140 | 1/1974 | Meyer-Bertenrath | 424/7 |
| 4,275,153 | 6/1981 | Gargiulo et al. | 435/13 |
| 4,279,810 | 7/1981 | Claeson et al. | 260/112.5 R |
| 4,336,186 | 6/1982 | Gargiulo et al. | 260/112.5 R |
| 4,557,862 | 12/1985 | Mangel et al. | 260/112 R |
| 4,640,893 | 2/1987 | Mangel et al. | 435/23 |
| 5,070,012 | 12/1991 | Nolan et al. | 435/6 |
| 5,208,148 | 5/1993 | Haugland et al | 435/14 |
| 5,290,682 | 3/1994 | Meneghini et al. | 435/25 |
| 5,330,889 | 7/1994 | Monget | 435/34 |
| 5,443,986 | 8/1995 | Haughland et al. | 435/4 |

FOREIGN PATENT DOCUMENTS

| | | |
|---|---|---|
| 1945663 | 3/1971 | Germany . |
| 9310461 | 5/1993 | WIPO . |

OTHER PUBLICATIONS

Rothe, G., Flow Cytometric Analysis of Protease Activiries in Vital Cells, Biol Chem Hoppe–Seyler, 373 Jul. 1992.
Dive, C., Improved Methodology for Intracellular Enzyme Reaction and Inhibition Kinetics by Flow Cytometry, Cytometry 8 552–561 1987.
Mitchell, G., Novel Rhodamine Tripeptide Substrate for Manual and Automated Colorimetric Prothrombin Time Test, Thrombosis Research, vol. 40, 339–349 1985.
Hegazi, F., Factors Affecting the Caseinolytic Activity of Lactobacillus CAsei and Lactobacillus Plantarum, Die Nahrung, vol. 31 No. 3, 199–206 1987.
Watson, Cytometry, vol. 1, No. 2, pp. 143–151 (1980).
Leytus et al, Biochem. J., vol. 209, pp. 299–307 (1983).
Leytus et al, Biochemica et Biophysica Acta, vol. 788, pp. 74–86 (1984).
Melhado et al, J. An. Chem. Soc., vol. 104, pp. 7299–7306.
Leytus et al, Biochem. J., vol. 215, pp. 253–260 (1983).
Kanaoka et al, Chem. Pharm. Bull, vol. 25, No. 2, pp. 362–363 (1977).
Morita et al, J. Biochem., vol. 82, pp. 1495–1498 (1977).
Mononen et al, Clinical Chemistry, vol. 40, No. 3, pp. 385–388 (1994).
Livingston et al, Biochemistry, vol. 20, No. 15, pp. 4298–4306 (1981).
Rothe et al, Biol. Chem. Hoppe–Seyler, vol. 373, pp. 547–554 (1992).
Mangel et al, Nature, vol. 361, pp. 274–275 (Jan. 21, 1993).
Huang et al ,The Journal of Histochemistry and Cytochemistry, vol. 41, No. 2, pp. 313–317 (1993).
Lottenberg et al, Methods in Enzymology, vol. 80, pp. 341–361 (1981).
Saifuku et al, Clinica Chimica Acta, vol. 84, No. ½, pp. 85–91 (1978).
Dive et al, Cytometry, vol. 8, pp. 552–561 (1987).
BioProbes 21–New Products and Applications from Molecular Probes, Inc., cover page, contents page and pp. 18–21 (Nov. 1994).
Duffy et al, Clinical Chemistry, vol. 38, No. 10, pp. 2114–2116 (1992).
Valet et al, Ann. NY Acad. Sci., vol. 677, pp. 233–251 (1993).
Cox et al, Cytometry, vol. 8, pp. 267–272 (1987).
Hjorth, Brain Topography, vol. 2, Nos. ½, pp. 57–61 (1989).
Windham et al, Journal of Computer Assisted Tomography, vol. 12, No. 1, pp. 1–9 (1988).

*Primary Examiner*—Ralph Gitomer
*Attorney, Agent, or Firm*—Mitchell E. Alter

[57] ABSTRACT

A method for assaying the activity of an enzyme inside a metabolically active whole cell is disclosed. The assay compound includes a leaving group and an indicator group. The leaving group is selected from the group comprising amino acids, peptides, saccharides, sulfates, phosphates, esters, phosphate esters, nucleotides, polynucleotides, nucleic acids, pyrimidines, purines, nucleosides, lipids and mixtures thereof. The indicator group is selected from compounds which have a first state when joined to the leaving group, and a second state when the leaving group is cleaved from the indicator group by the enzyme. Preferably, the indicator compounds are rhodamine 110, rhodol, and fluorescein and analogs of these compounds. A method of synthesizing the compound is also disclosed.

77 Claims, 45 Drawing Sheets
(7 of 45 Drawing(s) in Color)

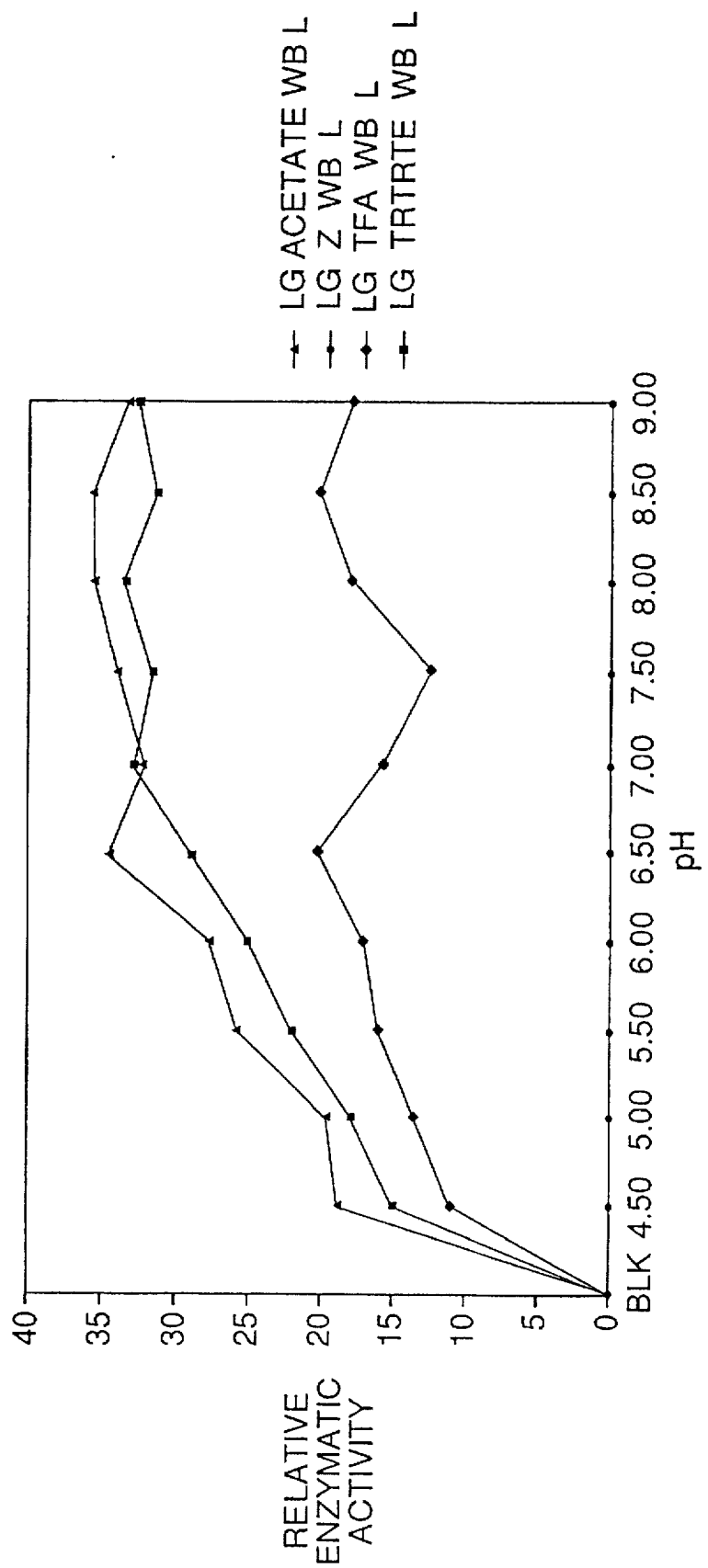

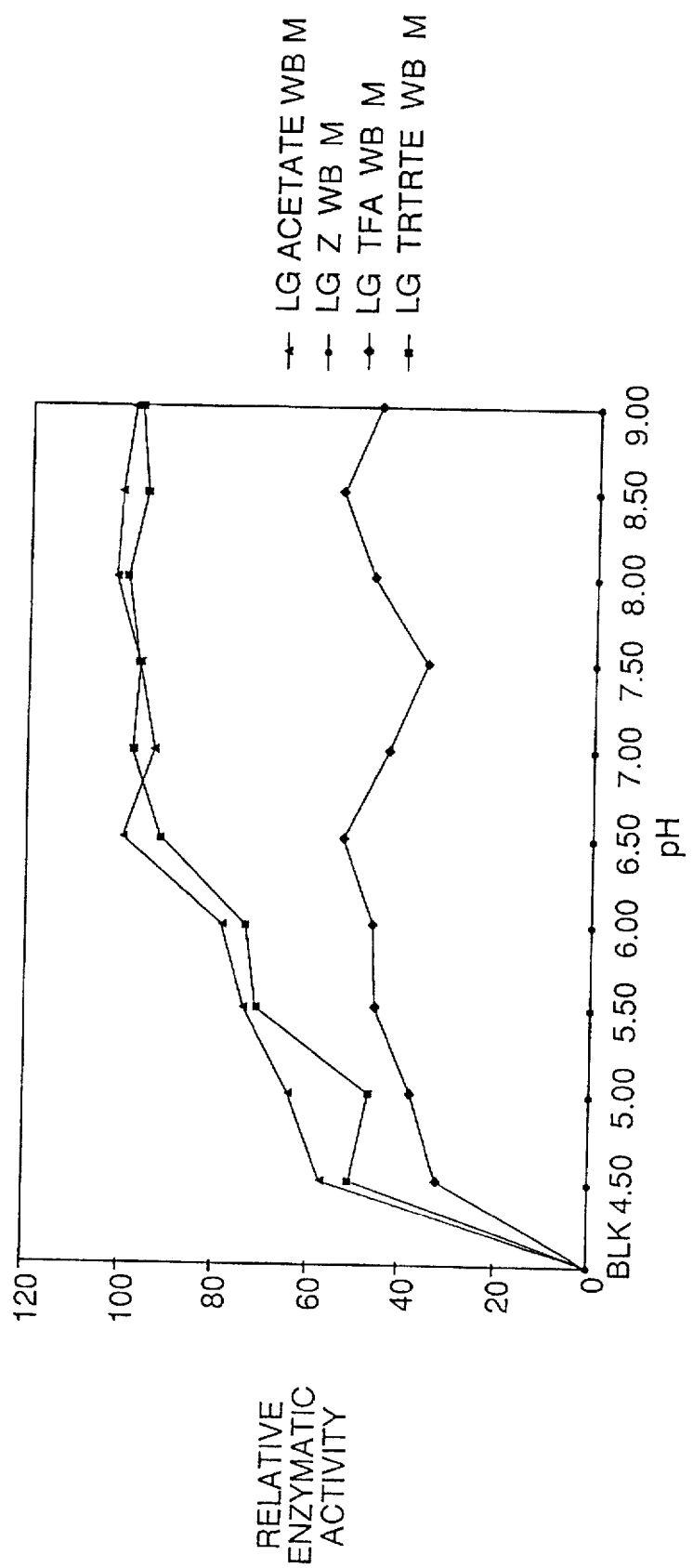

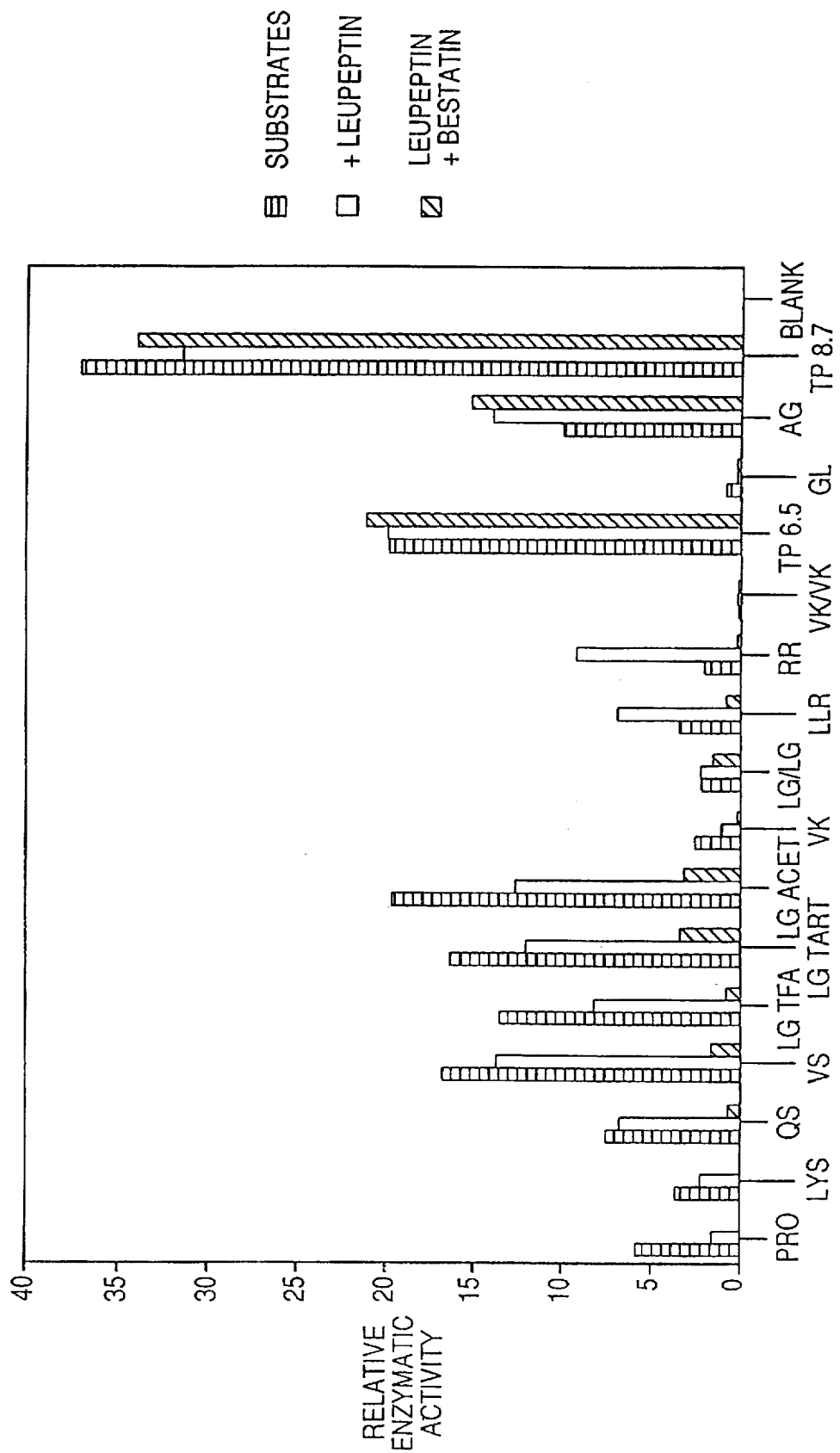

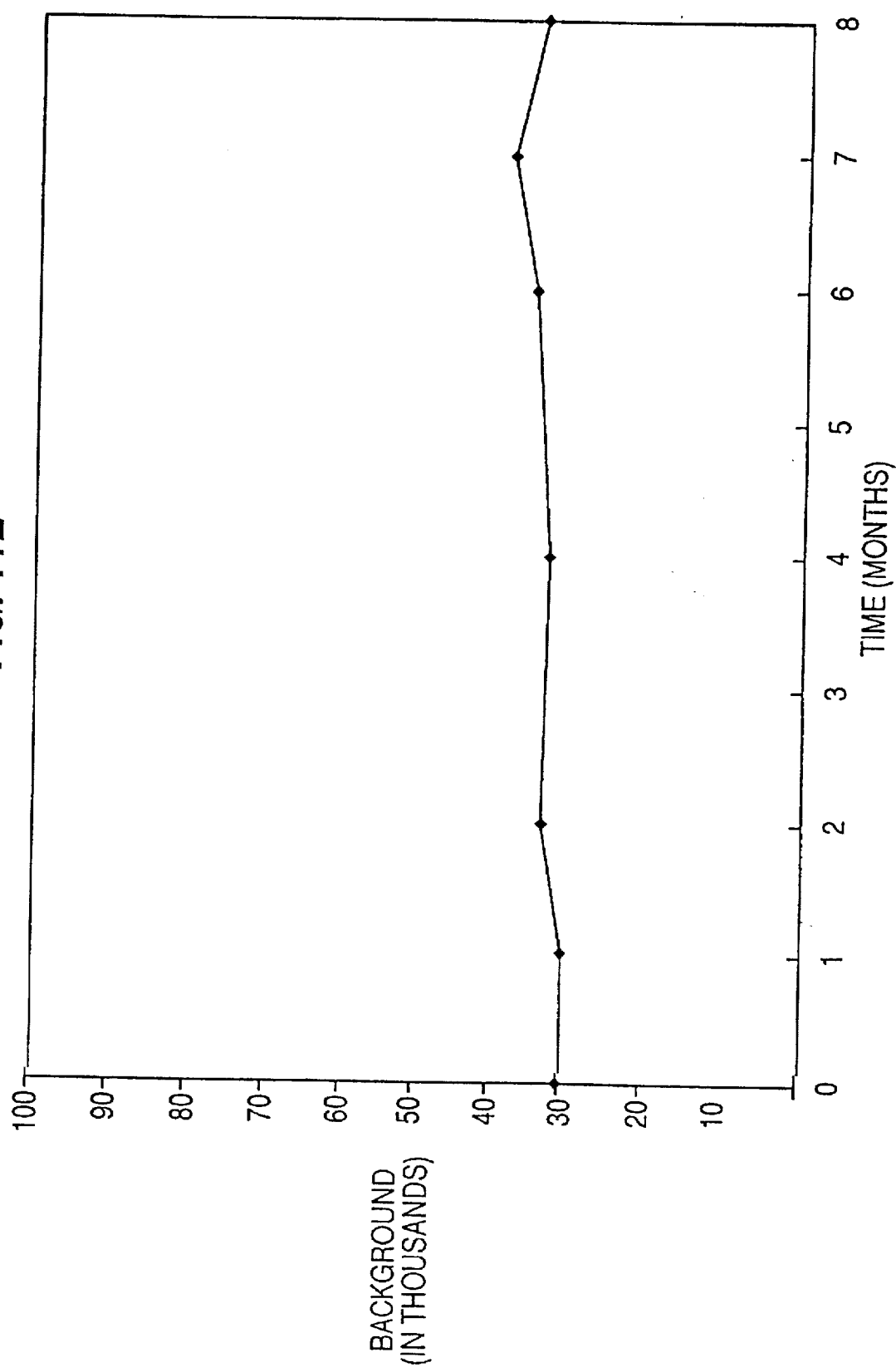

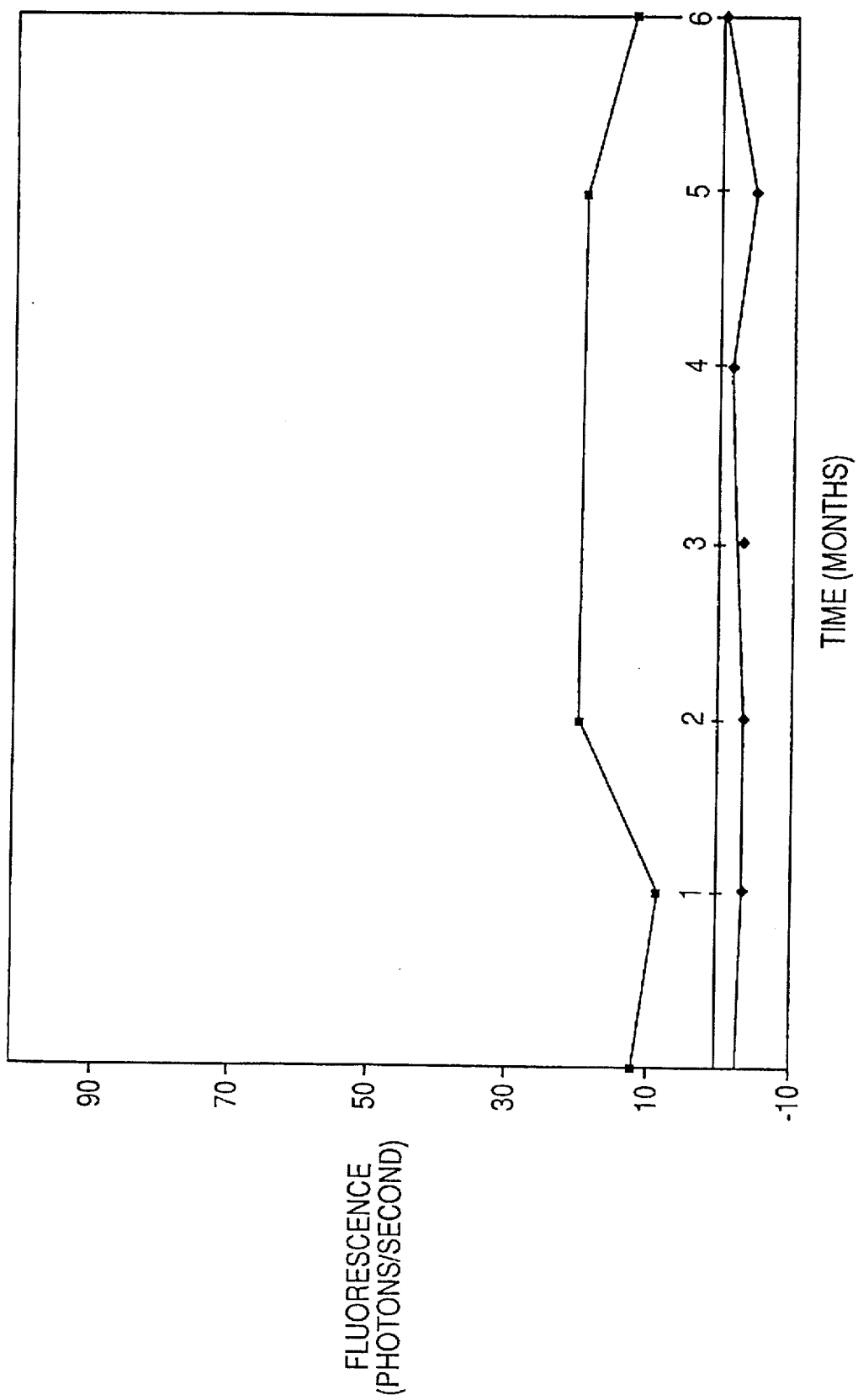

FIG. 14A

ANALYSIS OF VARIANCE VIA EIGENVECTORS

FULL COVARIANCE DATA MATRIX
DIMENSIONS: n+1 COLUMNS, nc * m ROWS

|  |  | NORMAL | DISEASE 1 | DISEASE 2 | ...... | DISEASE n |
|---|---|---|---|---|---|---|
| CELL TYPE 1 | ENZYME 1 |  |  |  |  |  |
|  | ENZYME 2 |  |  |  |  |  |
|  | ..... |  |  |  |  |  |
|  | ENZYME m |  |  |  |  |  |
| CELL TYPE 2 | ENZYME 1 |  |  |  |  |  |
|  | ENZYME 2 |  |  |  |  |  |
|  | ..... |  |  |  |  |  |
|  | ENZYME m |  |  |  |  |  |
|  |  | .... | .... | .... | .... | .... |
| CELL TYPE i | ENZYME 1 |  |  |  |  |  |
|  | ENZYME 2 |  |  |  |  |  |
|  | .... |  |  |  |  |  |
|  | ENZYME m |  |  |  |  |  |
|  |  | .... | .... | .... | .... | .... |
| CELL TYPE nc | ENZYME 1 |  |  |  |  |  |
|  | ENZYME 2 |  |  |  |  |  |
|  | .... |  |  |  |  |  |
|  | ENZYME m |  |  |  |  |  |

↓
EIGENVECTOR ANALYSIS 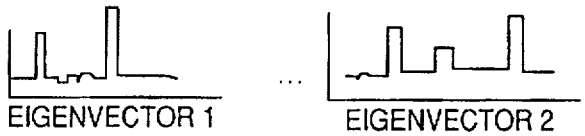
↓
EIGENVECTOR 1 ... EIGENVECTOR 2

REDUCED COVARIANCE DATA MATRIX
OF STRONGLY CONTRIBUTING FACTORS

DIMENSIONS: n+1 COLUMNS, m1+m2+... mnc ROWS;
$mi \leq m$, FOR ALL i

|  |  | NORMAL | DISEASE 1 | DISEASE 2 | ...... | DISEASE n |
|---|---|---|---|---|---|---|
| CELL TYPE 1 | ENZYME 1 |  |  |  |  |  |
|  | .... |  |  |  |  |  |
|  | ENZYME m1 |  |  |  |  |  |
| CELL TYPE 2 | ENZYME 1 |  |  |  |  |  |
|  | .... |  |  |  |  |  |
|  | ENZYME m2 |  |  |  |  |  |
|  |  | .... | .... | .... | .... | .... |
| CELL TYPE i | ENZYME 1 |  |  |  |  |  |
|  | .... |  |  |  |  |  |
|  | ENZYME mi |  |  |  |  |  |
|  |  | .... | .... | .... | .... | .... |
| CELL TYPE nc | ENZYME 1 |  |  |  |  |  |
|  | .... |  |  |  |  |  |
|  | ENZYME mnc |  |  |  |  |  |

PREDICTION OF DISEASE STATE BY NNLS

REDUCED COVARIANCE DATA MATRIX
OF STRONGLY CONTRIBUTING FACTORS
DIMENSIONS: n+1 COLUMNS, m1+m2+... mnc ROWS;
$mi < m$, FOR ALL i

NEURAL NETWORK FLOW CHART

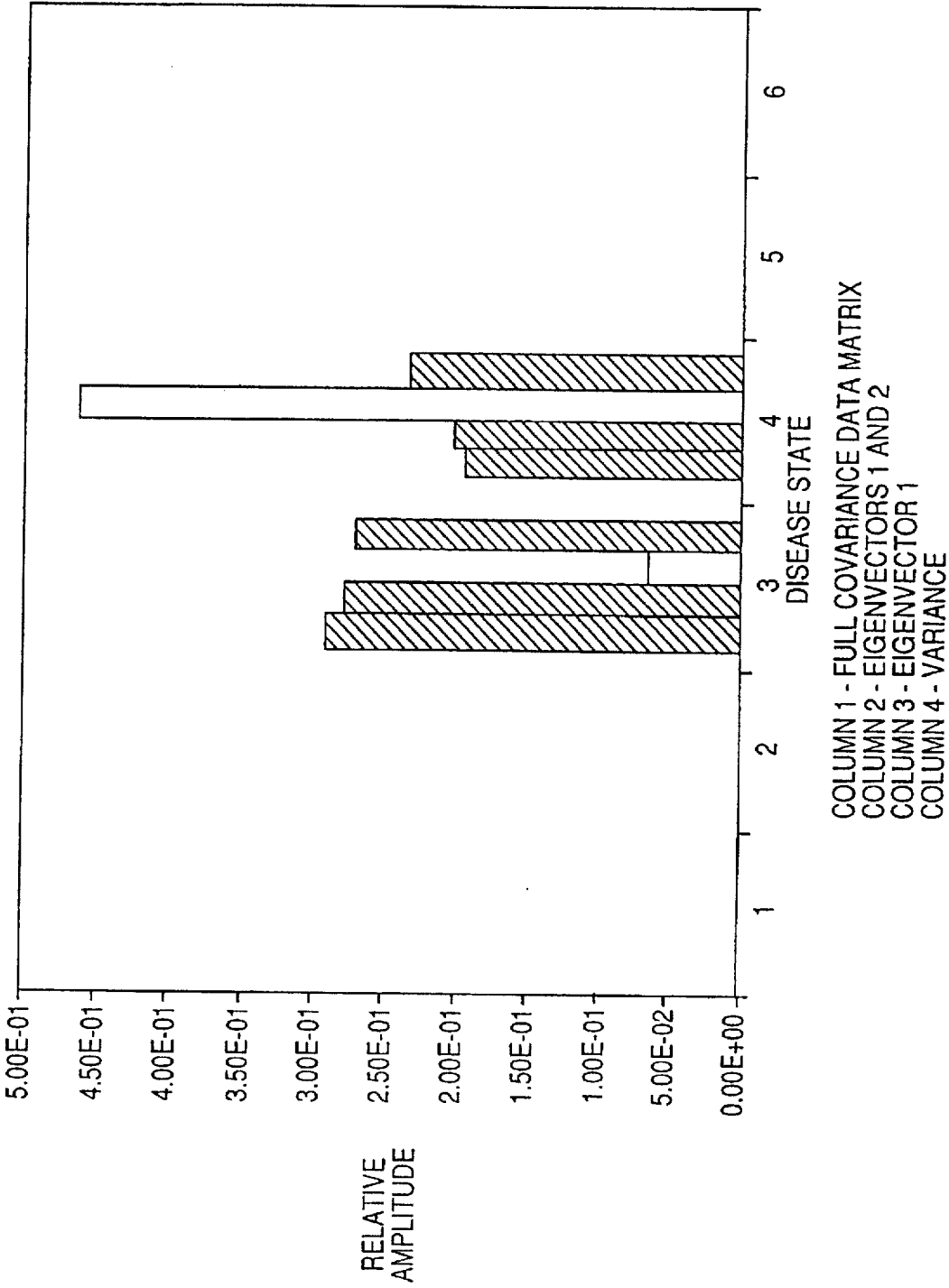

HARVARD RATIO - JR. RHEUMATOID ARTHRITIS

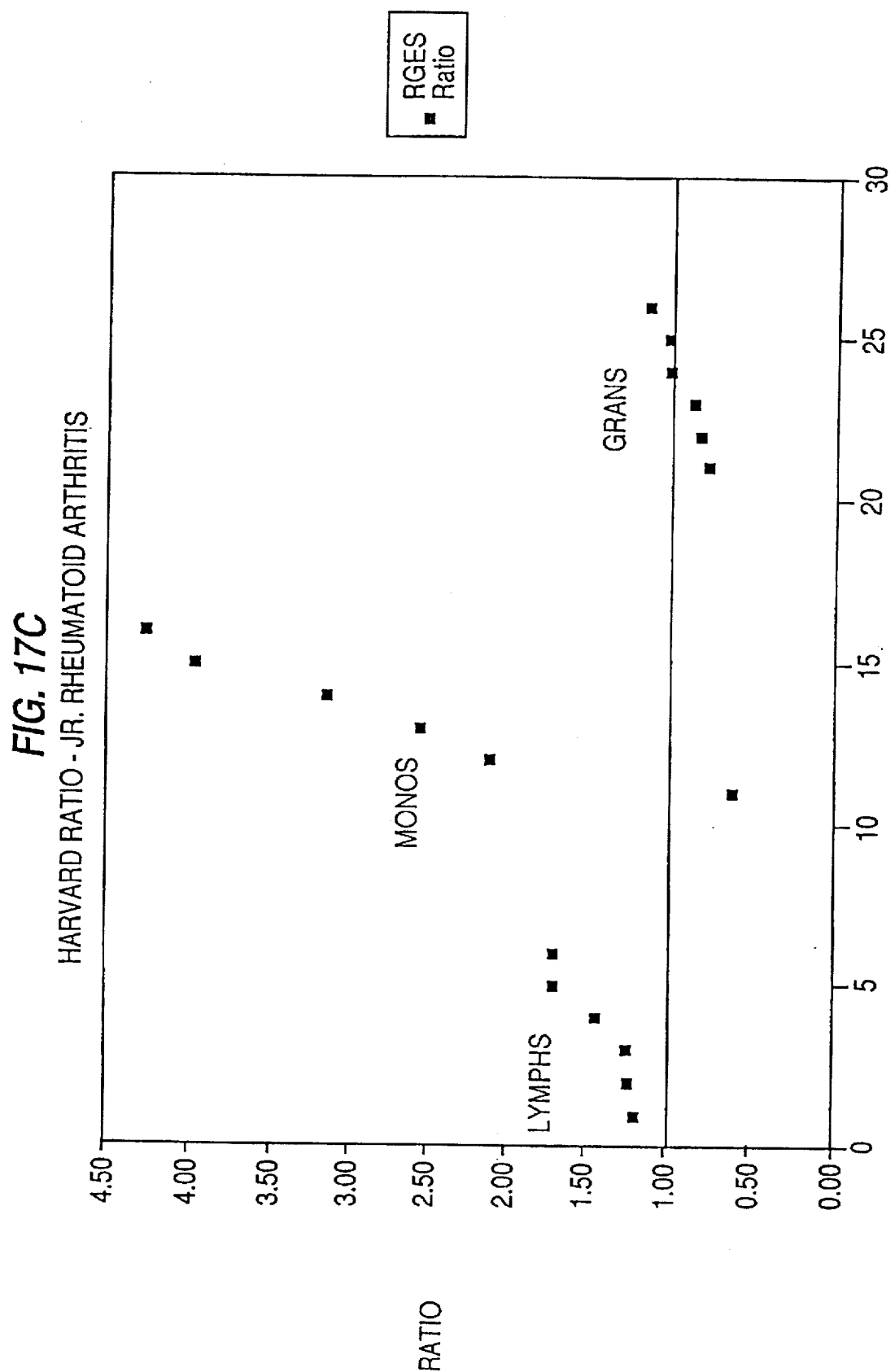

FIG. 18G

| | | PRIMARY PEAK | | | BIMODAL PEAK | | | PRIMARY PEAK | | | BIMODAL PEAK | | |
|---|---|---|---|---|---|---|---|---|---|---|---|---|---|
| SUBSTRATE | NORMAL GR MEAN NORMAL GRAND X (LY) | J94 8/25 J94 LYMPHS | J94 9/21 J94 LYMPHS | J94 10-12 J94 LYMPHS | J94 8/25 J94 LYMPHS BIMODAL | J94 9/21 J94 LYMPHS BIMODAL | J94 10-12 J94 LYMPHS BIMODAL | J94 9/6 J94 LYMPHS | J94 9/26 J94 LYMPHS | J94 10/13 J94 LYMPHS | J94 9/6 J94 LYMPHS BIMODAL | J94 9/26 J94 LYMPHS BIMODAL | J94 10/13 J94 LYMPHS BIMODAL |
| QS | 1.701 | 6.072 | | 1.98 | | | | 1.962 | | | | | |
| VS | 3.813 | 7.311 | | 4.44 | | | 1.34 | 2.842 | | | | | |
| GLY | 18.178 | 30.120 | 24.880 | 11.91 | | | | 11.380 | 22.760 | 12.23 | | | |
| LEU | 34.938 | | | 29.70 | | | | | | 26.26 | | | |
| CLOAC | 2.490 | 11.400 | 5.702 | 3.05 | 43.160 | 17.900 | | 5.552 | 12.550 | 1.98 | | | |
| DPO4 | 54.289 | | | 88.39 | | | | 30.570 | | | | | |
| DGLUC | 0.941 | | | 1.87 | 34.480 | | | 0.247 | | | | | |
| FDA | 13.384 | 32.180 | 22.880 | 14.22 | | | | 22.420 | 36.440 | 11.43 | | | |
| FDA-NAF | 17.980 | 33.790 | 24.500 | 12.43 | | | | 22.360 | 27.230 | 11.50 | | | |
| DIBUT 7.5 | 4.080 | 16.010 | 19.970 | 10.33 | | | | 12.950 | 11.160 | 9.41 | | | |
| DCFH-DAMES | 4.107 | 11.850 | 10.83 | 3.89 | | | | 14.640 | 25.040 | 3.07 | | | |
| DCFHMESPMA | 4.694 | | | 4.33 | | | | | | 3.17 | | | |

METHOD FOR DETERMINING ACTIVITY OF ENZYMES IN METABOLICALLY ACTIVE WHOLE CELLS

BACKGROUND OF THE INVENTION

1. Field of the Invention

This invention relates generally to cytoenzymology, and more particularly reagents for use in cytoenzymology as well as production and use of these reagents.

2. Description of the Background Art

Cytoenzymology is the study of enzymes as they function on and within cells. Previously, the study of enzymatic activity within cells has been pursued primarily by two indirect methods. According to a first method, the cell membrane is broken to create a cytosol of cellular components including the enzyme which is the object of study. Various tests are then performed to determine the activity of the enzyme, which tests can be performed on the cytosol or on the purified enzyme. According to a second method, the enzyme activity is determined from the study of extracellular events, such as the presence or lack of the products of enzyme activity.

According to the first method, various tests are performed to determine enzyme activity in the cytosol. One such test is to provide a substrate that is recognized by the enzyme, with a fluorescent compound which will undergo a detectable change when the substrate, or "leaving group", is cleaved from the compound by the enzyme. Mangel et al., U.S. Pat. Nos. 4,557,862 and 4,640,893, disclose rhodamine 110-based derivatives as fluorogenic substrates for proteinases. These compounds have the general formula:

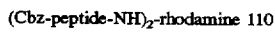

(Cbz-peptide-NH)$_2$-rhodamine 110 where the peptide includes known amino acids or amino acid derivatives, and "Cbz" refers to the blocking group benzyloxycarbonyl. When the amino groups of rhodamine 110 are blocked the compound is "quenched", and is relatively colorless and non-fluorescent. Cleavage of one of the peptides from the non-fluorescent bisamide substrate results in a 3500-fold increase in fluorescence intensity.

The rhodamine 110 substrates of Mangel et al. have been utilized to conduct cytoenzymological studies. G. Rothe et al., *Biol. Chem. Hoppe-Seyler*, 373, 544–547 (1992) describe the analysis of proteinase activities using the substituted peptide-rhodamine 110 derivatives of Mangel et al. Moreover, G. Valet et al, *Ann NY Acad Sci*, 667, 233–251 (1993), disclose the study of white cell and thrombocyte disorders with the rhodamine 110 derivatives of Mangel et al. The methods of Rothe and Valet have been used to conduct cytoenzymological studies on the activity of enzymes with cells, but the compounds utilized by Rothe and Valet are not suitable for the study of the activity of intracellular enzymes in vital cells. The Mangel et al. compounds cannot be efficiently solubilized and transmitted through the cell membrane in a manner which will produce a reliable assay. In addition, the Cbz group in the Mangel et al. compound is not recognized by the enzyme's active sites. Further, Mangel, et al., disclose the removal of the carbobenzyloxy group by treating the blocked peptide-indicator compound with 30% hydrobromide acid in acetic acid. However, the bromide salt is lethal to the cell and does not permit an assay for a metabolically active cell.

I. Mononen, et al., *Clin. Chem.*, 40(3), 385–388 (1994), describe the enzymatic diagnosis of aspartylglycosaminuria by the fluorometric assay of glycosylasparaginase in serum, plasma, and lymphocytes. The study was conducted on cytosols, and not whole cells, and utilized an asparagine-substituted 7-amino-4-methylcoumarin.

Dead or metabolically inactive cells can have as little as approximately one-quarter the enzymatic activity of living cells, Watson, J., "Enzyme Kinetic Studies in Cell Population Using Fluorogenic Substrates and Flow Cytometric Techniques", *Cytometry*, 1(2), p. 143 (1980). Further, because enzymes are frequently bound in highly organized enzyme pathways, the disruption and death of the cell can greatly affect enzyme activity. Current assays therefore have limited utility for determining enzyme activity in a living or metabolically active whole cell.

U.S. Pat. No. 5,070,012 to Nolan et al., describes a method of monitoring cells and trans-acting transcription elements. This method, however, is not designed for the monitoring of enzymes which are endogenous to the cell being tested. Rather, in this method a hypotonic solution is used to increase the permeability of the cell membrane thereby allowing an exogenous enzyme and other reagents (including a fluorogenic substrate) to be introduced into the cell. However, these severe hypotonic conditions significantly alter the normal state of the cell. The fluorogenic substrate described in this patent (fluoroscein digalactopyranoside) contains significant amounts of fluorescent impurities and must be bleached with a laser prior to use.

SUMMARY OF THE INVENTION

The present invention relates to an assay reagent for determining the activity of an enzyme in a metabolically active whole cell, said assay reagent comprising at least one water soluble assay compound having the ability to pass through a cell membrane or a water soluble physiologically acceptable salt thereof having the ability to pass through a cell membrane, said assay compound having a leaving group selected for cleavage by an enzyme to be analyzed and a fluorogenic indicator group being selected for its ability to have a non-fluorescent first state when joined to the leaving group, and a fluorescent second state excitable at a wavelength above 450 nm when the leaving group is cleaved from the indicator group by the enzyme, said assay reagent having a fluorescence less than the auto-fluorescence of a metabolically active cell and being stable for a minimum of 30 days when stored at 4° C., wherein said stability is defined as the compound having an increase in background fluorescence of ≦10%.

The present invention also relates to an assay reagent for determining the activity of an enzyme in a metabolically active whole cell, said assay reagent comprising at least one water soluble salt of an assay compound having the ability to pass through a cell membrane, said assay compound having a leaving group selected for cleavage by an enzyme to be analyzed and a fluorogenic indicator group being selected for its ability to have a first non-fluorescent state when joined to the leaving group, and a second fluorescent state excitable at a wavelength above 450 nm when the leaving group is cleaved from the indicator group by the enzyme, and said assay reagent having a fluorescence less than the auto-fluorescence of a metabolically active cell.

The present invention also relates to an assay reagent composition for determining the activity of an enzyme in a metabolically active whole cell, said assay reagent comprising at least one water soluble assay compound having the ability to pass through a cell membrane or a water soluble physiologically acceptable salt thereof having the ability to pass through a cell membrane, said assay compound having a leaving group selected for cleavage by an enzyme to be analyzed and a fluorogenic indicator group being selected for its ability to have a non-fluorescent first state when joined to the leaving group, and a fluorescent second state excitable at a wavelength above 450 nm when the leaving group is cleaved from the indicator group by the enzyme, and at least one additive selected from the group consisting of a buffer, an enzyme cofactor, an enzyme modulator, an enzyme inhibitor, an enzyme activator, a solubilizing component for said assay reagent, and a retention component for said assay reagent or products thereof, said assay reagent having a fluorescence less than the auto-fluorescence of a metabolically active cell.

This invention also relates to a method to produce an assay reagent for determining the activity of an enzyme in a metabolically active whole cell, in which the cell is contacted with the assay reagent. In a broad aspect, the invention relates to a method to make an assay compound for assaying the activity of an enzyme inside a metabolically active whole cell, said assay compound comprising an indicator group and a leaving group, said leaving group being selected for cleavage by said enzyme, comprising reacting a compound containing a leaving group selected from the group consisting of amino acids, peptides, saccharides, sulfates, phosphates, esters, phosphate esters, nucleotides, polynucleotides, nucleic acids, pyrimidines, purines, nucleosides, lipids and mixtures thereof and a blocking group, with an agent to form an intermediate complex containing a leaving group and a blocking group, reacting the intermediate complex with a compound containing an indicator group to form a reaction product; separating the reaction product from side reaction products, by-products and starting materials, removing blocking groups from the reaction product to obtain an assay compound having an indicator group and leaving group, optionally reacting the intermediate compound having an indicator group and leaving group with an acid or base to form a physiologically acceptable salt of said assay compound for assaying the activity of an enzyme inside a metabolically active whole cell, and purifying the assay compound or the physiologically acceptable salt thereof.

More specifically, the present invention is further related to a method for making an assay compound for assaying the activity of an enzyme inside a metabolically active whole cell, said assay compound comprising an indicator group and a leaving group, said leaving group being selected for cleavage by said enzyme, comprising reacting a compound containing a leaving group selected from the group consisting of amino acids, peptides, saccharides, esters, nucleotides, lipids and mixtures thereof, and a blocking group with an agent to form an intermediate complex containing a leaving group and a blocking group, reacting the intermediate complex with a compound containing an indicator group to form a reaction product, separating the reaction product from side reaction products, by-products and starting materials, removing the blocking group from the reaction product to obtain an assay compound having an indicator group and leaving group, and purifying the assay compound.

In another embodiment, the present invention is further related to a method for making an assay compound in a salt form for assaying the activity of an enzyme inside a metabolically active whole cell, said assay compound comprising an indicator group and a leaving group, said leaving group being selected for cleavage by said enzyme, comprising reacting a compound containing a leaving group selected from the group consisting of amino acids, peptides, phosphates, sulfates, esters, nucleotides and mixtures thereof, and a blocking group with an agent to form an intermediate complex containing a leaving group and a blocking group, reacting the intermediate complex with a compound containing an indicator group to form a reaction product, separating the reaction product from side reaction products, by-products and starting materials, removing the blocking group from the reaction product to obtain an assay compound having an indicator group and leaving group, reacting the intermediate compound having an indicator group and leaving group with an acid or a base to form a physiologically acceptable salt of said assay compound for assaying the activity of an enzyme inside a metabolically active whole cell, and purifying the physiologically acceptable salt of said assay compound.

The assay reagent has at least one assay compound having an indicator group and a leaving group. The leaving group is selected for cleavage by the enzyme to be assayed. The indicator group is in a first state when joined to the leaving group (e.g. the indicator is non-fluorescent), and is in a second state when the leaving group is cleaved from the indicator group by the enzyme (e.g. the indicator group is fluorescent).

The present invention also relates to a method for determining the activity of an endogenous enzyme in a metabolically active whole cell, comprising contacting a metabolically active whole cell with an assay reagent under conditions which allow said assay reagent to pass into said metabolically active whole cell, said assay reagent having at least one assay compound having the ability to pass through a cell membrane or a physiologically acceptable salt thereof having the ability to pass through a cell membrane, said assay compound comprising a fluorogenic indicator group and a leaving group, said leaving group being selected for cleavage by said enzyme, said indicator group being in a non-fluorescent first state when joined to said leaving group, and being in a fluorescent second state excitable at a wavelength above 450 nm when said leaving group is cleaved from said indicator group by said enzyme for a period of time sufficient for said assay reagent to be transferred into said cell and for said leaving group to be cleaved inside said cell from said indicator group by said enzyme, exposing said cell to light having a wavelength above 450 nm, and measuring fluorescence of said cell.

The present invention also relates to a method for detecting an abnormality in the activity of an enzyme in a metabolically active whole cell, comprising (a) contacting a reference, metabolically active whole cell having a normally functioning enzyme with a medium containing an assay reagent, said assay reagent having at least one water soluble assay compound having the ability to pass through a cell membrane or a water soluble physiologically acceptable salt thereof having the ability to pass through a cell membrane, said assay compound comprising a fluorogenic indicator group and a leaving group, said leaving group being selected for cleavage by said enzyme, said indicator group being in a non-fluorescent first state when bonded to said leaving group, and being in a fluorescent second state excitable at a wavelength above 450 nm when said leaving group is cleaved from said indicator group by said enzyme, for a period of time sufficient for said assay compound to be transferred into said cell and for said leaving group to be cleaved inside said cell from said indicator group by said enzyme, (b) sensing for said fluorescent second state of said indicator group for the reference, metabolically active whole cell to produce reference results, (c) contacting a test, metabolically active whole cell with said medium for said period of time, (d) sensing for said fluorescent second state of said indicator group for the test, metabolically active whole cell to produce test results, and (e) comparing the reference results of reference test, metabolically active whole cell in said step (b) with the test results obtained from said test metabolically active whole cell in said step (d).

The present invention also relates to a method of performing an assay for detecting the presence of a disease comprising (a) contacting a test, metabolically active whole cell with an assay reagent, said assay reagent containing at least one water soluble assay compound or water soluble physiologically acceptable salt thereof having a fluorogenic indicator group and a leaving group, said leaving group being selected for cleavage by a enzyme the activity of which changes with the presence of the disease, said indicator group being in a non-fluorescent first state when bonded to said leaving group, and being in a fluorescent second state excitable at a wavelength above 450 nm when said leaving group is cleaved from said indicator group by said enzyme for a period of time at least sufficient for said assay compound to be transferred into said cell and for said leaving group to be cleaved inside said cell from said indicator group by said enzyme, (b) sensing for said fluorescent second state of the indicator group for the test, metabolically active whole cell to produce test results, and (c) comparing the test results of said test metabolically active whole cell with reference results obtained from at least one of a diseased reference cell and a non-diseased reference cell.

The present invention also relates to a method for detecting an abnormality in the activity of an enzyme in a metabolically active whole cell, comprising (a) contacting a plurality of reference, metabolically active whole cells, each having at least one normally functioning enzyme with a medium containing an assay reagent, said assay reagent having at least one water soluble assay compound having the ability to pass through a cell membrane or a water soluble physiologically acceptable salt thereof having the ability to pass through a cell membrane, said assay compound comprising a fluorogenic indicator group and a leaving group, said leaving group being selected for cleavage by one of said at least one normally functioning enzymes, said indicator group being in a non-fluorescent first state when bonded to said leaving group, and being in a fluorescent second state excitable at a wavelength above 450 nm when said leaving group is cleaved from said indicator group by the one of said at least one normally functioning enzyme, for a period of time sufficient for said assay compound to be transferred into each of said plurality of reference, metabolically active whole cells for each of the at least one normally functioning enzymes for each of said plurality of reference, metabolically active whole cells to produce a matrix of reference results and for said leaving group to be cleaved inside of each of said plurality of reference, metabolically active whole cells from said indicator group by the one of said at least one normally functioning enzymes, (b) sensing for said fluorescent second state of said indicator group for each of the at least one normally functioning enzymes for each said plurality of reference, metabolically active whole cells to produce a matrix of reference results, (c) contacting a plurality of test, metabolically active whole cells, each having at least one normally functioning enzyme with said medium for said period of time, (d) sensing for said fluorescent second state of said indicator group for each of the at least one normal functioning enzyme for each of said plurality of test, metabolically active whole cells to produce a matrix of test results, and (e) comparing the matrix of test results of said plurality of test, metabolically active whole cells in said step (d) with the matrix of reference results obtained from said plurality of reference, metabolically active whole cells in said step (b).

The present invention also relates to a method of performing at least one or more assays for detecting the presence or absence of a disease comprising (a) contacting at least one or more test, metabolically active whole cells, each having at least one normally functioning enzyme, with one or more assay reagents, said assay reagent containing at least one water soluble assay compound or water soluble physiologically acceptable salt thereof having a fluorogenic indicator group and a leaving group, said leaving group being selected for cleavage by one of said at least one normally functioning enzyme the activity of which changes with the presence of the disease, said indicator group being in a non-fluorescent first state when bonded to said leaving group, and being in a fluorescent second state excitable at a wavelength above 450 nm when said leaving group is cleaved from said indicator group by the one of said at least one normally functioning enzyme for a period of time at least sufficient for said assay compound to be transferred into said cell and for said leaving group to be cleaved inside said cell from said indicator group by said enzyme, (b) sensing for said fluorescent second state of the indicator group for the test, metabolically active whole cell to produce a matrix of test results, and (c) comparing the matrix of test results of said test metabolically active whole cell with a matrix of reference results obtained from at least one of a diseased reference cell and a non-diseased reference cell.

The cell is contacted with the assay compound for a period of time sufficient for the assay reagent to be transferred into the cell and for the leaving group to be cleaved from the indicator group by the enzyme. The assay compound is capable of or enabled to pass through the membrane of the cell so that the enzyme, if present and active, can cleave the leaving group thereby forming the indicator compound which can be sensed from outside the cell.

The cell is then sensed for the first state or second state or both first and second states of the indicator group.

BRIEF DESCRIPTION OF THE DRAWINGS

The file of this patent contains at least one drawing executed in color. Copies of this patent with color drawings will be provided by the Patent and Trademark Office upon request and payment of the necessary fees.

There are shown in the drawings embodiments which are presently preferred, it being understood, however, that the invention is not limited to the precise instrumentalities and arrangements shown, wherein:

FIGS. 2A, 2B, 2C and 2D are charts illustrating the use of salts to enhance specificity;

FIGS. 3A, 3B, 3C and 3D are graphs illustrating the use of inhibitors in the reagent formula;

FIGS. 11A, 11B, 11C, 11D, 11E and 11F are graphs illustrating the storage stability of TFA salts of dipeptide derivatives of rhodamine 110;

FIGS. 12A, 12B, 12C and 12D are graphs illustrating the storage stability of acetate and tartrate salts of the Leu-Gly peptide derivative of rhodamine 110;

FIG. 14A illustrates reducing a full covariance data matrix to a reduced covariance data matrix of strongly contributing factors, by eigenvector analysis;

FIG. 16 illustrates a comparison of disease probabilities by performing 1) NNLS analysis on the full covariance data matrix, 2) NNLS analysis on a reduced covariance data matrix defined by eigenvectors 1 and 2, including 11 substrates, 3) NNLS analysis on a reduced covariance data matrix defined by eigenvector 1 above, including 6 substrates, and 4) squared deviation from the mean analysis on 6 substrates;

FIGS. 17A–17C are graphs of the ratio of a disease to the mean of the normal of all patients with the disease; and FIGS. 18A–18F illustrate a progression of disease during treatment and monitoring a return to normalcy and FIG. 18G is a summary of the data illustrated in FIGS. 18A–18F.

DETAILED DESCRIPTION OF THE PREFERRED EMBODIMENTS

Assay Compound

Figure 1A:
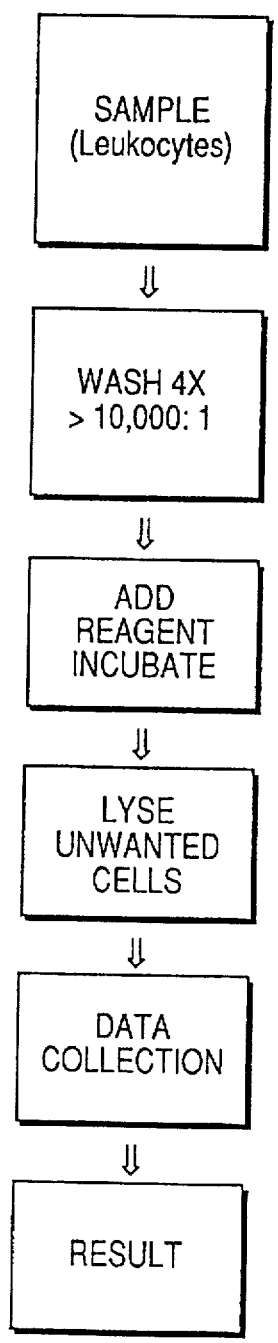
FIGS. 1A, 1B, 1C and 1D are flow charts of four assay protocols according to the invention.
Figure 1B:
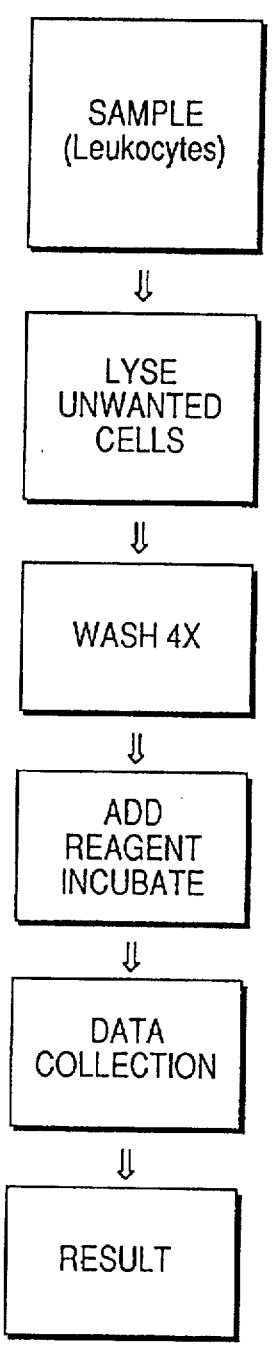
Figure 1C:
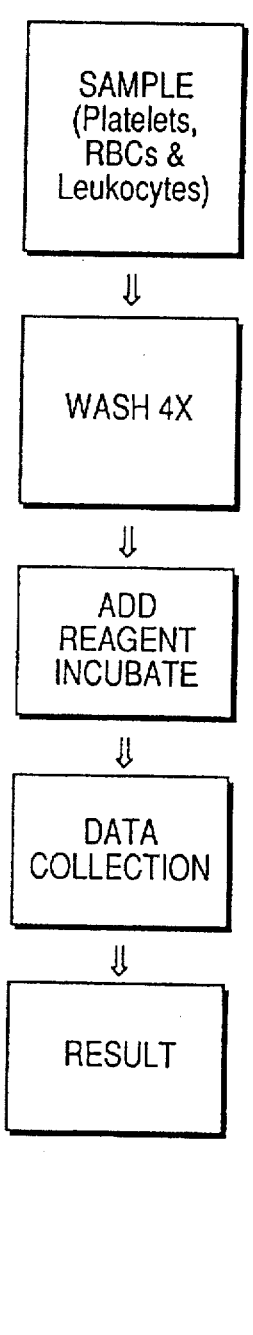
Figure 1D:
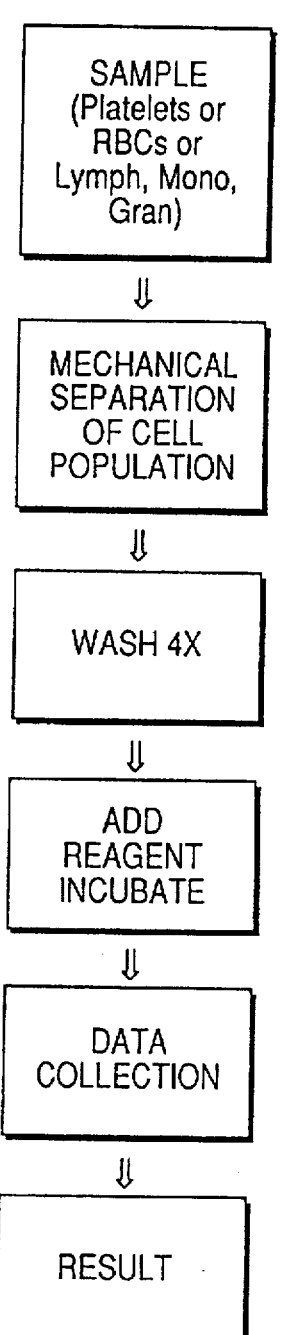

According to the present invention, an assay reagent is manufactured for determining the activity of an enzyme in a metabolically active whole cell. The assay reagent must be compatible with the cell such that the cell will remain metabolically active for at least the duration of the assay.

The assay reagent comprises at least one assay compound which is capable of passing through the cell wall. The assay compound must be small enough that it can be transmitted into the cell. An assay compound having a molecular weight of less than about 5,000 is presently preferred.

The assay compound contains a leaving group and an indicator group. The leaving group is selected for cleavage by the enzyme to be analyzed. The indicator group is selected for its ability to have a first state when joined to the leaving group, and a second state when the leaving group is cleaved from the indicator group by the enzyme. The indicator group is preferably excitable (caused to fluoresce) at a wavelength about the visible range, for example, at wavelength between about 450 to 500 nanometers (nm). The indicator group will usually emit in the range of about 480 to 620 nm, preferably 500 to 600 nm and more preferably 500 to 550 nm. Auto-fluorescence of the cell is most prevalent below about 500 nm.

Indicator groups

The indicator group is preferably derived from fluorogenic and chemiluminescent compounds. The indicator group should be quenched when joined to the leaving group. The term quenched means that the indicator group has almost no fluorescence or chemiluminescence when joined to the leaving group. When the leaving group is separated from the indicator group, the resulting indicator compound will have a fluorescence.

Suitable fluorogenic indicator compounds include xanthine compounds. Preferably, the indicator compounds are rhodamine 110; rhodol; and fluorescein. These compounds have the following structures:

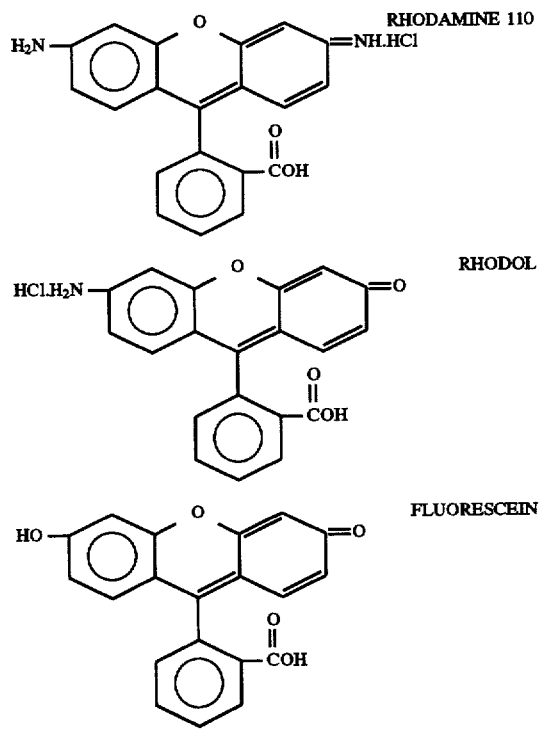

In addition, derivatives of these compounds which have the 4' or 5' carbon protected are acceptable indicator compounds. Preferred examples of the derivative compounds include 4'(5')thiofluorescein, 4'(5')-aminofluorescein, 4'(5')-carboxyfluorescein, 4'(5')-chlorofluorescein, 4'(5')-methylfluorescein, 4'(5')-sulfofluorescein, 4'(5')-aminorhodol, 4'(5')-carboxyrhodol, 4'(5')-chlororhodol, 4'(5')-methylrhodol, 4'(5')-sulforhodol; 4'(5')-aminorhodamine 110, 4'(5')-carboxyrhodamine 110, 4'(5')-chlororhodamine 110, 4'(5')-methylrhodamine 110, 4'(5')-sulforhodamine 110 and 4'(5')thiorhodamine 110. "4'(5')" means that at the 4 or 5' position the hydrogen atom on the carbon atom is substituted with a specific organic group or groups as previously listed.

Leaving groups

The leaving group is selected according to the enzyme that is to be assayed. The leaving group will have utility for assaying many kinds of cellular enzymes, including proteases, glycosidases, glucosidases, carbohydrases, phosphodiesterases, phosphatases, sulfatases, thioesterases, pyrophosphatases, lipases, esterases, nucleotidases and nucleosidases. For the purposes of this disclosure the term carbohydrases includes all enzymes which will hydrolyze a carbohydrate. Enzymes which do not recognize and cleave a leaving group, such as dehydrogenases and kinases, are not suitable for assays according to the invention. The enzymes to be measured can be those which are present in various cell preparations, enzymes found in cytosols, cell surface enzymes, cytoplasmic enzymes and cell nucleus (nuclear) enzymes. However, as will be discussed herein, the assay compounds are particularly useful for detecting intracellular enzymes in living cells.

The leaving group is selected from amino acids, peptides, saccharides, sulfates, phosphates, esters, phosphate esters, nucleotides, polynucleotides, nucleic acids, pyrimidines, purines, nucleosides, lipids and mixtures thereof. For example, a peptide and a lipid leaving group can be separately attached to a single assay compound such as rhodamine 110.

Other leaving groups suitable for the enzyme to be assayed can be determined empirically or obtained from the literature. See, for example, Mentlein, R., Staves, R., Rix-Matzen, H. and Tinneberg, H. R., "Influence of Pregnancy on Dipeptidyl Peptidase IV Activity (CD26 Leukocyte Differentiation Antigen) of Circulating Lymphocytes", *Eur. J. Clin. Chem. Clin. Biochem.*, 29, 477–480 (1991); Schön, E., Jahn, S., Kiessig, S., Demuth, H., Neubert, K., Barth, A., Von Baehr, R. and Ansorge, S., *Eur. J. Immunol.*, 17, 1821–1826 (1987); Ferrer-Lopez, P., Renesto, P., Prevost, M., Gounon, P. and Chignard, M., "Heparin Inhibits Neutrophil-Induced Platelet Activation Via Cathepsin", *J. Lab Clin. Med.* 119(3), 231–239 (1992); and Royer, G. and Andrews, J., "Immobilized Derivatives of Leucine Aminopeptidase and Aminopeptidase M.", *The J. of Biological Chemistry*, 248(5), 1807–1812 (1973). These references are hereby incorporated by reference in their entirety. Various leaving groups are shown in Table 1.

TABLE 1

| ENZYME | SUBSTRATES | SUB. CONC. (mM) | BUFFER | pH[1] RANGE (experiment) | pH[2] lit | COFACTOR | MODULATOR | INHIBITOR | mOSM | TIME (MIN) | IONIC STRG (μ) | FUNCTION OR INDICATION | CD |
|---|---|---|---|---|---|---|---|---|---|---|---|---|---|
| AminoPept A | (H-L-Asp)₂—Rho 110 .2TFA | 4.8 | Hanks | 7.5 | 7.0 | 1-5 mM CaCl₂ | | 10 mM CaCl₂ Amistatin I | 280-310 | 5 | .1530 | | |
| AminoPept B | (H-L-Glu)₂—Rho 110 .2TFA | | Hanks | | 7.0 | | | | 280-310 | 3 | | | |
| | (H-L-Arg)₂—Rho 110 .4TFA | 3.2 | Hanks | 8.0 ± .2 | 7.5 | NaCl 137 mM | | | 280-310 | 3 | | | |
| | (H-L-Cys)₂—Rho 110 .2TFA | | Hanks | | 7.5 | 1 mM DTT | | | 280-310 | 3 | | | |
| AminoPept M | (H-L-Ala)₂—Rho 110 .2TFA | 6.4 | Hanks | 7.0 | 7.5 | | | 10⁻⁴M Bestatin | 280-310 | 5 | 0.1530 | Leukemia | CD13 |
| | (H-L-Ala)₂-4'chloro-Rho 110 .2TFA | 6.4 | Hanks | 7.0 | 7.5 | | | 10⁻⁴M Bestatin | 280-310 | 5 | 0.1530 | Leukemia | CD13 |
| | H-L-Leu Rhodol .TFA | 2.4-3.2 | Hanks | 5.0-7.0 | 7.5 | | | 1.5 mM 1,10-Phenanthro-line | 280-310 | 1 | 0.1494 | | |
| | (H-L-Leu)₂ 4'chloro-Rho 110 .2TFA | 2.4-3.2 | Hanks | 5.0-7.0 | 7.5 | | | | 280-310 | 1 | 0.1494 | | |
| | (H-L-Leu)₂ Rho 110 .2TFA | 2.4-3.2 | Hanks | 5.0-7.0 | 7.5 | | | 56 mM 2,2 Dipyridyl 1 | 280-310 | 1 | 0.1494 | | CD13 |
| | (H-L-Met)₂ Rho 110 .2TFA | | Hanks | | 7.5 | | | | 280-310 | 5 | | | CD13 |
| AminoPept N | (H-Gly)₂ Rho 110 .2TFA | 6 | Hanks | 7.0-7.5 | 7.5 | | 1 mM DTE | | 280-310 | 5 | 0.1526 | | CD13 |
| | (H-Gly)₂ 4'chloro-Rho 110 .2TFA | 6 | Hanks | 7.0-7.5 | 7.5 | | 1 mM DTT | | 280-310 | 5 | 0.1526 | | CD13 |
| | (H-L-Pro)₂—Rho 110 .2TFA | 6 | Hanks | | 7.5 | | 1 mM DTE | | 280-310 | 5 | 0.1526 | | CD13 |
| | (H-L-Lys)₂ Rho 110 .4TFA | 2.4 | Hanks | 7.5 ± .2 | 7.5 | | | | 280-310 | 5 | 0.1490 | | CD13 |
| | (H-L-Lys)₂ Rho 110 .4TFA | 2.4 | Hanks | 5.5 ± .2 | 7.5 | | | | 280-310 | 5 | 0.1490 | | |
| | (H Gly)₂ Rho 110 .2TFA | 6.4 | Hanks | 5.5-6.0 | 7.5 | | | | 280-310 | 5 | 0.1506 | | |
| | (H-L-Ser)₂ Rho 110 .2TFA | 2.4 | Hanks | 5.0-6.5 | 7.5 | | | | 280-310 | 5 | 0.1526 | | |
| Neg Pro Control | (H-L-Pro)₂ Rho 110 .2TFA | 6 | Hanks | | 7.5 | | | | | | | | |
| DPP I | (H-L-Pro—Arg)₂ Rho 110 .4TFA | 6 | MES | 5.0-6.5 | 6.5 | | 1 mM DTE | | 280-310 | 10 | | | |
| | (H Gly—Arg)₂ Rho 110 .4TFA | 6 | MES | 5.0-6.5 | 6.5 | | 1 mM DTT | | 280-310 | 10 | | | |
| DPP II | (H-L Lys—Ala)₂ Rho 110 .4TFA | 2.0 | MES | 6.5 ± .5 | 6.5 | MgCl₂ Zn | DTE | Bestatin | 280-310 | 10 | 0.1019 | | |
| | (H-L-Lys—Ala)₂ Rho 110-Sulfo .4TFA | 2.0 | Mes | 6.5 ± .5 | 6.5 | MgCl₂ Zn | DTE | Bestatin | 280-310 | 10 | 0.1019 | | |
| | (H-L-Lys—Pro)₂ Rho 110 .4TFA | | MES | 5.5 | 6.5 | MgCl₂ Zn | DTE | | | | | | |
| | (H-L Ala—Pro)₂ Rho 110 .2TFA | 3.2 | MES | 5.5 | 6.5 | MgCl₂ Zn | DTE | Bestatin | 280-310 | 10 | 0.1229 | | |
| | (H-L Lys—Ala—Lys—Ala)₂ Rho 110 .6TFA | | MES | | 6.5 | | | | | | | | |
| DPP IV | (H-L Ala—Pro)₂ Rho 110 .2TFA | 2.4 | Gly—NaOH | 7.5 ± .5 | 8.7 | | | Gly—Pro 1.8 mM | 280-310 | 10 | 0.1449 | | CD26 |
| | (H-Gly—Pro)₂ Rho .2TFA | | Gly—NaOH | | 8.7 | | | | 280-310 | 10 | | | CD26 |
| | (H-L-Lys—Pro)₂ Rho 110 .4TFA | 4.0 | Gly—NaOH | | 8.7 | | 1 mM DTE | 3.6 mM Ala—Ala | 280-310 | 10 | 0.1449 | | CD26 |
| | (H-L-Ala—Ala)₂ Rho 110 .2TFA | | Gly—NaOH | 8.7 ± .2 | 8.7 | | | | 280-310 | 10 | | | |
| | (Z-Ala—Ala)₂ Rho 110 | | Gly—NaOH | 7.0-8.5 | 8.0 | | 1 mM DTE | | 280-310 | 10 | | | |
| | (H-L Ala—Ala—Ala—Ala)₂ Rho | | | | 8.7 | | 1 mM DTE | | 280-310 | 10 | | | CD26 |

TABLE 1-continued

| ENZYME | SUBSTRATES | SUB. CONC. (mM) | BUFFER | pH¹ RANGE (experiment) | pH² lit | COFACTOR | MODULATOR | INHIBITOR | mOSM | TIME (MIN) | IONIC STRG (μ) | FUNCTION OR INDICATION | CD |
|---|---|---|---|---|---|---|---|---|---|---|---|---|---|
| TriPeptidylPept Cathepsin B | (H-L-Ala—Ala—Arg)₂ Rho 110 .2TFA (H-L-Gln—Ser)₂ Rho 110 .2TFA | 3.6 | Gly—NaOH MES | 6.5–7.5 | 8.7 6.5 | | 1 mM DTE | 13 mM– 22 mM Leupeptin I | 280–310 280–310 | 10 10 | 0.1055 | Breast Cancer | |
| | (H-L-Gln—Ser)₂ Rho 110 .2TFA (H-L-Val—Ser)₂ Rho 110 .2TFA | 4.0 | MES MES | 5.5 ± .2 6.5–7.5 | 5.5 6.5 | | | 13 mM– 22 mM Leupeptin I Cystatin C | 280–310 280–310 | 10 10 | 0.1059 | Tumor Growth | |
| | (H-L-Leu—Gly)₂ Rho 110 .2Tartrate | 1.6–2.0 | MES | 6.0–6.5 | 6.5 | | | 13 mM– 22 mM Leupeptin I Cysteine 2 mM | 280–310 | 10 | 0.1037 | Progression | |
| | (H-L-Leu—Gly)₂ Rho 110 .2Acetate (H-L-Val—Lys)₂ Rho 110 .4TFA | 1.6 | MES MES | 5.0–6.0 | 5.5 6.5 | | 1 mM DTE | 13 mM– 22 mM Leupeptin I | 280–310 280–310 | 10 10 | 0.1072 | Lung Tumor | |
| | (H-L-Leu—Leu—Arg)₂ Rho 110 .4TFA | 6.4 | MES | | 6.5 | | | 13 mM– 22 mM Leupeptin I | 280–310 | 10 | 0.1232 | Leukemia | |
| | (H-L-Leu—Gly—Leu—Gly)₂ Rho 110 .2TFA | 6.4 | MES | | 6.5 | | | 13 mM– 22 mM Leupeptin I | 280–310 | 10 | 0.1083 | | |
| | (H-L-Val—Lys—Val—Lys)₂ Rho 110 .6TFA (H-L-Ala—Arg—Arg)₂ Rho 110 .6TFA | | | | 6.5 | | 1 mM DTE | Leupeptin I 1 mM EDTA | 280–310 280–310 | 10 10 | | | |
| | (H-L-Arg—Arg)₂ Rho 110 .6TFA | | | | | | | 13 mM– 22 mM Leupeptin | 280–310 | 10 | | Gastric Cancer | |
| Cathepsin B1 | (H-L-Leu—Leu—Arg)₂ Rho 110 .4TFA | 6.4 | MES | 7.0 ± .5 | 6.5 | | | 13 mM– 22 mM Leupeptin | 280–310 | 10 | 0.1232 | Smokers | |
| | (H-L-Ala—Arg—Arg)₂ Rho 110 .6TFA | | MES | | 6.5 | | | 13 mM– 22 mM Leupeptin | 280–310 | 10 | | | |
| Cathepsin C | (Z-Ala—Gly)₂ Rho 110 (H-L-Ala—Gly)₂ Rho 110 .2Acetate (H-L-Thr—Pro)₂ Rho 110 .2TFA (Z-Thr—Pro)₂ Rho 110 (H-L Pro—Arg)₂ Rho 110 .4TFA | 2.4 2.4 | Gly Gly Gly Gly | 7.5 ± .5 8.0–8.5 7.5–9.0 6.0–9.0 | 7.5 8.7 8.7 7.5 8.7 | | | | 280–310 280–310 280–310 280–310 280–310 | 10 10 10 10 10 | 0.1473 0.1473 | | |
| Cathepsin D | (H Gly—Leu)₂ Rho 110 .2FTA | 1.2 | MES | 5.0 ± .5 | 6.5 | | | 10 mM Pepstatin II | 280–310 | 10 | 0.1031 | Breast Cancer | |
| | (H-L-Thr—Pro)₂ Rho 110 .2TFA | 2.4 | MES | 5.0 ± .2 | 6.5 | | | | 280–310 | 10 | 0.1043 | MS | Liver Disease |
| Neutral Endo | (H Gly—Pro—Leu—Gly—Pro)₂ | 3.2 | MES | 7.0 ± .5 | 6.5 | | | | 280–310 | 10 | 0.1051 | Leuk (ALL) | CD10 |

TABLE 1-continued

| ENZYME | SUBSTRATES | SUB. CONC. (mM) | BUFFER | pH¹ RANGE (experiment) | pH² lit | COFACTOR | MODULATOR | INHIBITOR | mOSM | TIME (MIN) | IONIC STRG (μ) | FUNCTION OR INDICATION | CD |
|---|---|---|---|---|---|---|---|---|---|---|---|---|---|
| Peptidase | Rho 110 .2TFA | | | | | | Zinc Δ | | 280-310 | 10 | | | (CAL-LA) |
| | (H Gly—Phe—Gly—Ala)₂ Rho 110 .2TFA | | | | | | | | 280-310 | 10 | | | |
| | (H-L-Arg—Gly—Glu—Ser)₂ Rho 110 .4TFA | | | | | | | | | | | | |
| EndoPept I | (H-L-Arg)₂ Rho 110 .4TFA | | .1M Tris Hcl | | 7.5 | | | | 280-310 | 10 | | | |
| | (H-L-Glu—Gly—Arg)₂ Rho 110 .4TFA | | | | | | | | 280-310 | 10 | | | |
| EndoPept II | (H-L-Arg—Arg)₂ Rho 110 .6TFA | | PO4 | | 7.0 | | 1 mM DTE | | 280-310 | 10 | | | |
| | (H-L-Ala—Arg—Arg)₂ Rho 110 .6TFA | | | | | | 1 mM EDTA | | 280-310 | 10 | | | |
| Membrane Assoc. | (H-Gly—Ala—Ala)₂ Rho 110 .2TFA | | | | | | | | 280-310 | 10 | | | |
| EndoPept I Membrane Assoc | (H-L-Arg—Arg)₂ Rho 110 .6TFA | | | | | | | | 280-310 | 10 | | | |
| | (H-L-Ala—Arg—Arg)₂ Rho 110 .6TFA | | | | | | | | 280-310 | 10 | | | |
| EndoPept II Glutathione | (H-L-Glu—Cys—Gly)₂ Rho 110 .2TFA | | | | | | | | 280-310 | 10 | | | |
| Chymotrypsin | (H-L-Glu—Gly—Phe)₂ Rho 110 .2TFA | .1M Tris | | | 7.0 | | | PMSF | 280-310 | 10 | | | |
| Trypsin | (H-L-Arg)₂ Rho 110 .4TFA | | | | 7.0 | | | Antipain 13 mM- 22 mM Leupeptin | 280-310 | 10 | | | |
| | (H Gly—Gly—Arg)₂ Rho 110 .4TFA | | | | | | | | 280-310 | 10 | | | |
| Ester Proteinase | (N-Acetyl MET)₂ Rho 110 | .1M Tris | | | 6.5 | | | | 280-310 | 10 | | | |
| γ-GT | (γ-Glu)₂ Rho 110 .2TFA | .1M PO4 | | | 7.0 | | 1 mM Gly—Gly | | 280-310 | 10 | | | |
| Elastase | (H-L-Ala—Ala—Tyr)₂ Rho 110 .2TFA | | | | | | | α-1-Antitrypsin | 280-310 | 10 | | | |
| | (H-L-Ala—Ala—Pro—Ala)₂ Rho 110 .2TFA | | | | | | | | 280-310 | 10 | | | |
| | (H-L-Ala—Ala—Ala—Ala)₂ Rho 110 .2TFA | | | | | | | | 280-310 | 10 | | | |
| | (H-L-Ala—Pro—Ala)₂ Rho 110 .2TFA | | | | | | | | 280-310 | 10 | | | |
| Plasmin | (H-L-Ala—Phe—Lys)₂ Rho 110 .2TFA | | | | | | | 13 mM- 22 mM Leupeptin I | 280-310 | 10 | | | |
| | (H-L-Glu—Lys—Lys)₂ Rho 110 .6TFA | | | | | | | | 280-310 | 10 | | | |
| | (H-L-Val—Leu—Lys)₂ Rho 110 .4TFA | | | | | | | | 280-310 | 10 | | | |
| Urokinase | (H-Gly—Gly—Arg)₂ Rho 110 .4TFA | | | | | | | | 280-310 | 10 | | | |
| | (H-Gly—Arg)₂ Rho 110 .4TFA | | | | | | | | 280-310 | 10 | | | |
| HIV Protease | (H-L-Lys—Ala—Arg—Val)₂ Rho | | | | | | | | 280-310 | 10 | | | |

TABLE 1-continued

| ENZYME | SUBSTRATES | SUB. CONC. (mM) | BUFFER | pH¹ RANGE (experiment) | pH² lit | COFACTOR | MODULATOR | INHIBITOR | mOSM | TIME (MIN) | IONIC STRG (μ) | FUNCTION OR INDICATION | CD |
|---|---|---|---|---|---|---|---|---|---|---|---|---|---|
| | 110 .6TFA (H-L-Lys—Ala—Arg—Val—Phe)₂ Rho 110 .6TFA | | | | | | | | 280–310 | 10 | | | |
| v-Thrompsin | (H-L-Val—Pro—Arg)₂ Rho 110 .4TFA | | | | | | | PMSF | 280–310 | 10 | | | |
| Pancreatic | (H-L-Pro—Phe—Arg)₂ Rho 110 .4TFA | | | | | | | | 280–310 | 10 | | Breast Carcinoma growth cancer | |
| Cathepsin L | (H-L-Phe—Arg)₂ Rho 110 .4TFA | | | | | | | 13 mM– 22 mM Leupeptin | 280–310 | 10 | | Breast Carcinoma | |
| Cathepsin H | (H-L-Arg)₂ Rho 110 .4TFA | | MES | 8.0 ± .2 | | | | Bestatin | 280–310 | 10 | | | |
| Collagenase | (H-Gly—Pro—Leu—Gly—Pro)₂ Rho 110 .2TFA | | | 5.5 ± .2 | 5.5 | MgCl² | DTE | | 280–310 | 10 | .15 | | |
| Neutral Esterase | FL(palmitate)₂ | .1 | Hanks | 7.5 | | | | | 280–310 | 10 | | | |
| Acidic Esterase | | .1 | Mes | 6.5 | | | | | 280–310 | 10 | .10 | | |
| Acid Phosphatase | | .2 | Mes | 5.0 | | | | | 280–310 | 5 | .10 | | |
| Alkaline Phosphatase | FL(phosphate)₂.2NH₄⁺ | .2 | Gly | 8.7 | | | | | 280–310 | 5 | | | |
| Tartrate Resistant Phosphatase | FL(phosphate)₂.2NH₄⁺ | .2 | Tartrate Mes | 5.2 | | | | | 280–310 | 5 | .10 | Hairy Cell Leukemia | |
| Acid Phosphatase | FL(phosphate)₂.2NH₄⁺ | .1 | Mes | 5.0 | | | | | 280–310 | 5 | | | |
| Alkaline Phosphatase | Rho 110(phosphate)₂ | .1 | Gly | 8.7 | | | | | 280–310 | 5 | | | |
| Tartrate Resistant Phosphatase | Rho 110(phosphate)₂ | .1 | Tartrate Mes | 5.2 | | | | | 280–310 | 5 | | | |
| Neutral Non-specific Esterase | Fluorescein(acetate)₂ | .1 | Hanks | 7.5 | | | | | 280–310 | 3 | .15 | Monocytes, Megakaryocytes, Lymphocytes | |
| Acidic Non-specific Esterase | | .1 | Mes | 4.0–6.5 | | | | | 280–310 | 3 | .10 | | |
| Neutral Esterase | FL(propionate)₂ | .1 | Hanks | 7.5 | | | | | 280–310 | 3 | .15 | | |
| Acidic Esterase | | .1 | Mes | 6.5 | | | | | 280–310 | 3 | .10 | | |
| Neutral Chloro-acetate Esterase | FL(chloroacetate)₂ | .1 | Hanks | 7.5 | | | | | 280–310 | 3 | .15 | Immature Neutrophils & Mast cells | |
| Acidic Chloro-acetic Esterase | | .1 | Mes | 6.5 | | | | | 280–310 | 3 | .10 | | |
| Neutral Esterase I | FL(butyrate)₂ | .1 | Hanks | 7.5 | | | | | 280–310 | 3 | .15 | Monocytes & Megakaryocytes | |
| Acidic Esterase I | | .1 | Mes | 6.5 | | | | | 280–310 | 3 | .10 | | |

TABLE 1-continued

| ENZYME | SUBSTRATES | SUB. CONC. (mM) | BUFFER | pH¹ RANGE (experiment) | pH² lit | COFACTOR | MODULATOR | INHIBITOR | mOSM | TIME (MIN) | IONIC STRG ($\mu$) | FUNCTION OR INDICATION | CD |
|---|---|---|---|---|---|---|---|---|---|---|---|---|---|
| Neutral Esterase I | FL(chlorobutyrate)₂ | .1 | Hanks | 7.5 | | | | | 280–310 | 3 | .15 | | |
| Acidic Esterase I | | .1 | Mes | 6.5 | | | | | 280–310 | 3 | .10 | | |
| Neutral Esterase | FL(valerate)₂ | .1 | Hanks | 7.5 | | | | | 280–310 | 3 | .15 | | |
| Acidic Esterase | FL(hexanoate)₂ | .1 | Mes | 6.5 | | | | | 280–310 | 3 | .10 | | |
| Neutral Esterase | | .1 | Hanks | 7.5 | | | | | 280–310 | 3 | .15 | | |
| Acidic Esterase | FL(heptanoate)₂ | .1 | Mes | 6.5 | | | | | 280–310 | 3 | .10 | | |
| Neutral Esterase | | .1 | Hanks | 7.5 | | | | | 280–310 | 3 | .15 | | |
| Acidic Esterase | | .1 | Mes | 6.5 | | | | | 280–310 | 3 | .10 | | |
| Glyco-pyranosidase | (Acetyl-α-D-glucopyranosyl)₂ Rho 110 | .24 | Mes | 6.8 | | | | | 280–310 | 10 | | | |
| Glucuronidase | (B-D-glucuronide)₂ Rho 110 | .24 | Mes | 5.0 | | | | | 280–310 | 10 | | Leukemia | |
| Galacto-pyranosidase | (B-D-Galactopyranoside)₂ Rho 110 | .24 | Hanks | 7.5 | | | | | 280–310 | 10 | | | |
| Tyrosine Phosphatase | (H-L-Tyrosine Phosphate)₂ Rho 110 .2TFA | .1 | Hanks | 6.5 | | | | | 280–310 | 5 | | Cell Cycle Cell Division | |
| Serine Phosphatase | (H-L-Serine Phosphate)₂ Rho 110 .2TFA | .1 | Hanks | 6.5 | | | | | 280–310 | 5 | | Cell Cycle Cell Division | |
| Threonine Phosphatase | (H-L-Threonine Phosphate)₂ Rho 110 .2TFA | .1 | Hanks | 6.5 | | | | | 280–310 | 5 | | Cell Cycle Cell Division | |
| Neutral Esterase II | (N-Acetyl-L-Ala)₂FL | .1 | Hanks | 7.5 | | | | | 280–310 | 5 | | Monocytic Leukemias | |
| Acidic Esterase II | | .1 | Mes | 6.5 | | | | | 280–310 | | | | 45 RO |
| Adenosine Deaminase | (Adenosine) Rho 110 .2FTA | .1 | Mes | 6.0 | | | | | 280–310 | 10 | | AIDS | |
| Thymidine Deaminase | (Thymidine)₂ Rho 110 | .1 | Mes | 6.0 | | | | | 280–310 | 10 | | | |
| Cytosine Deaminase | (Cytosine)₂ Rho 110 .2TFA | .1 | Mes | 6.0 | | | | | 280–310 | 10 | | | |
| Guanine Deaminase | (Guanine)₂ Rho 110 .2TFA | .1 | Mes | 6.0 | | | | | 280–310 | 10 | | | |
| 5'Nucleotidase | (Adenosine Monophosphate)₂ Rho 110 .2TFA | .1 | Hanks | 7.5–9.0 | | | | | 280–310 | 10 | | Pap Smear | |
| Adenine Monophosphate Deaminase | Rho 110(AMP)₂.4NH₄⁺ | .1 | Mes | 6.0 | | | | | 280–310 | 10 | | AIDS | |
| Angiotensin Converting Enzyme | (Hippuryl-His—Leu)₂ Rho 110 | .1 | HEPES | 8.0 | | | | | 280–310 | 10 | | CALLA | |
| Cholinesterase | FL(Choline)₂ | .1 | Hanks | 8.0 | | Zn⁺⁺ | | | 280–310 | 10 | | | |
| Cholinesterase | FL(Butyl-Thiocholine)₂ | .1 | Hanks | 8.0 | | Zn⁺⁺ | | | 280–310 | 10 | | | |
| Acetyl Cholinesterase | FL(Acetyl-Choline)₂ | .1 | Hanks | 8.0 | | Zn⁺⁺ | | | 280–310 | 10 | | | |

TABLE 1-continued

| ENZYME | SUBSTRATES | SUB. CONC. (mM) | BUFFER | pH¹ RANGE (experiment) | pH² lit | COFACTOR | MODULATOR | INHIBITOR | mOSM | TIME (MIN) | IONIC STRG (μ) | FUNCTION OR INDICATION | CD |
|---|---|---|---|---|---|---|---|---|---|---|---|---|---|
| Nucleosidase | (Adenine)₂ Rho 110 .2TFA | .1 | Hanks | 7.4 | | | | | 280–310 | 10 | | Pap Smear | |
| Lipase | (Saturated Hydrocarbon)₂ Rho 110 | .1 | | | | | | | | | | | |
| Lipase | (Unsaturated Hydrocarbon)₂ Rho 110 | .1 | | | | | | | | | | | |
| Lipase | (Triacetin)₂ Rho 110 | .1 | Hanks | 7.7 | | | | | | | | | |
| Phospholipase | Rho 110 (Phosphatidyl-choline)₂ .2TFA | .1 | Hanks | 7.0 | | | | | 280–310 | 10 | .15 | | |
| Phospholipase C | Rho 110 (Phosphatidylinositol)₂ | .1 | Hanks | 7.0 | | | | | 280–310 | 10 | .15 | | |
| Phospholipase D | (Phosphatidyl-choline)₂ Rho 110 .2TFA | .1 | Hanks | 7.0 | | | | | 280–310 | 10 | .15 | | |
| Phospholipase A | (Phosphatidyl-choline)₂ Rho 110 .2TFA (H-L-thyroxine)₂ Rho 110 .2TFA | .1 | Hanks | 7.0 | | | | | 280–310 | 10 | .15 | | |

¹Range determined experimentally with cells
²pH from scientific literature using cytosol Preferred peptide leaving groups that react with cellular enzymes are included in Table 1. As examples, the enzymes glutamyltranspeptidase reacts with gammaglutamyl amino acid peptide giving gamma glutamic acid; trypsin cleaves the peptide at the arginine residue; aminopeptidase-M hydrolyzes the peptide at the aliphatic amino acid residue; and chymotrypsin cleaves the peptide at the phenylalanine residue.

It has been discovered that when the leaving group is a salt complex, it will significantly improve the transmission of the assay compound into the cell. The selection of an appropriate salt complex requires a consideration of the compatibility with the cell, solubility in the aqueous media, and cleavage by the enzyme. Particular care is required in the selection of the peptide salt since even isoenzymes have been found to be specific in their recognition of particular salts.

Leaving groups for saccharidases are preferably prepared by the synthesis of monosaccharides, oligosaccharides or polysaccharides comprising between one and about ten sugar residues of the D-configuration. Examples of useful sugars are monosaccharides-pentoses; ribose; deoxyribose; hexose: glucose, dextrose, galactose; oligosaccharides-sucrose, lactose, maltose and polysaccharides like glycogen and starch.

The sugar can be an alpha or beta configuration containing from 3 to 7 and preferably 5 to 6 carbon atoms. Analogs of these sugars can also be suitable for the invention. Preferably, the D-configuration of the monosaccharide or disaccharide is utilized. The monosaccharide or disaccharide can be natural or synthetic in origin.

Leaving groups for nucleases, nucleotidases, and nucleosidases are preferably prepared by the synthesis of nucleic acids, purines, pyrimidines, pentose sugars (i.e., ribose and deoxyribose) and phosphate ester. Examples are adenine, guanine, cytosine, uracil and thymine. Leaving groups for restriction enzymes would include poll/nucleotides.

The nucleic acids contain a purine or pyrimidine attached to a pentose sugar at the 1-carbon to N-9 purine or N-1 pyrimidine. A phosphate ester is attached to the pentose sugar at the 5' position. Analogs of these building blocks can also be used.

Leaving groups for lipases are preferably prepared by the synthesis of simple lipids, compound lipids or derived lipids. Simple lipids can be esters of fatty acids, triglycerides, cholesterol esters and vitamin A and D esters. Compound lipids can be phospholipids, glycolipids (cerebrosides), sulfolipids, lipoproteins and lipopolysaccharides. Derived lipids can be saturated and unsaturated fatty acids and mono or diglycerides. Analogs of these lipids can also be used.

Examples of lipids are: triglycerides—triolein, fatty acids—linoleic, linolenic and arachidonic; sterols—testosterone, progesterone, cholesterol; phospholipids—phosphatidic acid, lecithin, cephalin (phosphatidyl ethanolamine) sphingomyleins; glycolipids—cerebosides, gangliosides.

Leaving groups for esterases are preferably prepared by the synthesis of carboxylic acids comprising between 2 and 30 carbon atoms. The carboxylic acids can be saturated or unsaturated. The carboxylic acid preferably contains 2 to 24 carbons and more preferably 4 to 24 carbon atoms. Analogs of theses carboxylic acids can also be used. The carboxylic acids can be natural or synthetic in origin. Examples are butyric, caproic, palmitic, stearic, oleic, linoleic and linolenic.

Leaving groups for phosphatases are preferably prepared by the synthesis of phosphates, phosphatidic acids, phospholipids and phosphoproteins. Analogs of these compounds can also be used. Examples are ATP, ADP, AMP and cyclic AMP (c-AMP).

Leaving groups for peptidases are preferably prepared by the synthesis of peptides comprising between one and about ten amino acid residues of the L-configuration. Typically, it has been found that the synthesis of peptides having more than about six amino acids produces a low yield. However, where the yield is acceptable, peptides of greater length can be employed.

The amino acids preferably contain 2–10 and preferably 2–8 carbon atoms. Analogs of these amino acids can also be suitable for the invention. If the amino acids are chiral compounds, then they can be present in the D- or L- form or also as a racemate. Preferably, the L- configuration of the amino acid is utilized. The amino acids of the oligopeptide can be natural and/or of synthetic origin. Amino acids of natural origin, such as occur in proteins and peptide antibiotics, are preferred. Synthetic amino acids can also be used, such as pipecolic acid, cyclohexylalanine, phenylglycine, α-aminocyclohexylcarboxylic acid, hexahydrotyrosine, norleucine, or ethionine.

Protecting (Blocking) Groups

Protecting groups are preferably employed when synthesizing the leaving group to prevent undesired side reactions of the leaving group during synthesis of the assay compound. N-terminal protecting groups and polar organic protecting groups on the other portion of the amino acid molecule are used to prevent undesired side reactions of the amino acids during syntheses of the peptides. The protecting groups, also known as blocking groups, are removed prior to the assay, unless the presence of a particular blocking group or groups is found not to interfere with the assay.

The N-terminal protecting groups include an arylcarbonyl, alkylcarbonyl, alkoxycarbonyl, aryloxycarbonyl, aralkoxycarbonyl, arylsulfonyl, alkylsulfonyl, or other equivalents known to those skilled in the art of peptide syntheses. The polar organic protective groups include hydroxyl, guanidinyl, sulfhydryl and carboxyl or other equivalents known to those skilled in the art of peptide syntheses. Gross and Meienhofer, eds., *The Peptide*, 3(3–81) (Academic Press, New York, 1981), describe numerous suitable amine protecting groups.

Preferred examples of the N-terminal blocking groups include formyl, acetyl, trifluoroacetyl, benzyloxycarbonyl, phthaloyl, benzoyl, acetoacetyl, chloroacetyl, phenoxycarbonyl, carbobenzoxy, substituted benzyloxycarbonyl, tertiarybutyloxycarbonyl, isopropyloxycarbonyl, allyloxycarbonyl, phthaloyl, benzoyl, acetoacetyl, chloroacetyl, phenoxycarbonyl, methoxysuccinyl, succinyl, 2,4-dinitrophenol, dansyl, p-methoxybenzenesulfonyl, and phenylthio.

Preparation of Intermediate Complex

A compound containing a blocking group and a leaving group such as an amino acid is reacted with an agent to form an active intermediate complex. The leaving group is selected based on the leaving group desired in the final assay compound. Suitable agents are known to those skilled in the art of peptide chemistry. Examples of suitable agents include carbodiimides, (preferably 1-ethyl -3 - (3'-dimethylaminopropylcarbodiimide hydrochloride) and benzotriazolyl-N-oxy-tris (dimethylamino) phosphonium hexafluorophosphate (BOP reagent) and 1-hydroxybenzotriazole (HOBT reagent). The reagents are typically stirred in a flask at room temperature. The chemical structure of the intermediate complex is presently unknown. The presence of the complex can be confirmed by thin layer chromatography.

Preparation of Reaction Product

The intermediate complex is further reacted with a compound containing an indicator group (indicator compound) to form a reaction product. As appreciated by those skilled in the art of peptide chemistry, the indicator compound is dissolved in a solvent to facilitate the reaction with the intermediate complex. The reagents are typically stirred in a flask at room temperature for a time sufficient to form a reaction product. The reaction product can be confirmed by developing a thin layer chromatography (TLC) plate in an organic solvent. The reaction product should be a non-fluorescent compound. When the indicator group is rhodamine 110, rhodol or a derivative, the presence of the reaction product is confirmed by contacting the reaction product with an acidic solution, such as hydrochloric acid, which cleaves the leaving group thereby forming a colored product. When the indicator group is fluorescein or a derivative, the presence of the reaction product is confirmed by contacting the reaction product with a basic solution, such as sodium hydroxide, which cleaves the leaving group thereby forming a colored product. If only one spot on the TLC plate gives a positive test and there are no trace amounts of fluorescence or its derivatives, the reaction product is of acceptable purity for this stage of the process.

Purification of Reaction Product

The reaction product is then separated from other side reaction products, by-products and starting materials in the following manner. Preferably, the reaction product is concentrated to an oil under reduced pressure so as to remove volatile solvents that might be present. The reaction product oil is then redissolved in a minimum of an organic solvent, preferably chloroform, methylene chloride, and further separated from the other side reaction products, by-products and starting materials by normal phase preparative high pressure liquid chromatography (HPLC). Other conventional methods of separation can be employed. Separation of the reaction product is verified by TLC, as previously described, and analytical reverse phase HPLC. The reverse phase HPLC will depict the presence of one major band of reaction product.

The reaction product is separated from the other side reaction products, by-products and starting materials so that the reaction product can be further processed by having the blocking groups removed. If the reaction product is not sufficiently separated from the other side reaction products, by-products and starting materials, then a low yield of the assay compound containing an indicator group and leaving-group will be obtained. Moreover, the quality of the separation will have an effect on the amount of purification that will be subsequently necessary to obtain an assay compound for use in the metabolically active cell.

Removal of Blocking Group

The blocking group which is blocking (protecting) the leaving group is then removed from the reaction product to obtain an assay compound ("intermediate compound" if a salt is to be formed) which contains an indicator group and a leaving group. The reactions are conducted to obtain a free amino acid xanthine derivative by methods known to those skilled in the art. When the blocking group on the indicator group comprises benzyloxycarbonyl (CBZ), the blocking group is removed by a catalytic reaction of the reaction product in an organic solvent with hydrogen in the presence of palladium or platinum. Further details of this process are shown in Example 13. When the blocking group on the indicator group comprises 9-fluorenylmethyloxycarbonyl (FMOC), the blocking group is typically removed by the reaction of the reaction product in a polar solvent with an organic base. Further details of this process are shown in Example 1.

To confirm that the blocking group has been removed from the resulting intermediate compound, the intermediate compound is analyzed by analytical reverse phase HPLC. In addition, the resulting intermediate compound can be further confirmed by developing a thin layer chromatography plate in an organic solvent.

Physiologically Acceptable Salt Formation

This intermediate compound having an indicator group and leaving group is then reacted with an acid or a base to form an assay compound, which is a physiologically acceptable salt. It is important according to the method of the invention that the assay compounds be physiologically acceptable to the cell. The selection of the acid or base has a material affect on whether the resulting assay compound will be physiologically acceptable to the cell. In addition, it has been found that the selection of the acid affects the selectivity of the assay compound for the enzyme to be assayed.

It has been found that hydrogen bromide (HBr), even when buffered, kills cells. To confirm whether an acid will be appropriate to use, a selected acid is used to make an assay compound. The assay compound is then tested with a metabolically active cell to determine if viability (Trypan Blue; propidium iodide-fluorescein diacetate [PI-FDA]) over the assay time period is affected. Viability is confirmed with Trypan Blue or PI-FDA over a time period of 10 seconds to 30 minutes. If the viability of the cell sample at between one and three million cells/mL decreases by 10% then the salt of the compound is rejected and another salt of the assay compound is synthesized.

Preferably the acid that is used to form the salt is selected from the group consisting of hydrochloric, sulfuric, nitric, maleic, acetic, trifluoroacetic, tartaric acid, citric, succinic and p-toluenesulfonic acid. More preferably the acid is selected from the group consisting of acetic, trifluoroacetic, tartaric acid, and p-toluenesulfonic acid. Most preferably the acid is trifluoroacetic. When a base is used, ammonia or organic bases can be used. Most preferably, the base is ammonia.

Purification of the Assay Compound

The assay compound is purified, preferably by reverse phase HPLC. It is very important that the side reaction products, by-products and starting materials from the synthesis of the assay compound be removed which would diminish the utility of the assay. Non-physiologically acceptable impurities should be removed. In addition, the background noise generated from impurities should be less than the auto-fluorescence of a metabolically active cell.

It has been found that when a leaving group is present as an impurity, the leaving group can be an inhibitor to enzyme activity. Still further, metal impurities in any of the starting materials can poison the enzymes, prevent hydrolysis of the assay compound and interfere with the accuracy of the enzyme assay.

In addition, impurities will create background fluorescence which will add to the natural fluorescence of the cell to create a level of background noise which can interfere with the detection of enzyme generated fluorescence. Fluorescent impurities can be taken up by the cell, and a rate measurement of fluorescence against time will show a false rate of increasing fluorescence that is due only to this cellular uptake of fluorescent impurities. This is a particular problem if the assay is conducted to determine the presence or absence of an enzyme, since this impurity will indicate a rate of fluorescence which will falsely appear to be attributable to enzymatic activity.

The assay compound can be purified by techniques known in the art. As shown in Example 1, the purification of rhodamine 110 substrate can be accomplished by reverse phase column chromatography.

In the case of the preparation of salts of peptide-rhodamine 110 compounds, a significant level of impurities is created. These impurities include free indicator compound, monosubstituted rhodamine 110, blocked amino acids and peptides.

The fluorescence impurities should be removed to a level that they do not obscure the baseline detection of the enzyme in the cell. The baseline detection can be established by analyzing log dilutions of an indicator group. Preferably the impurities should be removed so that the fluorescence of the impurities is less than the auto-fluorescence of the metabolically active cell.

Assays for peptidases using assay compounds generate fluorescence generally in the range of $10^{-5}$ to $10^{-6}$ Molar free rhodamine 110. Therefore, it is preferred that the free rhodamine 110 and blocked peptide impurities in the assay reagent should be removed to a concentration of less than the fluorescence generated by about $1\times10^{-6}$M and more preferably less than the fluorescence generated by about $10^{-7}$ Molar free indicator group. This amounts to a 100,000 photon count using rhodamine 110 as a standard at $10^{-7}$–$10^{-8}$M, preferably $5\times10^{-8}$M in a 1 cm path length cuvette when measured over 10 min. on a photon counting spectrofluorometer manufactured by the SLM Company of Chicago, Ill. This corresponds to a use level on the flow cytometer where no cellular false positive can be detected for a 10 minute period at the highest sensitivity setting. In the case of the peptide-rhodamine 110 compounds, this has been found to require a concentration of impurities of less than one part per one hundred thousand, more preferably less than one part per five hundred thousand, most preferably less than one part per million. The presence of impurities causes a decrease in the storage stability of the compound, resulting in an increased autohydrolysis which leads to increased background fluorescence. A compound should be free of impurities such that when the compound (or reagent containing the compound) is stored at 4° C. for 30 days, preferably 90 days, more preferably 180 days, most preferably one year, the background fluorescence increases less than 10%, preferably less than 5%, most preferably less than 1% over these time periods, respectively. The purified compound or lyophilized reagent are stored in a sealed container over dry nitrogen under atmospheric pressure. The starting point in time for measuring stability is usually immediately after purification of the assay compound is completed but it can be any time such as immediately after the preparation of the assay reagent is completed.

Normal phase preparative HPLC procedures are presently preferred to separate peptide-indicator compound from the impurities. As is known in the art, solvents of varying polarity can be mixed in varying concentrations in order to more effectively separate the peptide-indicator compound from the various impurities. Thin layer chromatography (TLC) can be utilized to test for the presence of the rhodamine 110 substrate in the eluate. This is done by placing a drop of the eluent on the TLC plate, and then treating the spot with a suitable acid, such as HCl, to detect the presence of the rhodamine 110 substrate, which will turn bright yellow when treated with acid. Analytical reverse phase high pressure liquid chromatography is used to test the peptide-indicator product for purity, as evidenced by a single sharp band in the absorption spectrum.

Preparation of Assay Reagent

The assay reagent must be compatible with the metabolically active cell. The assay reagent should have an osmolality of from about 250 milliosmoles to 350 milliosmoles, preferably from about 275 milliosmoles to 320 milliosmoles. Further, the assay reagent will have an ionic strength between about 0.1 to 0.3 Mμ. In addition, the pH of the assay reagent will be between about 4.0 and 9.5, preferably between about 5.0 and 8.0. The preferred pH for assay compounds for particular enzymes is included in Table 1.

It has been further found that the efficacy of an intracellular assay is substantially improved by the addition of one or more components in the assay reagent. Examples of improvements include a reduction of reaction time, increased selectivity for the targeted enzyme, reduction of competing enzyme reactions, increasing signal of enzyme reaction, increasing reactivity of the assayed enzyme relative to other non-targeted enzymes, increasing the retention time of the indicator group within the cell and other similar advantageous results.

Additional components include buffers, cofactors, modulators, inhibitors, activators for increasing activity of the target enzymes over other non-targeted enzymes, solubilizing components and retention components can be included in the assay reagent to improve the enzyme assay results. These components are physiologically acceptable to the metabolically active whole cell that is being assayed.

The chemical nature of the buffer is important to the reactivity Of the assay compound with the cellular enzymes. For example, it has been found that Hanks solution is a better cellular buffer than cacodylic acid at 0.1M concentration for amino peptidase. More specifically, by utilizing Hanks solution, at pH 7.5, it has been further found that the assay compound has a higher sensitivity for the targeted enzyme. In addition, the assay compound hydrolysis by the enzyme occurs at an increased rate of reaction. Although Hanks solution contains calcium chloride at a concentration of 1.26 mM, calcium chloride has been found in the case of aminopeptidase to be inhibitory to the enzyme reaction with the assay compound, (H-L-Asp)$_2$ rhodamine 110, at concentrations of approximately 10 mM.

Buffer components that show no inhibitory effect to the cells can be used. Suitable buffer components are N-tris (hydroxymethyl)methyl-2-aminoethanesulfonic acid (TES), Hanks balanced salt and 2-N-morpholinoethanesulfonic acid (MES), tris-glycine, HEPES, glycine sodium hydroxide, and cacodylate. The preferred buffer components are MES for acidic solutions, Hanks for neutral solutions, and glycine sodium hydroxide for basic solutions. Preferred buffers for particular enzymes are included in Table 1. A metabolic energy source such as a sugar (glucose) can be added.

Cofactors are components not consumed in the enzymatic reactions, but are required to make the enzyme function.

Suitable cofactors include metals such as $Ca^{+2}$, $Zn^{+2}$, $Mg^{+2}$, $Fe^{+2}$ and $Mn^{+2}$. These cofactors can increase the selectivity of the enzyme for the leaving group. The cofactors can also be co-enzymes or vitamins. Preferred cofactors for particular enzymes are included in Table 1.

Modulators are components used to decrease the sensitivity of the enzyme for the leaving group. The modulators speed up or slow down the activity of an enzyme by changing the active site. Therefore, enzyme activity can be down-regulated, as in negative feedback inhibition by the leaving (stimulated) group inhibiting the original enzyme. For example, dithioerythritol (DTE) at 1 mM decreases the sensitivity of the substituted rhodamine 110 substrates containing the amino acids Pro, Gly, Gln-Ser, Val-Lys-Val-Lys, Ala-Ala, and Ala-Ala-Ala-Ala, but does not change the sensitivity of the leaving group for the enzyme where the substrate contains the amino acids Ala-Gly, and Leu-Gly. Dithiothreitol (DTT) has also been found to be an effective modulator. Preferred modulators for particular enzymes are included in Table 1.

Inhibitors and poisons (or toxins) are components that can be added to reduce the activity of non-targeted enzymes that provide competing reactions for the leaving group. Inhibitors are usually very selective for a particular enzyme. For example, EDTA only works with enzymes requiring $Ca^{+2}$, $Mg^{+2}$ and some other metals. Other examples of an inhibitor are bestatin, which selectively inhibits aminopeptidase and leupeptin which selectively inhibits cathepsin B. In addition, the monopeptide reagent contains approximately 137.9 mM per liter of sodium chloride. However, the addition of 7 mM of sodium chloride to the dipeptide reagent has a slightly inhibitory effect over the pH range of 6.5 to 8.7. Preferred inhibitors for particular enzymes are included in Table 1.

The assay compound must be soluble in the aqueous media. Solubility is measured by light scatter using the percent transmittance of light (or absorbance) through the mixture of the media and assay compound. As measured on a spectrophotometer, the assay compound should have a background color at a concentration to be used in an assay of less than 1000, preferably less than 800, and most preferably less than 500 milliabsorbance units at 340 nanometers (25° C.) blanked against distilled or deionized water. The assay compound will usually be used at a concentration of 0.5 to 10 mM. A useful concentration for determining solubility is 5 mM.

Preferably, a two fold excess quantity of the assay compound that will react with the enzyme during the time of the assay must be soluble in the aqueous media. An excess of assay compound is preferred. If an insufficient amount of the assay compound is provided, the enzyme reaction will completely hydrolyze the assay compound and the dynamic range of the assay will be limited. The resulting indicator compound will have a limited fluorescence duration. However, when an excess of the assay compound is employed, the enzyme reaction will continuously hydrolyze the assay compound and the fluorescence duration will continue during the enzyme reaction. This provides the advantage of having a longer time period in which to sense for one or more reaction states of the assay compound.

A solubilizing agent can be utilized with assay compounds for which salts are not available, or where such solubilizing agents will assist the transfer of the assay compound into a metabolically active cell. The solubilizing component is present in an amount effective to enable the assay compound to pass through the cell lipid bilayer without detrimentally affecting the cell. The solubilizing agent should be carefully chosen because the wrong solubilizing agent can cause lysis or cell death.

When the assay compound has a background color (at the concentration to be used in an assay) greater than 1,000, greater than 800 or greater than 500 milliabsorbance units, a solubility component may be used to lower the background color to less than 1,000, less than 800 or less than 500 milliabsorbance units. However, the concentration of the solubilizing component is limited. If a high concentration of the solubilizing component is used, metabolically active cells will be lysed. If a low concentration of the solubilizing component is used, sufficient solubility of the assay compound will not be attained. The effective amount of solubilizing component may be empirically determined, but is typically less than 10.0% by weight of the assay compound.

Suitable solubilizing components include non-ionic surfactants, polyethylene glycol, dimethyl sulfoxide (DMSO), and mannitol, as noted in Table 2. BRIJ 35 and TWEEN 20 are the tradenames for products from ICI Americas, Inc. PLURONIC 25 R8 is the tradename for a product from BASF Wyandotte. TRITON X100 is the tradename for a product from Rohm and Haas Company.

TABLE 2

| CONCEN-TRATION | COMMERCIAL NAME | CHEMICAL STRUCTURE |
| --- | --- | --- |
| 0.1% | BRIJ 35 (nonionic) | Polyoxyethylene lauryl ether |
| 0.2% | PLURONIC 25 R8 (non-ionic) | Ethylene oxide with hydrophobic base from propylene oxide and propylene glycol |
| 0.1% | TRITON X100 (non-ionic) | Octylphenoxy polyethoxy ethanol |
| 0.1% | TWEEN 20 (non-ionic) | Polyoxyethylene sorbitan monolaurate (polysorbate 20) |
| 0.1% | | Polyethylene Glycol |
| 5% | | Dimethyl Sulfoxide |
| 4.5% | | Mannitol |

When using a solubilizing component, certain difficulties have been encountered. While the solubilizing component facilitates the transmission of the assay compound into the metabolically active cell, the solubilizing component will also facilitate the expulsion of the fluorescent indicator group compound from the metabolically active cell. The expulsion of the indicator group will have the negative effect of permitting non-enzyme containing cells to absorb free dye. When this occurs, the accuracy of an enzyme assay is compromised.

In addition, the electronic configuration and polar nature of the liberated indicator dye influences its ability to be retained within the cell. Retention of the dye is important for proper detection.

A feature of the present invention used to avert the problem of cellular expulsion when using a solubilizing component, is for the assay reagent to include a retention component. The retention component will comprise at least one agent that will inhibit a cell pump mechanism for expressing extracellular material. Such cell pumps include the multiple drug response pump, calcium channel pump, sodium pump, potassium pump and ATPase pump. Suitable retention components include trifluoperazine.HCl, prochlorperazine.maleate, and chlorpromazine.HCl to inhibit the multiple drug response pump; verapamil.hydrochloride to inhibit the calcium channel pump; and digoxin ($C_{41}H_{64}O_{14}$), digoxin derivatives, such as ouabain ($C_{29}H_{44}O_{12}$), and strophatidin ($C_{23}H_{32}O_6$) to inhibit the sodium, potassium and ATPase pump.

The media in which the assay compound is dissolved must be compatible with the cell so that the cell can remain metabolically active in the media for at least the duration of the assay. The media is preferably sterile and free of endotoxin and chemicals that adversely affect the physiology of the cell. The assay compound is preferably completely soluble in the media at the concentration at which it is used. The assay compound is preferably used in concentrations up to the saturation or the suspension level or before turbidity occurs. The media may be physiological saline or a buffered solution (phosphate buffered saline) in which the assay compound and other additives are dissolved. The media should preferably include a buffer agent so that the pH of the assay mixture of metabolically active cells and assay compound is maintained at a point that is appropriate for the enzyme hydrolysis.

For storage purposes the compound and media mixture should be lyophilized under conditions where sublimation of the solvent occurs upon application of a vacuum. Applying a vacuum to the sample at a temperature where a liquid forms on the solid before going to a gas phase, referred to as "melt back" may cause degradation of the compound. Appropriate temperatures should be determined for each compound, and preferred temperatures are usually $-5°$ C. to $-35°$ C. for predominantly aqueous solutions. During the thermal cycle of lyophilization, heat may be applied after sublimation to drive off any additional moisture. The product temperature should never exceed the heat applied and the product should be brought to room temperature over 15 to 72 hours. The vacuum should be returned to atmospheric conditions by bleeding in dry nitrogen. The product is stoppered at atmospheric pressure and temperature. The lyophilized compound is stored at $4°$ C. to $8°$ C. and may be reconstituted using endotoxin-free deionized water.

Auto-hydrolysis, which is the nonspecific hydrolysis of the substrate, yields cellular fluorescence not derived from the target enzyme. Stability of the substrate compound has been demonstrated to be a key factor in preventing autohydrolysis.

The assay compound and/or the assay reagent should be sufficiently stable so that no auto-fluorescence or chemiluminescence is created by the degradation of the assay compound prior to cleavage by the enzyme. Preferably, when the assay compound or assay reagent is stored at $20°$ C. for 30 days, preferably 90 days, more preferably 180 days and most preferably one year, the reagent exhibits a photon count of 100,000 or less. Photons can be measured by using a 2 millimolar solution of assay compound in deionized water and a path length of 1 cm against a rhodamine 110 standard as previously described. Fluorescent impurities should account for less than 10% of the fluorescence generated during the assay.

An acceptable reagent should have the following three characteristics; (1) there should be a low level of native free fluorescence that is absorbed by the cells, non-specifically. Thus, there should be a low level of fluorescent impurities such as free indicator compounds. The acceptable and preferred levels of these impurities have already been described. (2) The reagent should be stable over time so that it does not need to be used shortly after it is prepared. Certain impurities and certain reagent additives can increase the rate of autohydrolysis which increases the fluorescence of the reagent. Acceptable and preferred stabilities have already been discussed. (3) The reagent should also have a high enough rate of reaction with the enzyme being measured so that fluorescence generated as a result of reaction between the enzyme and the reagent can be easily measured. In one aspect, the reaction rate should be sufficiently high that fluorescence generated as a result of cleavage of the leaving group inside the cell is at least 2 times, preferably at least 10 times, more preferably at least 50 times and most preferably at least 100 times greater than other non-specific fluorescence generated in the assay. In another aspect, the reagent should contain an unblocked assay compound which has a reaction rate which is at least 2 times, preferably at least 5 times, more preferably at least 100 times, most preferably at least 1000 times the reaction rate of a corresponding blocked assay compound. For example, the unblocked assay compounds of the present invention which contain unblocked amino and or peptide leaving groups have an enzymatic reaction rate which is considerably greater than the reaction rate of the corresponding compound wherein the amine group(s) on the leaving group is blocked by, for example, a Cbz group.

Types of Assays

It has been discovered that the assay reagent can be used to determine enzymatic activity of metabolically active whole cells to provide indication of the presence of a disease, of the progress of a disease, the efficacy of a drug, and cell differentiation.

It has been found that the activity of one or more enzymes changes with disease progression. Changes in the activity of one or more enzymes can be examined to provide an indication of the presence and progress of a disease. In addition, the measurement of the activity of certain enzymes can provide an indication of the response to certain drugs or treatments, since the activity of one or more enzymes will change if the drug is successfully fighting, modulating or treating the disease. Still further, it has been determined that differentiation of a cell can be determined by the presence of one or more selected enzymes.

Existing tests for the presence of a disease, progress of a disease, or efficacy of a drug require significant extracellular concentrations of the enzymes that are being measured. Usually, hours or days are required to allow extracellular concentrations to rise to detectable levels. The present invention has the further advantage of providing a method to produce a reagent for measuring the intracellular concentrations of enzymes. This enables the diagnostic assay to obtain analysis of the enzyme of interest in a shorter period of time and to monitor intracellular events as they are occurring.

Enzymatic assays are performed by contacting metabolically active cells with an assay reagent. The leaving group is selected to be one which can be cleaved from the indicator group by the targeted enzyme. The reaction occurs for a period of time sufficient for the leaving group to be cleaved from the indicator group by the targeted enzyme. Sensing for one or more reaction states confirms cleavage of the indicator group by the enzyme.

In some instances, one can characterize a disease, the progress of a disease, or efficacy of a treatment by sensing for only a single enzyme, as in the case where a disease is characterized by the presence or lack of activity of an enzyme. For instance, Hereditary Non-Spherocytic Hemolytic Anemia (HNSHA) is distinguished from hereditary spherocytosis by the fact that red blood cells are morphologically normal and manifest a normal osmotic fragility. Only in the case of pyrimidine 5'nucleotidase deficiency is the erythrocyte morphology changed to a basophilic stippling. (See Example 27) However, in most instances these conditions will be characterized by assaying for the activity of at least two enzymes. In practice, five or more enzymes will be used in a panel to serve as checks and to reduce the probability of false positive or false negatives since the activity of a targeted enzyme can be present in two different diseases. However, as the number of targeted enzymes are increased in the panel, the assay becomes more reliable or differentiable. The detection is more reliable because two different diseases will have different enzyme patterns.

Thus, there are at least two ways to run the assay of the present invention:

running a single assay and detecting a difference between the beginning state and the end state of a substrate, such as the cleavage of a single substrate by a target enzyme to yield free peptide and fluorescent indicator dye; and running a series of assays with a pattern matrix of several substrates reacted with an abnormal cell versus the same matrix reacted with a normal cell.

"Reliability" refers to the ability to make pattern matrix decisions without failure. Error in a single test may not, in fact, invalidate a pattern matrix. For a small set of assays, the assay provides an increased capability to differentiate states of abnormality.

The panel of selected enzymes are created by developing a range of normal values for enzymatic activities and ratios of enzymatic activities to each other. This panel will be used to compare the test results from the cell analyte. The enzyme activities from the examined cell analyte is compared to at least one of a reference/non-diseased cell or a reference/diseased cell to obtain an indication of a diseased state.

In other instances, the analysis of cellular enzymes involving classes of enzymes provides the ability to sort cells by type or morphology. As many as a thousand different enzymes may be operative in any given cell, but only a few dozen enzymes define the unique function or functions of any one cell type. Many enzymes are inhibited or missing from functionally different cells. Determination of proteases, glycosidases, glucosidases, carbohydrases, phosphodiesterases, sulfatases, thioesterases, pyrophosphatases, nucleotidases, nucleosidases, saccharidases, esterases, phosphatases, lipases and combinations thereof provides a matrix to rank cells by their functional activity.

Classification of normal cells morphologically can be made by determining key enzyme activities. For example, nucleated red blood cells (NRBC's) can be distinguished from non-nucleated red blood cells (RBC's) by determining dipeptidyl peptidase IV activity in the cell analyte. In NRBC's dipeptidyl peptidase IV activity will be present but in RBC's dipeptidyl peptidase IV activity will be absent. In addition, the age of RBC's can be determined by the presence or absence of adenosine deaminase or 5'nucleotidase.

In still other instances, the analysis of cellular enzymes involving classes of enzymes provides the ability to study cell proliferation. Cell proliferation is stimulated by growth factors. Cell proliferation is the ability of cells to divide and increase their numbers. Phases of cell division are under gene control and take a specified time period for each part of the division process. The time from one division to the next includes a randomly variable component. Different cell types require different growth factors in order to divide. All cells compete for growth factors. Cells are programmed for a certain number of divisions and then they die.

Abnormal cells that disobey normal constraints on cell division proliferate to form tumors in the body. They also appear transformed in cell culture. Cell transformation is often accompanied by mutation or over-express of specific oncogenes.

Some normal cells proliferate as part of their function. Signaling molecules are produced in the course of the inflammatory response and stimulate the bone marrow to produce more leukocytes. This regulation tends to be cell type specific. More specifically, some bacterial infections cause a selective increase in neutrophils, while infections from parasites cause a selective increase in eosinophils.

A blood cell differential can be constructed using this invention to determine cell types, immature cells, mature cells, abnormal cells due to drug interreaction and abnormal cells due to disease. For example, cell types can be identified by the assay of the present invention. For example, lymphocytes can be distinguished from monocytes or neutrophils by peroxidase activity. Lymphocytes will not show peroxidase activity while neutrophils will show peroxidase activity, and lymphocytes will not show esterase activity while neutrophils will show esterase activity. In addition, acetate esterase activity is present in monocytes that have been inhibited with sodium fluoride, but absent in neutrophils.

In addition, the analysis of cellular enzymes involving classes of enzymes provides the ability to study cell activation. Activation of T cells is a complex process involving various secreted proteins called interleukins which act as chemical mediators. Activation is thought to begin when the T cell stimulates the antigen presenting cell to secrete one or more interleukins. IL-1 mediator causes the T cell to stimulate its own proliferation by inducing it to secrete a growth factor IL-2, as well as synthesize IL-2 receptor to initiate proliferation.

Helper T cells are essential for B cell antibody response. Once activated by foreign antigen, the T cell presents the antigen to a B cell for antibody synthesis. Other Helper T cells secrete γ interferon which attracts macrophages and activates them to defend against infection by microorganisms. Diagnosis of infection from inflammation and inflammatory diseases has been achieved using the assay reagent in a pyrogen-free, sterile environment. Activation and proliferation agents, like phorbol myristate acetate (PMA), f-Met-Leu-Phe, IL-1, IL-2, GMCSF and γ interferon are added to the media and specific cell types are observed for response. Treatment regimes can also be monitored for effectiveness by using the assay reagent in conjunction with growth stimulators or signal peptides.

The present invention has potential use in the following clinical applications: diagnosis of cervical cancer, diagnosis of viral replication in HIV patients, diagnosis of HIV infected blood in blood supply, diagnosis of TB infected HIV patients, improved blood differential, differential diagnosis of viral from bacterial infections, differential diagnosis of Lupus from rheumatoid arthritis, differential diagnosis between rheumatoid arthritis from osteo arthritis, diagnosis of vasculitis, diagnosis of cardiovascular disease, monitoring of chemotherapeutic efficacy, diagnosis of Hodgkins Disease, confirmation of gene implantation and diagnosis of transplant rejection.

For a diagnosis of cervical cancer, several enzymes related to the presence of cervical cancer can be measured.

For a diagnosis of viral replication in patients, HIV replication in blood cells can be monitored. A sensitive measure of HIV replication can be important as a predictor of rapid movement into the AIDS state from the HIV infected stage of the disease. Since the virus replicates in the lymphocytes and monocytes, monitoring specific enzyme levels can make the monitoring both inexpensive and reproducible.

Identification of infected units in blood supply is one of the major goals of those responsible for the quality of blood supplied for transfusion to reduce the probability of HIV or Hepatitis infection. A low cost screening methodology can be devised whereby the blood can be subjected to HIV antibody testing and testing by the method of this invention.

In the management of AIDS patients, the early diagnosis of Tuberculosis is important to insure rapid recovery and to reduce the chance of further complications. The objective of such a test using this invention is to distinguish $TB^+HIV$ patients from $TB^-HIV$ patients. The early identification of the $TB^+HIV$ patients can permit administration of therapy to prevent additional complications in these immune deficient patients.

This invention also has utility for the differential diagnosis of viral from bacterial infections. Many patients have an elevated temperature and it is not known whether the temperature is from a viral or bacterial origin. The differential diagnosis between viral and bacterial infections assists the clinician in the management of these patients by allowing the physician to apply the proper therapy on an as needed basis.

This invention has further utility for differential diagnosis of Lupus from rheumatoid arthritis/drug monitoring in rheumatoid arthritis and Lupus patients. In the early course of disease, the symptoms for Lupus Erythematosis and rheumatoid arthritis are sufficiently similar that differential diagnosis of the disease is difficult, especially when a Lupus patient has early arthritic involvement. This has clinical consequences since it delays the administration of the correct therapy. Lupus can be a clinically aggressive disease and it is beneficial to the patient to have the correct diagnosis at an early date. These patients have different enzymes in activated states meaning that this methodology is the modality to use for a differential diagnosis. Additionally, monitoring the therapeutic application of steroid drugs can be of benefit to the patient.

This invention has still further utility for differential diagnosis between rheumatoid arthritis from osteo arthritis. Rheumatoid arthritis is an aggressive autoimmune disease which results in destruction of the panus of the joint. Osteo arthritis is a degenerative disease of the aging joint which is not immune mediated. Since immune cells migrate throughout the body, this methodology provides an early differential diagnosis between these two diseases. This is important since the correct therapy for each disease is different.

Moreover, this invention has utility for diagnosis of vasculitis. Vasculitis is an autoimmune disease of blood vessels generally in the extremities. Patients with this disease typically have nondescript complaints of pain which do not permit diagnosis until considerable damage has been completed on the vascular system by the immune cells. Since it is an autoimmune disease caused by circulating immune cells, the disclosed methodology can provide the needed information to make an early diagnosis.

Furthermore, this invention has utility for monitoring of cardiovascular disease. Atherosclerosis results in the deposition of platelets and other cellular components into the walls of coronary vessels. This process results in the loss of elasticity of the vessels and eventually in death. It has been shown that in these patients, as many as 20% of the platelets are in the activated state. Evaluation of platelets can permit the identification of patients with active atherosclerotic processes ongoing and permit administration of disease altering drugs.

Moreover, this invention has utility for monitoring of chemotherapeutic efficacy. Patients undergoing chemotherapeutic therapy have altered enzyme patterns which indicates that this change in enzyme levels can be used to monitor the effectiveness of chemotherapy.

In addition, this invention has utility for diagnosis of Hodgkins disease. The practice of this invention can be useful to monitor the stages of Hodgkins disease.

Furthermore, this invention has utility for diagnosis of transplant rejection. The practice of this invention can be useful to monitor the acceptance of an organ transplant. All patients are given immunosuppressants to prevent organ rejection and therefore it is difficult to distinguish infection from rejection.

Moreover, this invention has utility for monitoring for metastatic invasion. It has been found that tumor cells have different patterns of enzymes from normal cells in the same tissue. Identification of the types of enzymes is useful and important for predicting metastatic potential and invasion. Tumor cells in circulating blood can be useful to predict the progression of the disease.

Preparation of Metabolically Active Whole Cells

The assay reagent is reacted with a metabolically active whole cell analyte. The metabolically active whole cells are contained in tissue, blood, cell cultures or other cells containing constituents. Preferably, the metabolically active whole cells are separated into cell types. The metabolically active cells to be analyzed are isolated by known techniques such as differential lysis, differential centrifugation, and affinity columns. However, separation of the cells to be studied from other cells is not always essential.

The cells are usually washed to remove any extracellular enzymes, optionally with lysis or physical separation of unwanted cells. Several preferred techniques for accomplishing this are summarized in FIGS. 1A–1D.

The analysis of the segregated metabolically active cells provides specificity for a particular enzyme analysis. For example, when the metabolically active cell is a leukocyte blood cell, the method comprises separating the leukocyte cell from the cell analyte, washing the remaining leukocyte cell to remove any serum or plasma enzymes, contacting an assay reagent compound with the leukocyte cell, and determining fluorescence from the leukocyte cell (See FIG. 1B). A modification of this method comprises washing the cell analyte to remove any serum or plasma enzymes, contacting an assay compound with the cell analyte, separating the leukocyte blood cells from the cell analyte, and determining fluorescence from the leukocyte cells (See FIG. 1A). In addition, another method that can be used for cell analytes of leukocyte blood cells, nucleated erythrocyte blood cells and platelets analytes comprises washing the cell analyte to remove any serum or plasma enzymes, contacting an assay compound with the analyte and determining fluorescence from the analyte (See FIG. 1C).

To confirm that cells are metabolically active at the time of the assay, it is desirable that the viability of the cells be checked at the time of the assay. Several tests are useful to determine the viability of cells. Trypan blue is a blue stain which diffuses into the cell and is removed by cells if the cells are viable. Dead cells will not remove the dye and will take on a blue color. Propidium iodide is a DNA-RNA stain which, if the cell is dead and membranes are damaged, will penetrate the cell and stain the DNA-RNA. Fluorescein diacetate-propidium iodide will cause living cells to take on a green color because the fluorescein diacetate will be hydrolyzed, while dead cells become red from the propidium iodide. Red blood cells do not undergo cell division, and therefore a test for the presence of 2,3-diphosphoglucose dehydrogenase (which is an indicator of cell division) is a useful test for viability.

The assay of the present invention is particularly useful for measuring intracellular concentrations of enzymes in mammalian cells such as human cells. However, the assay should also be useful in various or other types of cells which have metabolic activity.

Assay Conditions

The concentration of the cells in the media should be high enough to provide a reading of the desired number of cells within the desired time period, taking into consideration the speed of the instrument that is being used. For current flow cytometry techniques, a concentration of about three million cells per milliliter is appropriate to yield a measurement of about 10,000–15,000 cells in about 1–2 minutes.

The assay compound is generally employed in concentrations in excess of the amount which can be completely hydrolyzed by the quantity of enzyme within the time of the assay. An assay compound concentration that is too high may have a negative effect on enzyme activity, since the leaving group can be a negative feedback inhibitor to enzyme activity.

The leaving group concentration in a cellular optimization is determined using Km (a known rate constant) and $V_{MAX}$ (maximum velocity) calculations. The leaving group is preferably present in an amount from about 2 to about $100 \times V_{MAX}$ and most preferably from about 2 to about 10 times the amount which can be completely hydrolyzed by the enzyme within the duration of the assay period. Preferred leaving group concentrations for particular enzymes are included in Table 1.

The assay may be conducted either as a rate determination or as an end point determination. Rate determinations are preferred, because they are generally less affected by autofluorescence. Consequently, a rate determination assay is more sensitive and precise. In a rate determination, the fluorescence of the assay compound-cell analyte mixture may be determined promptly after the cell analyte is contacted with the assay compound. The ability to see a signal and distinguish it from background noise determines the initial starting point of data collection and the final data point is preferably determined at the point where the slope of the reaction rate changes, typically more than 2%.

Most cellular reactions do not strictly obey zero-order kinetics. Most cellular enzymes show a delay between the time of exposure of the cells to the assay compound, and the ability to detect a signal that is greater than the background noise. Cellular enzymatic reactions that do not obey zero order kinetics are still useful measurements as first order, pseudo first order, or initial rate measurements. Multiple enzymes in a reaction (mixed reactions) are displayed by slope changes during the time course being monitored.

In an endpoint determination, the enzyme hydrolysis reaction is allowed to proceed for a predetermined length of time, usually at $V_{MAX}$. The reaction time can be calculated based on whether the reaction is zero order or first order kinetics using Michaelis—Menton methodology. Alternatively, the reaction time can also be adjusted by a different elapsed time for pseudo-first order reactions.

It has been determined that a number of factors will decrease the reliability of the assay, and yield false positive, or erroneous indications of enzymatic activity. These include (i) extended reaction between the cell analyte and the assay compound; (ii) another, non-targeted enzyme that is cleaving the leaving group; (iii) auto-hydrolysis of the assay compound; (iv) inhibitors or stimulators that are present and undetected; (v) cells that are no longer metabolically active, or dead; (vi) mixed populations of cells; (vii) a transfusion of the patient before sampling; (viii) non-specific dye uptake by negative cells; and (ix) background fluorescence. The creation of false negatives, or false indications of a lack of enzymatic activity, can be caused by (i) insufficient reaction between the cell analyte and the assay compound, (ii) a hypoosmotic media leading to a decrease in cell activity; (iii) a cell that is no longer metabolically active; (iv) burst cells; and (v) the presence of inhibitors to the target enzyme.

It has been further determined that assays will be significantly improved if reaction conditions are adjusted to maximize the activity of the assayed enzyme relative to other non-assayed enzymes which might otherwise compete for the leaving group. More specifically, the targeted enzyme can be involved in a chain cascade reaction of enzymes sequentially coupled to other enzymes, as in a multi-enzyme reaction cascade.

The reaction conditions can be adjusted to maximize the efficiency of the pathway, or to decrease the efficiency of competing pathways. Such conditions preferably include at least one of pH, choice of form of assay compound, temperature, osmotic pressure, ionic strength, and reaction time.

Figure 2C:
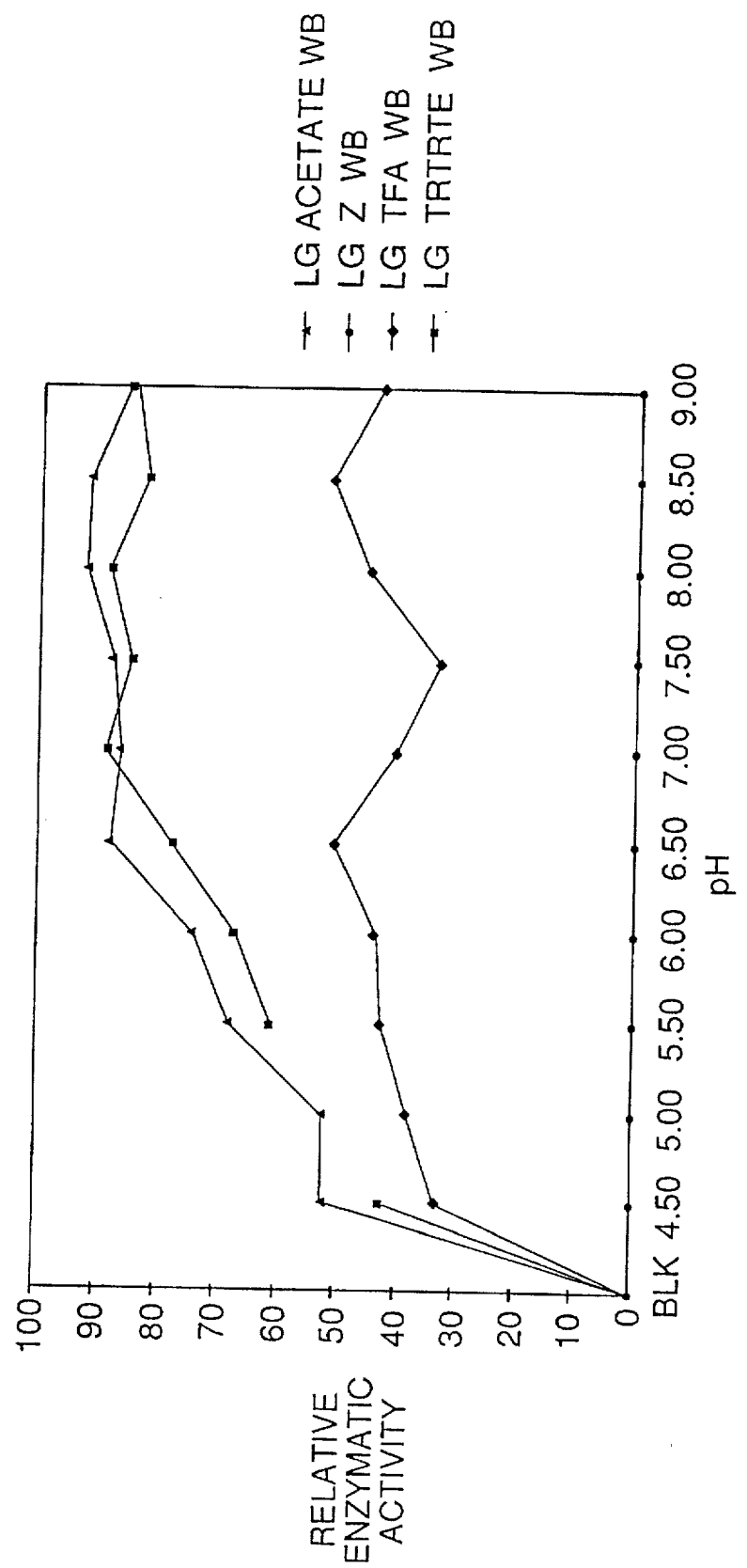
Figure 2D:
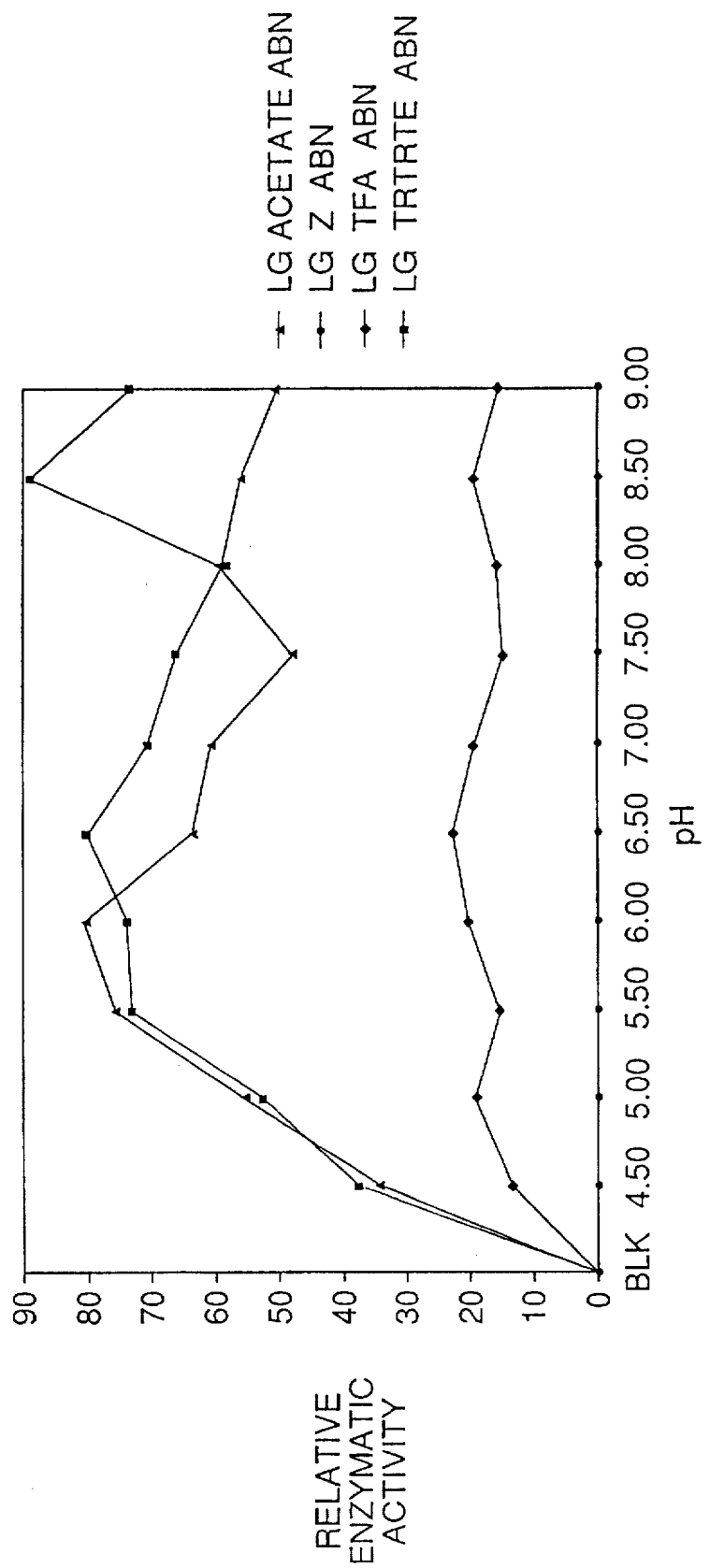
Figure 3A:
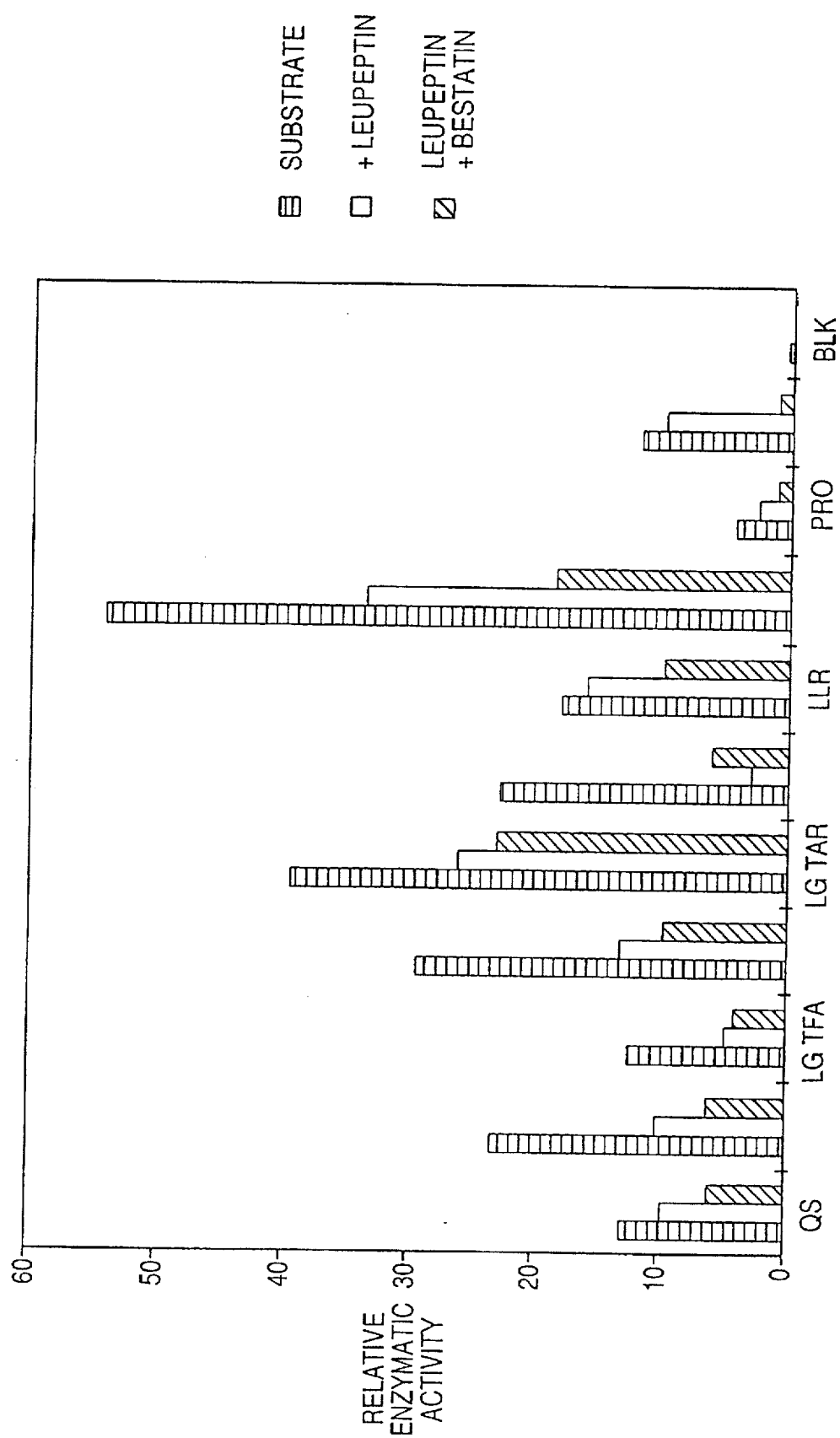
Figure 3B:
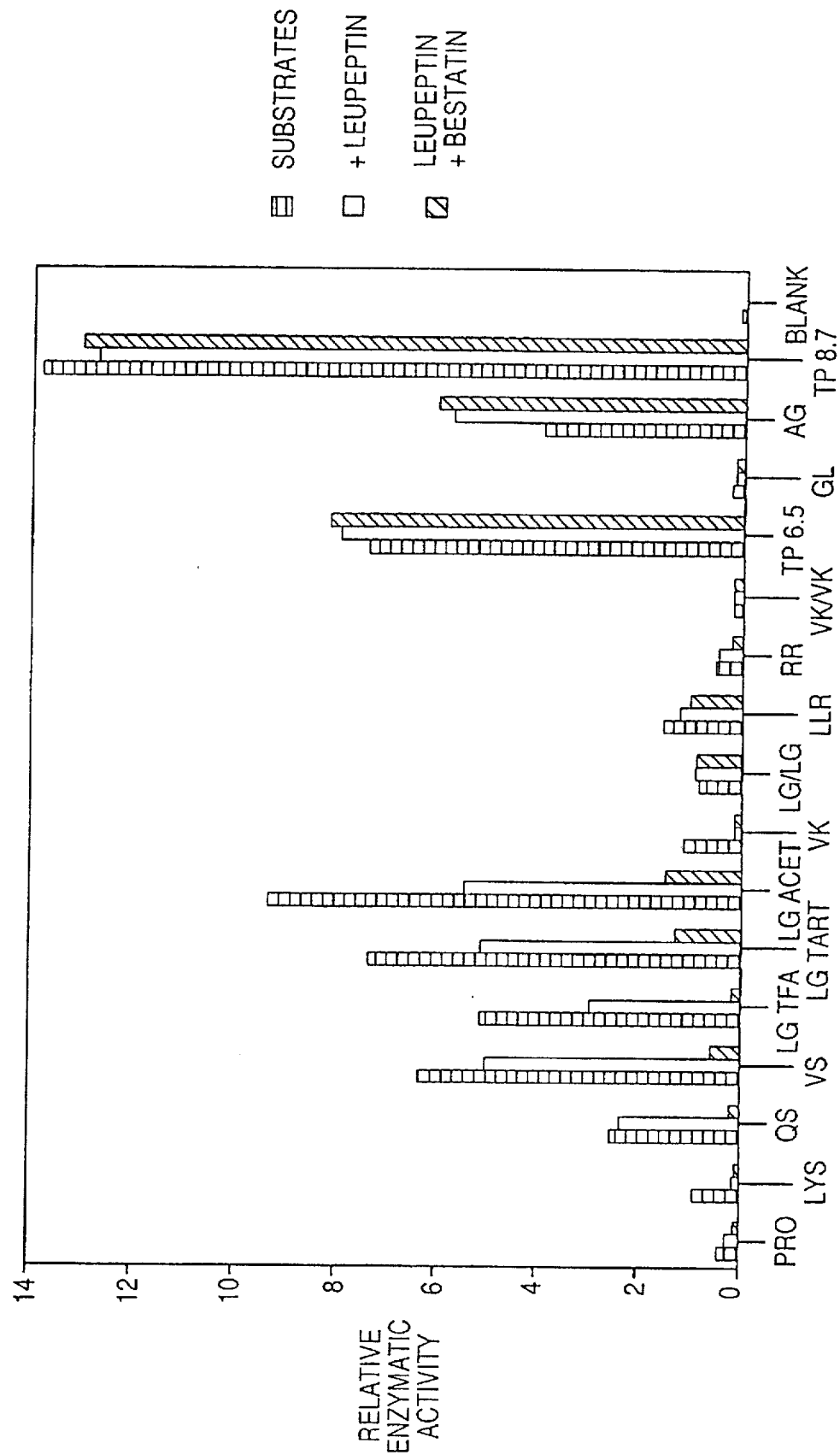
Figure 3C:
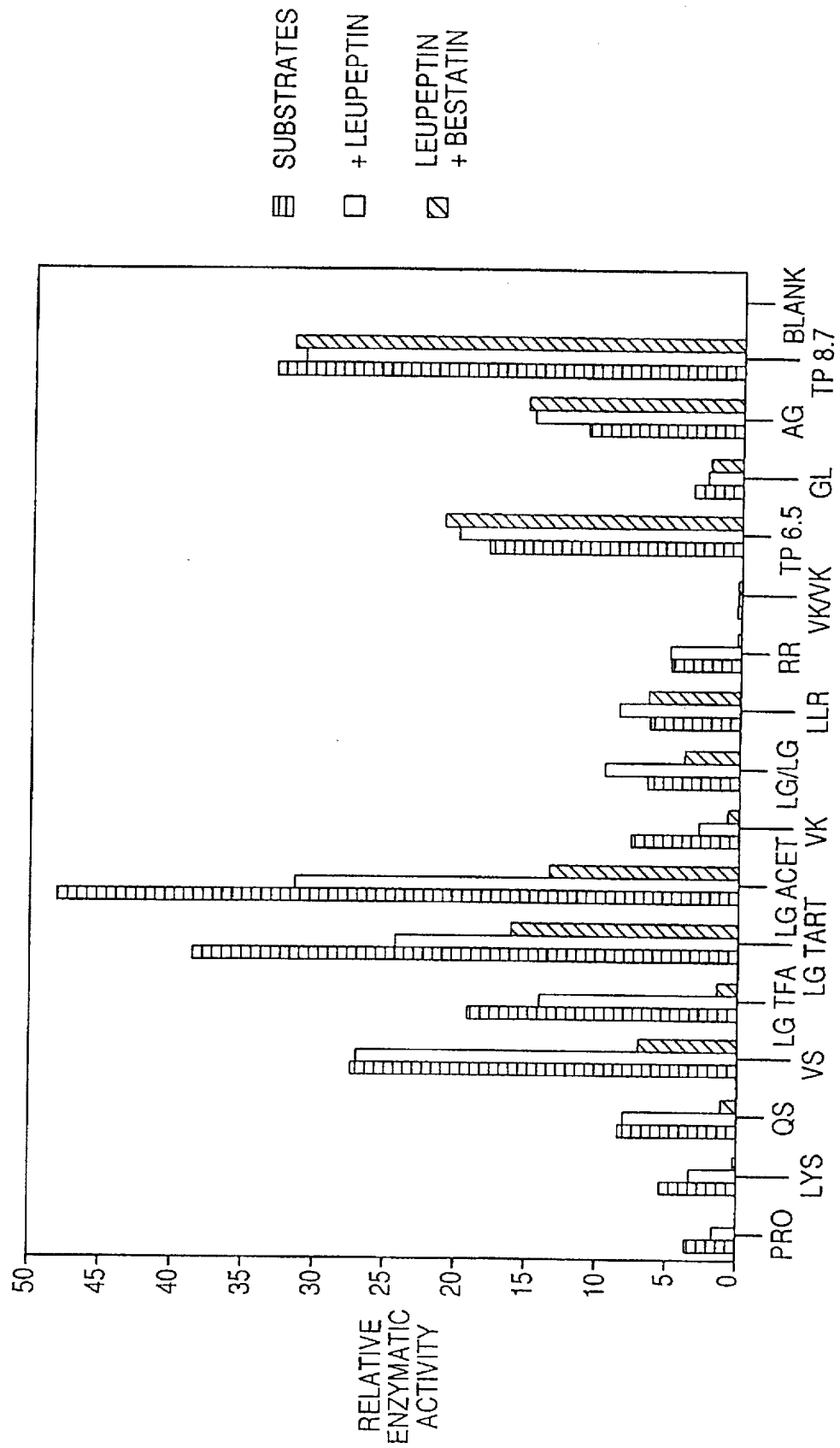

The pH at which an enzyme is most efficient can be determined from the literature, or determined empirically. As shown by FIG. 2, pH maxima can have two peaks (optima). Therefore, the selection of the appropriate pH should be made with care. In addition, care must be exercised when using pH information from the literature, because these values will usually be based on cytosol studies and not on intact, metabolically active whole cells. Therefore, it is preferable to use values from the literature only as a starting point, and then to determine the appropriate pH from this reference point. Generally, the pH will be between about 4.0 and 9.5. The pH of the assay mixture is controlled by dissolving the cell analyte and assay compound in an appropriate buffer. A list of preferred pH's for particular enzymes is included in Table 1.

The form of assay compound can be important since some enzymes require non-derivatized, natural structures for recognition of binding and reaction, whereas other enzymes are less selective. More specifically, derivatization and salt formation of the assay compound are important properties for solubilization, enzyme recognition and protection from auto-hydrolysis.

A reaction run using the same data collection window without the enzyme source will determine auto-hydrolysis of the substrate and therefore the potential for negative cells to absorb the dye non-specifically resulting in false positive.

The time of the assay is typically less than 30 minutes, preferably less than 20 minutes, usually between 5 seconds and 20 minutes, and most preferably between about 10 seconds and about 5 minutes. Some enzyme systems, such as esterase and phosphatase, can react with the assay compound in shorter periods of time due to concentrations of enzymes found in the cell. The reaction time should be limited so that the effects of cellular expulsion of the indicator compound will be avoided. Preferred time periods for assaying particular enzymes are included in Table 1.

The temperature at which the assay is performed must be physiologically acceptable to the cell. The temperature must be high enough to retain viability and to ensure enzyme activity, but not so high as to cause degradation or other deleterious reactions involving the leaving group, the enzyme, or other components of the mixture. Particular enzymes, or enzymes in particular pathways, are more reactive at particular temperatures. The temperature is preferably maintained between about 30° C. to about 40° C., more preferably between about 35° C. and about 38° C., and most preferably between about 36° C. to about 38° C. Preferred temperatures for a variety of enzymes are shown in Table 1.

The osmotic pressure of the assay mixture is controlled to be within physiological ranges from about 250 milliosmoles to 350 milliosmoles, preferably from about 275 milliosmoles to 320 milliosmoles. The osmotic pressure must be selected to maintain the viability of the metabolically active whole cell. Variations in osmotic pressures will result in lysis of the cell, severe shrinking or shriveling (crenation) when too low, and swelling or bursting (stomatolysing) of the cell when too high.

The ionic strength of the assay mixture should be selected so as to avoid shriveling crenating or bursting (stromatolysing) of the cells, and also to maximize the activity of the assayed enzyme relative to other, non-assayed enzymes. An ionic strength that is too low could deplete metals such as $Ca^{+2}$, $Mg^{+2}$, and $Zn^{+2}$, or cause insufficient amounts of anions such as $C^{-1}$, $NO_3^{-1}$, $SO_4^{-2}$ and $PO_4^{-3}$ which are the cofactors that can be used to improve enzymatic activity. The ionic strength of the assay reagent is preferably between about 0.1 to 0.3 Mμ. A list of preferred ionic strength values for particular enzymes is included in Table 1.

The fluorescence reading is made after the reaction has occurred or after a specific period of time. Typically, the reaction is stopped by immersing the reaction container in ice and water which cools the cells to about 0° C. Sensing for one or more reaction states by fluorescence determinations confirms cleavage of the indicator group by the enzyme.

The fluorescence determinations are performed on a Image Analysis System (IAS) or a Flow Cytometer (FC). The IAS is a microscope based system that measures fluorescence known to those skilled in the art. A representative example of an IAS is the Metamorph™ by Universal Imaging Corporation, West Chester, Penn. The structure and operation of flow cytometers is also well documented in the literature. Alternatives to traditional FC include slit-scan FC and stopped-flow FC. The type of instrument used to conduct the experiments described in the examples was a flow cytometer (for example, a Coulter Profile® flow cytometer manufactured by Coulter Corporation of Miami, Fla.). This flow cytometer measures fluorescence across the entire cell. Flow cytometric methods which measure fluorescence in only a part of the cell, such as slit scan flow cytometry, have significant utility in the invention because the background fluorescence is significantly reduced when measurements are focused on the region of the cell where the enzyme is located.

The fluorescence determinations can also be taken by a spectrofluorometer which has the capability to measure the very low fluorescence levels that are generated by the assay. The spectrofluorometer is tuned to the excitation and emission wavelengths of the particular indicator being used. Preferred compounds such as rhodamine 110 and fluorescein have excitation and emission wavelengths of about 495 to 498 nm (excitation) and 520 to 525 nm, respectively. The Model 8000C photon counting spectrofluorometer manufactured by the SLM company, a subsidiary of. Milton Roy (Chicago, Ill.) was used.

The flow cytometer can perform additional measurements in addition to a single wavelength fluorescence measurement. The flow cytometers can be equipped to measure fluorescence at two or more separate wavelengths. Such readings are useful to perform assays according to the invention when using more than one assay compound, or for using cell surface markers, such as monoclonal antibodies, to determine cell morphology. Additional wavelengths are useful to measure the activity of another enzyme, which can be a peptidase or a different enzyme such as a phosphatase, saccharidase, nucleotidase, esterase, or lipidase. Such additional tests are useful for simultaneously characterizing disease states, and for determining cell morphology and cell types.

Assay Protocols

Preferred sample preparations by which enzymes can be assayed using the reagents prepared according to the method of the invention have been developed. These sample preparations can be modified, and are included herein to disclose those procedures that are currently preferred.

The practice of the cell probe assay is divided into three parts: 1. Sample preparation, 2. Data Collection (i.e., Detection of Fluorescence) and 3. Results (i.e., Data Analysis).

1. Sample Preparation

Sample preparation can be divided into four different processes A, B, C and D which are illustrated in FIGS. 1A, 1B, 1C and 1D, respectively. The choice of sample preparation is dependent upon the user and the analyte. The four processes are:

Process A: Examination of leukocytes or tissue cells with erythrocyte contamination with postlysing.

A sample, consisting of whole blood (in EDTA, Heparin or ACD) or dissociated tissue or body fluids (synovial fluid) or cell culture media is obtained and stored in a manner so as not to decrease viability. The sample is washed sufficiently to remove plasma, media, body fluid, debris and extra-cellular enzymes. The wash media consists of a physiologically balanced buffered salt solution. The washed cells are incubated at 37° C. 50 μL of sample and 25 μL of substrate media are mixed together and allowed to incubate at 37° C. for a predetermined amount of time. At the end of the incubation period, unwanted cells are lysed with a lytic reagent, i.e., erythrocytes are removed. Compatible lytic systems are Q-Prep™, an acid lyse (formic acid/quench), Erythrolyse™, (acid lyse/detergent/quench) or hypotonic ammonium chloride. The sample is then measured for fluorescence. The referenced lyric systems are commercially available from Coulter Corporation, Miami, Fla.

Process B: Examination of leukocytes or tissue cells with erythrocyte contamination with prelysing.

A sample, consisting of whole blood (in EDTA, Heparin or ACD) or dissociated tissue or body fluids (synovial fluid) or cell culture media is obtained and stored in a manner so as not to decrease viability. Unwanted cells, i.e. erythrocytes, are lysed with a lytic reagent. Compatible lyric systems are acid lysed (formic acid/quench), IVCS lyse (quaternary ammonium salts)/quench or hypotonic ammonium chloride. The sample is washed sufficiently to remove plasma, media, body fluid, debris and extra-cellular enzymes. The wash media consists of a physiologically balanced buffered salt solution. The washed cells are incubated at 37° C. 50 μL of sample and 25 μL of substrate media are mixed together and allowed to incubate at 37° C. for a predetermined amount of time. At the end of the incubation period, the sample is then measured for fluorescence.

Process C: Examination of platelets, erythrocytes, leukocytes, dissociated tissue, body fluids and cell culture media.

A sample, consisting of whole blood (in EDTA, Heparin or ACD) or dissociated tissue or body fluids (synovial fluid) or cell culture media is obtained and stored in a manner so as not to decrease viability. The sample is washed sufficiently to remove plasma, media, body fluid, debris and extra-cellular enzymes. The wash media consists of a physiologically balanced buffered salt solution. The washed cells are incubated at 37° C. 50 µL of sample and 25 µL of substrate media are mixed together and allowed to incubate at 37° C. for a predetermined amount of time. At the end of the incubation period, the sample is then measured for fluorescence.

Process D: Examination of platelets, erythrocytes, leukocytes, dissociated tissue, body fluids and cell culture media using a mechanical separation to isolate a cell population.

A sample, consisting of whole blood (in EDTA, Heparin or ACD) or dissociated tissue or body fluids (synovial fluid) or cell culture media is obtained and stored in a manner so as not to decrease viability. A mechanical separation to isolate a specific cell population is performed, i.e., ficoll, differential centrifugation, differential precipitation. The sample is washed sufficiently to remove plasma, media, body fluid, debris and extra-cellular enzymes. The wash media consists of a physiologically balanced buffered salt solution. The washed cells are incubated at 37° C. 50 µL of sample and 25 µL of substrate media are mixed together and allowed to incubate at 37° C. for a predetermined amount of time. At the end of the incubation period, the sample is then measured for fluorescence.

2. Detection of Fluorescence

The instruments used to detect fluorescence are the flow cytometer or fluorescent microscope. There are four different instrument configurations for the flow cytometer, A, B, C and D. Any of the four configurations can be used with any one of the sample preparations described above. The choice of which configuration is selected is dependent upon the user and the information sought to be obtained. The four configurations are:

Configuration A

Configuration A analyzes the cells by size, granularity and single color. In the first configuration, the flow cytometer separates the cells by size and granularity. The activity of an enzyme is then assayed using the reagent compound. Two samples are allowed to proceed at different times and the reaction is stopped. The difference in fluorescence permits the calculation of a rate. Total population counts preferred are 20,000 to 500,000 cells. Use of light scatter or hematology parameters provide size and granularity separation. Intensity bitmap of desired populations and determination of fluorescent activity by single measurement point or multi-point measurement can be employed. Determine count, percentage and fluorescent intensity of a multi-modal population representing enzymatic activity.

Configuration B

Configuration B analyzes the cells by size, granularity and two colors. In the second configuration, the flow cytometer separates the cells by size and granularity. Cell morphology is determined by a fluorescence assay with a monoclonal antibody marker. The rate of the hydrolysis of the assay compound is then determined. Total population counts preferred are 20,000 to 500,000 cells. Use of light scatter or hematology parameters provide size and granularity separation. Intensity bitmap of desired populations and determination of fluorescent activity by single measurement or multi-point measurement can be employed. Determine count, percentage and fluorescent intensity of a multi-modal population representing enzymatic activity. The analysis is a 2-color analysis measuring enzymatic activity in one color and surface-marker antibody cell morphology in the other color.

Configuration C

Configuration C analyzes the cells by size, granularity, two colors and backgate fluorescence. Configuration 3 is a modification of the Duque method. Duque, R. E., "Flow Cytometric Analysis of Lymphomas and Acute Leukemias", *Annals of the New York Academy of Sciences, Clinical Flow Cytometry*, 677, pp. 309–325 (Mar. 20, 1993). The size and granularity of the cell are separated by a flow cytometer using light scatter and/or with surface markers, such as monoclonal antibodies. A series of cell populations are determined, with rearrangement of the histogram to identify the disease and normal cells. The activity of the enzyme is then assayed. Total population counts preferred are 20,000 to 500,000 cells. Use of light scatter or hematology parameters provide size and granularity separation. Intensity bitmap of desired populations and determination of fluorescent activity by single measurement point or multi-point measurement can be employed. Determine count, percentage and fluorescent intensity of a multi-modal population representing enzymatic activity. The analysis is a 2-color analysis measuring enzymatic activity in one color and surface-marker antibody cell morphology in the other color. Backgate fluorescence data on size and granularity to determine count and percent of diseased cells.

Configuration D

Configuration D analyzes activity of a population of cells over time. Total population counts preferred are 20,000 to 500,000. Use of light scatter or hematology parameters provide size and granularity separation. Intensity bitmap of desired populations and determination of fluorescent activity by single measurement point or multi-point measurement can be employed. Determine count, percentage and fluorescent intensity of a multi-modal population representing enzymatic activity. The analysis is a 2-color analysis measuring enzymatic activity in one color and surface-marker antibody cell morphology in the other color.

3. Data Analysis

The measured fluorescence intensity can be converted from mean channel fluorescence (in peak or integrated mode) to MESF (molecules of equivalent soluble fluorochrome, Flow Cytometry Standards Corp., San Juan, Puerto Rico) or International Units of hydrolysis per cell. A normal range of enzyme activity is established by assaying males and females in sufficient quantity to characterize the population levels statistically.

Various disease states are assayed for enzymatic activity and compared to the normal range. Three conditions will exist from this data:

1. Obvious increases or decreases in enzyme levels outside the normal range
2. Patterns of enzyme activities representing morphology
3. Patterns of enzyme activities representing disease states Artificial intelligence or Non-Negative Least Squares (NNLS) programs and analysis of variance (ANOVA) programs are useful in identifying patterns of enzyme activities representing morphology, cell types and patterns of enzyme activities representing disease states.

A first, and most obvious technique for disease diagnosis is identifying the absence or presence of a single enzyme.

One example of such a single enzyme diagnosis is the diagnosis for Gaucher's disease, which is diagnosed depending on the lack of a particular enzyme, namely, glucocerebrosidase.

The remaining techniques treat the absence or presence of a combination of enzymes as a complex interplay of metabolic systems, wherein each cell contains a group of enzymes, and the concentrations of these groups of enzymes are gaussian distributed, having a normal range or values, wherein values in disease states fall outside the normal range.

Analysis of Variance (ANOVA)

There are two steps in the mathematical analysis of the data. The first step is to analyze the variance in the data. The purpose of the analysis is to identify which combination of enzyme concentrations for various cell types are diagnostic of particular disease states or treatment modalities. (For simplicity, disease states and treatment modalities will be referred to collectively as disease states, henceforth).

To analyze the variance, each set of enzyme concentrations for each enzyme measured for each cell type is considered as a component of a composite measurement vector. A data matrix, such as the Full Covariance Data Matrix in FIG. 14A, including columns of basis measurement vectors known to characterize certain disease states is generated. The rows of the matrix represent the measurement vector components for each disease state under consideration. A variation across a row indicates that the various disease states affect cell metabolism such that the concentration of that enzyme in that cell type is changed; obviously such a difference provides information about the underlying disease state.

The data matrix needs to be developed for different disease states. Patients for the disease state data matrix can be first identified using conventional technologies. The disease state matrix can be expanded to include differentiation of stages of the disease as well as the influence of drug pharmokinetics on cellular function. Separate studies of drug pharmokinetics on human tissue culture cell lines can be performed to provide a reference.

The metabolism controlled by some enzymes in some cell types will be insensitive to disease state. Others will react collectively in a complex pattern with different enzymes in certain cells to produce a pattern of enzyme concentrations that will definitively characterize a particular disease state. The analysis of variance is necessary to select out that combination of enzymes in particular cells which are most useful in distinguishing among the various disease states spanned by the basis measurement vectors.

The selection of a relatively small number of components for the measurement vector is necessary to simplify the later analysis, reduce the number of physical measurements which must be made and to reduce the effects of spurious noise generated from the measurements and from individual variation among the same population. An example of the selected number of components is illustrated in FIG. 14A as the Reduced Covariance Data Matrix of Strongly Contributing Factors.

Squared Deviations From the Mean

The simplest way to analyze the variance is to compute the variance across the row for each row in the data matrix. Those rows with a high variance correspond to enzymes whose concentration in a particular cell type varies most strongly across the disease states under consideration. This method of analysis neglects any interaction of various enzymes with each other; however, it provides a simple, gross indication of which enzymes in which cell types are most affected by the disease state. This technique was used in the "Variance" column of Table 5.

Eigenvector or Principal Components Analysis of Variance

A more complete way to analyze variance is to compute the eigenvalues and eigenvectors of the data matrix, as described for example in J. D. Jobson, *Applied Multivariate Data Analysis*, Springer Verlag N.Y. (1992). Such an analysis is conventionally termed an eigenvector analysis or a principal components analysis (PCA). In practice, rather than on the data matrix, D, itself, the eigenvector analysis is performed on the covariance matrix of the data $(D-m)^t(D-m)$, where the superscript t refers to the transpose of the matrix and m is the vector whose components are the mean of each row of D. Each resulting eigenvector includes a particular weighted combination of the measurement vector components which act in concert with each other. Each eigenvector has a corresponding eigenvalue which is proportional to the total variance in the measurement which is accounted for by that eigenvector. Each eigenvector is also orthogonal or independent of every other eigenvector. This technique was used in the "Eigenvector 1" and "Eigenvector 2" columns of Table 5.

For the data matrices here, if the eigenvectors are arranged in order of decreasing eigenvalue, the vast majority of the variance is accounted for by the first several eigenvectors. Thus, the principal factors distinguishing the various disease states under consideration can be captured with a small number of combinations of the enzyme concentrations in the various cell types. FIG. 14A illustrates the process of developing the reduced covariance data matrix by eigenvector analysis.

An examination of the combination of measurement vector components contributing most to distinguishing different disease states, in light of the metabolic pathways linking the various enzymes, can be used to understand the underlying metabolic changes occurring with the various disease states. The foregoing eigenvector analysis is used to select from the entire series of measured enzyme concentrations for different cell types, the combination of enzymes which is most useful in characterizing the disease state.

Diagnosing Disease State, Based on Measurement NNLS

Once the measurement vector and data matrix are reformed with the selected (reduced number of) enzyme concentrations for particular cell types, measurements of patients with unknown diseases (presumed to be within the basis disease states of the data matrix) can be used to diagnose their disease state. Two methods are described here to accomplish the second step of the mathematical analysis of the data, the inference of disease state from the measurement vector: a Non-Negative Least Squares based algorithm (NNLS) and a neural net.

NNLS is a non-negatively constrained least squares solution to the problem of determining the disease state from the reduced measurement vector. The algorithm, which is disclosed in C. L. Lawson and R. J. Hanson, *Solving Least Squares Problems*, Prentice-Hall N.J. (1974) finds that linear combination of the basis measurement vectors which most closely fits, in a least squares sense, the measurement vector of the patient whose state is being diagnosed. The resulting solution is a vector the magnitude of whose components reflect the probability that the unknown disease state is each one of the basis disease states. The algorithm constrains the components of the solution vector to be non-negative; this constraint can be applied because the components of the vector represent probabilities, which by definition must be non-negative. The non-negativity constraint is extremely important in stabilizing the solution to this often mathematically ill-conditioned inversion problem.

Figure 14B:
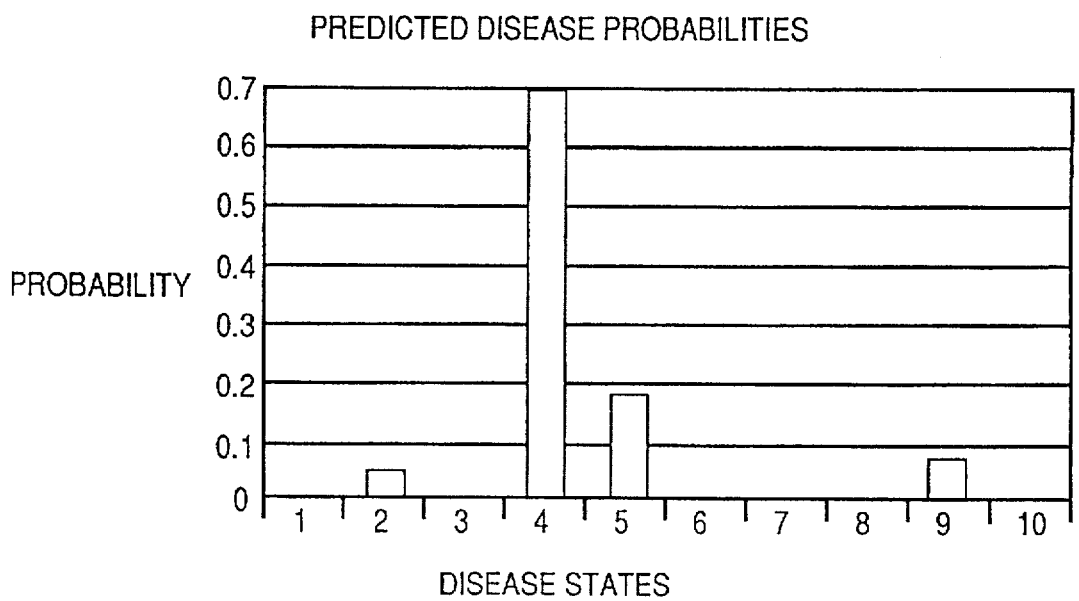
FIG. 14B illustrates the prediction of disease probabilities from the reduced covariance data matrix using Non-Negative Least Squares (NNLS) analysis.

Ideally, the solution vector has only a single non-zero component, in this case, the disease state corresponding to the chosen basis measurement vector is the diagnosis of the patient. Because of noise in the measurements and individual biological variation among individuals or because a patient is afflicted with more than one disease at a time, the solution vector provides a range of possibilities for the diagnosis; the component with the highest magnitude representing the most probable disease state, etc. FIG. 14B illustrates the process of extracting predicted disease state probabilities from the reduced covariance data matrix.

As illustrated in FIG. 14A, a database is obtained for both normal states and various disease states. An example of an array of values obtained for 5 cell types (lymphocytes, monocytes, platelets, granulocytes and erythrocytes) using 50 different enzyme assays is shown in Table 3A–3C. This Table further gives a mean value, two standard deviation low value and two standard deviation high value for each cell for each enzyme.

TABLE 3A

NORMAL LEUKOCYTE ENZYME ACTIVITY

| | | LYMPHS | | | MONOS | | | GRANS | | |
|---|---|---|---|---|---|---|---|---|---|---|
| | | Mean | Lo | Hi | Mean | Lo | Hi | Mean | Lo | Hi |
| Aminopep | LEU | 34.94 | 14.73 | 55.14 | 120.66 | 35.52 | 205.80 | 80.19 | 28.42 | 131.96 |
| Aminopep M | ALA | 75.85 | 47.46 | 104.25 | 172.33 | 107.51 | 237.15 | 149.02 | 85.05 | 212.98 |
| Pro Aminopep | PRO | 1.70 | 0.53 | 2.88 | 6.83 | 2.62 | 11.04 | 9.19 | 3.96 | 14.41 |
| Aminopep M | LYS | 1.16 | 0.33 | 1.99 | 7.56 | 3.83 | 11.29 | 4.27 | 0.00 | 8.88 |
| Aminopep M,N | GLY | 18.18 | 7.21 | 29.14 | 61.47 | 30.13 | 92.82 | 29.48 | 9.82 | 49.14 |
| Aminopep N | SER | 1.35 | 0.28 | 2.41 | 6.49 | 2.71 | 10.26 | 3.40 | 0.75 | 6.06 |
| Endopeptidase I | Z-ARG | 2.02 | 0.67 | 3.38 | 16.80 | 7.83 | 25.78 | 7.22 | 0.37 | 14.06 |
| Endopeptidase I | ARG | 1.47 | 0.50 | 2.45 | 10.34 | 5.13 | 15.54 | 5.16 | 0.23 | 10.10 |
| Aminopep A | ASP | 0.26 | 0.04 | 0.49 | 0.66 | 0.06 | 1.27 | 0.45 | 0.01 | 0.90 |
| Cathepsin B | VS | 3.81 | 0.57 | 7.06 | 19.61 | 2.86 | 36.36 | 8.27 | 2.68 | 13.87 |
| Cathepsin B | VS-M | 3.78 | 0.86 | 6.70 | 31.14 | 5.17 | 57.11 | 7.07 | 1.75 | 12.40 |
| Cathepsin B | VK | 1.87 | 0.05 | 3.69 | 20.38 | 0.00 | 54.92 | 5.10 | 0.65 | 9.54 |
| Cathepsin B | VK-M | 2.05 | 0.00 | 4.40 | 43.37 | 6.71 | 80.04 | 4.31 | 0.00 | 8.76 |
| Cathepsin B | QS | 1.70 | 1.06 | 2.34 | 10.66 | 4.02 | 17.30 | 4.67 | 2.08 | 7.25 |
| Cathepsin B | QS-M | 1.14 | 0.67 | 1.61 | 8.69 | 2.81 | 14.57 | 2.71 | 1.43 | 4.00 |
| Cathepsin B | LG | 13.83 | 6.56 | 21.09 | 44.56 | 22.50 | 66.62 | 29.99 | 11.28 | 48.69 |
| Cathepsin B | LG-M | 4.71 | 1.33 | 8.08 | 23.92 | 0.00 | 48.54 | 10.54 | 3.83 | 17.26 |
| Dipep Peptidase II | KA | 11.47 | 3.00 | 19.93 | 39.35 | 16.82 | 61.88 | 29.15 | 9.25 | 49.05 |
| Dipep Peptidase II | KA-M | 0.55 | 0.30 | 0.80 | 8.74 | 1.47 | 16.01 | 1.74 | 0.82 | 2.65 |
| Dipep Peptidase IV | Z-AA | 151.20 | 113.68 | 188.73 | 328.25 | 243.23 | 413.27 | 363.20 | 273.53 | 452.87 |
| Dipep Peptidase IV | Z-AA-M | 94.47 | 47.80 | 141.14 | 210.71 | 112.01 | 309.42 | 252.24 | 138.76 | 365.72 |
| Dipep Peptidase IV | Z-GP | 107.56 | 72.84 | 142.28 | 225.10 | 155.83 | 294.37 | 240.99 | 148.98 | 332.99 |
| Dipep Peptidase IV | Z-GP-M | 53.74 | 29.05 | 78.44 | 119.81 | 70.14 | 169.48 | 130.62 | 63.36 | 197.87 |
| Cathepsin D | GL | 9.42 | 3.84 | 15.00 | 41.78 | 20.02 | 63.54 | 29.16 | 11.99 | 46.33 |
| Cathepsin D | GL-M | 2.56 | 0.00 | 6.34 | 89.11 | 0.00 | 195.37 | 12.01 | 0.00 | 27.36 |
| Cathepsin C | Z-AG | 15.17 | 7.48 | 22.86 | 34.51 | 18.95 | 50.08 | 33.19 | 17.20 | 49.18 |
| Cathepsin C | Z-AG-M | 14.24 | 2.97 | 25.52 | 37.75 | 12.88 | 52.61 | 34.70 | 9.31 | 60.09 |
| Dipep Peptidase IV | AA-TFA | 56.95 | 3.01 | 110.89 | 158.31 | 31.98 | 284.63 | 154.81 | 25.75 | 283.87 |
| Dipep Peptidase IV | AA-M | 9.88 | 0.00 | 24.56 | 58.29 | 1.79 | 114.79 | 29.91 | 9.29 | 50.53 |
| Cathepsin D | Z-TP 6.5 | 21.97 | 8.98 | 34.96 | 49.69 | 22.25 | 77.13 | 58.05 | 24.15 | 91.96 |
| Cthepsin D | Z-TP 6.5-M | 20.62 | 9.03 | 32.22 | 45.70 | 21.61 | 69.80 | 55.07 | 23.22 | 86.91 |
| Cathepsin B | LLR | 4.09 | 0.00 | 9.90 | 54.32 | 28.31 | 80.32 | 9.46 | 0.00 | 23.73 |
| Cathepsin B | LLR-M | 3.38 | 0.50 | 6.26 | 62.85 | 14.37 | 111.33 | 7.58 | 0.00 | 24.34 |
| Cathepsin B | LGLG | 1.42 | 0.76 | 2.08 | 11.36 | 0.00 | 23.64 | 4.08 | 1.93 | 6.23 |
| Cathepsin B | LGLG-M | 1.34 | 0.38 | 2.29 | 40.74 | 0.00 | 98.16 | 3.24 | 1.12 | 5.37 |
| Esterase | FDA | 13.38 | 0.00 | 27.21 | 66.25 | 17.06 | 115.43 | 68.37 | 12.90 | 123.84 |
| Monocytic Esterase | FDA-NAF | 17.98 | 0.43 | 35.54 | 93.36 | 0.00 | 210.77 | 81.99 | 17.39 | 146.60 |
| Peroxidase | DCFH-DA MES | 4.11 | 0.68 | 7.53 | 12.28 | 2.23 | 22.34 | 7.49 | 0.95 | 14.04 |
| Activated Peroxidase | DCFH MES PMA | 4.69 | 0.98 | 8.41 | 22.18 | 0.00 | 48.35 | 11.02 | 0.00 | 28.46 |
| Collagenase | GPLGP | 8.97 | 3.64 | 14.30 | 23.38 | 10.98 | 35.79 | 16.88 | 6.80 | 26.96 |
| Collagenase | GPLGP-M | 7.89 | 2.40 | 13.37 | 23.32 | 10.36 | 36.28 | 13.82 | 4.39 | 23.24 |
| Collagenase | GFGA | 0.36 | 0.22 | 0.50 | 1.01 | 0.01 | 2.01 | 1.00 | 0.36 | 1.63 |
| Elastase | RGES | 1.43 | 0.75 | 2.12 | 8.37 | 4.28 | 12.46 | 3.96 | 2.09 | 5.83 |
| Glucosidase | DIGLUC | 0.94 | 0.42 | 1.46 | 5.58 | 0.25 | 10.91 | 2.35 | 0.10 | 4.60 |
| Acid Phospharase | PO4 5.0 | 54.29 | 17.08 | 91.49 | 148.32 | 61.42 | 235.23 | 85.42 | 13.42 | 157.42 |
| Galactidase | DIGALAC | 0.38 | 0.00 | 1.05 | 5.94 | 0.00 | 17.90 | 1.58 | 0.00 | 4.32 |
| Cathepsin C | Z-TP 8.7-M | 30.99 | 16.24 | 45.75 | 71.45 | 38.94 | 103.97 | 80.16 | 45.97 | 114.35 |
| Cathepsin C | Z-TP 8.7 | 35.01 | 24.75 | 45.26 | 76.00 | 53.89 | 98.11 | 82.35 | 59.36 | 105.33 |
| Glucosidase | DIGLUC (FL) | 0.23 | 0.15 | 0.32 | 1.89 | 0.00 | 4.55 | 0.45 | 0.07 | 0.83 |
| Neutral Butyrate | DIBUT 7.5 | | | | | | | | | |
| Acidic Butyrate | DIBUT 6.5 | 4.08 | 0.00 | 12.16 | 10.37 | 0.00 | 30.20 | 6.43 | 0.00 | 18.24 |
| Esterase | CHLOAC | 2.49 | 0.85 | 4.13 | 7.33 | 1.76 | 12.89 | 6.48 | 1.40 | 11.57 |
| Esterase | DIACET 6.5 | 109.89 | 39.37 | 180.41 | 634.00 | 322.46 | 745.54 | 408.88 | 251.29 | 566.46 |
| Esterase | DIACET 7.5 | 89.30 | 0.00 | 219.98 | 432.78 | 0.00 | 988.33 | 348.01 | 0.00 | 781.34 |
| Acidic Prop Esterase | DIPRO 6.5 | 86.11 | 0.00 | 216.26 | 441.65 | 0.00 | 1040.17 | 349.18 | 0.00 | 838.78 |
| Neutral Prop Esterase | DIPRO 7.6 | 96.34 | 0.00 | 219.08 | 489.27 | 0.00 | 1106.82 | 429.17 | 0.00 | 977.31 |
| Acidic Valerate Esterase | DIVAL 6.5 | 33.13 | 20.42 | 45.84 | 184.51 | 119.00 | 250.02 | 92.81 | 47.67 | 137.95 |
| Acidic Hex Esterase | DIHEX 6.5 | 15.10 | 4.22 | 25.97 | 72.87 | 24.73 | 121.00 | 33.84 | 11.39 | 56.29 |

TABLE 3A-continued

NORMAL LEUKOCYTE ENZYME ACTIVITY

| | | LYMPHS | | | MONOS | | | GRANS | | |
|---|---|---|---|---|---|---|---|---|---|---|
| | | Mean | Lo | Hi | Mean | Lo | Hi | Mean | Lo | Hi |
| Neutral Hex Esterase | DIHEX 7.5 | 7.54 | 0.00 | 15.15 | 37.22 | 10.06 | 64.37 | 17.57 | 2.89 | 32.24 |
| Acidic Hep Esterase | DIHEP 6.5 | 9.17 | 0.00 | 19.35 | 32.25 | 3.51 | 60.99 | 18.57 | 3.86 | 33.28 |
| Neutral Hep Esterase | DIHEP 7.5 | 9.73 | 0.00 | 19.52 | 36.15 | 7.40 | 64.89 | 20.41 | 0.92 | 39.89 |
| Acidic Pal Esterase | DIPAL 6.5 | 0.15 | 0.00 | 0.31 | 0.30 | 0.16 | 0.45 | 0.14 | 0.09 | 0.20 |
| Neutral Pal Esterase | DIPAL 7.5 | 0.14 | 0.00 | 0.29 | 0.30 | 0.13 | 0.47 | 0.14 | 0.10 | 0.19 |

TABLE 3B

NORMAL ERYTHROCYTE ENZYME ACTIVITY

| SUBSTRATE | ENZYME | MEAN | 2SD LO | 2SD HI |
|---|---|---|---|---|
| LEU | Aminopeptidase | 0.107 | 0.105 | 0.108 |
| ALA | Aminopeptidase M | 0.237 | 0.000 | 0.602 |
| PRO | Pro Aminopeptidase | 0.121 | 0.087 | 0.155 |
| LYS | Aminopeptidase M | 0.109 | 0.099 | 0.118 |
| GLY | Aminopeptidase M,N | 0.163 | 0.025 | 0.300 |
| SER | Aminopeptidase N | 0.107 | 0.107 | 0.107 |
| Z-ARG | Enodpeptidase I | 0.106 | 0.106 | 0.106 |
| ARG | Endopeptidase I | 0.106 | 0.104 | 0.107 |
| ASP | Aminopeptidase A | 0.106 | 0.106 | 0.106 |
| VS | Cathepsin B | 0.138 | 0.073 | 0.203 |
| VS-M | Cathepsin B | 0.176 | 0.027 | 0.324 |
| VK | Cathepsin B | 0.170 | 0.097 | 0.242 |
| VK-M | Cathepsin B | 0.129 | 0.093 | 0.164 |
| QS | Cathepsin B | 0.121 | 0.108 | 0.133 |
| QS-M | Cathepsin B | 0.116 | 0.113 | 0.119 |
| LG | Cathepsin B | 0.138 | 0.080 | 0.195 |
| LG-M | Cathepsin B | 0.131 | 0.129 | 0.132 |
| KA | Dipeptidylpeptidase II | 0.118 | 0.096 | 0.139 |
| KA-M | Dipeptidylpeptidase II | 0.110 | 0.104 | 0.116 |
| Z-AA | Dipeptidylpeptidase IV | 0.484 | 0.000 | 1.454 |
| Z-AA-M | Dipeptidylpeptidase IV | 0.411 | 0.000 | 1.227 |
| Z-GP | Dipeptidylpeptidase IV | 0.438 | 0.000 | 0.976 |
| Z-GP-M | Dipeptidylpeptidase IV | 0.334 | 0.000 | 0.818 |
| GL | Cathepsin D | 0.190 | 0.111 | 0.269 |
| GL-M | Cathepsin D | 0.286 | 0.000 | 0.734 |
| Z-AG | Cathepsin C | 0.225 | 0.000 | 0.482 |
| Z-AG-M | Cathepsin C | 0.171 | 0.115 | 0.226 |
| AA-TFA | Dipeptidylpeptidase IV | 0.144 | 0.070 | 0.218 |
| AA-M | Dipeptidylpeptidase IV | 0.131 | 0.097 | 0.165 |
| Z-TP6.5 | Cathepsin C | 0.132 | 0.098 | 0.166 |
| Z-TP6.5M | Cathepsin C | 0.168 | 0.070 | 0.265 |
| LLR | Cathepsin B | 0.225 | 0.000 | 0.529 |
| LLR-M | Cathepsin B | 0.476 | 0.000 | 1.492 |
| LGLG | Cathepsin B | 0.122 | 0.091 | 0.153 |
| LGLG-M | Cathepsin B | 0.150 | 0.059 | 0.241 |
| FDA | Esterase | 0.126 | 0.089 | 0.163 |
| FDA-NAF | Monocytic Esterase | 0.136 | 0.088 | 0.184 |
| DCFH-DAMES | Peroxidase | 0.286 | 0.000 | 0.764 |
| DCHFMESPMA | Activated peroxidase | 0.268 | 0.000 | 0.693 |
| GPLGP | Collagenase | 0.164 | 0.136 | 0.192 |
| GPLGP-M | Collagenase | 0.119 | 0.103 | 0.134 |
| GFGA | Collagenase | 0.131 | 0.073 | 0.188 |
| RGES | Elastase | 0.118 | 0.098 | 0.138 |
| DGLUC 49 | Glucosidase | 0.114 | 0.109 | 0.118 |
| DPO4 46 | Acid Phosphatase | 0.151 | 0.090 | 0.211 |
| GALAC 50 | Galactidase | 0.119 | 0.111 | 0.127 |
| TP8.7 M 48 | Cathepsin C | 0.212 | 0.000 | 0.467 |
| TP8.7 47 | Cathepsin C | 0.161 | 0.054 | 0.267 |
| FL GLUC | Glucosidase | 0.110 | 0.110 | 0.110 |

TABLE 3C

NORMAL PLATELET ENZYME ACTIVITY

| SUBSTRATE | ENZYME | MEAN | 2SD LO | 2SD HI |
|---|---|---|---|---|
| LEU | Aminopeptidase | 1.006 | 0.640 | 2.156 |
| ALA | Aminopeptidase M | 1.726 | 0.846 | 3.422 |
| PRO | Pro Aminopeptidase | 0.295 | 0.111 | 0.854 |
| LYS | Aminopeptidase M | 0.232 | 0.110 | 0.440 |
| GLY | Aminopeptidase M,N | 3.622 | 0.897 | 8.030 |
| SER | Aminopeptidase N | 0.309 | 0.135 | 0.579 |
| Z-ARG | Enodpeptidase I | 0.262 | 0.133 | 0.448 |
| ARG | Endopeptidase I | 0.268 | 0.128 | 0.499 |
| ASP | Aminopeptidase A | 0.403 | 0.170 | 1.274 |
| VS | Cathepsin B | 0.576 | 0.175 | 2.007 |
| VS-M | Cathepsin B | 0.592 | 0.180 | 1.622 |
| VK | Cathepsin B | 0.839 | 0.144 | 3.080 |
| VK-M | Cathepsin B | 0.486 | 0.153 | 1.343 |
| QS | Cathepsin B | 0.481 | 0.185 | 1.176 |
| QS-M | Cathepsin B | 0.499 | 0.280 | 1.194 |
| LG | Cathepsin B | 0.470 | 0.182 | 0.922 |
| LG-M | Cathepsin B | 0.438 | 0.143 | 1.032 |
| KA | Dipeptidylpeptidase II | 0.447 | 0.161 | 1.034 |
| KA-M | Dipeptidylpeptidase II | 0.277 | 0.126 | 0.562 |
| Z-AA | Dipeptidylpeptidase IV | 1.372 | 0.480 | 3.438 |
| Z-AA-M | Dipeptidylpeptidase IV | 1.199 | 0.545 | 3.253 |
| Z-GP | Dipeptidylpeptidase IV | 2.668 | 0.864 | 5.867 |
| Z-GP-M | Dipeptidylpeptidase IV | 1.415 | 0.481 | 3.883 |
| GL | Cathepsin D | 0.702 | 2.010 | 1.930 |
| GL-M | Cathepsin D | 0.511 | 0.254 | 1.235 |
| Z-AG | Cathepsin C | 7.900 | 0.411 | 21.322 |
| Z-AG-M | Cathepsin C | 5.113 | 0.280 | 13.295 |
| AA-TFA | Dipeptidylpeptidase IV | 0.622 | 0.218 | 1.274 |
| AA-M | Dipeptidylpeptidase IV | 0.350 | 0.145 | 0.684 |
| Z-TP6.5 | Cathepsin C | 2.105 | 0.251 | 4.841 |
| Z-TP6.5M | Cathepsin C | 2.348 | 0.347 | 5.889 |
| LLR | Cathepsin B | 2.150 | 0.484 | 5.562 |
| LLR-M | Cathepsin B | 0.434 | 0.239 | 0.886 |
| LGLG | Cathepsin B | 2.275 | 0.230 | 10.086 |
| LGLG-M | Cathepsin B | 4.013 | 0.211 | 9.648 |
| FDA | Esterase | 15.353 | 2.960 | 29.955 |
| FDA-NAF | Monocytic Esterase | 7.201 | 2.310 | 14.369 |
| DCFH-DAMES | Peroxidase | 0.764 | 0.317 | 1.840 |
| DCFH-DAATRIS | Super oxide dismutase | 3.556 | 1.640 | 7.982 |
| DCHFMESPMA | Activated peroxidase | 1.979 | 0.576 | 7.045 |
| DCFHTRISPMA | Activated super oxide dismutase | 5.111 | 1.870 | 12.045 |

Artificial Intelligence By Back Propagation (Neural Net)

An alternate method of analyzing the data is via neural net.

To determine the interrelationship of enzyme function in both the cell and cell type, the ratios of enzyme activities needs to be analyzed. To fully analyze all possible combinations of a data set, an artificial intelligence system such as "Neuroshell™" (Ward Systems Group Inc., Frederick, Md.) may be used.

The basic building block of artificial intelligence neural network technology is the simulated neuron, which processes a number of inputs to produce an output. Inputs and outputs are numeric values between 0 and 1 which represents positive stimulation close to 1 and negative stimulation close to 0. Inputs are data entered and outputs either come from other neurons or are displayed as results. The process by which the neuron processes its inputs to arrive at an output is usually a summation of inputs followed by a linear function applied to the sum. Independent neurons are of little use unless connected to a network of neurons called nodes. Nodes are layered and interconnected to receive information from each other. As each input node passes information to each other and the next layer, the values are weighed to represent the connection strength. To positively reinforce a connection the weight is raised and likewise to negatively reinforce or inhibit a connection the weight is lowered. The network processes data by accepting input patterns into input nodes or Defining Characteristics. The network produces output patterns which are called Classifying Characteristics. The user of the algorithm can adjust the output pattern by adjusting output thresholds. Feedback from the user determines whether the reinforcement is positive or negative. Learning in a neural network occurs when a set of input patterns (cell type and enzyme concentration) is given with a known output pattern (Disease state or Normal). This is called a sample case. The error between the predicted and actual outputs for a given output node is measured and the total error is one-half of the sum of the squares of the difference. The weights leading to this output node are modified slightly (specified by the user as learning rate, a percentage of the error to be used in the next iteration) during each iteration of a learning session in the direction required to produce a smaller error the next time the same pattern is presented. This is how the neural network "learns" Learning is continued until the consummate error of all output nodes falls below a learning threshold controlled by the user. Upon completion of learning, the network should be capable of reproducing the correct output pattern (disease or normal) when presented with one of the input patterns it has learned. Moreover, the network is capable of generalizing by recognizing an input pattern close to a pattern it has learned and produces an output close to a pattern it was trained to produce. A simple two layered network is incapable of learning complex patterns. Back propagation uses one or more layers of hidden nodes and a nonlinear function algorithm The weight applied to the nodes must then be back propagated through all layers of the nodes. The number of hidden nodes is determined by the user for a specific problem. If too few hidden nodes are used, then all the unique situations found in the sample case will not be explored and if too many are used, learning will never complete. The neural network approach provides the opportunity to look at ratios of cell types and enzyme levels in all possible combinations for both disease and health using a simple format.

Progression of a disease during treatment to monitor "return to normalcy" or further increase in stage or complication with additional disease states can be done by monitoring the NNLS predictive disease probabilities over time or the value of the Neural Network score as it approaches normalcy or the three-dimensional plotting of cell-type enzyme activity patterns comparison to normal. Recurrent Neural Networks may also be used for time series data. Examples of these types are the Probabilistic Neural Network (PNN), General Regression Neural Network (GRNN) and the Kohonen-Realty Neural Network.

Figure 15:
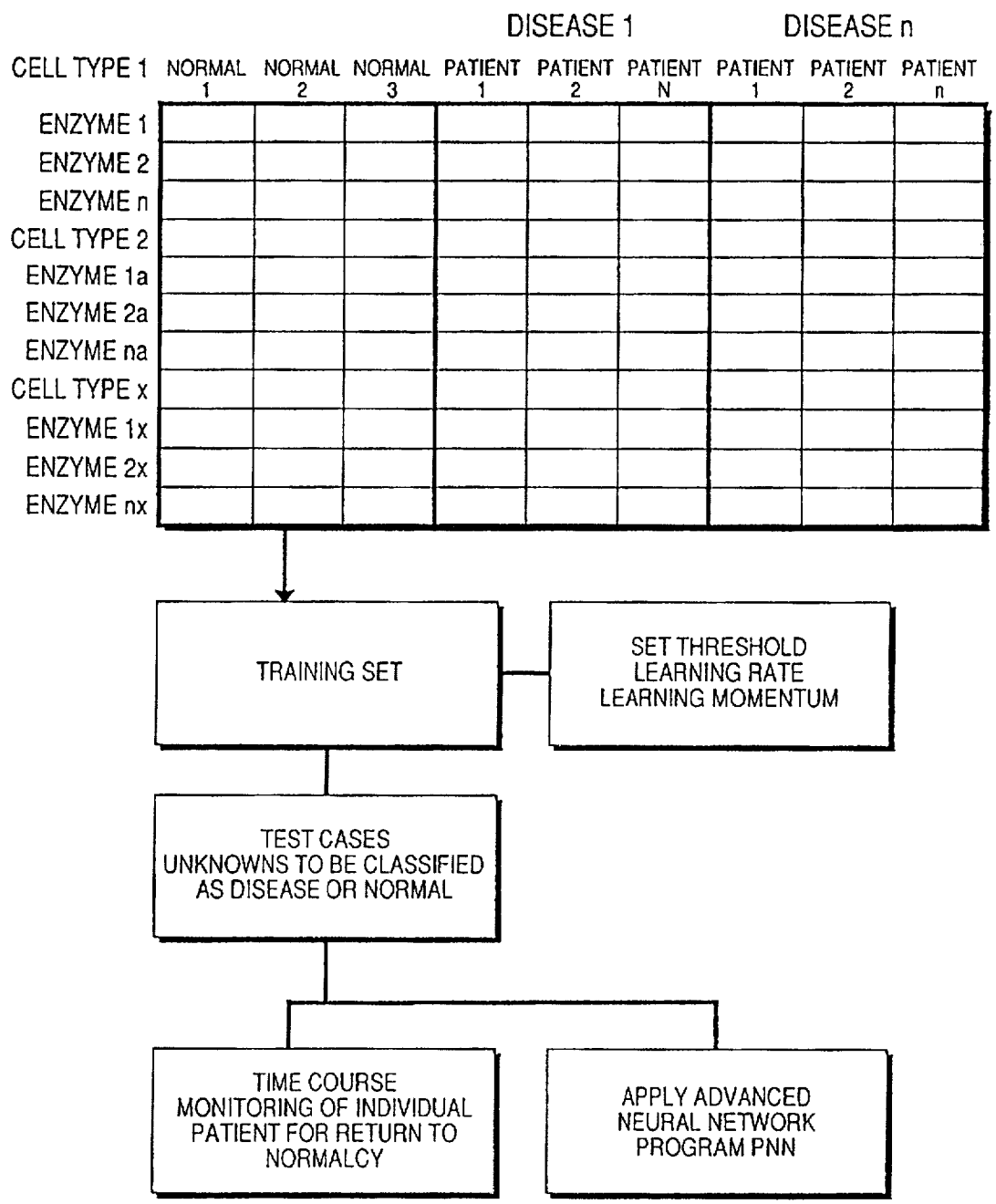
FIG. 15 illustrates a full covariance data matrix being fed to a Neural Network to predict disease probabilities.

One embodiment of an analysis system using neural networks is illustrated in FIG. 15. The same database illustrated in FIG. 14A using the ANOVA technique is also used in the neural network implementation. The database is input into this neural network has a training set and the user sets a threshold, learning rate, and learning momentum. Once the neural network has "learned" on the plurality of sample cases, a test case is input to the neural network including an unknown to be classified as a disease state or normal state. Based on what the neural network as learned with a plurality of sample cases, the neural network outputs the best predictor of the test case. The neural network may also be utilized to perform time course monitoring of an individual patient for return to normalcy, using an advanced probabilistic neural network (TNN) program.

Look-Up Tables

An alternative to the NNLS and Neural Net analyses described above uses Look-Up tables and is similar to the Expert System described in "White Cell and Thrombocyte Disorders—Standardized Self-learning Flow Cytometric List Mode Data Classification with the CLASSIF1 Program System", Valet et al, Ann. N.Y. Acad. Sci., 677:233–251 (1993).

Definitions

As used herein, either individually or as part of a larger group, "alkyl" means a linear, cyclic, or branched-chain aliphatic moiety of one to 10 carbon atoms; "substituted alkyl" means an alkyl group having a substituent containing a heteroatom or heteroatoms such as N, O, or S; "aryl" means an aromatic moiety, e.g., phenyl, of 6 to 18 carbon atoms, unsubstituted or substituted with one or more alkyl, substituted alkyl, nitro, alkoxy, or halo groups; and "alkaryl" means an aryl moiety of 7 to 19 carbons having an aliphatic substituent, and optionally, other substituents such as one or more alkyl, substituted alkyl, alkoxy or amino groups. "Aralkyl" means a linear or branched-chain aliphatic moiety of six to 18 carbon atoms comprising an aryl group or groups.

The following common chemical abbreviations are used in the examples:

t-BOC=tertiarybutyloxycarbonyl

EDAC=1-ethyl-3-(3'-dimethylaminopropyl-carbodiimide)-hydrochloride

FMOC=9-fluorenylmethyloxycarbonyl

BOP=benzotriazoly-N-oxy-tris(dimethylamino)-phosphonium-hexafluorophosphate

HBOT=1-hydroxybenzotriazole

HPLC=High pressure liquid chromatography

TLC=Thin layer chromatography

V:V=Volume to volume

The amino acids are abbreviated as follows:

| Amino Acid | Abbreviation |
| --- | --- |
| L-alanine | Ala or A |
| L-arginine | Arg or R |
| L-asparagine | Asn or N |
| L-aspartic acid | Asp or D |
| L-cysteine | Cys or C |
| L-glutamic acid | Glu or E |
| L-glutamine | Gln or Q |
| glycine | Gly or G |
| L-histidine | His or H |
| L-isoleucine | Ile or I |

-continued

| Amino Acid | Abbreviation |
| --- | --- |
| L-leucine | Leu or L |
| L-lysine | Lys or K |
| L-methionine | Met or M |
| L-phenylalanine | Phe or F |
| L-proline | Pro or P |
| L-serine | Ser or S |
| L-threonine | Thr or T |
| L-tryptophan | Trp or W |
| L-tyrosine | Tyr or X |
| L-valine | Val or V |

The synthesis of the assay compounds can be further understood by reference to the Examples. It will be appreciated, however, that the invention is not limited to the described examples, and that other methods of preparation could be suitable to prepare reagents according to the invention.

Example 1
Preparation of Monopeptide Derivative of Rhodamine 110 Employing the EDAC Procedure A 10-fold excess of a FMOC amino acid is placed into a round bottom flask containing a 50:50 pyridine-dimethylformamide solution (V:V) and stirred until a complete solution occurs. To this stirred solution is added a 12-fold excess of EDAC and the admixture is stirred for 30 minutes. A solution of rhodamine 110 dissolved in a minimum of a 50:50 pyridine-dimethylformamide (V:V) is added dropwise to the reaction solution. This addition requires 15–20 minutes and the reaction solution is allowed to stir at room temperature overnight. The solution is concentrated under reduced pressure to an oil. This oil is dissolved into an appropriated organic solvent and the product is purified by normal phase HPLC, using solvents of increasing polarity (methylene chloride, 1% methanol-chloroform, 2% methanol-chloroform, etc.). The eluate containing the product is concentrated under reduced pressure affording a crystalline material and the purity and identity are checked by analytical reverse phase high pressure liquid chromatography and thin layer chromatography.

Figure 10A:
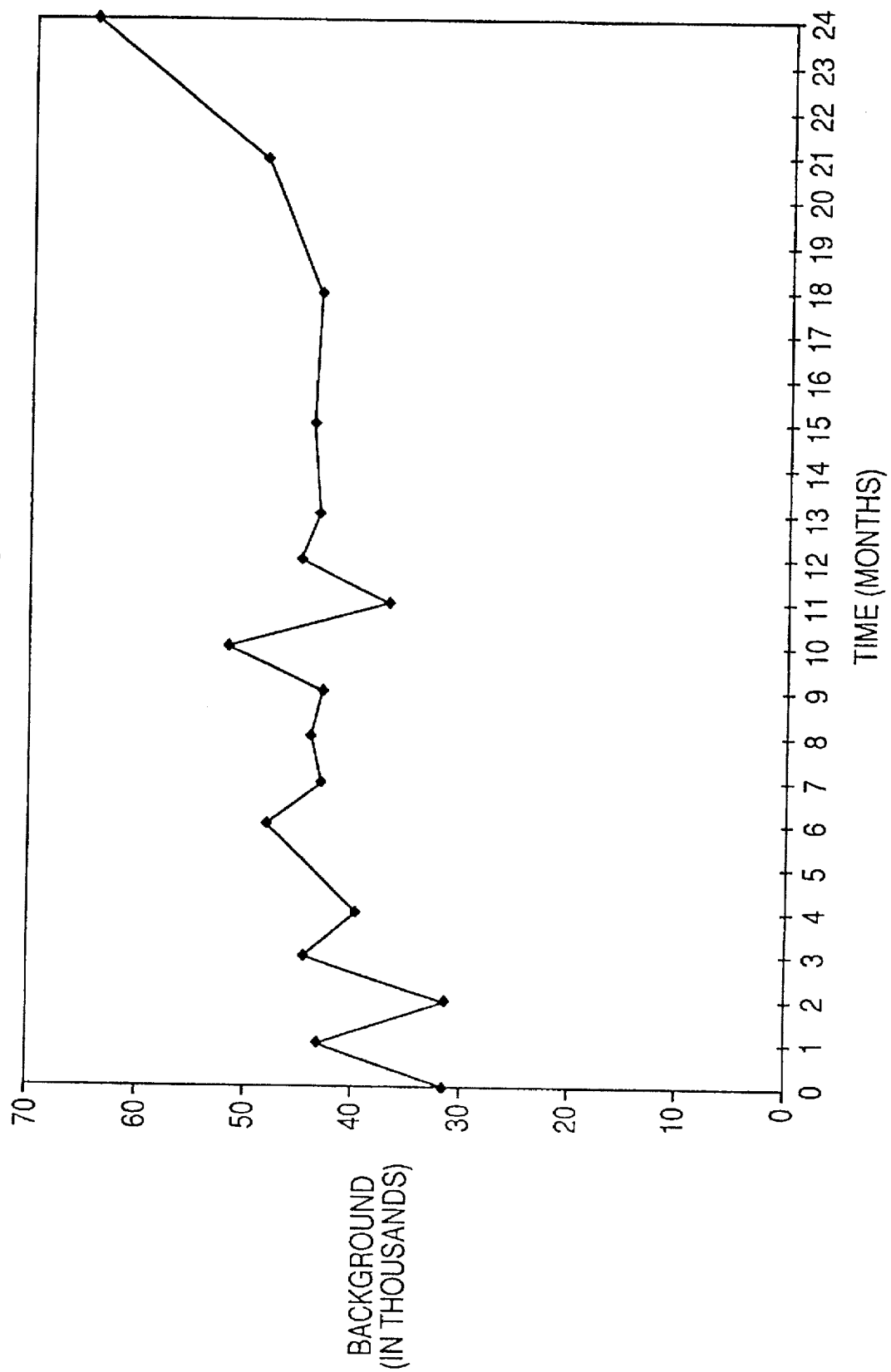
FIGS. 10A and 10B are graphs illustrating the storage stability of a monopeptide-TFA salt derivative of rhodamine 110.
Figure 10B:
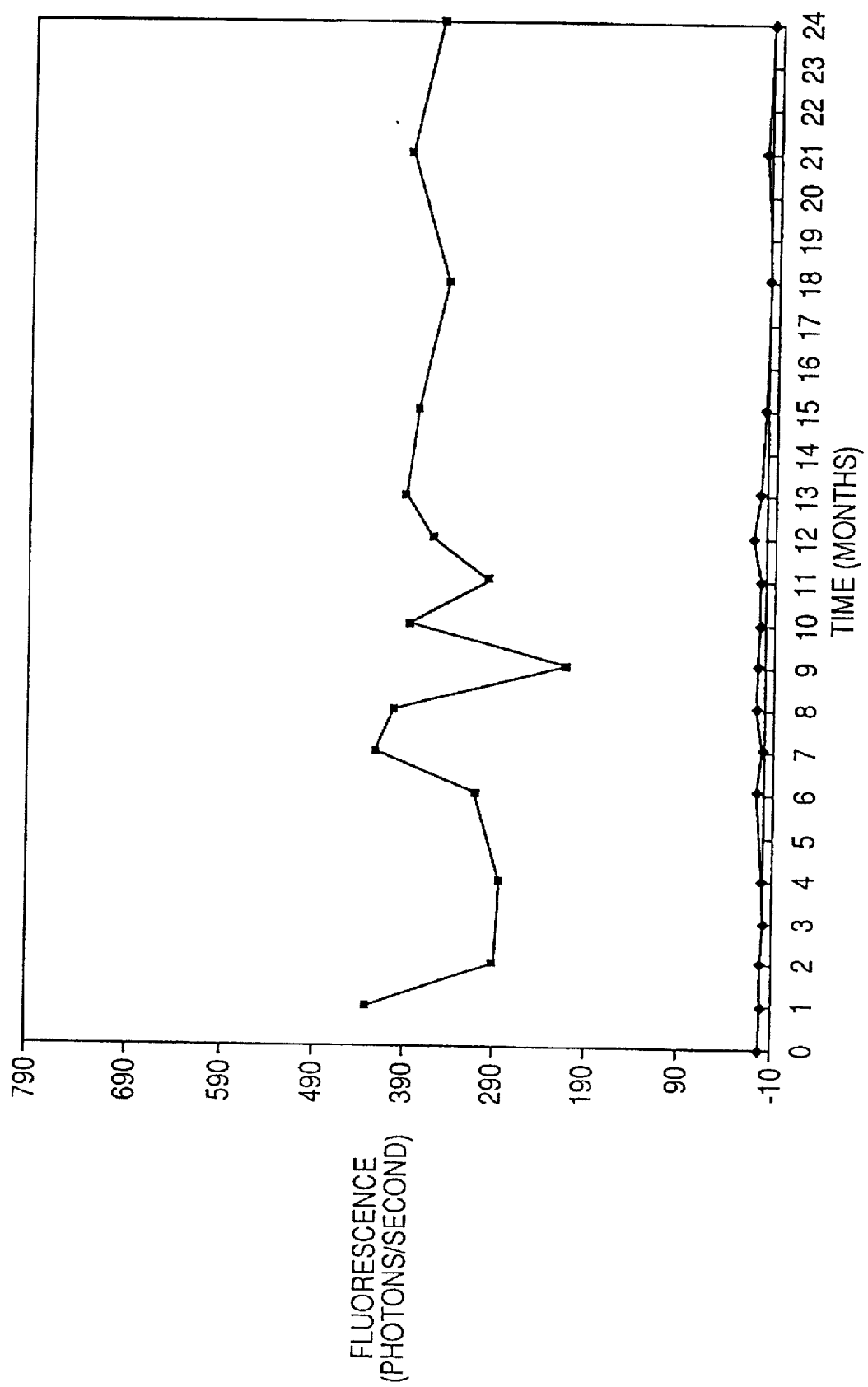

The crystalline material is treated with a 5% solution of piperidine dissolved in dimethylformamide. The reaction is stirred for 45 minutes and concentrated under reduced pressure. The resulting solid is triturated several times with pentane and then dissolved in a minimum of methanol and a 5-fold excess of trifluoroacetic acid is added. The solution is concentrated under reduced pressure to dryness and the resulting solid is centrifuged with cold diethyl ether until the ether triturate has a pH=7. If the monopeptide is polar, then the remaining protective group is removed by treating with a 30 to 50% trifluoroacetic acid solution in methylene chloride for four hours at room temperature. The solution is concentrated under reduced pressure to dryness and the resulting solid is centrifuged with cold diethyl ether until the ether triturate has a pH=7. A final purification of this trifluoroacetic acid substrate is effected with reverse phase HPLC, using solvents of decreasing polarity (water, acetonitrile, trifluoroacetic acid). The eluate containing the product is concentrated under reduced pressure and the aqueous solution is lyophilized. The product's purity and identity are checked by analytical reverse phase high pressure liquid chromatography, thin layer chromatography, and photon counting spectrofluorometry. The purity and stability of the product are also measured by monitoring the background fluorescence, autohydrolysis and enzymatic activity using the product as a substrate after storage of the product at FIGS. 10A and 10B illustrate the stability and purity of a monopeptide-TFA salt derivative Proline-rhodamine 110 which was prepared by the procedure described in this Example. Stability (background fluorescence) is shown in FIG. 10A. Autohydrolysis (diamonds) and enzyme rate (squares) are shown in FIG. 10B.

Figure 11A:
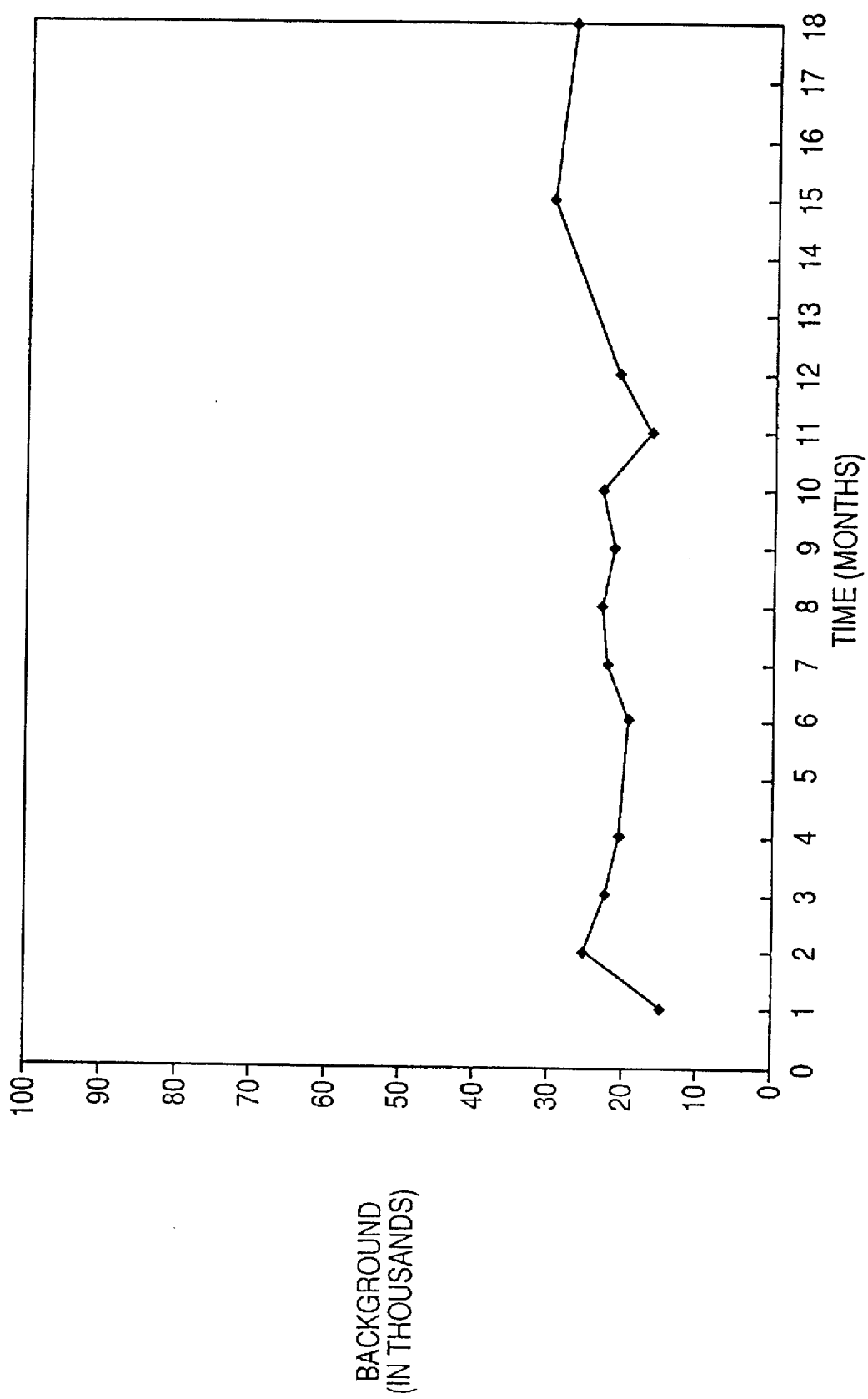
Figure 11B:
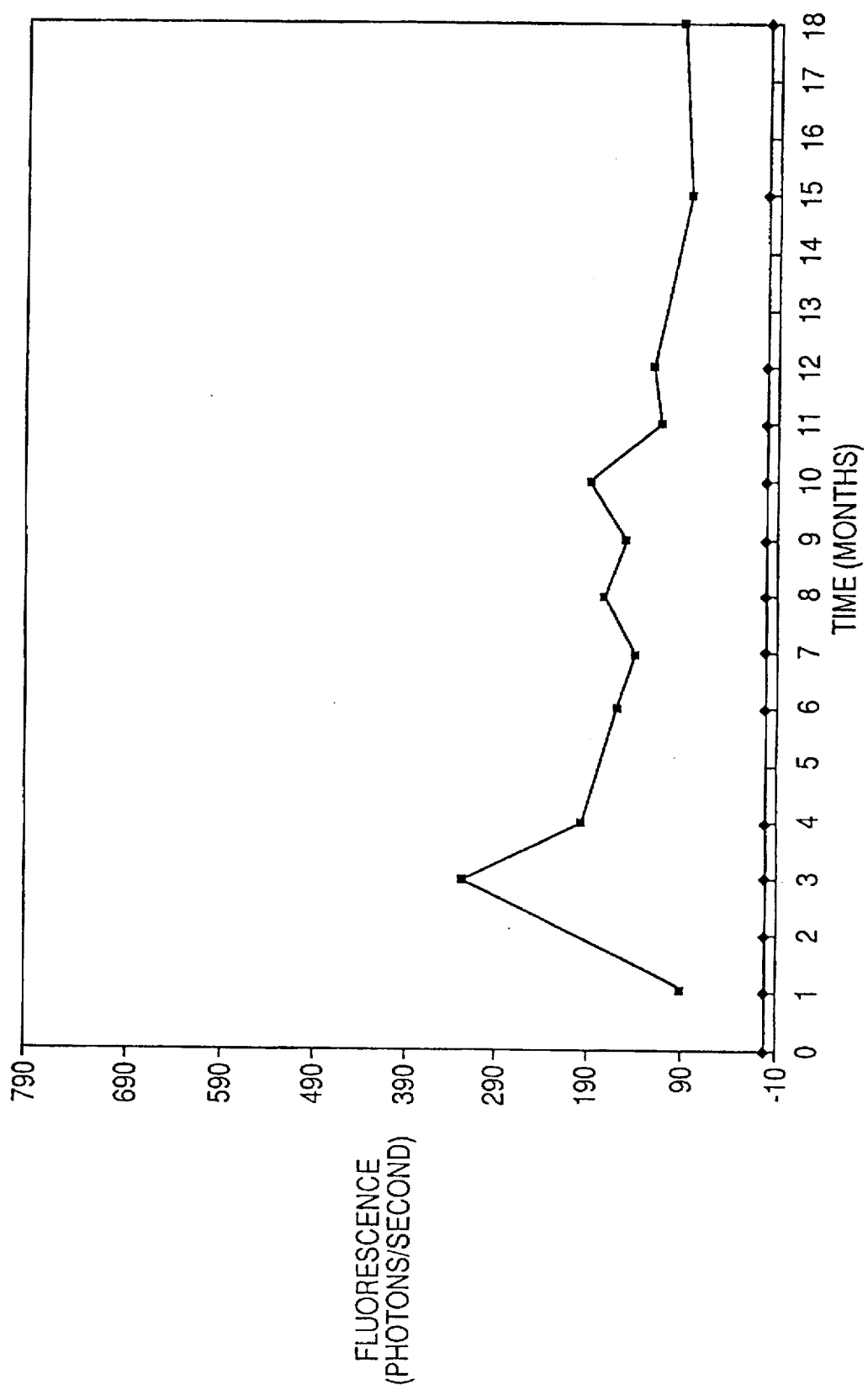
Figure 11C:
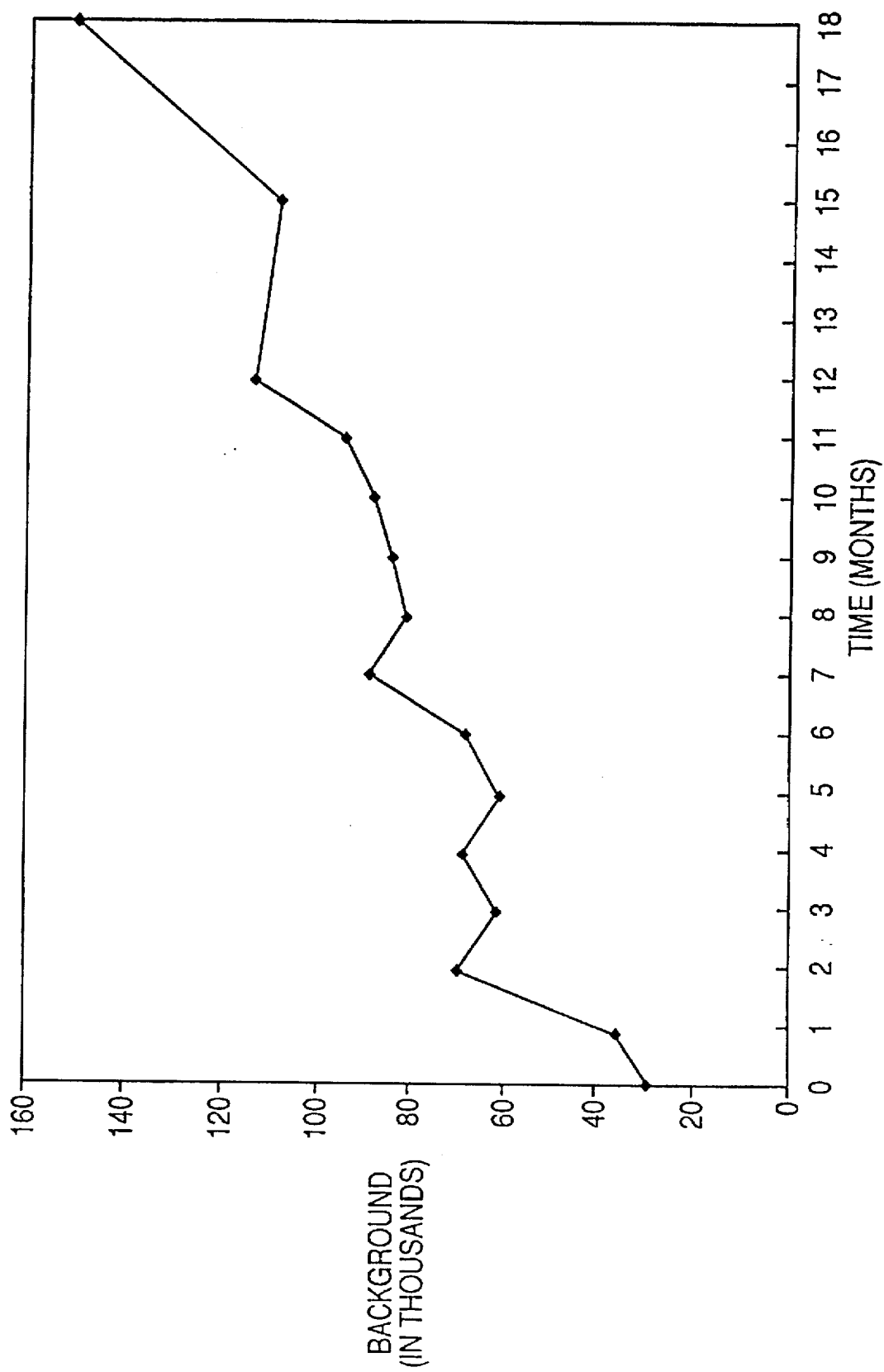
Figure 11D:
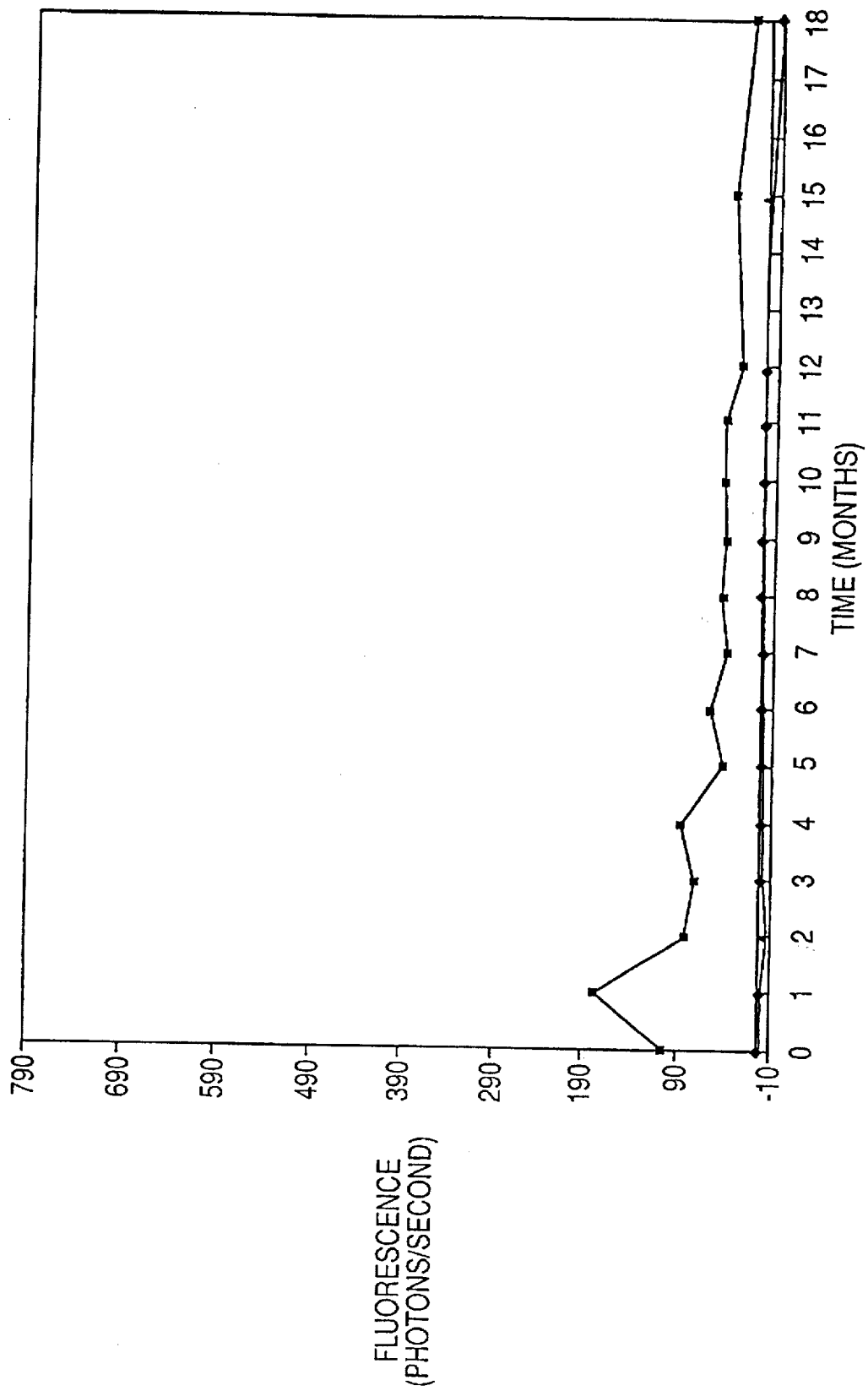

Example 2
Preparation of Dipeptide Derivative of Rhodamine 110 Employing the EDAC Procedure A 6-fold excess of the FMOC amino acid is placed into a round bottom flask containing a 50:50 pyridine-dimethylformamide solution (V:V) and stirred several minutes. To this well-stirred solution is added a 12-fold excess of EDAC and the admixture is stirred an additional 30 minutes. A solution of the monopeptide of rhodamine 110 dissolved in a minimum of 50:50 pyridine-dimethylformamide solution (V:V) is added dropwise over a period of 15 to 20 minutes. The reaction is stirred at room temperature for 16 hours and then concentrated to an oil under reduced pressure. This oil is dissolved in a minimum of an organic solvent and the crude product is purified by normal phase HPLC. The eluate containing the desired product is collected and concentrated under reduced pressure affording a crystalline material and the purity and identity are checked by analytical reverse phase high pressure liquid chromatography and thin layer chromatography. The FMOC blocking group is removed by dissolving the solid in a 5% piperidine-dimethylformamide solution and stirred at room temperature for one hour. The solution is concentrated to dryness under reduced pressure. The resulting solid is triturated several times with pentane to remove the FMOC polymer. The solid is dissolved in a minimum of methanol and a 5-fold excess of trifluoroacetic acid is added. The solution is concentrated to dryness and the resulting solid is centrifuged with cold diethyl ether until the ether triturate has a pH=7. If the dipeptide is polar, then the remaining protective group(s) is removed by treating with a 30 to 50% trifluoroacetic acid solution in methylene chloride for four hours at room temperature. The solution is concentrated under reduced pressure to dryness and the resulting solid is centrifuged with cold diethyl ether until the ether triturate has a pH=7. A final purification of this trifluoroacetic acid substrate is effected with reverse phase HPLC. The eluate containing the product is concentrated under reduced pressure and the aqueous solution is lyophilized. The product's purity and identity are checked by analytical reverse phase high pressure liquid chromatography, thin layer chromatography and photon counting spectrofluorometry. The purity and stability of the product are also measured by monitoring the background fluorescence, autohydrolysis and enzymatic activity using the product as a substrate after storage of the product at FIGS. 11A–11F illustrate the stability and purity of the TFA salts of several dipeptide derivatives of rhodamine 110 prepared by the procedure described in this Example. The FIGURES describe the following:

FIG. 11A (background fluorescence, Val-Lys.TFA);

FIG. 11B (autohydrolysis and enzyme rate, Val-Lys.TFA);

FIG. 11C (background fluorescence, Val-Ser.TFA);

FIG. 11D (autohydrolysis and enzyme rate, Val-Ser.TFA);

FIG. 11E (background fluorescence, Leu-Gly.TFA); and

Figure 11F:
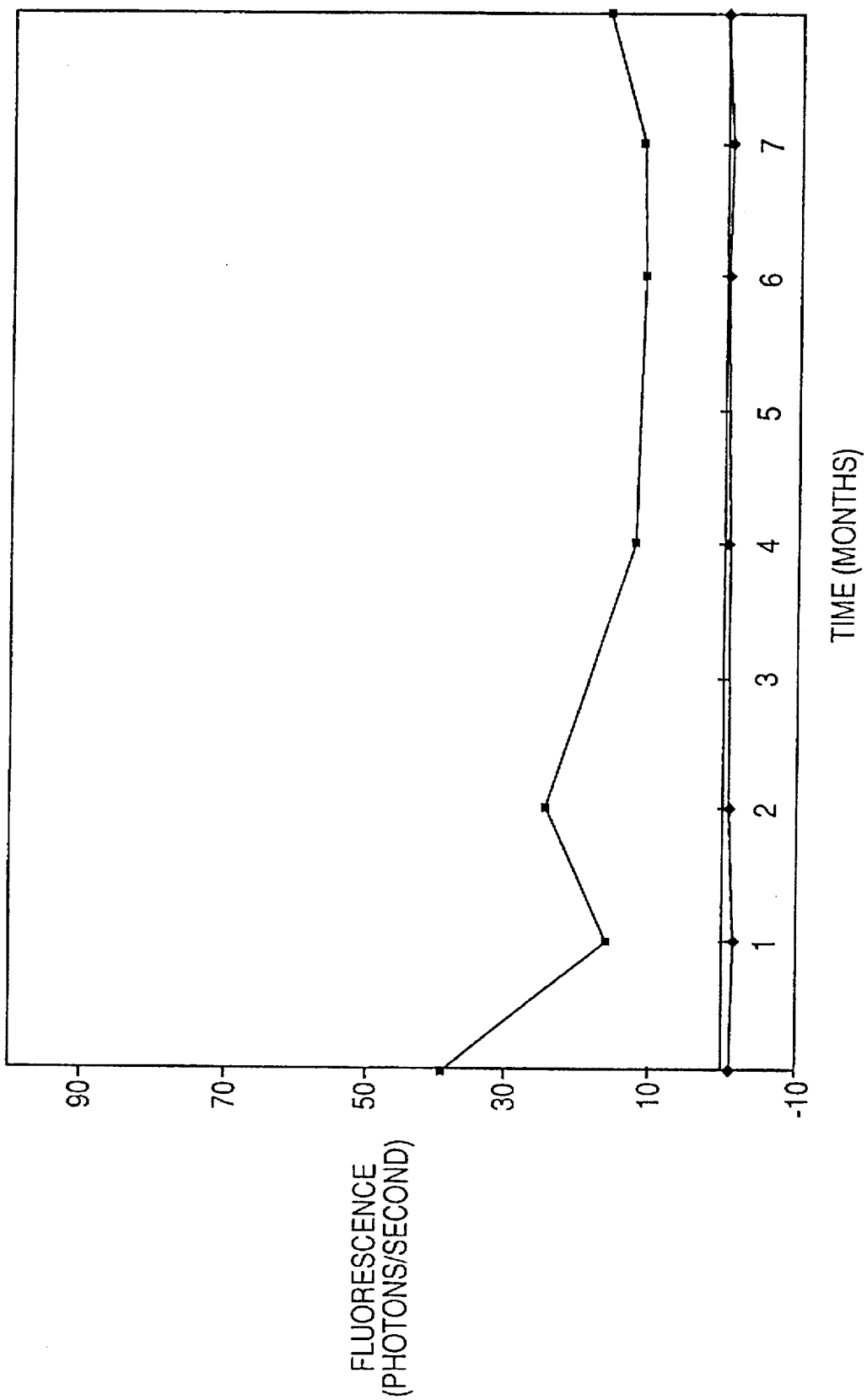

FIG. 11F (autohydrolysis and enzyme rate, Leu-Gly.TFA).

Example 3
Preparation of Polypeptide Derivative of Rhodmine 110 Employing the EDAC Procedure A 6-fold excess of the FMOC polyamino acid is placed into a round bottom flask containing a 50:50 pyridine-dimethylformamide solution (V:V) and stirred until solution occurs. To this well stirred solution is added a 12-fold excess of EDAC and the admixture is stirred an additional 30 minutes. A solution of the monopeptide of rhodamine 110 dissolved in a minimum of 50:50 pyridine-dimethylformamide solution (V:V) is added dropwise over a period of 15 to 20 minutes. The reaction is stirred at room temperature for 16 hours and then concentrated to an oil under reduced pressure. The oil is dissolved in a minimum of an organic solvent and the crude product is purified by normal phase HPLC. The eluate containing the desired product is collected and concentrated under reduced pressure affording a crystalline material and the purity and identity are checked by analytical reverse phase high pressure liquid chromatography and thin layer chromatography. The FMOC blocking group is removed by dissolving the solid in a 5% piperidine dimethylformamide solution and stirred at room temperature for one hour. The solution is concentrated under reduced pressure to dryness under reduced pressure. The resulting solid is triturated several times with pentane to remove the FMOC polymer. The solid is dissolved in a minimum of methanol and a 5-fold excess of trifluoroacetic acid is added. The solution is concentrated under reduced pressure to dryness and the resulting solid is centrifuged with cold diethyl ether until the ether triturate has a pH=7. If the polypeptide is polar then the remaining group(s) is removed by treating with a 30 to 50% trifluoroacetic acid solution for four hours at room temperature. The solution is concentrated under reduced pressure to dryness, and the resulting solid is centrifuged with cold diethyl ether until the ether triturate has a pH=7. A final purification of this trifluoroacetic acid substrate is effected with reverse phase HPLC. The eluate containing the product is concentrated under reduced pressure and the aqueous solution is lyophilized. The product's purity and identity are checked by analytical reverse phase high pressure liquid chromatography, thin layer chromatography and photon counting spectrofluorometry.

Example 4

Preparation of a Dipeptide Derivative of Rhodamine 110 Employing the HOBT-BOP Procedure A 4-fold excess of the FMOC amino acid, and a 4-fold excess of HOBT and BOP are placed into a round bottom flask containing a 0.6 millimolar solution of N-methylmorpholine in dimethylformamide and stirred for 10–15 minutes. To this solution is added dropwise a solution of the monopeptide of rhodamine 110 dissolved in a minimum amount of a 0.6 millimolar solution of N-methylmorpholine in dimethylformamide. This addition requires 5–10 minutes, and the reaction is stirred at room temperature for four hours. The reaction solution is concentrated under reduced pressure to an oil. This oil is dissolved in methylene chloride and the crude product is purified by normal phase HPLC. The eluate containing the desired product is collected and concentrated under reduced pressure affording a crystalline material. The purity and identify of this material are checked by analytical reverse phase HPLC and thin layer chromatography. The FMOC blocking is removed by dissolving the solid in a 5% piperidine-dimethylformamide solution and stirred at room temperature for one hour. The solution is concentrated under reduced pressure, and the resulting solid is triturated several times with pentane to remove the FMOC polymer. The remaining solid is dissolved in a minimum of methanol and a 5-fold excess of trifluoroacetic acid is added. The solution is concentrated under reduced pressure and the resulting solid is centrifuged with cold diethyl ether until the ether triturate has a pH=7. If the dipeptide is polar then the remaining protective group(s) is removed by treating with a 30 to 50% trifluoroacetic acid solution in methylene chloride for four hours at room temperature. The solution is concentrated under reduced pressure to dryness, and the resulting solid is centrifuged with cold diethyl ether until the ether triturate has a pH=7. A final purification of this trifluoroacetic acid substrate is effected with reverse phase HPLC. The eluate containing the product is concentrated under reduced pressure and the aqueous solution is lyophilized. The product's purity and identity are checked by analytical reverse phase high pressure liquid chromatography, thin layer chromatography and photon counting spectrofluorometry.

Example 5

Preparation of a Polypeptide Derivative of Rhodamine 110 lEmploying the HOBT-BOP Procedure A 4-fold excess of the FMOC polypeptide and a 4-fold excess of HOBT and BOP are placed into a round bottom flask containing a 0.6 millimolar solution of N-methylmorpholine in dimethylformamide and stirred for 10–15 minutes. To this solution is added dropwise a solution of the monopeptide rhodamine 110 dissolved in a minimum amount of a 0.6 millimolar solution of N-methylmorpholine in dimethylformamide. This addition requires 5–10 minutes, and the reaction is stirred at room temperature for four hours. The reaction solution is concentrated under reduced pressure to an oil. This oil is dissolved in methylene chloride and the crude product is purified by normal phase HPLC. The eluate containing the desired product is collected and concentrated under reduced pressure affording a crystalline material. The purity and identify of this material are checked by analytical reverse phase HPLC and thin layer chromatography. The FMOC blocking is removed by dissolving the solid in a 5% piperidine-dimethylformamide solution and stirred at room temperature for one hour. The solution is concentrated under reduced pressure, and the resulting solid is triturated several times with pentane to remove the FMOC polymer. The remaining solid is dissolved in a minimum of methanol and a 5-fold excess of trifluoroacetic acid is added. The solution is concentrated under reduced pressure and the resulting solid is centrifuged with cold diethyl ether until the ether triturate has a pH=7. If the polypeptide is polar then the remaining protective group(s) is removed by treating with a 30 to 50% trifluoroacetic acid solution in methylene chloride for four hours at room temperature. The solution is concentrated under reduced pressure to dryness, and the resulting solid is centrifuged with cold diethyl ether until the ether triturate has a pH=7. A final purification of this trifluoroacetic acid substrate is effected with reverse phase HPLC. The eluate containing the product is concentrated under reduced pressure and the aqueous solution is lyophilized. The product's purity and identify are checked by analytical reverse phase HPLC, thin layer chromatography and photon counting spectrofluorometry.

Example 6

Preparation of p-Aminobenzoic Acid Derivative of Rhodamine 110

A molar quantity of p-Aminobenzoic Acid is placed into a round bottom flask containing a small quantity of dioxane and stirred until a complete solution occurs. A 10% molar excess solution of sodium carbonate, dissolved in water, is added. To this well-stirred solution is added dropwise a molar solution of 9-fluorenylmethyloxycarbonylchloride dissolved in a minimum of dioxane. This addition requires 10 to 15 minutes and the reaction solution is allowed to stir an additional four (4) hours. The reaction is diluted with water and extracted (3) times with diethyl ether. The aqueous layer is cooled in an ice water bath and the pH is adjusted to two (2) with a 10% solution of hydrochloric acid. The resulting colorless precipitate is filtered and recrystallized from an acetone solution. A TLC of the colorless, crystalline product showed only one (1) quenched spot and obtained in a yield of 68%.

A 6-fold excess of the FMOC-p-amino acid is placed into a round bottom flask containing a 50:50 pyridine-dimethylformamide solution (V:V) and stirred until a complete solution occurs. To this stirred solution is added a 12-fold excess of EDAC and the admixture is stirred for 30 minutes. A solution of rhodamine 110, dissolved in a minimum of a 50:50 pyridine-dimethylformamide (V:V) is added dropwise to the reaction solution. This addition requires 15–20 minutes, and the reaction solution is concentrated under reduced pressure to an oil and dissolved in a small amount of chloroform. The crude product is purified by normal phase HPLC and the product is eluted in a 5% methanol-chloroform solution. This eluate is concentrated under reduced pressure, and the resulting colorless solid dried in vacuo affording a 60% yield of the product. This material is treated with a 5% solution of piperidine dissolved in dimethylformamide. The resulting solution is stirred at room temperature for one (1) hour and concentrated under reduced pressure. The resulting solid is triturated several times with pentane, dissolved in a minimum of methanol and a 5-fold excess of trifluoroacetic acid is added. The solution is concentrated to dryness and the resulting solid is centrifuged with cold diethyl ether until the ether triturate has a pH of seven (7). The trifluoroacetate salt is dried in vacuo overnight affording a yield of 74.5%. The product's purity and identify are checked by analytical reverse phase high pressure liquid chromatography, thin layer chromatography and photon counting spectrofluorometry.

Example 7

Preparation of Tetraacetyl-α-D-Glucopyranosyl Derivative of Rhodamine 110 and Tetrabenzoyl-α-D-Glucopyranosyl Derivative of Rhodamine 110

A 10-fold excess of the respective protected tetraacetyl (or tetrabenzoyl) α-D-glucopyranosyl bromides is placed into a round bottom flask containing a 50:50 pyridine-dimethylformamide solution (V:V) and warmed and stirred until a complete solution occurs. To this stirred solution is added a 12-fold excess of EDAC and the admixture is stirred for 30 minutes. A solution of rhodamine 110, dissolved in a minimum of a 50:50 pyridine-dimethylformamide (V:V) is added dropwise to the reaction solution. This addition requires 15 to 20 minutes. The reaction solution is allowed to stir for 24 hours and concentrated under reduced pressure to an oil. The crude product is dissolved in chloroform and purified by normal phase HPLC. The tetraacetyl-α-D-glucopyranosyl derivative is eluted in a 1% methanol-chloroform solution. The tetrabenzoyl-α-D-glucopyranosyl derivative is eluted in a 3% methanol-chloroform solution. The product is isolated by concentrating the respective eluates under reduced pressure and drying in vacuo overnight. The yield of the tetraacetyl-α-D-glucopyranosyl rhodamine 110 is 30% and the yield of the tetrabenzoyl-α-D-glucopyranosyl rhodamine 110 is almost quantitative (100%). The product's purity and identity are checked by analytical reverse phase high pressure liquid chromatography, thin layer chromatography and photon counting spectrofluorometry.

Example 8

Preparation of N-Butyl Ester Derivative of Fluorescein

A 3.4 fold excess of n-butyrylanhydride is placed into a round bottom flask containing a minimum amount of tetrahydrofuran and stirred for several minutes. A one molar equivalent of fluorescein is added, followed by 10 mL of triethylamine and solution occurs. The reaction solution is stirred an additional 30 minutes and then concentrated under reduced pressure to an oil. The oil is dissolved in a minimum of chloroform and the crude product is purified by normal phase HPLC. The product is eluted with a 0.5% methanol-chloroform solution and the eluate is concentrated under reduced pressure affording a yield of a colorless solid of 63%. The product's purity and identity are checked by analytical reverse phase high pressure liquid chromatography, thin layer chromatography and photon counting spectrofluorometry.

Example 9

Preparation of Chloroacetyl Ester Derivative of Fluorescein

A 10-fold excess of chloroacetic anhydride is placed into a round bottom flask containing a minimum amount of tetrahydrofuran and stirred for several minutes. A solution of fluorescein, dissolved in a minimum amount of tetrahydrofuran and a 2-fold excess of triethylamine, is added dropwise to the reaction mixture. This addition required 10 to 15 minutes and the reaction solution is allowed to stir overnight. The solution is concentrated under reduced pressure to an oil. This oil is dissolved in a minimum amount of methylene chloride and the crude product is purified by normal phase HPLC. The desired product is eluted in a 100% methylene chloride solution, and this eluate concentrated under reduced pressure. This solid is dried in vacuo for 16 hours affording a quantitative yield (100%) of the desired product. The product's purity and identity are checked by analytical reverse phase high pressure liquid chromatography, thin layer chromatography and photon counting spectrofluorometry.

Example 10

Preparation of n-Palmityl Ester Derivative of Fluorescein

A 2.5-fold excess of palmitic acid is placed into a round bottom flask containing a minimum amount of tetrahydrofuran and stirred for several minutes. To this solution is added a 3-fold excess of EDAC and the mixture stirred for 30 minutes. A solution of fluorescein dissolved in a minimum amount of tetrahydrofuran is added dropwise to the reaction mixture. This addition required 15 to 20 minutes and the reaction mixture is allowed to stir overnight. The reaction mixture is concentrated under reduced pressure to an oil. This oil is dissolved in chloroform and extracted three (3) times with a 5% aqueous sodium bicarbonate solution. The organic layer is dried over magnesium sulfate, filtered and concentrated to dryness. This crude product is purified by normal phase HPLC and the product is eluted with 100% chloroform. This eluate is concentrated under reduced pressure and the resulting solid is dried in vacuo affording 400 mg (9% yield). The product's purity and identity are checked by analytical reverse phase high pressure liquid chromatography, thin layer chromatography and photon counting spectrofluorometry.

An elemental analysis for carbon and hydrogen, by Galbraith Laboratories, Inc. of Knoxville, Tenn., gave the following results: Formula: $C_{52}H_{72}O_7 \cdot \frac{1}{2}H_2O$ MW=817.075

| Theoretical | Found |
|---|---|
| C = 76.34 | C = 76.36; 76.51 |
| H = 8.99 | H = 9.01; 9.05 |

Example 11

Preparation of Diphenylphosphate Derivative of Rhodamine 110

A 6.6-fold excess of diphenylchlorophosphate is placed into a round bottom flask containing a very small amount of pyridine and stirred several minutes in an ice-water bath. To this well-stirred, cold solution is added rhodamine 110 and a white precipitate is formed immediately. The stirring is continued for an hour and the reaction mixture is placed in the refrigerator for 48 hours. The reaction mixture is treated with water and extracted twice with chloroform. The combined chloroform extracts are dried over magnesium sulfate, filtered and concentrated under reduced pressure. The crude product is purified by normal phase HPLC. The desired product is eluted in a 1% methanol-chloroform solution, and this eluate is concentrated under reduced pressure to an oil. This oil is dissolved in ammonia, and the resulting aqueous solution is lyophilized affording the ammonium salt of the product in a 66% yield. The product's purity and identity are checked by analytical reverse phase high pressure liquid chromatography, thin layer chromatography and photon counting spectrofluorometry.

Example 12

Preparation of Diphenylphosphate Derivative of Fluorescein

A 6.6-fold excess of diphenylchlorophosphate is placed into a round bottom flask containing a very small amount of pyridine and stirred several minutes in an ice-water bath. To this well-stirred, cold solution is added fluorescein and a white precipitate is formed immediately. Stirring is continued for one (1) hour and the reaction mixture placed in the refrigerator for 48 hours. The reaction mixture is treated with water and extracted twice with chloroform. The combined chloroform extracts are dried over magnesium sulfate, filtered and concentrated to dryness under reduced pressure. The resulting solid is dissolved in a minimum amount of chloroform and the crude product is purified by normal phase HPLC. The product is eluted in a 1% methanol-chloroform solution and this solution concentrated under reduced pressure. The colorless solid is treated with ammonia and lyophilized, affording the ammonium salt in a yield of 95%. The product's purity and identity are checked by analytical reverse phase high pressure liquid chromatography, thin layer chromatography and photon counting spectrofluorometry.

Example 13

Preparation of Trifluoroacetyl Ester Derivative of 4'(5') Carboxyfluorescein

A 10-fold excess of trifluoroacetic anhydride is placed into a round bottom flask containing a minimum amount of tetrahydrofuran and stirred several minutes. A 30% pyridine-tetrahydrofuran solution, containing the 4'(5') carboxyfluorescein, is added dropwise over 10 to 15 minutes. The solution is allowed to stir overnight and concentrated under reduced pressure. The resulting oil is dissolved in chloroform, extracted three times with water and the organic layer dried over magnesium sulfate. This is filtered, concentrated to a small volume under reduced pressure and the crude product purified by normal phase HPLC. The product is eluted in a 4% methanol-chloroform solution. This is concentrated under reduced pressure and resulting solid dried in vacuo for 15 hours affording an 83% yield. The product's purity and identity are checked by analytical reverse phase high pressure liquid chromatography, thin layer chromatography and photon counting spectrofluorometry.

Example 14

Preparation of Diphenylphosphate Ester Derivative of 4'(5') Carboxyfluorescein

A 15-fold excess of chlorodiphenylphosphate is added to a solution of 4'(5')carboxyfluorescein, dissolved in 8 mL of pyridine over a period of 10 to 15 minutes. The reddish-colored solution turns a light yellow and a precipitate is formed. Stirring is continued for two hours and the mixture is allowed to cool in the refrigerator overnight. To this mixture is added 100 mL of water and the mixture extracted three times with chloroform. The combined chloroform extracts are dried over magnesium sulfate, filtered and concentrated under reduced pressure to an oil. This oil is dissolved in a minimum amount of methylene chloride, and the crude product is purified by normal phase HPLC. The desired product is eluted in a 1% methanol-chloroform solution, and this eluate is concentrated under reduced pressure. The resulting solid is dried in vacuo for 16 hours affording a yield of 95%. The product's purity and identity are checked by analytical reverse phase high pressure liquid chromatography, thin layer chromatography and photon counting spectrofluorometry.

Example 15

Preparation of H-L-Leucine Trifluoroacetate Salt Derivative of Rhodol

A 10-fold excess of benzyloxycarbonyl-L-leucine is placed into a round bottom flask containing a 50:50 pyridine-dimethylformamide solution (V:V) and stirred until a complete solution occurs. To this stirred solution is added a 12-fold excess of EDAC and the admixture is stirred for 30 minutes. A solution of rhodol hydrochloride, dissolved in a minimum of a pyridine-dimethylformamide solution (V:V), is added dropwise to the reaction solution. This addition required 10 to 15 minutes and the reaction is allowed to stir at room temperature overnight The solution is concentrated under reduced pressure to an oil. This oil is dissolved into chloroform and extracted three (3) times with water and organic layer dried over magnesium sulfate. This is filtered, concentrated to a very small volume under reduced pressure and purified by normal phase HPLC. The product is eluted in a 2% methanol-chloroform solution. This eluate is concentrated under reduced pressure and the resulting colorless, crystalline solid, dried in vacuo, affords a 33.4% yield of the product and the product's purity and identity are checked by analytical reverse phase high pressure liquid chromatography and thin layer chromatography. This material is dissolved into a small volume of isopropyl alcohol and catalytically reduced with a small amount of 10% palladium on carbon as the catalyst in a Paar shaker apparatus for 16 hours. The alcohol solution is carefully filtered and a 2-fold excess of trifluoroacetic acid is added. This solution is concentrated to dryness under reduced pressure and the resulting solid is centrifuged with cold diethyl ether until the ether triturate has a pH of 7. The colorless trifluoroacetate salt is dried in vacuo overnight, affording a 92.48% yield. The product's purity and identity are checked by analytical reverse phase high pressure liquid chromatography, thin layer chromatography and photon counting spectrofluorometry.

Example 16

Preparation of (H-LEU-GLY)$_2$ Rhodamine 110 Acetate and Tartrate Salts

A 10-fold excess of FMOC glycine is placed into a round bottom flask containing a 50:50 pyridine-dimethylformamide solution (v:v) and stirred until a complete solution occurs. To this stirred solution is added a 12-fold excess of EDAC and the admixture is stirred for 30 minutes. A solution of rhodamine 110 is dissolved in a minimum of a 50:50 pyridine-dimethylformamide solution (v:v) and is added dropwise to the reaction solution. This addition requires 15–20 minutes, and the reaction is allowed to stir at room temperature overnight. The solution is concentrated under reduced pressure to an oil. This oil is dissolved in a small amount of methylene chloride, and the product is purified by normal phase HPLC. The product is eluted from the column in a 1% methanol-chloroform solution. This eluate is concentrated under reduced pressure, and the resulting solid dried in vacuo affording an 85% yield of the product. The purity and identity are checked by analytical reverse phase high pressure liquid chromatography and thin layer chromatography. This material is treated with a 5% solution of piperidine dissolved in dimethylformamide. The resulting solution is stirred at room temperature for one (1) hour and concentrated under reduced pressure. The resulting solid is triturated several times with pentane and product dried in vacuo. A TLC of this material showed only one quenched spot which is positive to concentrated hydrochloric acid.

A four (4) fold excess of FMOC-L-leucine is placed into a round bottom flask containing a 50:50 pyridine-dimethylformamide solution (v:v) and stirred until a complete solution occurs. To this stirred solution is added an eight (8) fold excess of EDAC and the admixture is stirred for 30 minutes. A solution of (H-GLY)$_2$ rhodamine 110 (from above) dissolved in a minimum of a 50:50 pyridine-dimethylformamide solution (v:v) is added dropwise to the reaction solution. This addition requires 15–20 minutes, and the reaction is allowed to stir at room temperature for six (6) hours. The solution is concentrated under reduced pressure to an oil. This oil is dissolved in chloroform, and the product is purified by normal phase high pressure liquid chromatography. The product is eluted from the column in a 2% methanol-chloroform solution. This eluate is concentrated under reduced pressure, and the resulting solid dried in vacuo affording a 74% yield. The purity and identity are checked by analytical reverse phase high pressure liquid chromatography and thin layer chromatography. This material is treated with a 5% solution of piperidine dissolved in dimethylformamide. The resulting solution is stirred at room temperature for one (1) hour and concentrated under reduced pressure. The solid is triturated several times with pentane and dried in vacuo. One half of this material is dissolved in a small amount of methanol and a 10% excess of acetic acid is added. Ether is added to this solution and cooled in an ice-water bath. The resulting colorless solid is filtered, washed with ether and centrifuged with ether until the pH=7. The crystalline salt is dried in vacuo according a 61% yield.

The remaining one-half of the material (from above) is dissolved in a small amount of methanol and a 10% excess of L-tartaric acid dissolved in a very small amount of methanol is added. This solution is cooled in an ice-water bath and ether is added. The resulting crystalline material is filtered, washed with ether and centrifuged with ether until the pH=7. The resulting colorless salt is dried in vacuo affording a 42% yield.

The free fluorescence and identity of the acetate and tartrate salts of these rhodamine 110 substrates are checked by analytical reverse phase high pressure liquid chromatography, thin layer chromatography and photon counting spectrofluorometry.

Figure 12A:
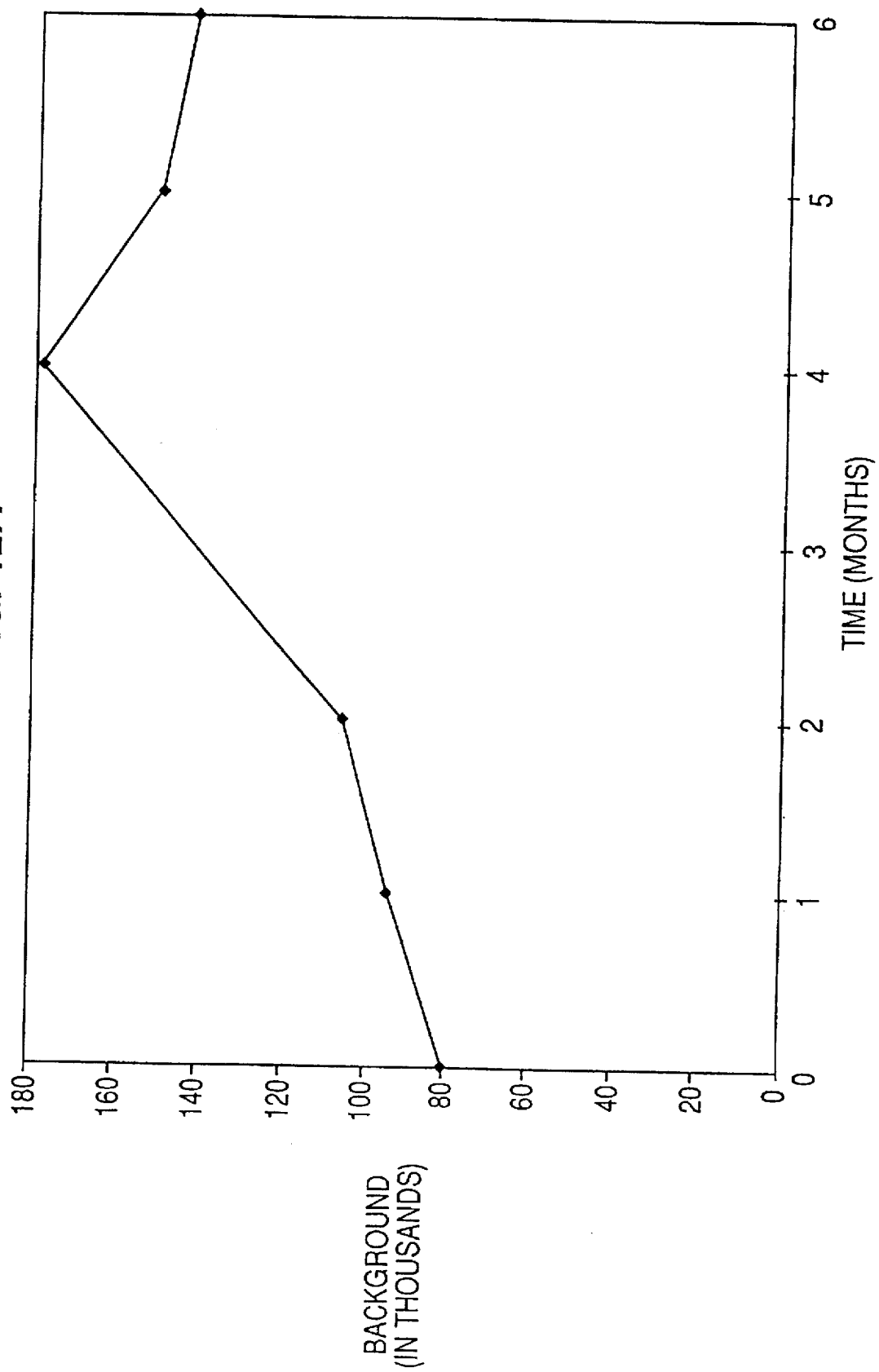
Figure 12C:
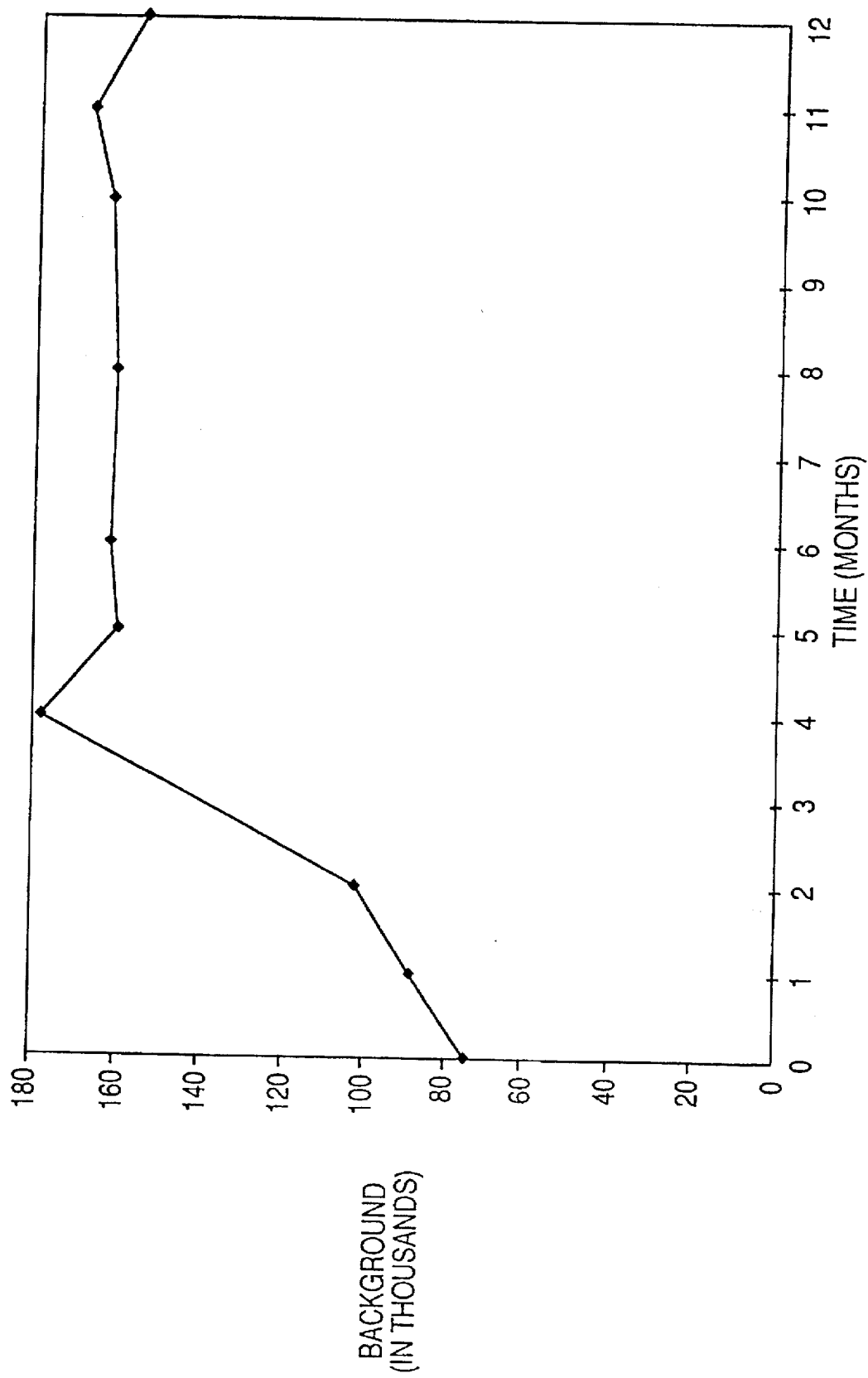

The acetate and tartrate salts thus prepared have the following characteristics, respectively: native free fluorescence, 63,000 and 61,000 photons; autohydrolysis rate when measured at 37° C. using a 1 cm path length, −5.56 and −3.8 change in photons per second; and enzymatic reaction rate of cathepsin B at 37° C., +128 and +138 change in photons per second. The purity and stability of acetate and tartrate salts of (LeuGly)$_2$ rhodamine 110 as demonstrated by assessment of autohydrolysis, background fluorescence and enzymatic activity after storage at 4° C. are illustrated in FIGS. 12A–12D as follows:

FIG. 12A (background fluorescence, Leu-Gly.acetate);

FIG. 12B (autohydrolysis and enzyme rate, Leu-Gly.acetate);

FIG. 12C (background fluorescence, Leu-Gly.tartrate); and

Figure 12D:
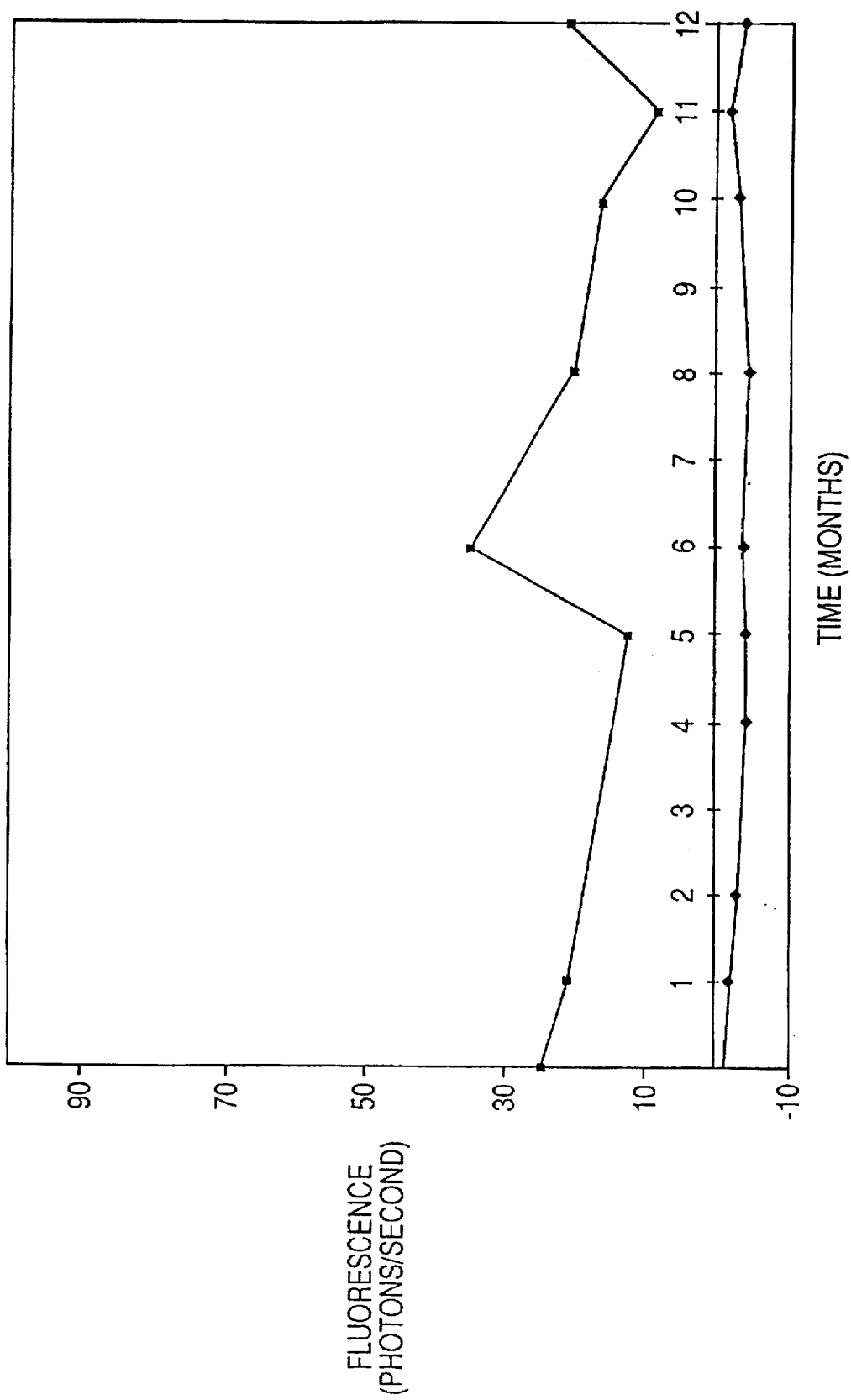

FIG. 12D (autohydrolysis and enzyme rate, Leu-Gly.tartrate).

Example 17

Preparation of the Free Amine of (Lys-Ala)$_2$ Rhodamine 110

Figure 13A:
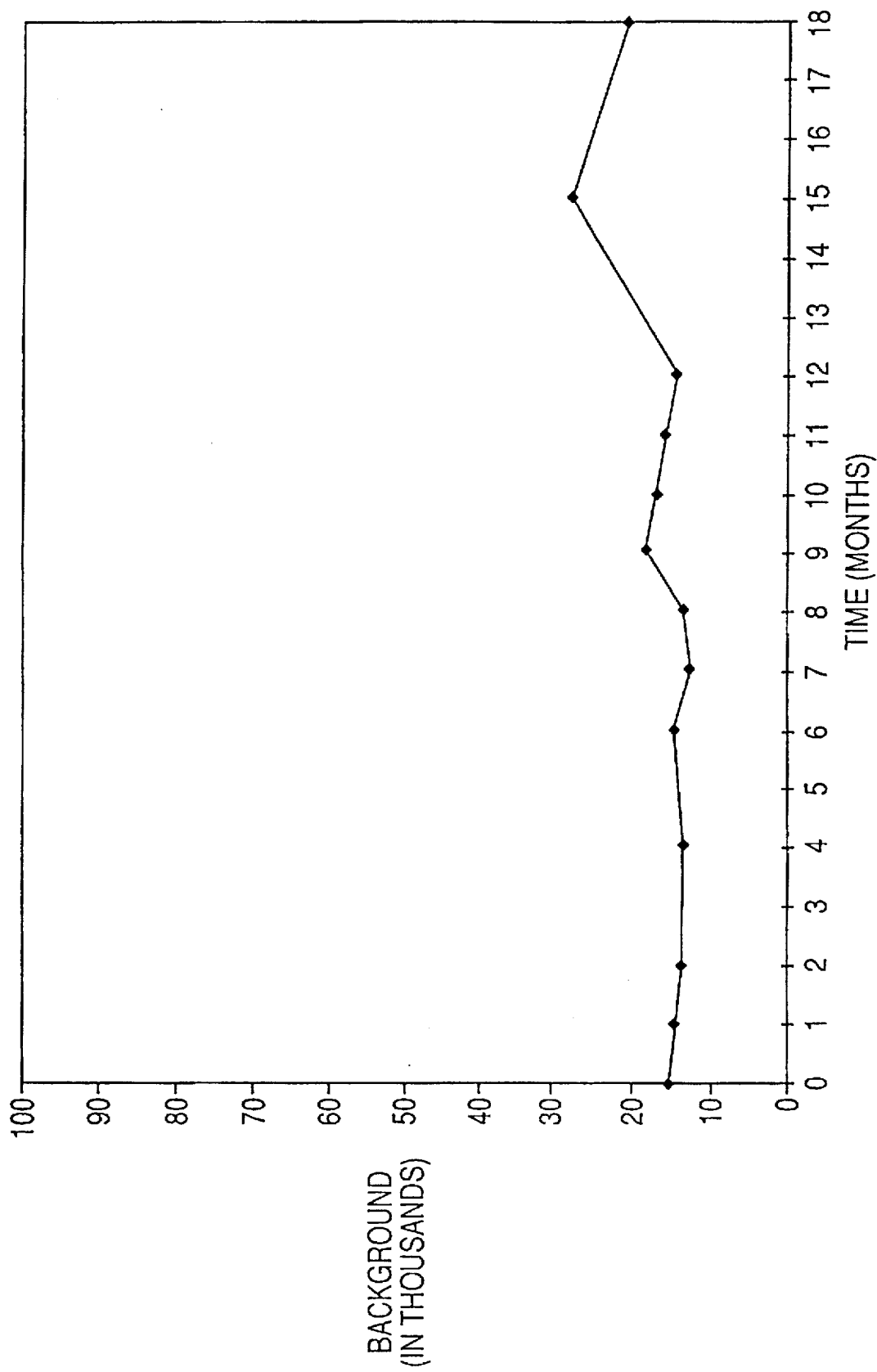
FIGS. 13A and 13B are graphs illustrating the storage stability of free-amine peptide derivatives of rhodamine 110.
Figure 13B:
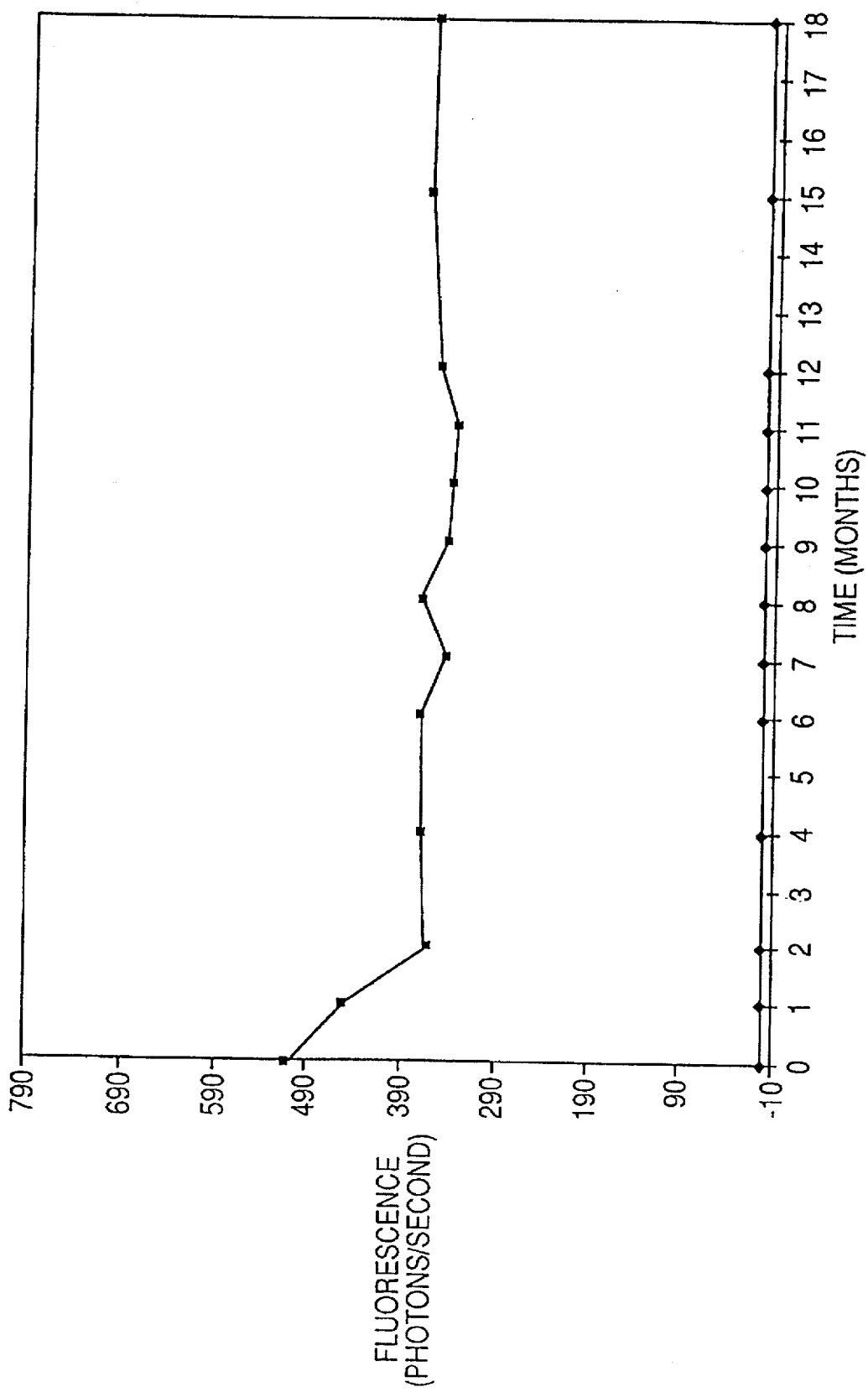

A 10-fold excess of the FMOC L-lysineεBOC amino acid is placed into a round bottom flask containing a 50:50 pyridine-dimethylformamide solution (V:V) and stirred several minutes. To this well-stirred solution is added a 20-fold excess of EDAC and the admixture is stirred an additional 30 minutes. A solution of (Ala)$_2$ rhodamine 110 dissolved in a minimum of 50:50 pyridine-dimethylformamide solution (V:V) is added dropwise over a period of 15 to 20 minutes. The reaction is stirred at room temperature for 16 hours and then concentrated to an oil under reduced pressure. This oil is dissolved in a minimum of an organic solvent and the crude product is purified by normal phase HPLC. The eluate containing the desired product is collected and concentrated under reduced pressure affording a crystalline material. A TLC of this material is run to check for purity and identity. The BOC protecting group is removed by dissolving the solid into a 50% solution of trifluoroacetic acid in methylene chloride. The reaction is stirred at room temperature for one hour, and the purity of the reaction product is checked by thin layer chromatography. The TLC did not show any of the BOC group. The acid solution is concentrated under reduced pressure to dryness. Several washes with fresh methylene chloride and reconcentrations under reduced pressure are performed to generate a crystalline solid. The FMOC blocking group is removed by dissolving the solid in a 5% piperidine-dimethylformamide solution and stirred at room temperature for one hour. The solution is concentrated to dryness under reduced pressure. The resulting solid is triturated several times with pentane to remove the FMOC polymer and the product is dried in vacuo to constant weight affording a yield of 98.62%. The purity of this material is checked by reverse phase HPLC, thin-layer chromatography and photon counting spectrofluorometry. The stability and purity of the product is further determined by monitoring the autohydrolysis, background fluorescence and enzymatic activity with the product as a substrate after storage of the product at 4° C. FIGS. 13A and 13B illustrate the stability of the free amine of (Lys-Ala)₂ rhodamine 110 which was prepared by the procedure described in this Example. FIG. 13A shows background fluorescence and FIG. 13B shows autohydrolysis and enzyme rate.

Example 18

Use of Different Salts to Enhance Specificity

The use of salts to identify cellular enzymes is very important. pH optimas are different demonstrating different enzymes or isoenzymes. Different salts from within the same pH range may give different reactivities. Z-groups, which are not salts but covalent organic compounds, show relatively little activity and no pH optima. See FIGS. 2A-2D, using cathepsin B as a target enzyme.

Example 19

Use of inhibitors in the Reagent Formula

Use of inhibitors of the targeted enzyme has been shown to prove substrate specificity. More specifically, when an inhibitor eliminated the targeted enzyme signal, it was reasoned that the targeted enzyme activity was measured without the inhibitor. The disclosed enzyme assay contemplates the use of interfering reaction inhibitors to increase and maintain specificity.

To improve a Cathepsin D response, inhibitors to aminopeptidase and Cathepsin B are added to the substrate most specific for Cathepsin D. Conversely, adding a Cathepsin D inhibitor to an assay for Cathepsin D requires measurement before and after inhibitor addition thus requiring two (2) measurements per assay. The opposite approach only requires one measurement. See FIGS. 3A-3D.

Example 20

Immune Competence

Figure 4A:
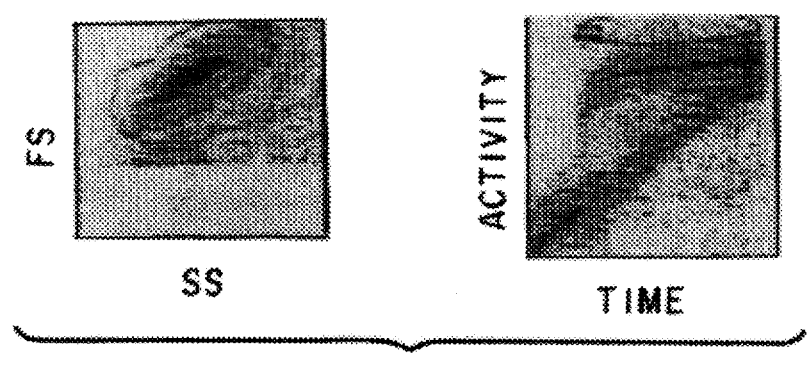
FIGS. 4A and 4B are photomicrographs of normal Ficoll prepared lymphocytes and acute lympholytic Ficoll prepared lymphocytes, respectively, which illustrate use of an assay according to the invention to determine immune competence and the difference in enzyme activity between normal lymphocytes and acute lymphocytic leukemia lymphocytes.
Figure 4B:
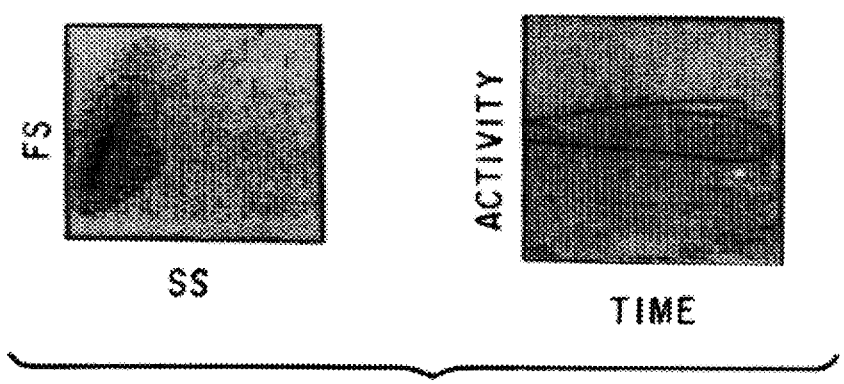

The cell's ability to fight off an invader lies within its genetics and therefore cell type. The "readiness" however of any genetically capable group of cells to defend is different. A measure of this "readiness" is manifest in the available proteolytic enzymes contained within vacuoles or on the surface of the cell. The assay compound hydrolysis rate increases with increased mass of enzymes giving a picture of immune competence both in number of cells and activity level. FIG. 4A shows cell size (fs), granularity (ss) and amino peptidase activity (log fluorescence at 525 nm v. time) using Leu rhodamine 110-TFA as a substrate in normal Ficoll prepared lymphocytes. FIG. 4B shows the same data for acute lympholytic Ficoll prepared lymphocytes. The cells tested in FIG. 4B have lost their enzymatic activity. Images were generated using Universal Imaging.

Example 21

Leukemia

Figure 5A:
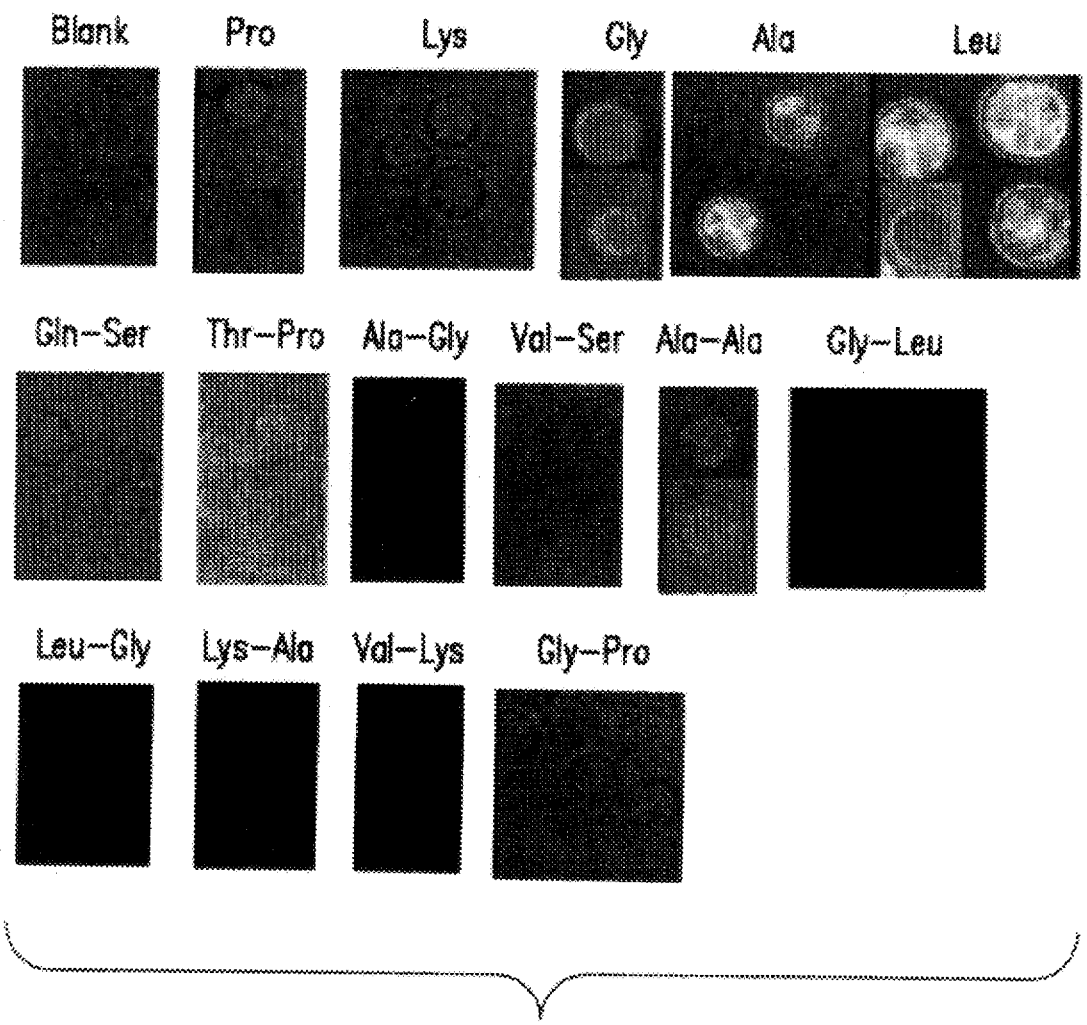
FIGS. 5A and 5B are color photomicrographs which illustrate use of an assay according to the invention to provide an indication of leukemia.
Figure 5B:
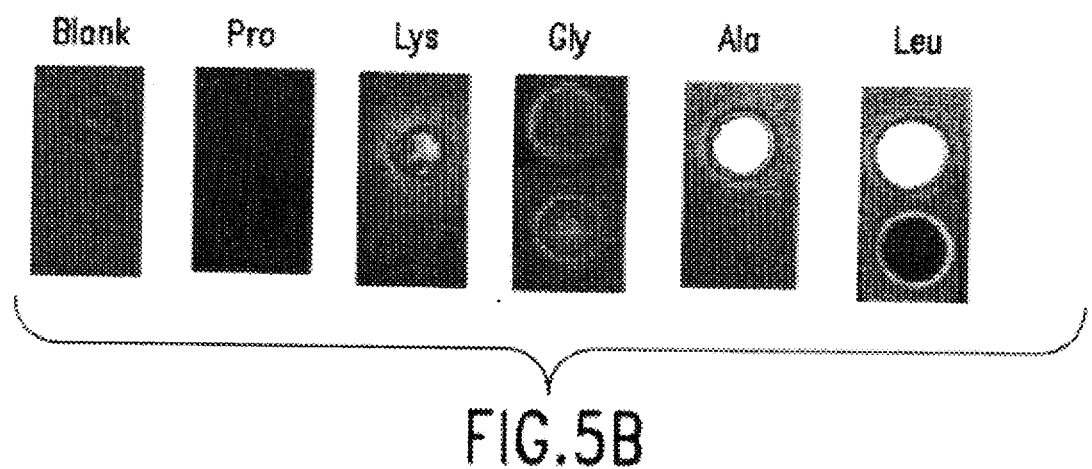

A panel of assay compounds are assembled consisting of pro-aminopeptidase; aminopeptidase M (Pro, Lys, Gly, Ala, Leu), Cathepsin D (Gly-Leu, Thr-Pro), Cathepsin B (Gln-Ser, Leu-Gly, Val-Ser, Val-Lys), Cathepsin C (Ala-Gly) and dipeptidyl peptidase II (Lys-Ala, Gly-Pro, Ala-Ala). Values for these assay compounds outside the normal range are considered diagnostic for leukemia. In addition, the ratios of these enzyme readings to one another provide information on further classifying the leukemia into myelogenous or lymphocytic and monitoring the course of the disease. Values may be both higher or lower than the normal range. FIG. 5A shows results obtained when normal leukocytes are tested with various rhodamine 110-monopeptide and rhodamine 110-dipeptide compounds. All compounds except (Lys-Ala)₂ rhodamine 110 are TFA salts. (Lys-Ala)₂ rhodamine 110 was a free amine derivative. FIG. 5B shows results obtained when leukemia cells are tested with various rhodamine 110-monopeptide compounds.

Example 22

Sepsis

Figure 6A:
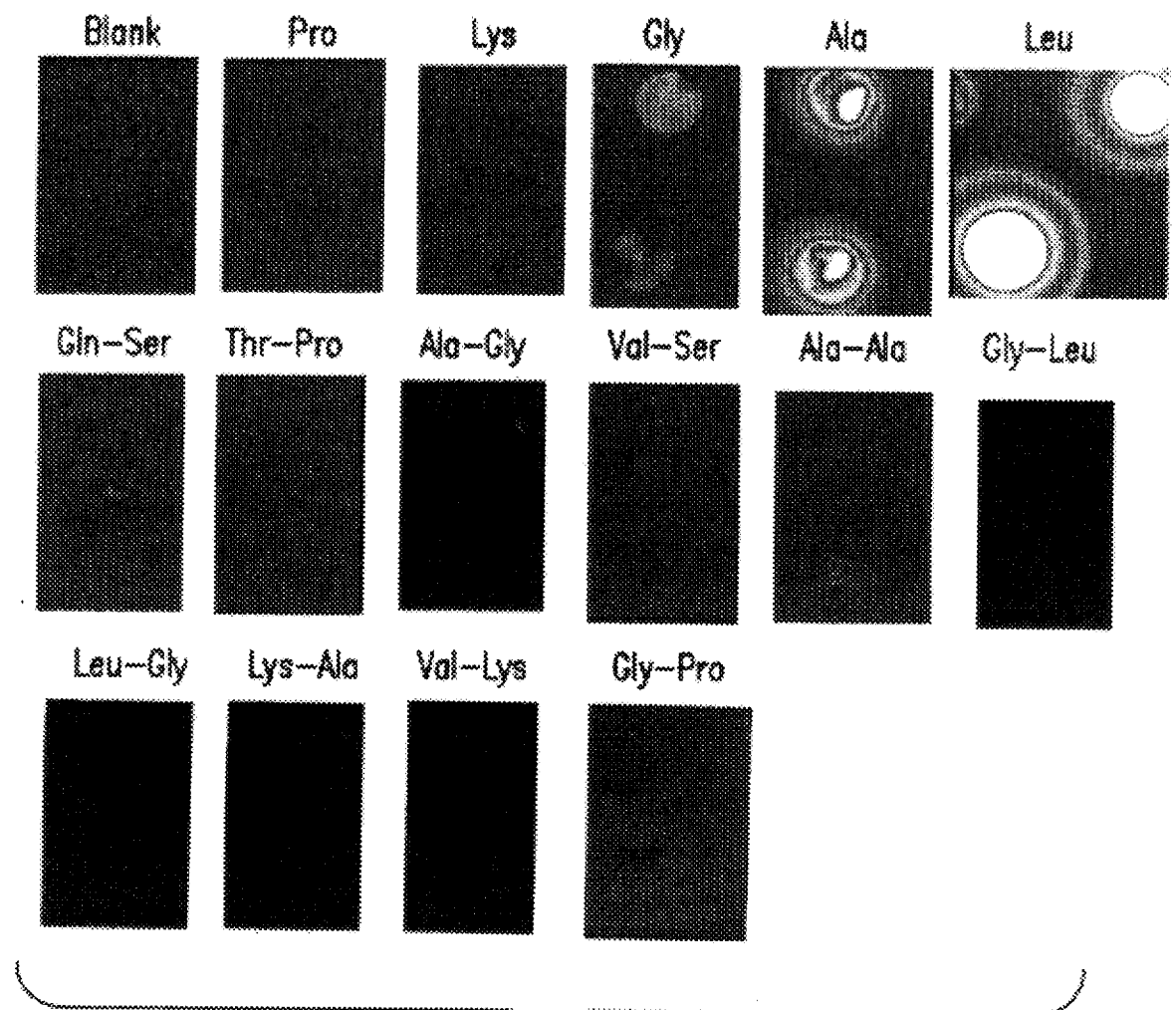
FIGS. 6A and 6B are color photomicrographs which illustrate use of an assay to provide an indication of sepsis.
Figure 6B:
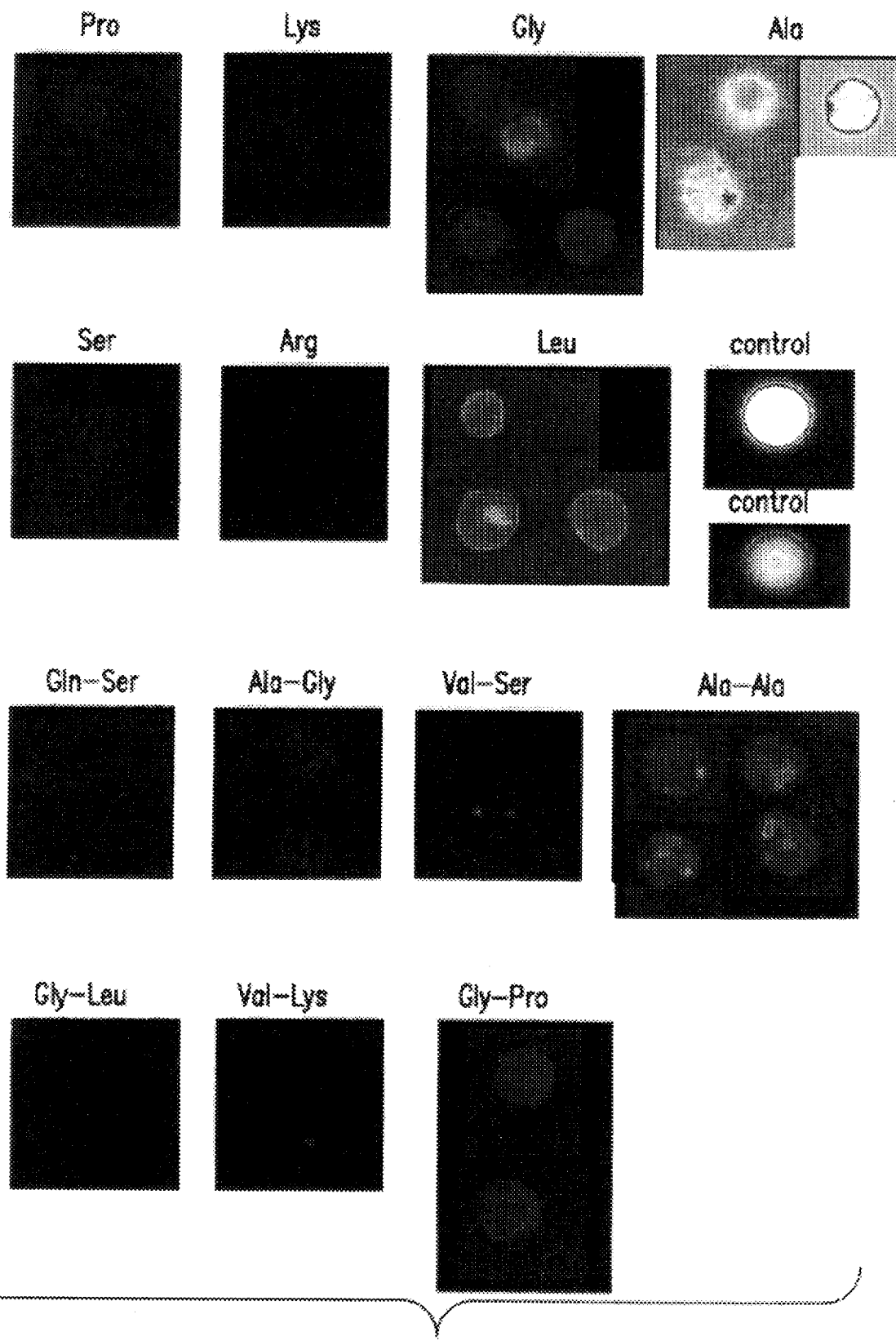

A panel of assay compounds are assembled consisting of aminopeptidase (Leu, Pro, Lys, Gly, Ala), dipeptidyl peptidase II (Gly-Pro, Lys-ala, Ala-Ala), Cathepsin C (Ala-Gly) and Cathepsin B (Leu-Gly, Val-Lys, Val-Ser and Gln-Ser) and cathepsin D (Gly-Leu and Thr-Pro). Values for these substrates outside the normal range are considered diagnostic for sepsis. FIG. 6A shows results obtained when cells from a patient that had been shot by a gun and who was experiencing sepsis were treated with various rhodamine 110-monopeptide and dipeptide compounds. FIG. 6B shows results obtained when umbilical cord blood cells from a newborn infant were treated with various rhodamine 110-monopeptide and dipeptide compounds. All compounds except (Lys-Ala)₂ rhodamine 110 are TFA salts. (Lys-Ala)₂ rhodamine 110 was a free amine derivative.

Example 23

TB Infection

A panel of assay compounds are assembled consisting of Ala-aminopeptidase and Lys-aminopeptidase, Dipeptidyl peptidase IV (Ala-Ala)₂ rhodamine 110 and Cathepsin D to indicate possible TB infection in AIDS related cases.

A panel Of enzymatic substrates is performed consisting of Ala-aminopeptidase and Lys-aminopeptidase, Dipeptidyl peptidase IV (Ala-Ala)₂ rhodamine 110 and Cathepsin D to indicate possible TB infection in AIDS related cases. The results are reported in Table 4 below:

TABLE 4

| | NORMALS | | | HIV + PATIENTS | | | |
|---|---|---|---|---|---|---|---|
| SUBSTRATE | MEAN DELTA FL | SD | N | MEAN DELTA FL | SD | N | P 2 TAIL |
| GLN—SER**** | 11.9 | 4.4 | 14 | 13.7 | 7.2 | 13 | N.S. |
| GLN—SER* | 6.1 | 2.6 | 14 | 12.7 | 12.9 | 17 | <0.060 |
| VAL—SER**** | 24.6 | 5.3 | 14 | 32.5 | 14.7 | 7 | N.S. |
| LYS—ALA¹ | 112.6 | 43.5 | 12 | 121.5 | 62.9 | 7 | N.S. |
| LYS—ALA² | 7.6 | 1.7 | 12 | 7.9 | 3.7 | 13 | N.S. |
| THR—PRO**** | 295.0 | 140.9 | 7 | 204.4 | 106.1 | 6 | N.S. |
| ALA—GLY**** | 48.0 | 44.1 | 11 | 39.9 | 43.7 | 6 | N.S. |
| ALA—GLY* | 31.6 | 27.0 | 13 | 29.7 | 24.8 | 13 | N.S. |
| THR—PRO**** | 87.2 | 95.8 | 13 | 62.9 | 99.2 | 13 | N.S. |
| THR—PRO* | 17.3 | 18.5 | 13 | 10.2 | 8.7 | 17 | N.S. |
| GLY—PRO**** | 46.7 | 42.8 | 17 | 18.4 | 9.2 | 13 | <0.020 |
| GLY—PRO* | 50.9 | 45.9 | 17 | 21.4 | 15.5 | 19 | <0.025 |
| ALA—ALA**** | 158.4 | 47.5 | 9 | 110.1 | 31.6 | 16 | <0.020 |
| ALA—ALA* | 25.6 | 7.6 | 13 | 26.3 | 10.2 | 13 | N.S. |
| GLY—LEU**** | 9.5 | 4.7 | 17 | 16.3 | 11.1 | 17 | <0.030 |
| LEU—GLY** | 143.0 | 132.7 | 13 | 104.1 | 98.4 | 13 | N.S. |
| LEU—GLY*** | 162.4 | 146.9 | 13 | 111.9 | 99.8 | 13 | N.S. |
| VAL—LYS**** | 22.7 | 16.1 | 15 | 17.7 | 10.4 | 13 | N.S. |
| GLYCINE**** | 101.1 | 101.2 | 11 | 62.4 | 73.3 | 13 | N.S. |
| ALANINE**** | 132.0 | 140.4 | 13 | 59.0 | 31.3 | 17 | <0.095 |
| LYSINE**** | 10.5 | 3.7 | 12 | 7.4 | 3.8 | 17 | <0.040 |

TABLE 4-continued

| | NORMALS | | | HIV + PATIENTS | | | |
|---|---|---|---|---|---|---|---|
| SUBSTRATE | MEAN DELTA FL | SD | N | MEAN DELTA FL | SD | N | P 2 TAIL |
| PROLINE**** | 11.4 | 4.3 | 10 | 11.0 | 5.0 | 13 | N.S. |
| LEUCINE**** | 259.6 | 99.6 | 8 | 130.5 | 99.5 | 9 | <0.020 |

*BESTATIN + TFA RHODAMINE 110
**TARTRATE
***ACETATE
****TFA-RHODAMINE 110
[1] Rho 110-free amine
[2] Rho 110-free amine + bestatin Example 24

Metastatic Potential in Solid Tumors

Figure 7:
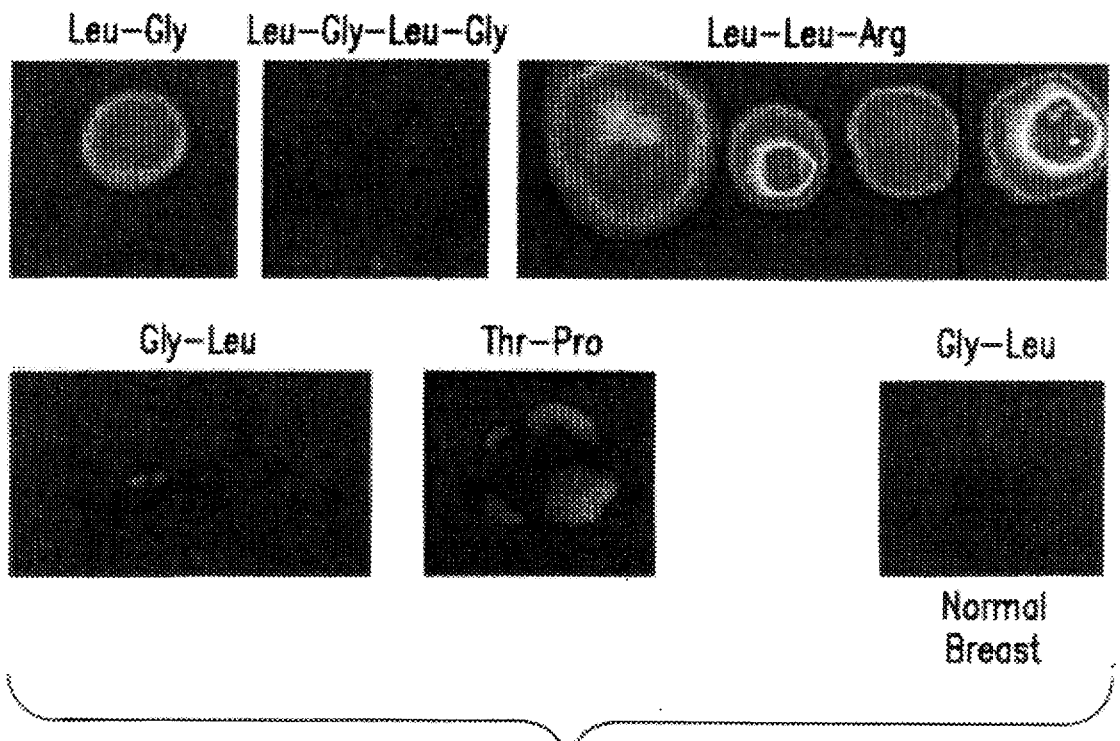
FIG. 7 is a color photomicrograph which illustrates the use of an assay to provide an indication of the metastatic potential of tumors.

A panel of assay compounds are assembled consisting of Cathepsin B markers (Gln-Ser, Val-Ser), Cathepsin C (Thr-Pro), Dipeptidyl peptidase IV (Ala-Ala) and Leu-aminopeptidase to predict metastatic potential in solid tumors. The results obtained when breast tumor cells (and one normal breast control cell sample) are treated with TFA salts of various rhodamine 110-peptide compounds are shown in FIG. 7.

Example 25

Monitoring Drug Treatment

Figure 8A:
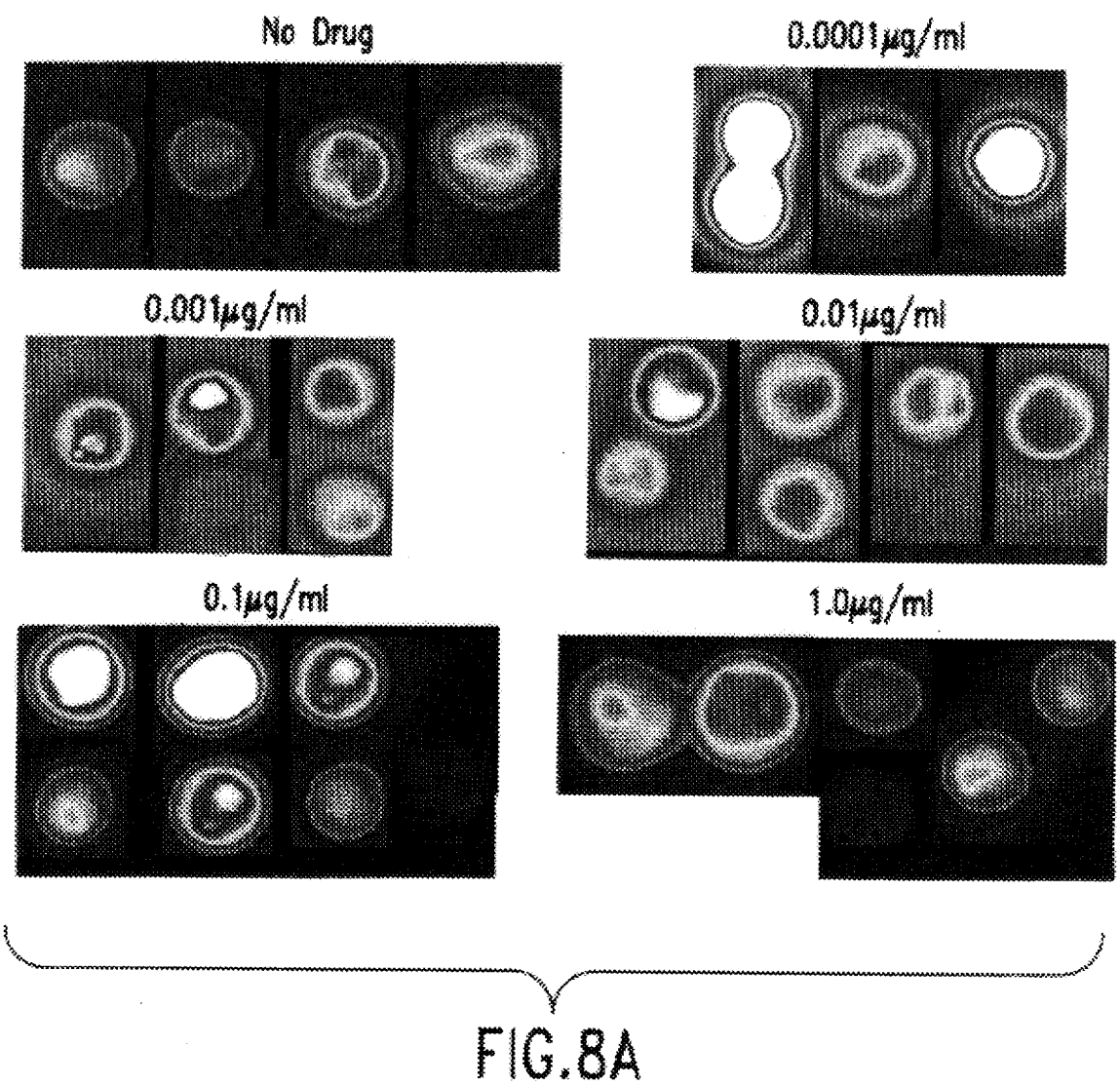
FIGS. 8A and 8B are color photomicrographs which illustrate the use of assays to monitor drug treatment.
Figure 8B:
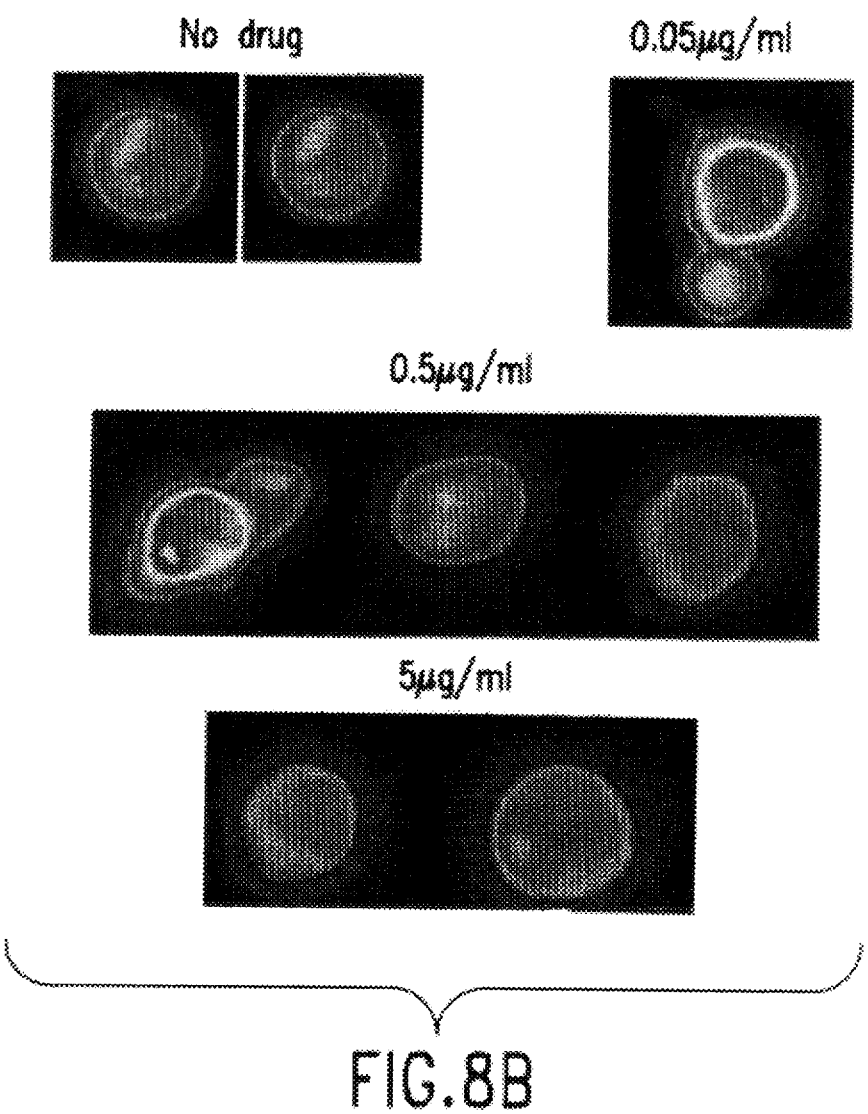

An assay compound can be used to monitor drug treatment. Enzymatic activity according to drug target, i.e., protein synthesis, can diminish over time and increase dramatically depending on dose of drug. The results obtained when Raji cells which had been exposed to various concentrations of cyclophosphamide for 48 hours are treated with Leu-rhodamine 110 for 1 minute are shown in FIG. 8A. The results obtained when Raji cells, which had been exposed to various concentrations of vincristine for 48 hours, are treated with a TFA salt of Leu-rhodamine 110 for i minute and aminopeptidase activity is measured are shown in FIG. 8B.

Example 26

Macrophage Activation

Figure 9:
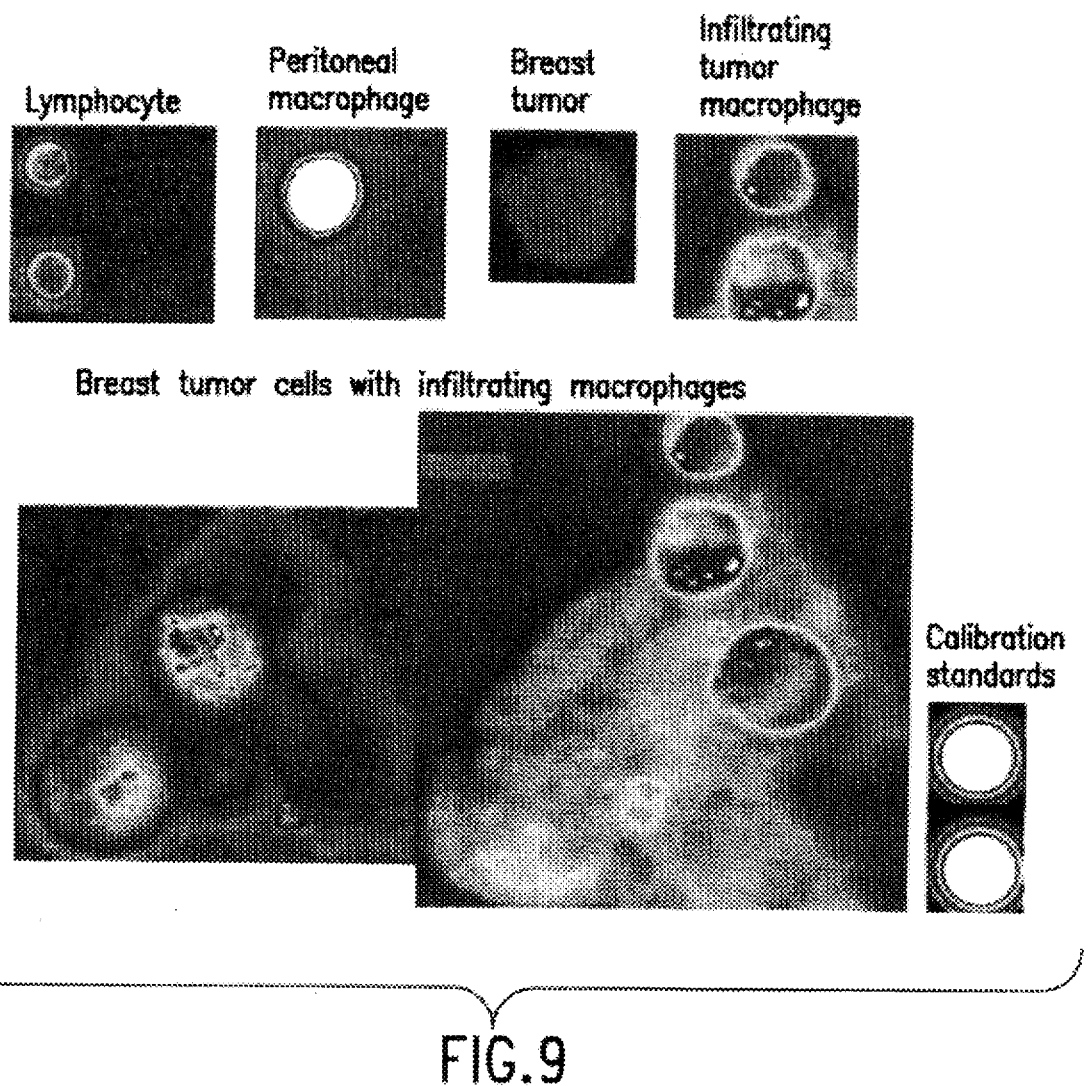
FIG. 9 is a color photomicrograph which illustrates the use of assays to provide an indication of macrophage activation.

FIG. 9 illustrates the use of assays to provide an indication of macrophage activation. Using a mouse model, various types of cells used to study metastatic versus non-metastatic breast tumors, were treated with Leu-rhodamine 110 substrate and amino peptidase activity was measured. The results obtained are shown in FIG. 9.

Example 27

Red Blood Cell Adenosine Deaminase (ADA) and Relationship To Hereditary Non-Spherocytic Hemolytic Anemia (HNSHA) Disease Hereditary deficiencies of glycolytic enzymes or related pathways in the erythrocyte are characterized by the disease hemolytic anemia. Hereditary Non-Spherocytic Hemolytic Anemia is distinguished from Hereditary Spherocytosis by the fact that red blood cells are morphologically normal and manifest a normal osmotic fragility. Only in the case of pyrimidine 5' nucleotidase deficiency is the erythrocyte morphology changed to a basophilic stippling.

Deficiencies of ADA are well-known causes of immunodeficiency. In cases where ADA is greatly increased to levels as high as 100 times normal but other tissues have normal levels in the same individual, the clinical disease is HNSHA. The high ADA depletes the erythrocytes of vital adenine nucleotides, impairing their metabolism. The residual enzyme structure is normal and the gene is normal but attaching the promoter to a reporter gene produced increased levels of enzyme.

The structure of Adenosine is:

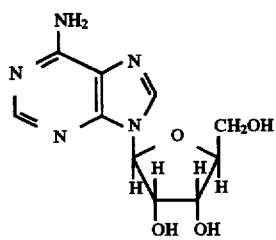

The enzyme adenosine deaminase removes the $NH_2$ and replaces it with a hydroxyl:

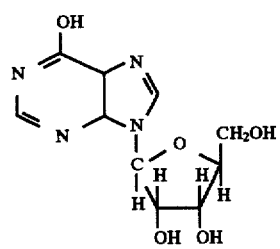

The assay compound using rhodamine 110 is then:

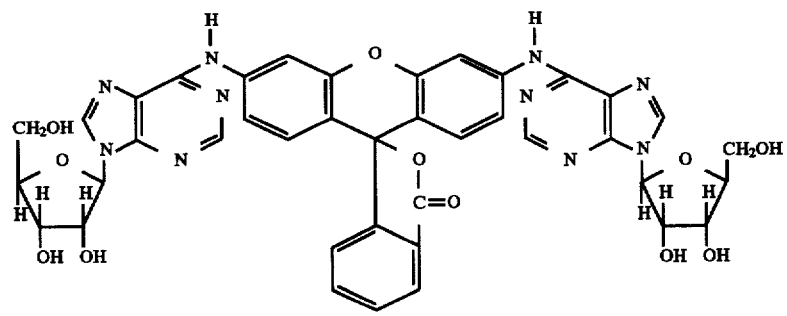

Hydrolysis by ADA leaves 2 Inosine and 1 rhodamine 110:

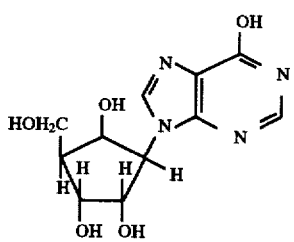

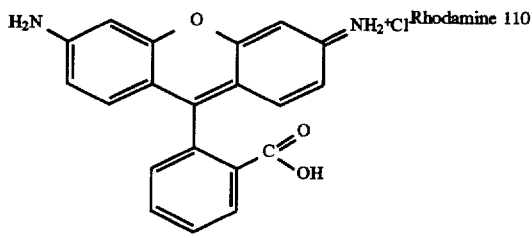

To assay vital cells for ADA activity, a blood sample (containing platelets, erythrocytes and leukocytes) is washed to remove plasma, debris, dead cells and extra cellular enzymes. The sample is incubated at 37° C. in the wash media.

A media is prepared for the assay reagent using Hanks balanced salts at pH 7.0. The aqueous buffer media is adjusted to isosmotic conditions. The ionic strength is adjusted to 0.1 to 0.3μ by additions of salts. Appropriate cofactors including divalent cations such as $Ca^{2+}$, $Mg^{2+}$ and $Ba^{2+}$ are added for ADA to maximize the hydrolysis rate. The assay compound is added at excess for the quantities of enzyme analyzed. (A time-course activity assay is used to determine correct fluorescence intensity data collection, usually between 10 seconds and 10 minutes, as well as, appropriate assay compound concentration.)

The structure of pyrimidine 5'nucleotide is:

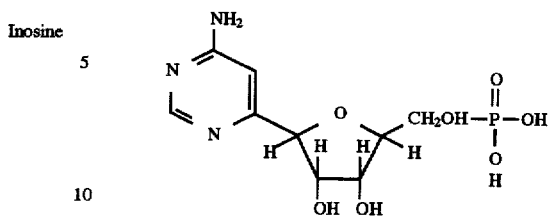

The enzyme pyrimidine 5'nucleotidase removes the phosphate group from the compound:

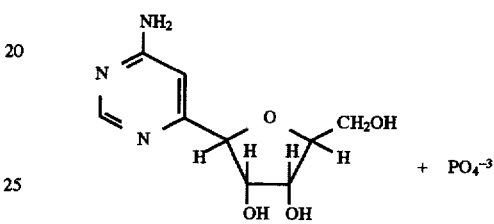

The assay reagent using fluorescein is then:

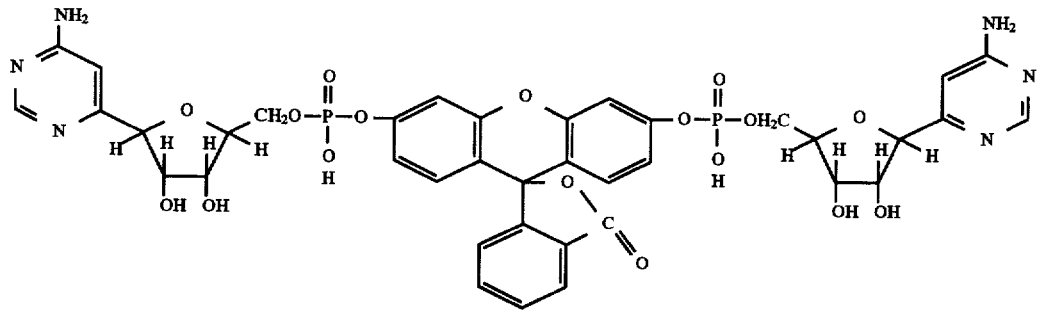

The washed, pre-incubated blood sample is added to the media, incubated at 37° C. and fluorescent intensity is measured at the predetermined time on erythrocytes. The fluorescence found on platelets and leukocytes are disregarded. Separation of cell types is aided by size discrimination.

Comparison of "normal" erythrocytic ADA activity to those in HNSHA disease state demonstrates a 100-fold increase in ADA activity.

To assay vital cells for pyrimidine-5'-nucleotidase, a blood sample containing platelets, erythrocytes, leukocytes and plasma is washed to remove plasma, debris, dead cells and extracellular enzymes. The sample is pre-incubated at 37° C. in the wash media.

A media is prepared for the assay reagent using glycine-sodium hydroxide buffer at pH 8.5. The aqueous buffer media is adjusted to isosmotic conditions. The ionic strength is adjusted to 0.1 to 0.3μ by addition of salts. Appropriate cofactors of calcium chloride and magnesium sulfate are added for pyrimidine 5'nucleotidase to maximize the hydrolysis rate. The assay compound is added at excess for the quantities of enzyme to be analyzed. Other Michaelis-Menten parameters are determined to provide correct data collection window.

The washed pre-incubated blood sample is added to the media, incubated at 37° C. and fluorescent intensity is measured on erythrocytes. Erythrocytes are identified visually under a microscope using morphological indicators. Erythrocytes are identified using a flow cytometer by size and granularity discrimination or 2-color assay monoclonal antibody for erythrocytes.

Comparison of "normal" erythrocytes pyrimidine 5'nucleotidase to those in HNSHA shows a deficiency of enzyme in HNSHA.

Example 28

Proinsulin or Pre-proinsulin Inside Cell

Insulin is synthesized as a single chain polypeptide—pre-proinsulin. The signal sequence "pre" becomes cleaved during synthesis on the rough endoplasmic reticulum, and no mutations are known that cause disturbances of removing signal sequences, because such mutations probably would be lethal.

Proinsulin is characterized by the presence of a C-peptide that joins the two A and B chains of the mature insulin molecule. Mutations occur mostly at the two critical junctions where the C-peptide is attached to the A and B insulin chains by two pairs of basic amino acids. Such defects have been recognized in families with hyperinsulinemia. The defect is inherited in an autosomal dominant pattern, and probably involves the loss of one of the basic amino acid residues that makes it impossible to cleave the proinsulin molecule at the mutation site, which results in the presence of a two-chained intermediate of proinsulin molecules secreted into the blood plasma.

Clinically occurring glucose intolerance with abnormally high ratios of proinsulin-like material to insulin (9 to 10 as compared with normal values of approximately 0.25) are due to a loss of Arg 65 and loss of the protective activity causing acetylation of Lys 64 which make it impossible to cleave the C-peptide from the A chain of insulin. It is supposed that substitution of Arg 65 of the proinsulin molecule results in failure of cellular enzymes to cleave correctly the C-peptide from the A chain of insulin. Use of a specific substrate, designed for this cleavage site, can be diagnostic for the defect, as well as prognostic for genetic treatment.

Example 29

Hairy Cell Leukemia

Acid-tartaric buffer in phosphate substrate is used to confirm hairy cell leukemia. "Tartaric Resistant Acid Phosphatase" is a cellular component found in hairy cell leukemia. Design of a buffer system, using tartrate in the buffer and a phosphate substrate, confirms presence of this disease with a positive result.

Example 30

Cathepsin B

Cathepsin B substrates Gln-Ser, Val-Ser, Leu-Gly, Val-Lys specific for isoenzymes of Cathepsin B. The use of isoelectric focusing for Cathepsin B enzyme and nitrocellulose transfer of these isoenzymes, similar to Western blot, provides a solid support to test substrate activity. Examination of substrate activity, based on design of the dye molecule, determines isoenzyme specificity based on structure.

To prepare the reagent for measuring cathepsin B activity, an assay compound such as Val-Lys-rhodamine 110-TFA is dissolved in 100% DMSO at a stock concentration of 1.6 mM. The stock solution is then diluted 20-fold [with 10 mM MES buffer at pH 6.0] to give a reagent concentration of 0.08 mM. To the 0.08 mM solution the following reagents are added. 0.5 mM Bestatin as an aminopeptidase inhibitor, 1.0 mM dithiothretol as activator, 1.0 mM $CaCl_2$ and 1.0 $MgCl_2$ as cofactors and 247 mM Mannitol as a bulking reagent for lyophilization. The complete reagent mixture is lyophilized during which process the DMSO is effectively removed and the lyophilized mixture is reconstituted using endotoxin-free deionized water.

Example 31

Response to Modulators

The use of cellular response modifiers, i.e., PMA (phorbol myristate acetate), interleukins and interferons in the pre-incubation step provides information on cellular response. If the cell function is normal the response to the modulator will, for selected enzyme substrates, be in defined ranges. If abnormal, the measured response will be higher or lower.

To make the reagent, the assay compound dichlorofluoroscein diacetate is dissolved in 100% DMSO at 6.0 mM as a stock solution. The stock solution is diluted 100-fold with 10 mM MES at pH 6.0 to give a reagent concentration of 0.06 mM. 0.032 mM PMA is added as a cell-activator and 247 mM Mannitol is added as a bulking agent for lyophilization. The reagent mixture is lyophilized which effectively removes the DMSO and reconstituted with endotoxin-free deionized water.

Example 32

Use in Conjunction with Genetic Analysis Techniques

The methods to determine the activity of an enzyme using the assays described above are also useful when used in independent combination with genetic analysis techniques including, polymerase chain reaction (PCR), transcription mediated amplification (TMA), ligase chain reaction (LCR) and fluorescent in situ hybridization (FISH). The results obtained using these genetic analysis techniques can be used both for confirmation of diagnostic conclusions based on measurements of enzymatic activities in cells, as determined with the assays previously described herein, and for the differentiation of purely functional pathologies and functional pathologies having an underlying genetic cause.

Example 33

Statistical Analysis and Diagnosis of Normal and Diseased States based on Cellular Enzymatic Activity A normal in house adult donor pool was drawn, recording sex and determining that no known disease state was present at the time of sample draw. Criteria for rejecting samples included patients under medication, patients with infection or inflammation of any type, colds and flu as well as any known medical illness such as cancer, heart ailment and high blood pressure. A donor list of 75 patients has been developed and a mean and 2 sd range established. A subgroup of "super normals" was developed from this list by examining the 75 patients to determine which group falls closest to the mean for all enzymes in all cell types tested. These patients were used as the "wellness index" or best group of "normalcy" patients. If a study required the use of children or newborns then this same format was used to develop a data base for these age groups. It was noted that the normal range was different in the different age groups. These groups were also screened for criteria, for example in the newborns an apgarde value greater than 8, with a normal delivery, 48 hour stay in the hospital and no clinical diseases diagnosed in the mother was considered normal.

The next task was to develop a similar data base for different disease states. These were clinically diagnosed using conventional technology to identify the disease. The patient samples were assayed using the same protocol as the normal samples. The patients were not transfused and the sample was less than 4 hours old at analysis. All cell type information was collected with all enzyme assays. Staging of the disease was noted where available and all drug treatments were also recorded. Drug pharmokinetics were determined by the appropriate reference to estimate the drug's possible influence on cellular function. Separate studies using the drugs on human tissue culture cell lines were also used to determine their effect on specific cell types and provide reference. Untreated patient samples were separated into their own group and compared to drug treatment protocols. The goal of the studies was early prediction of disease states as well as monitoring of treatment modalities.

The data from the collected samples was organized into tables containing rows of cell type and enzyme concentration. As illustrated in Table 5, the first seven columns contain either individual patients with a disease or the mean of patients with a disease. Calculation of the sum of the squares, the covariance or the correlation of the rows then indicated which enzyme and what cell type gave the largest difference and therefore the most descriptive indicator of the disease. This approach used the Non-Negative Least Squares method and the ANOVA method. Eigenvectors were then determined for an unknown to predict the most likely disease for the unknown. FIG. 16 shows the prediction of an unknown (actually diagnosed as JRA) from a group of inflammatory diseases (Kawasaki #1, Lupus #2, Juvenile Rheumatoid Arthritis #3, Dermatomyositis #4, Rheumatic Fever #5, and Inflammatory Bowel Disease #6) using the full data matrix versus reduced data matrices using respectively: the enzyme/cell type combinations identified by eigenvector 1 alone, eigenvector 1 and 2 together, or the analysis based on squared deviations from the mean (variance) alone.

TABLE 5

LYMPHOCYTES

| SUBSTRATE | Kawasaki's Ratio Dis. Lymphs. | Lupus Ratio Lymphs | JRA Ratio Lymphs | Dermatomyositis Ratio Lymphs | Rheumatic Fever Lymphs | Inflam. Bowel Dis. Lymphs | Eigen Vector 1 | Eigen Vector 2 | Variance | Inflam Dis Lymphs |
|---|---|---|---|---|---|---|---|---|---|---|
| LEU | 0.93 | 1.93 | 1.64 | 1.36 | 1.05 | 1.34 | | | | 0.72 |
| ALA | 1.05 | 1.16 | 1.59 | 1.16 | 1.18 | 1.53 | | | | 1.07 |
| GLY | 1.94 | 1.64 | 0.17 | 1.30 | 2.09 | 1.97 | | | | 0.16 |
| VK | 1.19 | 1.25 | 1.60 | 1.39 | 0.74 | 1.08 | | | | 1.29 |
| VK-M | 0.83 | 0.99 | 7.71 | 0.97 | 0.68 | 0.66 | 3 | | 5 | 4.64 |
| KA | 1.53 | 1.93 | 0.10 | 1.39 | 1.19 | 1.75 | | | | 0.07 |
| KA-M | 1.32 | 1.06 | 1.46 | 1.93 | 2.07 | 1.63 | | | | 2.06 |
| Z-GP | 2.90 | 1.93 | 1.29 | 1.73 | 3.23 | 1.73 | | | | 1.07 |
| Z-GP-M | 3.44 | 2.09 | 1.30 | 3.45 | 4.09 | 3.80 | | | | 1.04 |
| Z-TP6.5 | 5.85 | 2.30 | 2.89 | 3.87 | 7.19 | 3.03 | | | | 1.71 |
| FDA | 0.28 | 1.01 | 1.17 | 1.06 | 0.90 | 0.87 | | | | 0.80 |
| FDA-NAF | 0.30 | 0.74 | 0.21 | 1.14 | 0.97 | 0.89 | | | | 0.16 |
| DCHFMESPMA | 0.09 | 0.63 | 0.38 | 0.52 | 0.34 | 0.40 | | | | 0.31 |
| GFGA | 2.15 | 1.25 | 2.03 | 2.14 | 2.14 | 2.16 | | | | 1.40 |
| RGES | 1.43 | 1.84 | 1.43 | 2.06 | 2.04 | 1.96 | | | | 1.23 |
| DGLUC | 0.25 | 0.78 | 0.82 | 0.72 | 0.97 | 1.04 | | | | 0.45 |
| DPO4 | 0.62 | 0.90 | 0.82 | 0.64 | 0.77 | 0.87 | | | | 0.45 |
| GALAC | 2.46 | 1.30 | 2.28 | 2.34 | 2.24 | 2.39 | | | | 1.40 |

MONOCYTES

| SUBSTRATE | Kawasaki's Dis. Monos | Lupus Ratio Monos | JRA Ratio Monos | Dermatomyositis Ratio Monos | Rheumatic Fever Monos | Inflam. Bowel Dis. Lymphs | Eigen Vector 1 | Eigen Vector 2 | Variance | Inflam. Dis. Monos |
|---|---|---|---|---|---|---|---|---|---|---|
| LEU | 0.57 | 44.44 | 1.44 | 1.35 | 0.96 | 1.13 | 1 | | 1 | 0.65 |
| ALA | 1.36 | 6.17 | 1.31 | 0.99 | 1.08 | 1.43 | 5 | | | 0.94 |
| GLY | 3.83 | 6.00 | 1.11 | 1.01 | 2.06 | 1.84 | 6 | | | 0.35 |
| VK | 5.38 | 1.64 | 5.94 | 1.42 | 1.32 | 3.08 | | 7 | | 2.32 |
| VK-M | 0.25 | 11.37 | 3.49 | 3.45 | 8.67 | 1.41 | 2 | 6 | 3 | 1.87 |
| KA | 2.22 | 6.93 | 0.54 | 1.04 | 2.39 | 1.95 | 4 | | | 0.25 |
| KA-M | 7.08 | 14.08 | 12.14 | 1.65 | 15.36 | 4.10 | 3 | 1 | 2 | 1.44 |
| Z-GP | 4.06 | 1.88 | 1.34 | 1.50 | 3.56 | 1.64 | | | | 0.98 |
| Z-GP-M | 4.47 | 1.92 | 1.79 | 3.05 | 2.99 | 3.33 | | | | 0.73 |
| Z-TP6.5 | 6.40 | 2.29 | 8.33 | 3.12 | 5.37 | 2.83 | | 4 | | 3.06 |
| FDA | 0.41 | 1.01 | 1.55 | 0.94 | 0.53 | 0.98 | | | | 0.47 |
| FDA-NAF | 0.58 | 0.83 | 0.35 | 1.03 | 0.89 | 1.11 | | | | 0.13 |
| DCHFMESPMA | 0.13 | 0.48 | 0.38 | 0.47 | 0.35 | 0.46 | | | | 0.24 |
| GFGA | 1.77 | 2.18 | 2.29 | 2.01 | 1.36 | 3.42 | | | | 1.67 |
| RGES | 4.65 | 3.03 | 3.98 | 5.22 | 6.52 | 6.02 | | | | 0.61 |
| DGLUC | 0.35 | 0.38 | 1.13 | 0.73 | 2.91 | 4.62 | | | | 0.28 |
| DPO4 | 0.51 | 0.69 | 1.13 | 0.79 | 1.09 | 1.30 | | | | 0.28 |
| GALAC | 8.40 | 1.17 | 3.81 | 2.14 | 1.80 | 4.93 | | | 6 | 1.87 |

TABLE 5-continued

| | GRANULOCYTES | | | | | | | | | |
|---|---|---|---|---|---|---|---|---|---|---|
| SUBSTRATE | Kawasaki's Dis. Grans | Lupus Ratio Grans | JRA Ratio Grans | Dermatomyositis Ratio Grans | Rheumatic Fever Grans | Inflam. Bowel Dis. Lymphs | Eigen Vector 1 | Eigen Vector 2 | Variance | Inflam. Dis. Grans |
| LEU | 0.33 | 2.03 | 1.43 | 1.31 | 0.98 | 1.11 | | | | 0.58 |
| ALA | 1.31 | 1.08 | 1.21 | 0.97 | 1.03 | 1.26 | | | | 0.80 |
| GLY | 2.30 | 1.42 | 0.30 | 1.12 | 0.56 | 1.78 | | | | 0.17 |
| VK | 1.30 | 1.04 | 1.26 | 1.12 | 0.60 | 1.08 | | | | 0.85 |
| VK-M | 0.72 | 0.89 | 9.49 | 0.15 | 0.48 | 0.64 | | 2 | 4 | 3.39 |
| KA | 0.99 | 1.64 | 0.10 | 1.16 | 1.02 | 1.32 | | | | 0.05 |
| KA-M | 1.32 | 1.01 | 1.13 | 1.02 | 0.17 | 1.58 | | | | 1.37 |
| Z-GP | 2.54 | 1.82 | 1.24 | 1.44 | 2.51 | 1.47 | | | | 0.83 |
| Z-GP-M | 2.83 | 1.94 | 1.46 | 2.76 | 2.98 | 2.68 | | | | 0.66 |
| Z-TP6.5 | 4.21 | 2.19 | 5.70 | 2.79 | 4.73 | 2.20 | | | 5 | 2.01 |
| FDA | 0.31 | 1.01 | 1.12 | 0.92 | 0.67 | 0.93 | | | | 0.50 |
| FDA-NAF | 0.39 | 0.72 | 0.23 | 0.97 | 0.80 | 0.96 | | | | 0.08 |
| DCHFMESPMA | 0.05 | 0.31 | 0.38 | 0.34 | 0.14 | 0.28 | | | | 0.13 |
| GFGA | 1.93 | 0.10 | 2.26 | 1.85 | 2.10 | 2.78 | | | | 1.77 |
| RGES | 0.36 | 1.36 | 1.01 | 1.62 | 1.54 | 1.60 | | | | 0.76 |
| DGLUC | 0.22 | 0.77 | 0.98 | 1.18 | 0.13 | 1.64 | | | | 0.38 |
| DPO4 | 0.69 | 0.71 | 0.98 | 0.88 | 0.24 | 1.22 | | | | 0.38 |
| GALAC | 2.32 | 1.01 | 3.42 | 1.76 | 1.16 | 2.35 | | | | 1.37 |

In the above Table the following abbreviations are used:

LEU—(Leu)$_2$ Rho 110

ALA—(Ala)$_2$ Rho 110

GLY—(Gly)$_2$ Rho 110

VK—(Val-Lys)$_2$ Rho 110

VK-M—(Val-Lys)$_2$ Rho 110 (modified)

KA—(Lys-Ala)$_2$ Rho 110

KA-M—(Lys-Ala)$_2$ Rho 110

Z-GP—(carbobenzyloxycarbonyl-Gly-Pro)$_2$ Rho 110

Z-GP-M—(carbobenzyloxycarbonyl-Gly-Pro)$_2$ Rho 110 (modified)

Z-TP6.5—(carbobenzyloxycarbonyl-Thr-Pro)$_2$ Rho 110 (pH 6.5)

FDA—fluorescein diacetate

FDA-NAF—fluorescein diacetate in a buffer containing sodium fluoride

DCHFMESPMA—dichlorofluorescein in MES buffer plus phorbolmyristate acetate

GFGA—(Gly-Phe-Gly-Ala)$_2$ Rho 110

RGES—(Arg-Gly-Glu-Ser)$_2$ Rho 110

DGLUC—(D-glucose)$_2$ fluorescein

DPO4—(PO$_4$)$_2$ fluorescein

GALAC—(D-galactose)$_2$ fluorescein

The reagents designated as "-M" or "modified" contain cofactors, modulators, inhibitors, etc. as shown in Table 1.

As illustrated from FIG. 16, utilizing only the eigenvector 1 and 2 or the squared deviation from the means analysis provides the correct diagnosis, whereas eigenvector 1 alone cannot distinguish from diseases #3 and #4. From Table 5, using three cell types and 18 enzyme concentrations, it is apparent that only six or eleven values are necessary to classify the unknown sample. The information most informative to the disease diagnosis came from the monocyte cell type and cathepsin, aminopeptidase and dipeptidyl peptidase enzymes.

Example 34

Analysis and Diagnosis of Normal and Diseased States using Artificial Intelligence Artificial intelligence was used to analyze data of cellular enzyme functions, and determine normal and disease states. Peptidases were used to distinguish leukemia from non-leukemia (output pattern). For input patterns lymphocyte and granulocyte cell types were used with aminopeptidases, cathepsins and dipeptidylpeptidase enzyme activities. In this Example, illustrated in Tables 6A–6C, three normals and three leukemia patients were used as known output patterns for the neural network to learn (in practice, the larger the learning set the more accurate unknown prediction will be). Unknowns were then presented to the learned algorithm as shown in the test case examples. Clinical diagnosis was confirmed by physicians. The trained neural network was able to correctly classify the leukemia from the non-leukemia.

TABLE 6A

THE USE OF PEPTIDASES TO DISTINGUISH LEUKEMIA FROM NON-LEUKEMIA

Aminopeptidases are Pro, Lys, Gly, ala; Cathpsin B and Gln/Ser, Val/Ser and Leu/gly; Cathepsin C is Thr/.Pro and Dipeptidylpeptidase IV is Gly/Pro.
The results of this study shows 100% predictability of leukemia when tested against normal and various diseases as specified.

LEARNED CASES:

Substrates: Pro, Lys, Gly, Ala, Gln/Ser, Thr/Pro, Val/Ser, Leu/Gly and Gly/Pro

| Patients: | ID # | DIAGNOSIS** |
|---|---|---|
| 1. | N191 | Normal |
| 2. | N192 | Normal |
| 3. | N193 | Normal |
| 4. | J4 | Acute Leukemia |
| 5. | J5 | Acute Myelogenous Leukemia |
| 6. | J4 | Acute Leukemia |

TEST CASES:

| Patients: | ID # | DIAGNOSIS** |
|---|---|---|
| 1. | J4 | Acute Leukemia |
| 2. | J19 | Chronic Lymphocytic Leukemia |
| 3. | J22 | Acute Myelogenous Leukemia |

TABLE 6A-continued

THE USE OF PEPTIDASES TO DISTINGUISH LEUKEMIA FROM NON-LEUKEMIA

Aminopeptidases are Pro, Lys, Gly, ala; Cathpsin B and Gln/Ser, Val/Ser and Leu/gly; Cathepsin C is Thr/.Pro and Dipeptidylpeptidase IV is Gly/Pro.
The results of this study shows 100% predictability of leukemia when tested against normal and various diseases as specified.

| | | |
|---|---|---|
| 4. | N199* | Normal |
| 5. | N200 | Normal |
| 6. | N201 | Normal |
| 7. | N206 | Normal |
| 8. | P68 | Abnormal - Tachycardia |
| 9. | P69 | Abnormal - Pancreatic Cancer |
| 10. | N191 | Normal |
| 11. | N192 | Normal |
| 12. | N193 | Normal |
| 13. | J4 | Acute Leukemia |
| 14. | J5 | Acute Myelogenous Leukemia |
| 15. | J4 | Acute Leukemia |
| 16. | P70 | Abnormal - Cirrhosis/Hemobilia |
| 17. | P71 | Abnormal - Acute Pyelonephritis |
| 18. | N194 | Normal |
| 19. | N195 | Normal |
| 20. | N197 | Normal |
| 21. | N202 | Normal |
| 22. | J22 | Acute Myelogenous Leukemia |

*Normal donor later found to have cervical cancer
Diagnosis provided by Jackson memorial Hospital: Normal donors were in-house employees

TABLE 6B

TEST CASE #4

Synopsis: Lymphs and Grans were used on Learn and Test cases with the following results:

| | | SCORE | |
|---|---|---|---|
| I.D. # | Negative | Leukemic | Diagnosis |
| 1 J4 | | 81.4 | Acute Leukemia |
| 2 J19 | | 100 | Chronic Lymphocytic Leukemia |
| 3 J22 | | 77.9 | Acute Myelogenous Leukemia |
| 4 N199* | 63.5 | | Normal |
| 5 N200 | 100 | | Normal |
| 6 N201 | 100 | | Normal |
| 7 N206 | 100 | | Normal |
| 8 P68 | 100 | | Tachycardia |
| 9 P69 | 100 | | Pancreatic Cancer |
| 10 N191 | 100 | | Normal |
| 11 N192 | 100 | | Normal |
| 12 N193 | 100 | | Normal |
| 13 J4 | | 100 | Acute Leukemia |
| 14 J5 | | 99.4 | Acute Myelogenous Leukemia |
| 15 J4 | | 99.3 | Acute Leukemia |
| 16 P70 | 100 | | Cirrhosis/Hemobilia |
| 17 P71 | 100 | | Acute Pyelonephritis |
| 18 N194 | 95.6 | | Normal |
| 19 N195 | 100 | | Normal |
| 20 N197 | 99 | | Normal |
| 21 N202 | 98.5 | | Normal |
| 22 J22 | | 72.4 | Acute Myelogenous Leukemia |

PREDICTION: 100%

| | Non-Leukemic | Leukemic |
|---|---|---|
| Dx Non-Leukemic | 15/15 | 0/15 |
| Dx Leukemic | 0/7 | 7/7 |

*Normal donor later found to have cervical cancer.

TABLE 6C

CLASSIFICATION OF NEW CASES

| J4 11/21/91 ACUTE LEUK. | | J5 11/27/91 A M L | | P70 CIRRHOSIS/HEMOBILIA | | P71 AC. PYELONEPHRITIS | |
|---|---|---|---|---|---|---|---|
| 2.72 | GP Lymphs | 3.40 | GP Lymphs | 6.68 | GP Lymphs | 3.55 | GP Lymphs |
| 0.47 | PRO L | 0.89 | PRO L | 0.56 | PRO L | 0.52 | PRO L |
| 0.77 | LYS L | 5.71 | LYS L | 1.02 | LYS L | 0.91 | LYS L |
| 14.02 | GLY L | 28.36 | GLY L | 54.84 | GLY L | 41.93 | GLY L |
| 86.00 | ALA L | 92.44 | ALA L | 141.87 | ALA L | 109.26 | ALA L |
| 0.05 | QS L | 0.07 | QS L | 0.04 | QS L | 0.05 | QS L |
| 2.30 | TP L | 1.32 | TP L | 1.89 | TP L | 1.86 | TP L |
| 0.05 | VS L | 0.05 | VS L | 0.04 | VS L | 0.08 | VS L |
| 0.16 | LG L | 0.23 | LG L | 0.79 | LG L | 0.68 | LG L |
| 10.75 | GP Grans | 8.95 | GP Grans | 16.42 | GP Grans | 11.07 | GP Grans |
| 5.77 | PRO G | 5.92 | PRO G | 0.66 | PRO G | 6.33 | PRO G |
| 3.01 | LYS G | 14.86 | LYS G | 2.33 | LYS G | 4.17 | LYS G |
| 27.79 | GLY G | 56.33 | GLY G | 88.42 | GLY G | 59.35 | GLY G |
| 193.43 | ALA G | 194.85 | ALA G | 236.23 | ALA G | 185.37 | ALA G |
| 0.22 | QS G | 1.24 | QS G | 0.19 | QS G | 0.51 | QS G |
| 5.96 | TP G | 2.72 | TP G | 4.02 | TP G | 4.37 | TP G |
| 0.37 | VS G | 1.13 | VS G | 0.26 | VS G | 0.69 | VS G |
| 0.85 | LG G | 2.51 | LG G | 2.20 | LG G | 4.00 | LG G |
| 0.00 | NORMAL | 0.63 | NORMAL | 100.00 | NORMAL | 100.00 | NORMAL |
| 100.00 | LEUKEMIC | 99.37 | LEUKEMIC | 0.00 | LEUKEMIC | 0.00 | LEUKEMIC |

| N194 NORMAL | | N195 NORMAL | | N197 NORMAL | | N202 NORMAL | |
|---|---|---|---|---|---|---|---|
| 5.22 | GP Lymphs | 5.24 | GP Lymphs | 5.97 | GP Lymphs | 6.61 | GP Lymphs |
| 0.86 | PRO L | 0.88 | PRO L | 0.57 | PRO L | 0.89 | PRO L |
| 0.93 | LYS L | 1.07 | LYS L | 0.70 | LYS L | 0.71 | LYS L |
| 39.76 | GLY L | 48.18 | GLY L | 42.96 | GLY L | 44.55 | GLY L |
| 97.02 | ALA L | 118.81 | ALA L | 96.36 | ALA L | 118.37 | ALA L |

TABLE 6C-continued

CLASSIFICATION OF NEW CASES

| | | | | | | | |
|---|---|---|---|---|---|---|---|
| 0.02 | QS L | 0.04 | QS L | 0.06 | QS L | 0.01 | QS L |
| 1.82 | TP L | 1.90 | TP L | 1.96 | TP L | 2.49 | TP L |
| 0.07 | VS L | 0.06 | VS L | 0.11 | VS L | 0.04 | VS L |
| 2.06 | LG L | 1.93 | LG L | 1.79 | LG L | 1.28 | LG L |
| 12.49 | GP Grans | 13.31 | GP Grans | 15.85 | GP Grans | 14.44 | GP Grans |
| 3.75 | PRO G | 4.70 | PRO G | 3.76 | PRO G | 4.96 | PRO G |
| 1.56 | LYS G | 2.53 | LYS G | 1.59 | LYS G | 13.22 | LYS G |
| 60.30 | GLY G | 79.13 | GLY G | 76.88 | GLY G | 66.22 | GLY G |
| 164.00 | ALA G | 221.28 | ALA G | 188.20 | ALA G | 201.17 | ALA G |
| 0.07 | QS G | 0.21 | QS G | 0.24 | QS G | 0.08 | QS G |
| 3.77 | TP G | 3.74 | TP G | 3.82 | TP G | 4.44 | TP G |
| 0.29 | VS G | 0.37 | VS G | 0.58 | VS G | 0.24 | VS G |
| 3.52 | LG G | 4.11 | LG G | 4.41 | LG G | 2.70 | LG G |
| 95.56 | NORMAL | 100.00 | NORMAL | 99.02 | NORMAL | 98.62 | NORMAL |
| 4.46 | LEUKEMIC | 0.00 | LEUKEMIC | 1.00 | LEUKEMIC | 1.32 | LEUKEMIC |

| J22 12/9/91 AML | | J4 12/2/91 A L | |
|---|---|---|---|
| 3.01 | GP Lymphs | 3.80 | GP Lymphs |
| 0.44 | PRO L | 0.29 | PRO L |
| 1.20 | LYS L | 1.81 | LYS L |
| 27.14 | GLY L | 27.32 | GLY L |
| 83.48 | ALA L | 68.10 | ALA L |
| 0.02 | QS L | 0.01 | QS L |
| 1.02 | TP L | 1.46 | TP L |
| 0.04 | VS L | 0.03 | VS L |
| 0.61 | LG L | 0.18 | LG L |
| 11.52 | GP Grans | 11.08 | GP Grans |
| 3.53 | PRO G | 3.59 | PRO G |
| 1.90 | LYS G | 4.09 | LYS G |
| 38.47 | GLY G | 47.74 | GLY G |
| 157.48 | ALA G | 139.53 | ALA G |
| 0.24 | QS G | 0.44 | QS G |
| 2.51 | TP G | 2.59 | TP G |
| 0.32 | VS G | 0.14 | VS G |
| 1.94 | LG G | 0.79 | LG G |
| 27.64 | NORMAL | 0.31 | NORMAL |
| 72.43 | LEUKEMIC | 99.81 | LEUKEMIC |

| J4 12/3/91 ACUTE LEUK. | | J19 11/27/91 C L L | | J22 12/2/91 A M L | | N199 NORMAL | |
|---|---|---|---|---|---|---|---|
| 4.17 | GP Lymphs | 1.73 | GP Lymphs | 1.73 | GP Lymphs | 5.55 | GP Lymphs |
| 0.24 | PRO L | 0.44 | PRO L | 0.40 | PRO L | 1.02 | PRO L |
| 1.64 | LYS L | 0.98 | LYS L | 0.74 | LYS L | 0.33 | LYS L |
| 31.51 | GLY L | 11.39 | GLY L | 24.50 | GLY L | 30.68 | GLY L |
| 74.64 | ALA L | 47.78 | ALA L | 84.42 | ALA L | 91.07 | ALA L |
| 0.06 | QS L | 0.06 | QS L | 0.02 | QS L | 0.02 | QS L |
| 1.18 | TP L | 0.50 | TP L | 0.99 | TP L | 1.86 | TP L |
| 0.04 | VS L | 0.01 | VS L | 0.01 | VS L | 0.03 | VS L |
| 0.19 | LG L | 0.02 | LG L | 0.02 | LG L | 0.85 | LG L |
| 1.28 | GP Grans | 1.39 | GP Grans | 13.98 | GP Grans | 13.41 | GP Grans |
| 3.68 | PRO G | 5.50 | PRO G | 4.03 | PRO G | 4.85 | PRO G |
| 3.19 | LYS G | 4.41 | LYS G | 1.41 | LYS G | 0.95 | LYS G |
| 48.53 | GLY G | 48.80 | GLY G | 34.02 | GLY G | 45.00 | GLY G |
| 138.89 | ALA G | 143.11 | ALA G | 157.12 | ALA G | 157.30 | ALA G |
| 0.19 | QS G | 1.16 | QS G | 0.10 | QS G | 0.05 | QS G |
| 1.93 | TP G | 2.95 | TP G | 2.33 | TP G | 3.71 | TP G |
| 0.23 | VS G | 2.83 | VS G | 0.22 | VS G | 0.14 | VS G |
| 1.06 | LG G | 36.35 | LG G | 1.56 | LG G | 2.02 | LG G |
| 18.76 | NORMAL | 0.00 | NORMAL | 22.16 | NORMAL | 63.52 | NORMAL |
| 81.42 | LEUKEMIC | 100.00 | LEUKEMIC | 77.90 | LEUKEMIC | 36.50 | LEUKEMIC |

| N200 NORMAL | | N201 NORMAL | | N206 NORMAL | | P68 TACHYCARDIA | |
|---|---|---|---|---|---|---|---|
| 5.38 | GP Lymphs | 6.53 | GP Lymphs | 7.09 | GP Lymphs | 5.92 | GP Lymphs |
| 0.74 | PRO L | 1.10 | PRO L | 1.28 | PRO L | 0.70 | PRO L |
| 0.90 | LYS L | 1.05 | LYS L | 1.65 | LYS L | 1.51 | LYS L |
| 42.28 | GLY L | 45.32 | GLY L | 55.56 | GLY L | 59.29 | GLY L |
| 101.38 | ALA L | 106.72 | ALA L | 122.71 | ALA L | 1471.10 | ALA L |
| 0.01 | QS L | 0.02 | QS L | 0.04 | QS L | 0.02 | QS L |
| 2.39 | TP L | 1.88 | TP L | 2.89 | TP L | 1.90 | TP L |

TABLE 6C-continued

CLASSIFICATION OF NEW CASES

| | | | | | | | |
|---|---|---|---|---|---|---|---|
| 0.06 | VS L | 0.07 | VS L | 0.28 | VS L | 0.05 | VS L |
| 1.55 | LG L | 1.57 | LG L | 3.12 | LG L | 0.78 | LG L |
| 12.74 | GP Grans | 15.92 | GP Grans | 17.96 | GP Grans | 16.08 | GP Grans |
| 4.04 | PRO G | 6.42 | PRO G | 6.13 | PRO G | 7.19 | PRO G |
| 1.46 | LYS G | 2.06 | LYS G | 3.11 | LYS G | 3.09 | LYS G |
| 59.39 | GLY G | 75.48 | GLY G | 91.93 | GLY G | 100.00 | GLY G |
| 171.06 | ALA G | 206.06 | ALA G | 232.57 | ALA G | 276.07 | ALA G |
| 0.06 | QS G | 0.09 | QS G | 0.27 | QS G | 0.33 | QS G |
| 4.69 | TP G | 4.23 | TP G | 5.98 | TP G | 5.63 | TP G |
| 0.24 | VS G | 0.32 | VS G | 1.03 | VS G | 0.33 | VS G |
| 3.40 | LG G | 3.14 | LG G | 6.01 | LG G | 2.52 | LG G |
| 100.00 | NORMAL | 100.00 | NORMAL | 100.00 | NORMAL | 100.00 | NORMAL |
| 0.00 | LEUKEMIC | 0.00 | LEUKEMIC | 0.00 | LEUKEMIC | 0.00 | LEUKEMIC |
| P69 PANCREATIC CA | | N191 NORMAL | | N192 NORMAL | | N193 NORMAL | |
| 6.80 | GP Lymphs | 4.14 | GP Lymphs | 3.00 | GP Lymphs | 3.00 | GP Lymphs |
| 0.66 | PRO L | 0.69 | PRO L | 1.14 | PRO L | 0.95 | PRO L |
| 1.22 | LYS L | 1.18 | LYS L | 0.56 | LYS L | 0.52 | LYS L |
| 67.38 | GLY L | 43.57 | GLY L | 37.47 | GLY L | 39.30 | GLY L |
| 130.34 | ALA L | 95.72 | ALA L | 103.31 | ALA L | 100.50 | ALA L |
| 0.31 | QS L | 0.02 | QS L | 0.03 | QS L | 0.03 | QS L |
| 2.26 | TP L | 2.14 | TP L | 2.12 | TP L | 2.33 | TP L |
| 0.18 | VS L | 0.14 | VS L | 0.08 | VS L | 0.09 | VS L |
| 2.00 | LG L | 2.42 | LG L | 3.45 | LG L | 1.56 | LG L |
| 16.21 | GP Grans | 11.20 | GP Grans | 11.22 | GP Grans | 8.87 | GP Grans |
| 5.70 | PRO G | 4.34 | PRO G | 4.34 | PRO G | 4.75 | PRO G |
| 2.14 | LYS G | 1.20 | LYS G | 1.20 | LYS G | 1.43 | LYS G |
| 88.04 | GLY G | 73.20 | GLY G | 48.67 | GLY G | 63.33 | GLY G |
| 204.02 | ALA G | 177.32 | ALA G | 154.84 | ALA G | 178.64 | ALA G |
| 0.37 | QS G | 0.19 | QS G | 0.15 | QS G | 0.14 | QS G |
| 4.21 | TP G | 4.73 | TP G | 4.62 | TP G | 4.96 | TP G |
| 0.57 | VS G | 0.64 | VS G | 0.40 | VS G | 0.44 | VS G |
| 3.53 | LG G | 5.37 | LG G | 6.78 | LG G | 3.55 | LG G |
| 100.00 | NORMAL | 100.00 | NORMAL | 100.00 | NORMAL | 98.77 | NORMAL |
| 0.00 | LEUKEMIC | 0.00 | LEUKEMIC | 0.00 | LEUKEMIC | 1.23 | LEUKEMIC |

TABLE 7

ABERRANT ENZYME ACTIVITIES IN 10 FEBRILE CHILDREN

| PATIENTS | | P88 | P89 | P92 | P95 | P96 | P97 | P99 | P101 | P102 | P103 |
|---|---|---|---|---|---|---|---|---|---|---|---|
| | | | | | LYMPHS | | | | | | |
| 1 | Leu | + | + | + | + | + | o | o | + | o | + |
| 2 | Ala | o | o | o | | | o | | | o | o |
| 3 | Pro | | | o | | | o | | | | o |
| 4 | Lys | | | o | | | o | | | | o |
| 5 | Gly | o | — | o | | | o | | | o | o |
| 6 | Ser | | | o | | | o | | | | o |
| 7 | Arg | | | o | o | — | + | o | | o | o |
| 8 | Arg-TFA | | | o | | | o | | | | o |
| 9 | Asp | | | o | | | o | | | | o |
| 10 | Val/Ser | | | — | o | o | o | + | — | — | o |
| 11 | Val/Ser-M | | | o | | | o | | | | o |
| 12 | Val/Lys | o | o | o | — | o | o | + | o | o | o |
| 13 | Val/Lys-M | o | o | o | + | + | + | | o | o | o |
| 14 | Gln/Ser | | | o | | | o | | | | o |
| 15 | Gln/Ser-M | | | o | | | o | | | | o |
| 16 | Leu/Gly | | | o | — | — | o | + | — | | o |
| 17 | Leu/Gly-M | | | o | | | o | | | | o |
| 18 | Lys/Ala | o | o | o | o | o | o | o | | o | o |
| 19 | Lys/Ala-M | o | o | o | o | o | o | + | | o | o |
| 20 | Z-Ala/Ala | | | — | — | — | — | o | — | o | — |
| 21 | Z-Ala/Ala-M | | | — | | | — | | | | |
| 22 | Z-Gly/Pro | o | — | — | — | — | o | | — | | |
| 23 | Z-Gly/Pro-M | — | — | | | | | | | | |
| 24 | Gly/Leu | | | o | | | o | | | | o |
| 25 | Gly/Leu-M | | | o | | | o | | | | o |
| 26 | Ala/Gly | — | — | — | — | — | — | o | | o | o |

TABLE 7-continued

ABERRANT ENZYME ACTIVITIES IN 10 FEBRILE CHILDREN

| PATIENTS | | P88 | P89 | P92 | P95 | P96 | P97 | P99 | P101 | P102 | P103 |
|---|---|---|---|---|---|---|---|---|---|---|---|
| 27 | Ala/Gly-M | | | − | | | − | | | | − |
| 28 | Ala/Ala-TFA | | | o | | | o | | | | o |
| 29 | Ala/Ala-M | | | o | | | o | | | | o |
| 30 | TP 6.5 | − | − | − | | | o | | | | o |
| 31 | TP 6.5-M | | | | | | o | | | | o |
| 32 | LLR | | | o | | | o | | | | o |
| 33 | LLR-M | | | | | | | | | | |
| 34 | LGLG | | | o | | | o | | | | o |
| 35 | LGLG-M | | | | | | | | | | |
| 36 | FDA | o | + | + | + | + | o | o | + | o | + |
| 37 | FDA-NaF | o | + | + | + | + | o | o | + | o | + |
| 38 | DCFH | o | + | + | + | + | o | o | + | o | + |
| 40 | DCFH_PMA | o | + | + | + | + | + | o | + | o | + |
| 42 | GPLGP | o | o | − | | | − | | | o | − |
| 43 | GPLGP-M | | | − | | | o | | | | o |
| 44 | GFGA | o | o | o | | | o | | | | o |
| 45 | RGES | o | o | o | o | + | o | o | o | o | o |
| 46 | DGLUC | o | o | o | | | | | | | − |
| 47 | DPO4 | o | o | o | o | − | o | o | o | o | o |
| 48 | GALAC | o | o | o | | | o | | | | o |
| 49 | TP 8.7-M | | | − | | | o | | | | o |
| 50 | TP 8.7 | | | | | | o | | | | o |
| 51 | DIGLUC | | | o | | | o | | | | |
| | | Enteritis | Viral Stomatitis | Adenitis | Viral Syndrome | Viral Syndrome | Pyelonephritis | Viral Syndrome | Fever — Unknown Origin | UTI | Viral Syndrome |

| MONOS | | | | | | | | | | | |
|---|---|---|---|---|---|---|---|---|---|---|---|
| 1 | Leu | + | + | + | + | + | + | o | + | o | + |
| 2 | Ala | o | o | + | | | + | | | + | o |
| 3 | Pro | | | o | | | o | | | | o |
| 4 | Lys | | | + | | | o | | | | + |
| 5 | Gly | o | o | o | | | + | | | | o |
| 6 | Ser | | | o | | | o | | | | + |
| 7 | Arg | | | + | o | o | o | o | | o | + |
| 8 | Arg-TFA | | | + | | | o | | | | + |
| 9 | Asp | | | o | | | o | | | | o |
| 10 | Val/Ser | | | − | − | o | − | + | − | − | o |
| 11 | Val/Ser-M | | | | | | − | | | | o |
| 12 | Val/Lys | − | − | o | o | o | o | + | o | − | + |
| 13 | Val/Lys-M | − | o | − | o | o | o | | − | | − |
| 14 | Gln/Ser | | | o | | | o | | | | + |
| 15 | Gln/Ser-M | | | − | | | − | | | | o |
| 16 | Leu/Gly | | | o | | o | o | + | o | | o |
| 17 | Leu/Gly-M | | | − | | | o | | | | o |
| 18 | Lys/Ala | o | o | o | o | o | + | o | + | o | o |
| 19 | Lys/Ala-M | − | − | − | − | − | − | o | | o | − |
| 20 | Z-Ala/Ala | | | − | − | o | o | o | − | o | o |
| 21 | Z-Ala/Ala-M | | | o | | | o | | | | o |
| 22 | Z-Gly/Pro | o | o | − | o | o | o | o | − | o | o |
| 23 | Z-Gly/Pro-M | − | o | − | | | o | | | | o |
| 24 | Gly/Leu | | | o | | | o | | | | o |
| 25 | Gly/Leu-M | | | − | | | o | | | | o |
| 26 | Ala/Gly | − | o | − | o | o | o | o | | o | o |
| 27 | Ala/Gly-M | | | − | | | o | | | | o |
| 28 | Ala/Ala-TFA | | | | | | + | | | | + |
| 29 | Ala/Ala-M | | | − | | | o | | | | o |
| 30 | TP 6.5 | − | − | − | | | o | | | | o |
| 31 | TP 6.5-M | | | − | | | o | | | | o |
| 32 | LLR | | | o | | | o | | | | + |
| 33 | LLR-M | | | | | | | | | | |
| 34 | LGLG | | | o | | | o | | | | o |
| 35 | LGLG-M | | | − | | | − | | | | + |
| 36 | FDA | o | + | + | + | + | + | o | + | o | + |
| 37 | FDA-NaF | o | + | + | + | + | o | + | + | o | + |
| 38 | DCFH | o | + | + | + | + | + | o | + | o | + |
| 40 | DCFH_PMA | o | + | + | + | + | + | o | + | o | + |
| 42 | GPLGP | − | o | − | | | − | | | | − |
| 43 | GPLGP-M | | | o | | | + | | | | + |
| 44 | GFGA | o | o | o | | | o | | | | o |
| 45 | RGES | − | o | + | o | o | o | o | − | o | o |
| 46 | DGLUC | − | o | − | | | | | | | + |
| 47 | GPO4 | o | + | + | + | | o | o | + | o | + |
| 48 | GALAC | o | o | o | | | o | | | | o |
| 49 | TP 8.7-M | | | − | | | o | | | | o |

TABLE 7-continued

ABERRANT ENZYME ACTIVITIES IN 10 FEBRILE CHILDREN

| PATIENTS | | P88 | P89 | P92 | P95 | P96 | P97 | P99 | P101 | P102 | P103 |
|---|---|---|---|---|---|---|---|---|---|---|---|
| 50 | TP 8.7 | | | − | | | o | | | | o |
| 51 | DIGLUC | | | + | | | o | | | | + |
| | | Enteritis | Viral Stomatitis | Adenitis | Viral Syndrome | Viral Syndrome | Pyelonephritis | Viral Syndrome | Fever — Unknown Origin | UTI | Viral Syndrome |

GRANS

| | | P88 | P89 | P92 | P95 | P96 | P97 | P99 | P101 | P102 | P103 |
|---|---|---|---|---|---|---|---|---|---|---|---|
| 1 | Leu | + | + | + | + | + | o | o | + | o | + |
| 2 | Ala | o | o | + | | | + | | | o | o |
| 3 | Pro | | | o | | | o | | | | o |
| 4 | Lys | | | + | | | + | | | | o |
| 5 | Gly | o | o | o | | | o | | | o | o |
| 6 | Ser | | | + | | | o | | | | o |
| 7 | Arg | | | + | o | o | + | + | | o | + |
| 8 | Arg-TFA | | | + | | | + | | | | + |
| 9 | Asp | | | o | | | o | | | | o |
| 10 | Val/Ser | | | − | − | o | o | + | | − | o |
| 11 | Val/Ser-M | | | o | | | o | | | | o |
| 12 | Val/Lys | − | − | o | − | o | + | + | o | o | o |
| 13 | Val/Lys-M | − | o | o | + | + | o | | o | − | o |
| 14 | Gln/Ser | | | + | | | o | | | | + |
| 15 | Gln/Ser-M | | | + | | | o | | | | o |
| 16 | Leu/Gly | | | o | − | o | o | + | o | o | − |
| 17 | Leu/Gly-M | | | − | | | − | | | | − |
| 18 | Lys/Ala | o | o | o | o | o | o | o | + | o | o |
| 19 | Lys/Ala-M | o | o | o | o | o | o | o | o | o | o |
| 20 | Z-Ala/Ala | | | − | − | o | o | o | | o | o |
| 21 | Z-Ala/Ala-M | | | o | | | o | | | | o |
| 22 | Z-Gly/Pro | o | | − | − | o | o | o | | | o |
| 23 | Z-Gly/Pro-M | − | | − | | | o | | | | o |
| 24 | Gly/Leu | | | o | | | + | | | | o |
| 25 | Gly/Leu-M | | | o | | | o | | | | o |
| 26 | Ala/Gly | + | o | o | o | o | o | o | | o | o |
| 27 | Ala/Gly-M | | | − | | | o | | | | o |
| 28 | Ala/Ala-TFA | | | + | | | + | | | | + |
| 29 | Ala/Ala-M | | | o | | | o | | | | o |
| 30 | TP 6.5 | − | − | − | | | | | | | o |
| 31 | TP 6.5-M | | | − | | | o | | | | o |
| 32 | LLR | | o | | | | o | | | | o |
| 33 | LLR-M | | | | | | | | | | |
| 34 | LGLG | | | o | | | o | | | | o |
| 35 | LGLG-M | | | o | | | o | | | | o |
| 36 | FDA | o | + | + | + | + | + | o | + | o | + |
| 37 | FDA-NaF | o | + | + | + | + | o | + | + | o | + |
| 38 | DCFH | o | + | + | + | + | + | o | + | o | + |
| 40 | DCFH_PMA | o | + | + | + | + | + | o | + | o | + |
| 42 | GPLGP | o | o | − | | | − | | | o | − |
| 43 | GPLGP-M | | | − | | | o | | | | o |
| 44 | GFGA | o | o | o | | | o | | | | o |
| 45 | RGES | o | + | + | o | o | o | o | o | o | o |
| 46 | DGLUC | o | + | + | | | o | | | | + |
| 47 | GPO4 | o | + | + | o | o | o | o | + | o | + |
| 48 | GALAC | o | o | o | | | o | | | | o |
| 49 | TP 8.7-M | | | − | | | o | | | | o |
| 50 | TP 8.7 | | | | | | o | | | | o |
| 51 | DIGLUC | | | o | | | o | | | | o |
| | | Enteritis | Viral Stomatitis | Adenitis | Viral Syndrome | Viral Syndrome | Pyelonephritis | Viral Syndrome | Fever — Unknown Origin | UTI | Viral Syndrome |

Figure 17A:
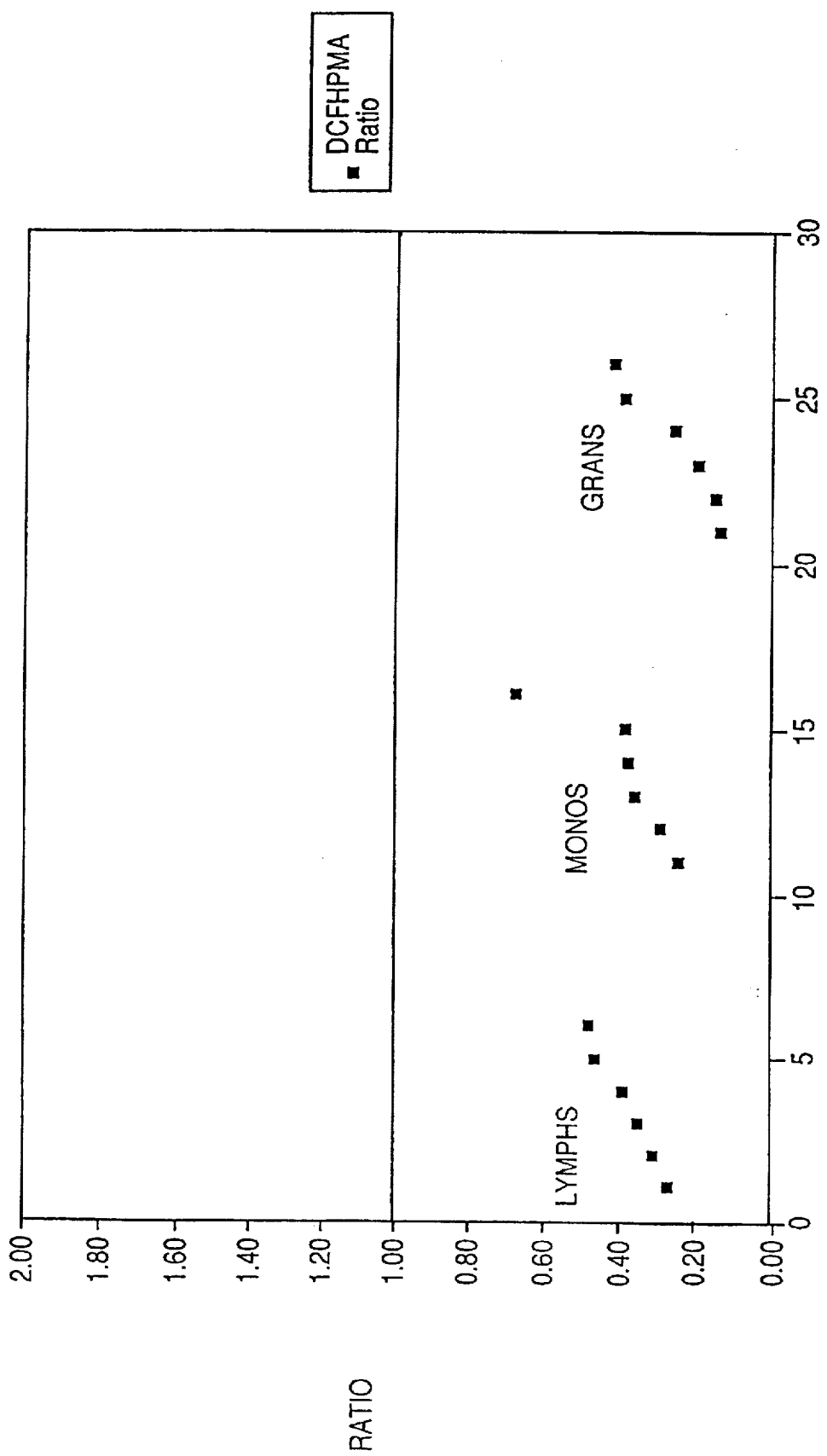
Figure 17B:
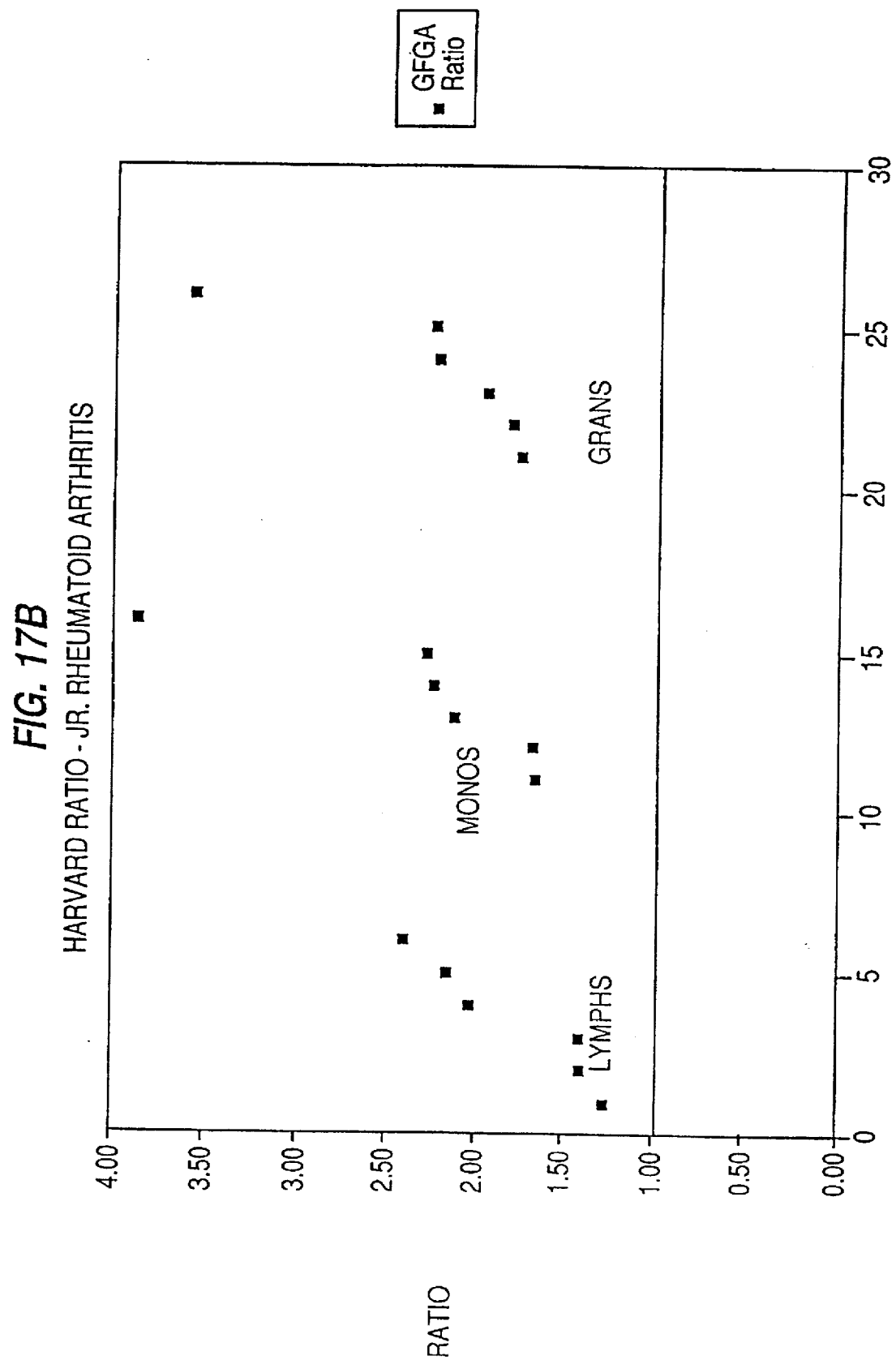

\+ >0.25 Increase over normal range
− >0.25 Decrease over normal range
o No Change The use of neural networks has also been used to reduce a large data set (3 cell types×45 enzyme assays×5 or more diseases) to only the important cell types and enzyme assays for classification of a disease. This can be visualized by graphing the ratio of the diseases to the mean of the normal of all patients with the disease, as illustrated in FIGS. 17A, 17B and 17C to reduce the data set, as illustrated in Table 5, and providing an HLA score sheet, illustrated in Table 7, showing greater than ±25% of the mean normal enzyme activity for that cell type.

Example 35

Figure 18A:
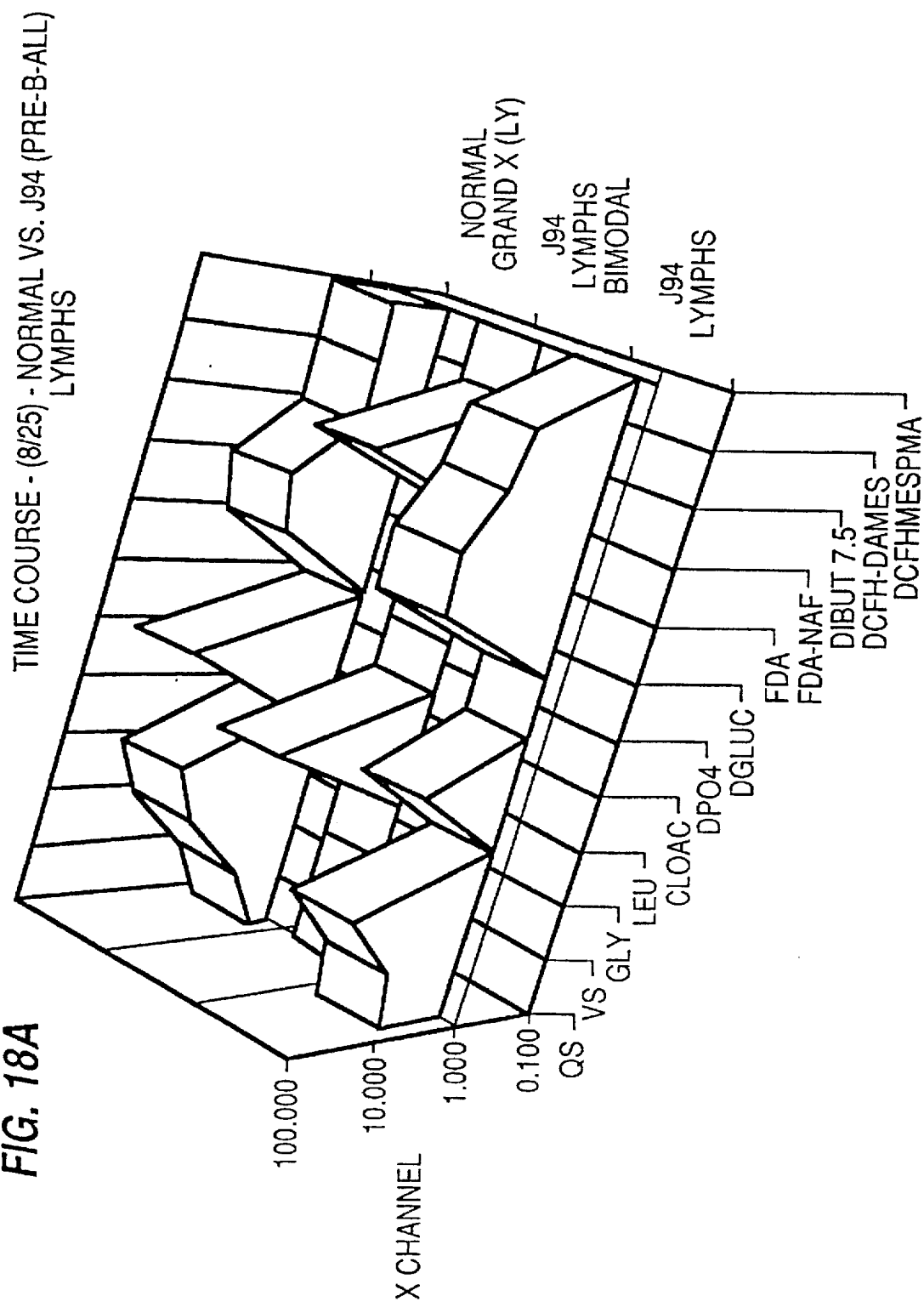
Figure 18B:
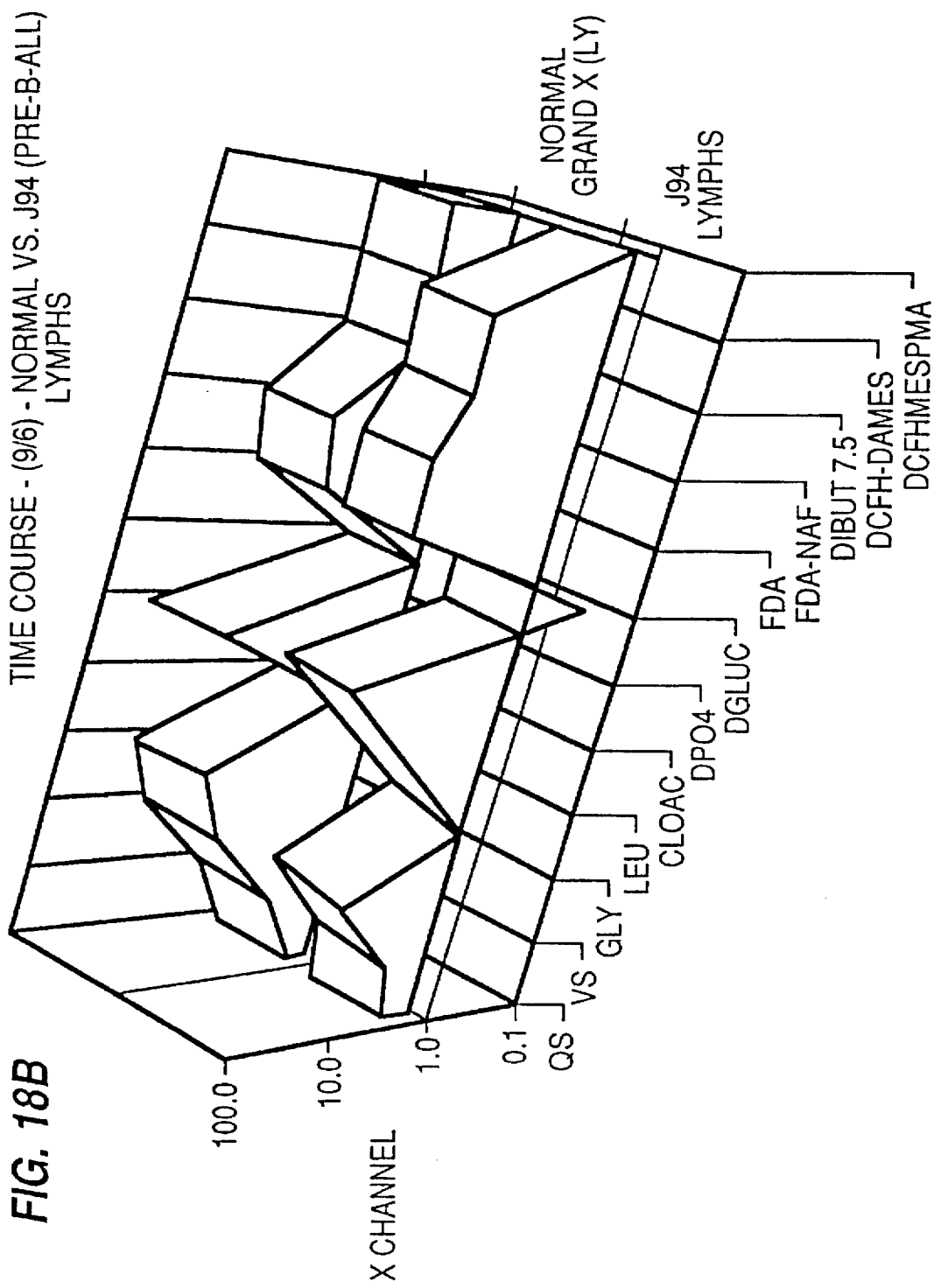
Figure 18C:
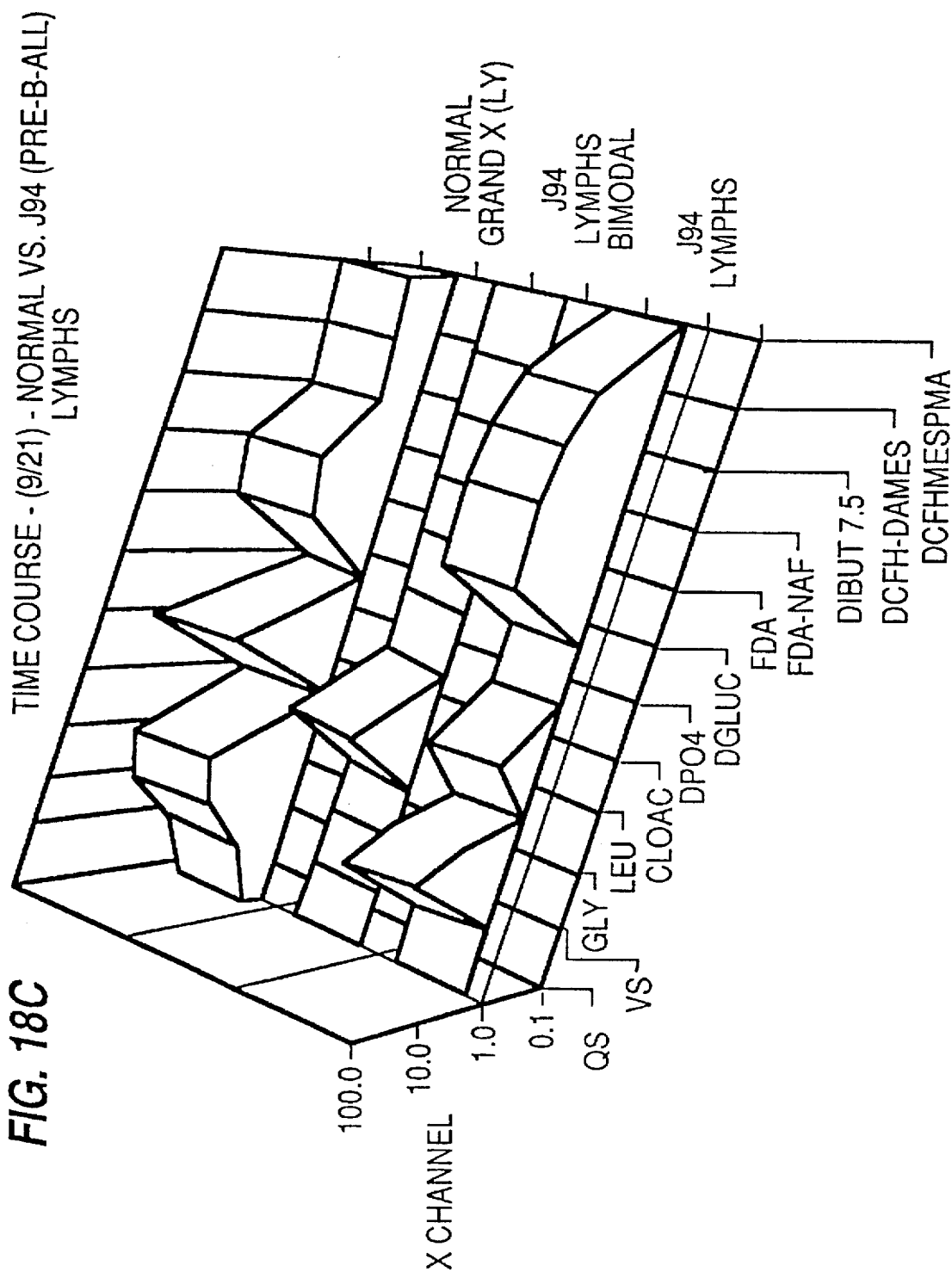
Figure 18D:
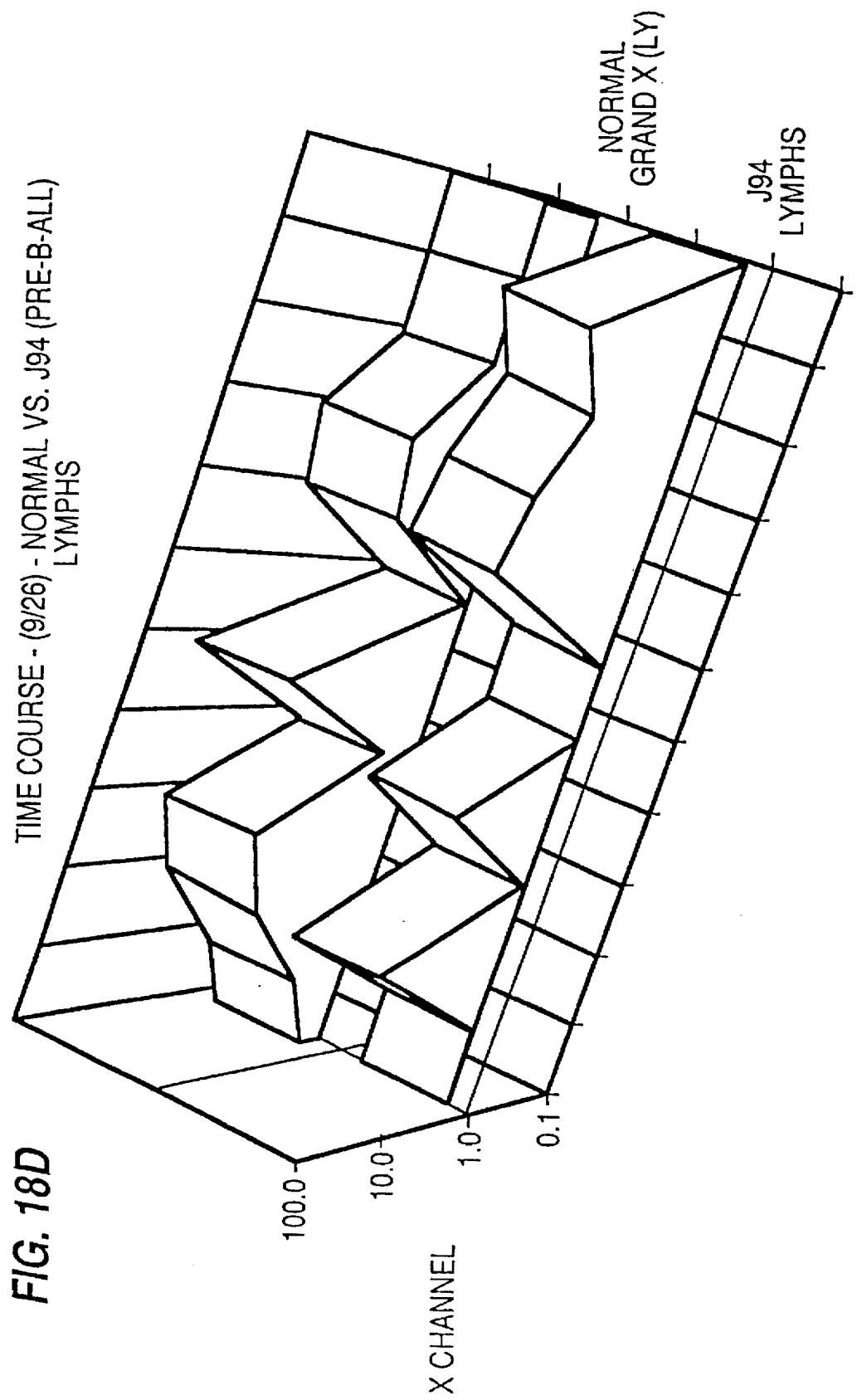
Figure 18E:
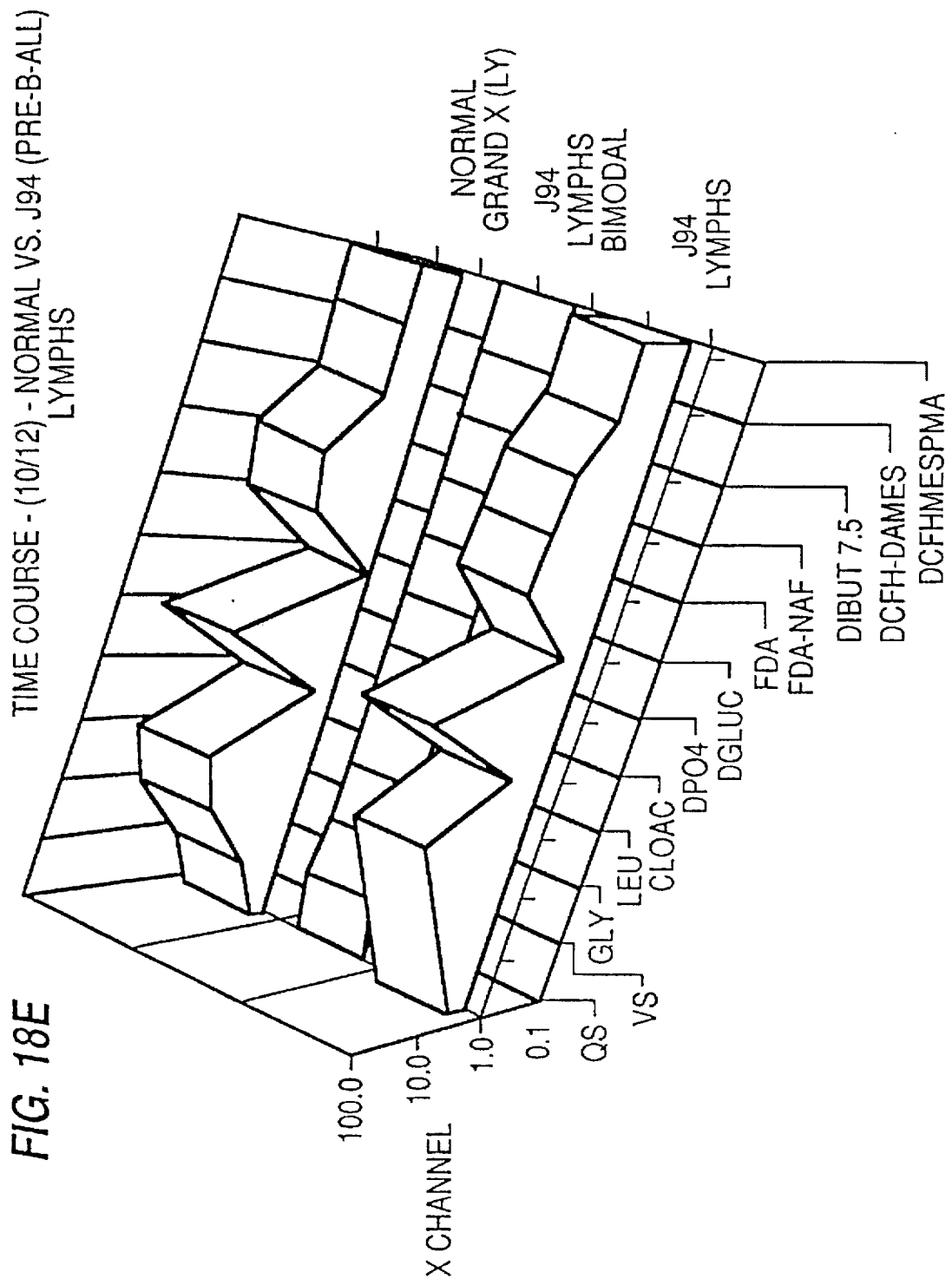
Figure 18F:
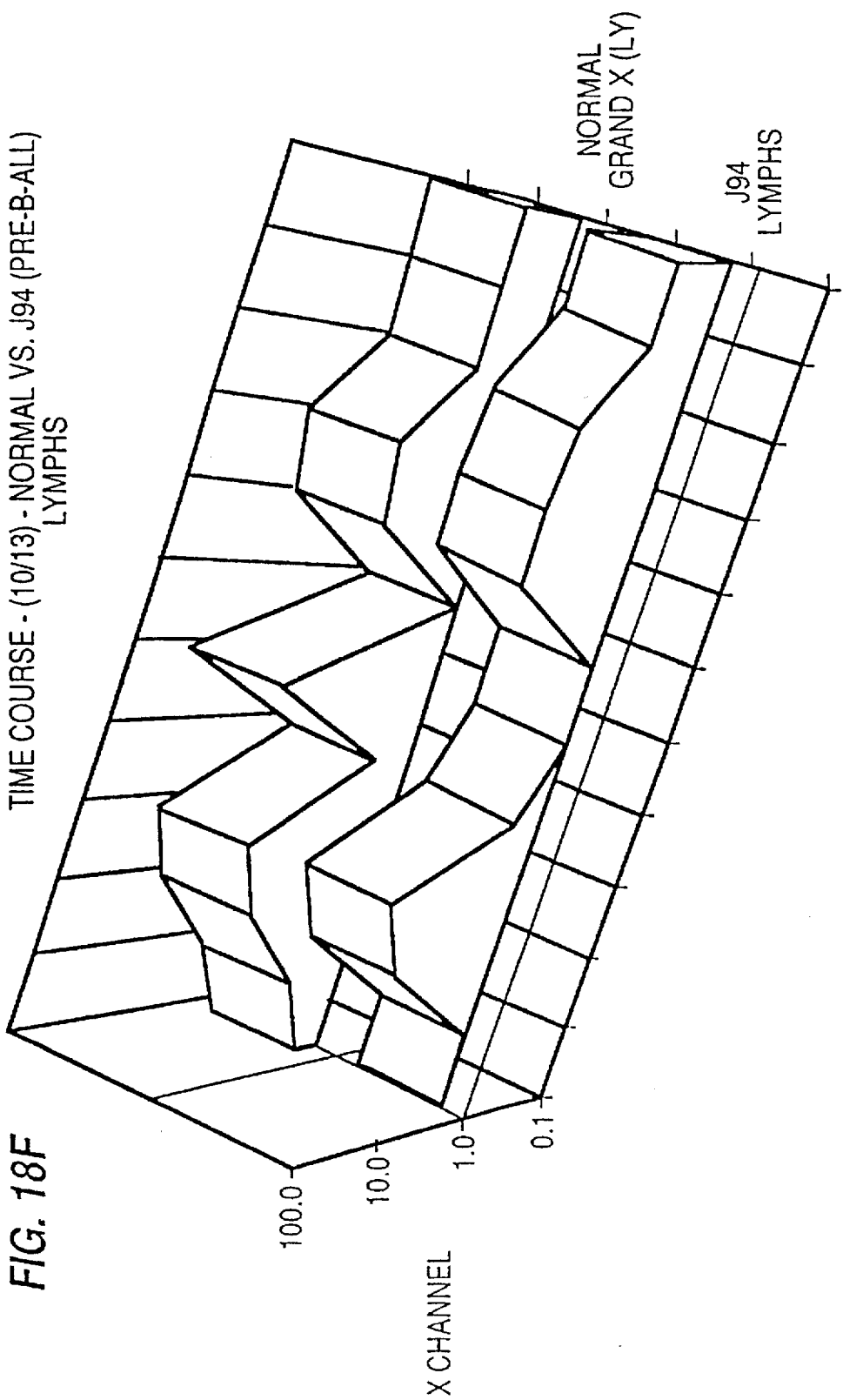

Determination of Disease Progression Using Artificial Intelligence Based Analysis of Cellular Enzyme Function Progression of disease during treatment and monitoring a return to normalcy during treatment are shown in FIGS. 18A–18F and the raw data is summarized in FIG. 18G. The time measurements were monitored by three-dimensional plotting of cell-type enzyme activity patterns of the sample values and normal values. FIG. 18A illustrates raw data for lymphocyte cells of a particular patient as compared to the normal data. The raw data in FIG. 18A was taken on August 25. FIG. 18B illustrates the raw data of the diseased patient as compared with normal data on September 6. Similarly, FIGS. 18C–18F illustrate raw data for the diseased patient as compared to normal data on September 21, September 26, October 12, and October 13, respectively. The time progression illustrated in FIGS. 18A–18F clearly indicates by October 13, the raw data of the "diseased patient" is now virtually identical to the normal data. The increase in stage or complication with additional disease states may also be performed in a manner similar to that illustrated in FIGS. 18A–18F.

All patents and publications referred to in this application are hereby incorporated by reference in their entirety.

The invention has been described with reference to the preferred embodiments. It should be understood, however, that the invention is not so limited, and the scope of the invention should be determined with reference to the following claims, rather than to the foregoing specification.

We claim:

1. A method for detecting the presence or absence of an abnormality in the activity of an enzyme in a metabolically active whole cell, comprising:
   (a) contacting a reference, metabolically active whole cell having a normally functioning enzyme with a medium containing a cell permeable water soluble assay compound having the ability to pass through a cell membrane or a water soluble physiologically acceptable salt thereof having the ability to pass through a cell membrane, said assay compound comprising a fluorogenic indicator group and an unblocked leaving group, said leaving group being selected for cleavage by said enzyme, said indicator group being in a non-fluorescent first state when bonded to said leaving group, and being in a fluorescent second state excitable at a wavelength above 450 nm when said leaving group is cleaved from said indicator group by said enzyme, for a period of time sufficient for said assay compound to be transferred into said cell and for said leaving group to be cleaved inside said cell from said indicator group by said enzyme, wherein said assay compound has sufficient purity so that fluorescence of impurities in said assay compound is less than autofluorescence of the metabolically active whole cell;
   (b) sensing for said fluorescent second state of said indicator group for the reference, metabolically active whole cell to produce reference results;
   (c) contacting a test, metabolically active whole cell with said medium for said period of time;
   (d) sensing for said fluorescent second state of said indicator group for the test, metabolically active whole cell to produce test results; and
   (e) comparing the reference results of reference test, metabolically active whole cell in said step (b) with the test results obtained from said test metabolically active whole cell in said step (d) thereby detecting the presence or absence of said abnormality in activity of said enzyme in said metabolically active whole cell.

2. The method of claim 1, wherein said step (b) includes measuring an intensity of said fluorescent second state against time.

3. The method of claim 1, wherein said step (b) includes measuring a magnitude of said fluorescent second state at a point of time.

4. The method of claim 1, wherein said step (e), the test results and the reference results are compared to a genetic analysis of the test, metabolically active whole cell.

5. The method of claim 1, wherein said step (e) is performed by a computer.

6. The method of claim 5, wherein the computer includes a neural network with back propagation for classifying the test results.

7. The method of claim 5, wherein the computer includes an expert system with Look-Up tables for classifying the test results.

8. The method of claim 1, said step (e) including performing a Non-Negative Least Squares technique on the test results and the reference results to classify the test results.

9. The method of claim 1, said step (e) including performing an analysis of variance technique on the test results and the reference results to classify the test results.

10. The method of claim 9, wherein the analysis of variance technique includes determining a plurality of eigenvectors and eigenvalues.

11. The method of claim 1, said step (e) including performing an analysis of variance technique on the test results and the reference results to obtain a reduced set of test results and reference results.

12. The method of claim 11, said step (e) further including performing a non-Negative Least Squares technique on the reduced set of test results and reference results to classify the test results.

13. The method of claim 11, said step (e) further including inputting the reduced set of test results and reference results to a Neural Network with back propagation to classify the test results.

14. The method of claim 11, said step (e) further including inputting the reduced set of test results and reference results to an expert system with Look-Up tables to classify the test results.

15. The method of claim 1, wherein said step (e) compares the test results and the reference results to monitor enzyme activity representing morphology or cell type of the test, metabolically active whole cell.

16. The method of claim 1, wherein said step (e) compares the test results and the reference results to monitor enzyme activity of the test, metabolically active whole cell over time.

17. The method of claim 1, wherein said step (e) diagnoses the test, metabolically active whole cell for leukemia, wherein the leaving group includes at least one member selected from the group consisting of Pro, Lys, Gly, Ala, Gln-Ser, Thr-Pro, Val-Ser, Leu-Gly, and Gly-Pro and the test, metabolically active whole cell is a lymphocyte cell or a granulocyte cell.

18. A method of performing an assay for detecting the presence or absence of a disease which is characterized by an abnormal enzyme activity comprising:
   (a) contacting a test, metabolically active whole cell with a cell permeable water soluble assay compound or water soluble physiologically acceptable salt thereof having a fluorogenic indicator group and an unblocked leaving group, said leaving group being selected for cleavage by an enzyme the activity of which changes with the presence of the disease, said indicator group being in a non-fluorescent first state when bonded to said leaving group, and being in a fluorescent second state excitable at a wavelength above 450 nm when said leaving group is cleaved from said indicator group by said enzyme for a period of time at least sufficient for said assay compound to be transferred into said cell and for said leaving group to be cleaved inside said cell from said indicator group by said enzyme, wherein said assay compound has sufficient purity so that fluorescence of impurities in said assay compound is less than autofluorescence of the metabolically active whole cell;

(b) sensing for said fluorescent second state of the indicator group for the test, metabolically active whole cell to produce test results; and (c) comparing the test results of said test metabolically active whole cell with reference results obtained from at least one of a diseased reference cell and a non-diseased reference cell thereby detecting the presence or absence of said disease in said test, metabolically active whole cell.

19. The method of claim 18, wherein said step (b) includes measuring an intensity of said fluorescent second state against time.

20. The method of claim 18, wherein said step (b) includes measuring a magnitude of said fluorescent second state at a particular point of time which is less than 20 minutes after said cells are contacted with said assay reagent.

21. The method of claim 18, wherein said step (c), the test results and the reference results are compared to a genetic analysis of the test, metabolically active whole cell.

22. The method of claim 18, wherein said step (c) is performed by a computer.

23. The method of claim 22, wherein the computer includes a neural network with back propagation for classifying the test results.

24. The method of claim 22, wherein the computer includes an expert system with look-up tables for classifying the test results.

25. The method of claim 18, said step (c) including performing a non-linear least squares technique on the test results and the reference results to classify the test results.

26. The method of claim 18, said step (c) including performing an analysis of variance technique on the test results and the reference results to classify the test results.

27. The method of claim 26, wherein the analysis of variance technique includes determining a plurality of eigenvectors and eigenvalues.

28. The method of claim 18, said step (c) including performing an analysis of variance technique on the test results and the reference results to obtain a reduced set of test results and reference results.

29. The method of claim 28, said step (c) further including performing a Non-Negative Least Squares technique on the reduced set of test results and reference results to classify the test results.

30. The method of claim 28, said step (c) further including inputting the reduced set of test results and reference results to a Neural Network with back propagation to classify the test results.

31. The method of claim 28, said step (c) further including inputting the reduced set of test results and reference results to an expert system with Look-Up tables to classify the test results.

32. The method of claim 18, wherein said step (c) compares the test results and the reference results to monitor enzyme activity representing morphology or cell type of the test, metabolically active whole cell.

33. The method of claim 18, wherein said step (c) compares the test results and the reference results to monitor enzyme activity of the test, metabolically active whole cell over time.

34. The method of claim 18, wherein said step (c) diagnoses the test, metabolically active whole cell for leukemia, wherein the leaving group includes at least one member selected from the group consisting of Pro, Lys, Gly, Ala, Gln-Ser, Thr-Pro, Val-Ser, Leu-Gly, and Gly-Pro and the test, metabolically active whole cell is a lymphocyte cell or a granulocyte cell.

35. The method of claim 18, wherein cells are classified into cell types after determining the activity of an endogenous enzyme.

36. The method of claim 35, wherein enzymes are measured which distinguish nucleated red blood cells from non-nucleated red blood cells.

37. A method for detecting the presence or absence of an abnormality in the activity of an enzyme in a metabolically active whole cell, comprising:

(a) contacting a plurality of reference, metabolically active whole cells, each having at least one normally functioning enzyme with a medium containing a cell permeable water soluble assay compound having the ability to pass through a cell membrane or a water soluble physiologically acceptable salt thereof having the ability to pass through a cell membrane, said assay compound comprising a fluorogenic indicator group and an unblocked leaving group, said leaving group being selected for cleavage by one of said at least one normally functioning enzyme, said indicator group being in a non-fluorescent first state when bonded to said leaving group, and being in a fluorescent second state excitable at a wavelength above 450 nm when said leaving group is cleaved from said indicator group by the one of said at least one normally functioning enzyme, for a period of time sufficient for said assay compound to be transferred into each of said plurality of reference, metabolically active whole cells for each of the at least one normally functioning enzyme, for each of said plurality of reference, metabolically active whole cells to produce a matrix of reference results and for said leaving group to be cleaved inside of each of said plurality of reference, metabolically active whole cells from said indicator group by the one of said at least one normally functioning enzyme, wherein said assay compound has sufficient purity so that fluorescence of impurities in said assay compound is less than autofluorescence of the metabolically active whole cell;

(b) sensing for said fluorescent second state of said indicator group for each of the at least one normally functioning enzyme for each said plurality of reference, metabolically active whole cells to produce a matrix of reference results;

(c) contacting a plurality of test, metabolically active whole cells, each having at least one normally functioning enzyme with said medium for said period of time;

(d) sensing for said fluorescent second state of said indicator group for each of the at least one normal functioning enzyme for each of said plurality of test, metabolically active whole cells to produce a matrix of test results; and (e) comparing the matrix of test results of said plurality of test, metabolically active whole cells in said step (d) with the matrix of reference results obtained from said plurality of reference, metabolically active whole cells in said step (b) thereby detecting the presence or absence of said abnormality in the activity of an enzyme in said metabolically active whole cell.

38. The method of claim 37, wherein said step (b) includes measuring an intensity of said fluorescent second state against time.

39. The method of claim 37, wherein said step (b) includes measuring a magnitude of said fluorescent second state at a point of time.

40. The method of claim 37, wherein said step (e), the matrix of test results and the matrix of reference results are compared to a genetic analysis of the plurality of test, metabolically active whole cells.

41. The method of claim 37, wherein said step (e) is performed by a computer.

42. The method of claim 41, wherein the computer includes a Neural Network with back propagation for classifying the matrix of test results.

43. The method of claim 41, wherein the computer includes an expert system with Look-Up tables for classifying the matrix of test results.

44. The method of claim 37, said step (e) including performing a Non-Negative Least Squares technique on the matrix of test results and the matrix of reference results to classify the matrix of test results.

45. The method of claim 37, said step (e) including performing an Analysis of Variance technique on the matrix of test results and the matrix of reference results to classify the matrix of test results.

46. The method of claim 45, wherein the analysis of variance techniques includes determining a plurality of eigenvectors and eigenvalues.

47. The method of claim 39, said step (e) including performing an analysis of variance technique on the test results and the reference results to obtain a reduced set of test results and reference results.

48. The method of claim 47, said step (e) further including performing a Non-Negative Least Squares technique on the reduced set of test results and reference results to classify the test results.

49. The method of claim 47, said step (e) further including inputting the required set of test results and reference results to a Neural Network with back propagation to classify the test results.

50. The method of claim 47, said step (e), further including inputting the reduced set of test results and reference results to an expert system with Look-Up tables to classify the test results.

51. The method of claim 37, wherein said step (e) compares the matrix of test results and the matrix of reference results to monitor enzyme activity representing morphology or cell type of the plurality of test, metabolically active whole cells.

52. The method of claim 37, wherein said step (e) compares the matrix of test results and the matrix of reference results to monitor enzyme activity of the plurality of test, metabolically active whole cells over time.

53. The method of claim 37, wherein said step (e) diagnoses the plurality of test, metabolically active whole cells for leukemia, wherein the at least one normally functioning enzyme includes Pro, Lys, Gly, Ala, Gln-Ser, Thr-Pro, Val-Ser, Leu-Gly, and Gly-Pro and the plurality of test, metabolically active whole cells include lymphocyte cells and granulocyte cells.

54. A method of performing an assay for detecting the presence or absence of a disease characterized by an abnormal enzyme activity comprising:

(a) contacting a test, metabolically active whole cell with at least one cell permeable water soluble assay compound or water soluble physiologically acceptable salt thereof having a fluorogenic indicator group and an unblocked leaving group, said leaving group being selected for cleavage by one of said at least one normally functioning enzyme the activity of which changes with the presence of the disease, said indicator group being in a non-fluorescent first state when bonded to said leaving group, and being in a fluorescent second state excitable at a wavelength above 450 nm when said leaving group is cleaved from said indicator group by the one of said at least one normally functioning enzyme for a period of time at least sufficient for said assay compound to be transferred into said cell and for said leaving group to be cleaved inside said cell from said indicator group by said enzyme wherein said assay compound has sufficient purity so that fluorescence of impurities in said assay compound is less tan autofluorescence of the metabolically active whole cell;

(b) sensing for said fluorescent second state of the indicator group for the test, metabolically active whole cell to produce a matrix of test results; and (c) comparing the matrix of test results of said test metabolically active whole cell with a matrix of reference results obtained from at least one of a diseased reference cell and a non-diseased reference cell thereby detecting the presence or absence of said disease in said test, metabolically active whole cell.

55. The method of claim 54, wherein said step (b) includes measuring an intensity of said fluorescent second state against time.

56. The method of claim 54, wherein said step (b) includes measuring a magnitude of said fluorescent second state at a point of time.

57. The method of claim 54, wherein in said step (c), the test results and the reference results are compared to obtain a genetic analysis of the test, metabolically active whole cell.

58. The method of claim 54, wherein said step (c) is performed by a computer.

59. The method of claim 58, wherein the computer includes a Neural Network with back propagation for classifying the matrix of test results.

60. The method of claim 59, wherein the computer includes an expert system with Look-Up tables for classifying the matrix of test results.

61. The method of claim 54, said step (c) including performing a Non-Negative Least Squares technique on the matrix of test results and the matrix of reference results to classify the matrix of test results.

62. The method of claim 54, said step (c) including performing an Analysis of Variance technique on the matrix of test results and the matrix of reference results to classify the matrix of test results.

63. The method of claim 62, wherein the analysis of variance technique includes detecting a plurality of eigenvectors and eigenvalues.

64. The method of claim 54, said step (c) including performing an analysis of variance technique on the test results and the reference results to obtain a reduced set of test results and reference results.

65. The method of claim 64, said step (c) further including performing a Non-Negative Least Squares technique on the reduced set of test results and reference results to classify the test results.

66. The method of claim 64, said step (c) further including inputting the reduced set of test results and reference results to a Neural Network with back propagation to classify the test results.

67. The method of claim 64, said step (c) further including inputting the reduced set of test results and reference results to an expert system with Look-Up tables to classify the test results.

68. The method of claim 54, wherein said step (c) compares the matrix of test results and the matrix of reference results to monitor enzyme activity representing morphology or cell type of the test, metabolically active whole cell.

69. The method of claim 54, wherein said step (c) compares the matrix of test results and the matrix of reference results to monitor enzyme activity of the test, metabolically active whole cell over time.

70. The method of claim 54, wherein said step (c) diagnoses the test, metabolically active whole cell for leukemia, wherein the at least one normally functioning enzymes include Pro, Lys, Gly, Ala, Gln-Ser, Thr-Pro, Val-Ser, Leu-Gly, and Gly-Pro and the test, metabolically active whole cell is a lymphocyte cell or a granulocyte cell.

71. A method for measuring the activity of an enzyme in a metabolically active whole cell, comprising:

(a) contacting a reference, metabolically active whole cell having a normally functioning enzyme with a medium containing a cell permeable water soluble assay compound or a cell permeable water soluble physiologically acceptable salt thereof, said assay compound having a solubility such that when a salt of the compound is dissolved in the aqueous media used in the assay at the concentration used in the assay, the solution has a background color of less than 1000 milliabsorbance units at 340 nm at 25° C. blanked against distilled or deionized water, said assay compound or physiologically acceptable salt thereof having the ability to pass through a cell membrane, said assay compound comprising a fluorogenic indicator group and a leaving group, said leaving group being selected for cleavage by said enzyme, said indicator group being in a non-fluorescent first state when bonded to said leaving group, and being in a fluorescent second state excitable at a wavelength above 450 nm when said leaving group is cleaved from said indicator group by said enzyme, for a period of time sufficient for said assay compound to be transferred into said cell and for said leaving group to be cleaved inside said cell from said indicator group by said enzyme, wherein said assay compound has sufficient purity so that fluorescence of impurities in said assay compound is less than autofluorescence of the metabolically active whole cell;

(b) sensing for said fluorescent second state of said indicator group for the reference, metabolically active whole cell to produce reference results;

(c) contacting a test, metabolically active whole cell with said medium for said period of time;

(d) sensing for said fluorescent second state of said indicator group for the test, metabolically active whole cell to produce test results; and (e) comparing the reference results of reference test, metabolically active whole cell in said step (b) with the test results obtained from said test metabolically active whole cell in said step (d) thereby measuring the activity of said enzyme in said metabolically active whole cell.

72. A method for measuring the activity of an enzyme in a metabolically active whole cell, comprising:

(a) contacting a reference, metabolically active whole cell having a normally functioning enzyme with a medium containing a cell permeable water soluble purified assay compound which is purified to an extent that background noise generated from impurities is less than autofluorescence of a metabolically active whole cell, said compound having the ability to pass through a cell membrane or a water soluble physiologically acceptable salt thereof having the ability to pass through a cell membrane, said assay compound comprising a fluorogenic indicator group and a leaving group, said leaving group being selected for cleavage by said enzyme, said indicator group being in a non-fluorescent first state when bonded to said leaving group, and being in a fluorescent second state excitable at a wavelength above 450 nm when said leaving group is cleaved from said indicator group by said enzyme, for a period of time which is sufficient for said assay compound to be transferred into said cell and for said leaving group to be cleaved inside said cell from said indicator group by said enzyme;

(b) sensing for said fluorescent second state of said indicator group for the reference, metabolically active whole cell to produce reference results;

(c) contacting a test, metabolically active whole cell with said medium for said period of time;

(d) sensing for said fluorescent second state of said indicator group for the test, metabolically active whole cell to produce test results; and (e) comparing the reference results of reference test, metabolically active whole cell in said step (b) with the test results obtained from said test metabolically active whole cell in said step (d) thereby measuring the activity of said enzyme in said metabolically active whole cell.

73. A method for measuring the activity of an enzyme in a metabolically active whole cell, comprising:

(a) contacting a reference, metabolically active whole cell having a normally functioning enzyme with a medium containing a cell permeable water soluble assay compound or a water soluble physiologically acceptable salt thereof, said assay compound or physiologically acceptable salt thereof having the ability to pass through a cell membrane, said assay compound comprising a fluorogenic indicator group and a leaving group, said leaving group being selected for cleavage by said enzyme, said indicator group being in a non-fluorescent first state when bonded to said leaving group, and being in a fluorescent second state excitable at a wavelength above 450 nm when said leaving group is cleaved from said indicator group by said enzyme, for a period of time sufficient for said assay compound to be transferred into said cell and for said leaving group to be cleaved inside said cell from said indicator group by said enzyme, wherein said assay compound has sufficient purity so that fluorescence of impurities in said assay compound is less than autofluorescence of the metabolically active whole cell;

(b) sensing for said fluorescent second state of said indicator group for the reference, metabolically active whole cell to produce reference results;

(c) contacting a test, metabolically active whole cell with said medium for said period of time;

(d) sensing for said fluorescent second state of said indicator group for the test, metabolically active whole cell to produce test results; and (e) comparing the reference results of reference test, metabolically active whole cell in said step (b) with the test results obtained from said test metabolically active whole cell in said step (d) thereby measuring the activity of said enzyme in said metabolically active whole cell.

74. The method of claim 1, 18, 37, 54, 71, 72 or 73, wherein said fluorescence of impurities in said assay compound are less than the autofluorescence of the metabolically active whole cell such that said fluorescence is less than the fluorescence generated by $1\times10^{-6}$M free rhodamine 110.

75. The method of claim 1, 18, 37, 54, 71, 72 or 73, wherein said fluorescence of impurities in said assay compound are less than the autofluorescence of the metabolically active whole cell such that said fluorescence is less than the fluorescence generated by $1\times10^{-7}$M free rhodamine 110.

76. The method of claim 1, 18, 37, 54, 71, 72 or 73, wherein said fluorogenic indicator group is selected from rhodamine 110, rhodol, fluorescein and derivatives of rhodamine 110, rhodol, fluorescein.

77. The method of claim 76, wherein said derivatives of rhodamine 110, rhodol, fluorescein is selected from 4'(5') thiofluorescein, 4'(5')-aminofluorescein, 4'(5')-carboxyfluorescein, 4'(5')-chlorofluorescein, 4'(5')-methylfluorescein, 4'(5')-sulfofluorescein, 4'(5')-aminorhodol, 4'(5')-carboxyrhodol, 4'(5')-chlororhodol, 4'(5')-methylrhodol, 4'(5')-sulforhodol; 4'(5')-aminorhodamine 110, 4'(5')-sulforhodamine 110 and 4'(5') thiorhodamine 110.

* * * * *